US012454695B2

(12) United States Patent
Schmidt et al.

(10) Patent No.: US 12,454,695 B2
(45) Date of Patent: Oct. 28, 2025

(54) FUSION POLYPEPTIDES COMPRISING INTERLEUKIN 12 AND A METAL-HYDROXIDE BINDING POLYPEPTIDE

(71) Applicant: Ankyra Therapeutics, Inc., Boston, MA (US)

(72) Inventors: Michael Schmidt, Wellesley, MA (US); Grigorios Zarbis-Papastoitsis, Watertown, MA (US); Karl Dane Wittrup, Boston, MA (US); Darrell Irvine, Arlington, MA (US)

(73) Assignee: Ankyra Therapeutics, Inc., Boston, MA (US)

( * ) Notice: Subject to any disclaimer, the term of this patent is extended or adjusted under 35 U.S.C. 154(b) by 848 days.

(21) Appl. No.: 17/736,431

(22) Filed: May 4, 2022

(65) Prior Publication Data

US 2022/0372495 A1 Nov. 24, 2022

Related U.S. Application Data

(60) Provisional application No. 63/184,620, filed on May 5, 2021.

(51) Int. Cl.

| | |
|---|---|
| ***C07K 14/54*** | (2006.01) |
| ***A61K 38/00*** | (2006.01) |
| ***A61P 35/00*** | (2006.01) |
| ***C07K 16/18*** | (2006.01) |
| ***C07K 16/28*** | (2006.01) |
| ***C12N 15/62*** | (2006.01) |

(52) U.S. Cl.

CPC .............. *C12N 15/62* (2013.01); *A61P 35/00* (2018.01); *C07K 14/5434* (2013.01); *C07K 16/18* (2013.01); *C07K 16/2866* (2013.01); *A61K 38/00* (2013.01); *C07K 2319/00* (2013.01)

(58) Field of Classification Search

CPC .... C12N 15/62; C07K 14/5434; C07K 16/18; C07K 16/2866; C07K 2319/00; C07K 14/54

See application file for complete search history.

(56) References Cited

FOREIGN PATENT DOCUMENTS

| | | | |
|---|---|---|---|
| WO | WO-2020/068261 | A1 | 4/2020 |
| WO | WO-2020/263399 | A1 | 12/2020 |
| WO | WO-2022/235755 | A2 | 11/2022 |

OTHER PUBLICATIONS

Agarwal, Y. et al., Intratumourally injected alum-tethered cytokines elicit potent and safer local and systemic anticancer immunity. Nat Biomed Eng., 6(2):129-143 (2022).

Brunati, A. et al., Novel consensus sequence for the Golgi apparatus casein kinase, revealed using proline-rich protein-1 (PRP1)-derived peptide substrates, Biochem J., 351 Pt 3(Pt 3):765-8 (2000).

Chang, Z. and Chen, Y., Synthetic Immunoreceptors for Cancer Therapy and Beyond, Trends Mol Med., 23(5):430-450 (2017).

Cutrera, J. et al., Safe and effective treatment of spontaneous neoplasms with interleukin 12 electro-chemo-gene therapy, J Cell Mol Med., 19(3):664-75 (2015).

Cutrera, J. et al., Safety and efficacy of tumor-targeted interleukin 12 gene therapy in treated and non-treated, metastatic lesions, Curr Gene Ther., 15(1):44-54 (2014).

Lasa-Benito, M., et al., Golgi apparatus mammary gland casein kinase: monitoring by a specific peptide substrate and definition of specificity determinants, FEBS Lett., 382(1-2):149-52 (1996).

Lasek, W., et al., Interleukin 12: still a promising candidate for tumor immunotherapy?, Cancer Immunol Immunother., 63(5):419-35 (2014).

Liu, S. et al., NK cell-based cancer immunotherapy: from basic biology to clinical development, J Hematol Oncol., 14(1):7 (2021).

Mercier, J. et al., Structure primaire de la caséine s1-bovine. Séquence complète [Primary structure of bovine s1 casein. Complete sequence], Eur J Biochem., 23(1):41-51 (1971).

Mercier, J.C., Phosphorylation of caseins, present evidence for an amino acid triplet code posttranslationally recognized by specific kinases, Biochimie, 63(1):1-17 (1981).

Milling, L. et al., Delivering safer immunotherapies for cancer, Adv Drug Deliv Rev., 114:79-101 (2017).

Momin, N. et al., Anchoring of intratumorally administered cytokines to collagen safely potentiates systemic cancer immunotherapy, Sci Transl Med., 11(498): 26 pages (2019).

Morefield, G. et al., Effect of phosphorylation of ovalbumin on adsorption by aluminum-containing adjuvants and elution upon exposure to interstitial fluid, Vaccine, 23(12):1502-6 (2005).

Nastala, C. et al., Recombinant IL-12 administration induces tumor regression in association with IFN-gamma production, J Immunol., 153(4):1697-706 (1994).

Paoloni, M. et al., Defining the Pharmacodynamic Profile and Therapeutic Index of NHS-IL12 Immunocytokine in Dogs with Malignant Melanoma, PLoS One, 10(6):e0129954 (2015).

Rohaan, M. et al., Adoptive cellular therapies: the current landscape, Virchows Arch., 474(4):449-461 (2019).

Sreelatha, A. et al., The secretory pathway kinases, Biochim Biophys Acta, 1854(10 Pt B):1687-93 (2015).

Tagliabracci, V. et al., A Single Kinase Generates the Majority of the Secreted Phosphoproteome, Cell, 161(7):1619-32 (2015).

Tagliabracci, V. et al., Secreted kinase phosphorylates extracellular proteins that regulate biomineralization, Science, 336(6085):1150-3 (2012).

Ullrich, K. et al., Immunology of IL-12: An update on functional activities and implications for disease, EXCLI J., 19:1563-1589 (2020).

(Continued)

*Primary Examiner* — Elly-Gerald Stoica

(74) *Attorney, Agent, or Firm* — Morgan, Lewis & Bockius LLP

(57) ABSTRACT

The present disclosure provides surprisingly useful fusion polypeptides including an immunomodulatory moiety and a metal-hydroxide binding moiety, as well as various related technologies, including methods of making and of using such fusion polypeptides.

20 Claims, 57 Drawing Sheets

Specification includes a Sequence Listing.

(56) References Cited

OTHER PUBLICATIONS

Von Rueden, S. and Fan, T., Cancer-Immunity Cycle and Therapeutic Interventions-Opportunities for Including Pet Dogs With Cancer, Front Oncol., 11:773420 (2021).

International Search Report for PCT/US2022/027617, 8 pages (Nov. 28, 2022).

Written Opinion for PCT/US2022/027617, 10 pages (Nov. 28, 2022).

| Name | Sequence | Tag |
|---|---|---|
| ABP10 | GGGGSFQSEEQQGGGSGGSEEGGMESEESNGGGSGGSEEGGGGS **(SEQ ID NO: 90)** | HHHHHH **(SEQ ID NO: 98)** |
| ABP20 | GGGGSGGGGSEESEESEESEEGGGGS **(SEQ ID NO: 119)** | HHHHHH **(SEQ ID NO: 98)** |
| ABP20-G4 | GGGGSGGGGSEEGGGGSEEGGGGSEEGGGGSEEGGGGS **(SEQ ID NO: 82)** | HHHHHH **(SEQ ID NO: 98)** |
| ABP20-G4-GS20 | GGGGSGGGGSGGGGSGGGGSEEGGGGSEEGGGGSEEGGGGSEEGGGGS **(SEQ ID NO: 120)** | HHHHHH **(SEQ ID NO: 98)** |

Figure 3C

| Name | Sequence | Tag |
|---|---|---|
| ABP20-G4 | GGGGSGGGGSEEGGGGSEEGGGGSEEGGGGSEEGGGGS (**SEQ ID NO: 82**) | HHHHHH (**SEQ ID NO: 98**) |
| ABP20-G4-6x | GGGGSGGGGSEEGGGGSEEGGGGSEEGGGGSEEGGGGSEEGGGGSEEGGGGS (**SEQ ID NO: 83**) | HHHHHH (**SEQ ID NO: 98**) |
| ABP20-G4-8x | GGGGSGGGGSEEGGGGSEEGGGGSEEGGGGSEEGGGGSEEGGGGSEEGGGGSEEGGGGSEEGGGGS (**SEQ ID NO: 84**) | HHHHHH (**SEQ ID NO: 98**) |
| ABP20-6x | GGGGSGGGGSEESEESEESEESEESEEGGGGS (**SEQ ID NO: 85**) | HHHHHH (**SEQ ID NO: 98**) |
| ABP20-8x | GGGGSGGGGSEESEESEESEESEESEESEESEEGGGGS (**SEQ ID NO: 86**) | HHHHHH (**SEQ ID NO: 98**) |
| ABP20-G4-SEEE | GGGGSGGGGSEEEGGGSEEEGGGSEEEGGGSEEEGGGS (**SEQ ID NO: 87**) | HHHHHH (**SEQ ID NO: 98**) |
| ABP20-G4-SEEA | GGGGSGGGGSEEAGGGSEEAGGGSEEAGGGSEEAGGGS (**SEQ ID NO: 88**) | HHHHHH (**SEQ ID NO: 98**) |
| ABP20-G4-SEEQ | GGGGSGGGGSEEQGGGSEEQGGGSEEQGGGSEEQGGGS (**SEQ ID NO: 89**) | HHHHHH (**SEQ ID NO: 98**) |
| ABP10 | GGGGSFQSEEQQGGGSGGSEEGGMESEESNGGGSGGSEEGGGGS (**SEQ ID NO: 90**) | HHHHHH (**SEQ ID NO: 98**) |
| ABP10-GS | GGGGSGGSEEGGGGGSGGSEEGGGGSEEGGGGGSGGSEEGGGG (**SEQ ID NO: 91**) | HHHHHH (**SEQ ID NO: 98**) |
| ABP10-GE | GGGGEGGSEEGGGGGEGGSEEGGGGSEEGGGGGEGGSEEGGGG (**SEQ ID NO: 92**) | HHHHHH (**SEQ ID NO: 98**) |
| ABP20-G8-GS | GGGGEGGGGSEEGGGSGGGGSEEGGGSGGGGSEEGGGSGGGGSEEGGGG (**SEQ ID NO: 93**) | HHHHHH (**SEQ ID NO: 98**) |
| ABP20-G8-GE | GGGGEGGGGSEEGGGEGGGGSEEGGGEGGGGSEEGGGEGGGGSEEGGGG (**SEQ ID NO: 94**) | HHHHHH (**SEQ ID NO: 98**) |
| ABP20-G4-GE | GGGGEGGGGSEEGGGGSEEGGGGSEEGGGGSEEGGGG (**SEQ ID NO: 95**) | HHHHHH (**SEQ ID NO: 98**) |
| ABP20-G4-6x-GE | GGGGEGGGGSEEGGGGSEEGGGGSEEGGGGSEEGGGGSEEGGGGSEEGGGG (**SEQ ID NO: 96**) | HHHHHH (**SEQ ID NO: 98**) |
| ABP20-G4-8x-GE | GGGGEGGGGSEEGGGGSEEGGGGSEEGGGGSEEGGGGSEEGGGGSEEGGGGSEEGGGGSEEGGGG (**SEQ ID NO: 97**) | HHHHHH (**SEQ ID NO: 98**) |

Figure 5 mIL12-ABP10-K mIL12-ABP20-G4-8x-GE-K

| | Peak elution time | | |
|---|---|---|---|
| Molecule | Pre-AEX | Post-AEX | Post-AEX + phosphatase |
| mIL12-ABP10-K | 16.7 | 16.6 | 14.2 |
| mIL12-ABP20-G4-8x-GE-K | 19.5 | 19.4 | 15.6 |

Figure 10C

| Fraction | % of pool | PO4/protein |
|---|---|---|
| No Fam20C control | | 0.6 |
| 110 | | 2.4 |
| 111 | | 3.7 |
| 112 | 24 | 4.6 |
| 113 | 20 | 5.8 |
| 114 | 17 | 6.2 |
| 115 | 14 | 6.3 |
| 116 | 11 | 6.4 |
| 117 | 9 | 6.9 |
| POOL (112-118) | | 5.7 |

Figure 17B

Dashed line represents 12,500 ng/mL theoretical concentration of free protein if all protein elutes off alum Dashed line represents 12,500 ng/mL theoretical concentration of free protein if all protein elutes off alum

| | | | Alum retention | | HEK-Blue-IL12 | | |
|---|---|---|---|---|---|---|---|
| Fraction | % of pool | PO4/protein (mean) | % Retained – Run 1 | % Retained – Run 2 | EC50 – No alum | EC50 w/ alum | % max signal |
| 110 | | 2.4 | 11 | 50 | 6 | 10 | 100 |
| 111 | | 3.7 | 78 | 81 | | | |
| 112 | 24 | 4.6 | 95 | 95 | 7 | 18 | 100 |
| 113 | 20 | 5.8 | 99 | 96 | | | |
| 114 | 17 | 6.2 | 100 | 99 | 10 | 25 | 79 |
| 115 | 14 | 6.3 | 100 | 99 | | | |
| 116 | 11 | 6.4 | | | | | |
| 117 | 9 | 6.9 | 100 | 100 | 17 | 32 | 50 |

Figure 20

| Fraction | Conc (mg/mL) | PO4/protein |
|---|---|---|
| 645 | 7.4 | 5.8 |
| 650 | 13.9 | 5.8 |
| 655 | 12.7 | 6.3 |
| 660 | 10 | 8.4 |
| 665 | 4.8 | 8.8 |

| Alum retention |
|---|
| % Retained – 24 hours |
| 70 |
| 91 |
| 99 |
| 99 |
| |

| HEK-Blue-IL12 | |
|---|---|
| EC50 – No alum | EC50 w/ alum |
| 3.5 | 5 |
| 3.6 | 6.4 |
| 3.4 | 8.6 |
| 3.4 | 14 |
| | |

Figure 22

| Q-HP elution fraction | PO4/protein (malachite green) | % retained on alum at 24 hours | HEK-Blue-IL12 EC50 (ng/mL) | |
|---|---|---|---|---|
| | | | No alum | + alum |
| f90 | 0.4 | | | |
| f91 | 2.0 | 28 | | |
| f92 | 4.5 | 65 | | |
| f93 | 5.5 | 97 | 2.5 | 6.5 |
| f93.5 | 6.5 | 99 | | |
| f94 | 6.8 | 100 | | 9.4 |
| f94.5 | 8.3 | 100 | | 9.0 |
| f95 | 9.4 | 100 | 3.0 | 14.4 |
| f96 | 10.3 | 100 | | 16.5 |
| f97 | 10.8 | 100 | 3.9 | 30.1 |
| f98 | 12.2 | | | |
| f99 | 11.3 | | | |

Figure 25

SEQUENCE LISTING

```
<160> NUMBER OF SEQ ID NOS: 144

<210> SEQ ID NO 1
<211> LENGTH: 313
<212> TYPE: PRT
<213> ORGANISM: Mus sp.

<400> SEQUENCE: 1

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
```

```
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310


<210> SEQ ID NO 2
<211> LENGTH: 193
<212> TYPE: PRT
<213> ORGANISM: Mus sp.

<400> SEQUENCE: 2

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala


<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15
```

<210> SEQ ID NO 4
<211> LENGTH: 521
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

Met Trp Glu Leu Glu Lys Asp Val Tyr Val Val Glu Val Asp Trp Thr
1 5 10 15

Pro Asp Ala Pro Gly Glu Thr Val Asn Leu Thr Cys Asp Thr Pro Glu
20 25 30

Glu Asp Asp Ile Thr Trp Thr Ser Asp Gln Arg His Gly Val Ile Gly
35 40 45

Ser Gly Lys Thr Leu Thr Ile Thr Val Lys Glu Phe Leu Asp Ala Gly
50 55 60

Gln Tyr Thr Cys His Lys Gly Gly Glu Thr Leu Ser His Ser His Leu
65 70 75 80

Leu Leu His Lys Lys Glu Asn Gly Ile Trp Ser Thr Glu Ile Leu Lys
85 90 95

Asn Phe Lys Asn Lys Thr Phe Leu Lys Cys Glu Ala Pro Asn Tyr Ser
100 105 110

Gly Arg Phe Thr Cys Ser Trp Leu Val Gln Arg Asn Met Asp Leu Lys
115 120 125

Phe Asn Ile Lys Ser Ser Ser Ser Ser Pro Asp Ser Arg Ala Val Thr
130 135 140

Cys Gly Met Ala Ser Leu Ser Ala Glu Lys Val Thr Leu Asp Gln Arg
145 150 155 160

Asp Tyr Glu Lys Tyr Ser Val Ser Cys Gln Glu Asp Val Thr Cys Pro
165 170 175

Thr Ala Glu Glu Thr Leu Pro Ile Glu Leu Ala Leu Glu Ala Arg Gln
180 185 190

Gln Asn Lys Tyr Glu Asn Tyr Ser Thr Ser Phe Phe Ile Arg Asp Ile
195 200 205

Ile Lys Pro Asp Pro Pro Lys Asn Leu Gln Met Lys Pro Leu Lys Asn
210 215 220

Ser Gln Val Glu Val Ser Trp Glu Tyr Pro Asp Ser Trp Ser Thr Pro
225 230 235 240

His Ser Tyr Phe Ser Leu Lys Phe Phe Val Arg Ile Gln Arg Lys Lys
245 250 255

Glu Lys Met Lys Glu Thr Glu Glu Gly Cys Asn Gln Lys Gly Ala Phe
260 265 270

Leu Val Glu Lys Thr Ser Thr Glu Val Gln Cys Lys Gly Gly Asn Val
275 280 285

Cys Val Gln Ala Gln Asp Arg Tyr Tyr Asn Ser Ser Cys Ser Lys Trp
290 295 300

Ala Cys Val Pro Cys Arg Val Arg Ser Gly Gly Gly Gly Ser Gly Gly
305 310 315 320

Gly Gly Ser Gly Gly Gly Gly Ser Arg Val Ile Pro Val Ser Gly Pro
325 330 335

Ala Arg Cys Leu Ser Gln Ser Arg Asn Leu Leu Lys Thr Thr Asp Asp
340 345 350

Met Val Lys Thr Ala Arg Glu Lys Leu Lys His Tyr Ser Cys Thr Ala

```
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala
        515                 520


<210> SEQ ID NO 5
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190
```

```
Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser His His
        515                 520                 525

His His His His
    530


<210> SEQ ID NO 6
<211> LENGTH: 571
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Trp Glu Leu Glu Lys Asp Val Tyr Val Val Glu Val Asp Trp Thr
1               5                   10                  15
```

-continued

```
Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430
```

```
Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Phe Gln
        515                 520                 525

Ser Glu Glu Gln Gln Gly Gly Gly Ser Gly Gly Ser Glu Glu Gly Gly
    530                 535                 540

Met Glu Ser Glu Glu Ser Asn Gly Gly Gly Ser Gly Gly Ser Glu Glu
545                 550                 555                 560

Gly Gly Gly Gly Ser His His His His His His
                565                 570


<210> SEQ ID NO 7
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220
```

```
Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Ser Glu Glu Ser Glu Glu Ser Glu Glu Gly Gly
    530                 535                 540

Gly Gly Ser His His His His His His
545                 550
```

<210> SEQ ID NO 8
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
```

-continued

```
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445
```

```
Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Gly Gly Gly Gly Ser Glu Glu Gly Gly Gly Gly
    530                 535                 540

Ser Glu Glu Gly Gly Gly Gly Ser Glu Glu Gly Gly Gly Gly Ser His
545                 550                 555                 560

His His His His His
                565


<210> SEQ ID NO 9
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
```

```
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Gly Gly Gly Gly Ser Gly Gly Gly Gly Ser Glu Glu Gly
    530                 535                 540

Gly Gly Gly Ser Glu Glu Gly Gly Gly Gly Ser Glu Glu Gly Gly Gly
545                 550                 555                 560

Gly Ser Glu Glu Gly Gly Gly Gly Ser His His His His His His
                565                 570                 575
```

<210> SEQ ID NO 10
<211> LENGTH: 579
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

```
Met Trp Glu Leu Glu Lys Asp Val Tyr Val Val Glu Val Asp Trp Thr
1               5                   10                  15
```

-continued

```
Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
```

```
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Gly Gly Gly Gly Ser Glu Glu Gly Gly Gly Gly
    530                 535                 540

Ser Glu Glu Gly Gly Gly Gly Ser Glu Glu Gly Gly Gly Gly Ser Glu
545                 550                 555                 560

Glu Gly Gly Gly Gly Ser Glu Glu Gly Gly Gly Gly Ser His His His
                565                 570                 575

His His His


<210> SEQ ID NO 11
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
```

```
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Gly Gly Gly Gly Ser Glu Glu Gly Gly Gly Gly
    530                 535                 540

Ser Glu Glu Gly Gly Gly Gly Ser Glu Glu Gly Gly Gly Gly Ser Glu
545                 550                 555                 560

Glu Gly Gly Gly Gly Ser Glu Glu Gly Gly Gly Gly Ser Glu Glu Gly
                565                 570                 575

Gly Gly Gly Ser Glu Glu Gly Gly Gly Gly Ser His His His His His
            580                 585                 590

His
```

<210> SEQ ID NO 12
<211> LENGTH: 559
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 12

Met Trp Glu Leu Glu Lys Asp Val Tyr Val Val Glu Val Asp Trp Thr
1 5 10 15

Pro Asp Ala Pro Gly Glu Thr Val Asn Leu Thr Cys Asp Thr Pro Glu
20 25 30

Glu Asp Asp Ile Thr Trp Thr Ser Asp Gln Arg His Gly Val Ile Gly
35 40 45

Ser Gly Lys Thr Leu Thr Ile Thr Val Lys Glu Phe Leu Asp Ala Gly
50 55 60

Gln Tyr Thr Cys His Lys Gly Gly Glu Thr Leu Ser His Ser His Leu
65 70 75 80

Leu Leu His Lys Lys Glu Asn Gly Ile Trp Ser Thr Glu Ile Leu Lys
85 90 95

Asn Phe Lys Asn Lys Thr Phe Leu Lys Cys Glu Ala Pro Asn Tyr Ser
100 105 110

Gly Arg Phe Thr Cys Ser Trp Leu Val Gln Arg Asn Met Asp Leu Lys
115 120 125

Phe Asn Ile Lys Ser Ser Ser Ser Ser Pro Asp Ser Arg Ala Val Thr
130 135 140

Cys Gly Met Ala Ser Leu Ser Ala Glu Lys Val Thr Leu Asp Gln Arg
145 150 155 160

Asp Tyr Glu Lys Tyr Ser Val Ser Cys Gln Glu Asp Val Thr Cys Pro
165 170 175

Thr Ala Glu Glu Thr Leu Pro Ile Glu Leu Ala Leu Glu Ala Arg Gln
180 185 190

Gln Asn Lys Tyr Glu Asn Tyr Ser Thr Ser Phe Phe Ile Arg Asp Ile
195 200 205

Ile Lys Pro Asp Pro Pro Lys Asn Leu Gln Met Lys Pro Leu Lys Asn
210 215 220

Ser Gln Val Glu Val Ser Trp Glu Tyr Pro Asp Ser Trp Ser Thr Pro
225 230 235 240

His Ser Tyr Phe Ser Leu Lys Phe Phe Val Arg Ile Gln Arg Lys Lys
245 250 255

Glu Lys Met Lys Glu Thr Glu Glu Gly Cys Asn Gln Lys Gly Ala Phe
260 265 270

Leu Val Glu Lys Thr Ser Thr Glu Val Gln Cys Lys Gly Gly Asn Val
275 280 285

Cys Val Gln Ala Gln Asp Arg Tyr Tyr Asn Ser Ser Cys Ser Lys Trp
290 295 300

Ala Cys Val Pro Cys Arg Val Arg Ser Gly Gly Gly Gly Ser Gly Gly
305 310 315 320

Gly Gly Ser Gly Gly Gly Gly Ser Arg Val Ile Pro Val Ser Gly Pro
325 330 335

Ala Arg Cys Leu Ser Gln Ser Arg Asn Leu Leu Lys Thr Thr Asp Asp
340 345 350

Met Val Lys Thr Ala Arg Glu Lys Leu Lys His Tyr Ser Cys Thr Ala
355 360 365

Glu Asp Ile Asp His Glu Asp Ile Thr Arg Asp Gln Thr Ser Thr Leu
370 375 380

Lys Thr Cys Leu Pro Leu Glu Leu His Lys Asn Glu Ser Cys Leu Ala
385 390 395 400

```
Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Ser Glu Glu Ser Glu Glu Ser Glu Glu Ser Glu
    530                 535                 540

Glu Ser Glu Glu Gly Gly Gly Gly Ser His His His His His His
545                 550                 555


<210> SEQ ID NO 13
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
```

```
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Ser Glu Glu Ser Glu Glu Ser Glu Glu Ser Glu
    530                 535                 540

Glu Ser Glu Glu Ser Glu Glu Ser Glu Glu Gly Gly Gly Gly Ser His
545                 550                 555                 560

His His His His His
                565
```

<210> SEQ ID NO 14
<211> LENGTH: 565
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
```

```
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Glu Gly Gly Gly Ser Glu Glu Glu Gly Gly Gly
    530                 535                 540

Ser Glu Glu Glu Gly Gly Gly Ser Glu Glu Glu Gly Gly Gly Ser His
545                 550                 555                 560

His His His His His
                565


<210> SEQ ID NO 15
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190
```

```
Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Ala Gly Gly Gly Ser Glu Glu Ala Gly Gly Gly
    530                 535                 540

Ser Glu Glu Ala Gly Gly Gly Ser Glu Glu Ala Gly Gly Gly Ser His
545                 550                 555                 560

His His His His His
                565
```

<210> SEQ ID NO 16
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400
```

```
Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Gly Gly Ser Glu Glu Gln Gly Gly Gly Ser Glu Glu Gln Gly Gly Gly
    530                 535                 540

Ser Glu Glu Gln Gly Gly Gly Ser Glu Glu Gln Gly Gly Gly Ser His
545                 550                 555                 560

His His His His His
                565


<210> SEQ ID NO 17
<211> LENGTH: 570
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190
```

```
Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Ser Gly Gly
        515                 520                 525

Ser Glu Glu Gly Gly Gly Gly Gly Ser Gly Gly Ser Glu Glu Gly Gly
    530                 535                 540

Gly Gly Ser Glu Glu Gly Gly Gly Gly Gly Ser Gly Gly Ser Glu Glu
545                 550                 555                 560

Gly Gly Gly Gly His His His His His His
                565                 570
```

<210> SEQ ID NO 18
<211> LENGTH: 570
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 18

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400
```

Thr Arg Glu Thr Ser Ser Thr Thr Arg Gly Ser Cys Leu Pro Pro Gln
405 410 415

Lys Thr Ser Leu Met Met Thr Leu Cys Leu Gly Ser Ile Tyr Glu Asp
420 425 430

Leu Lys Met Tyr Gln Thr Glu Phe Gln Ala Ile Asn Ala Ala Leu Gln
435 440 445

Asn His Asn His Gln Gln Ile Ile Leu Asp Lys Gly Met Leu Val Ala
450 455 460

Ile Asp Glu Leu Met Gln Ser Leu Asn His Asn Gly Glu Thr Leu Arg
465 470 475 480

Gln Lys Pro Pro Val Gly Glu Ala Asp Pro Tyr Arg Val Lys Met Lys
485 490 495

Leu Cys Ile Leu Leu His Ala Phe Ser Thr Arg Val Val Thr Ile Asn
500 505 510

Arg Val Met Gly Tyr Leu Ser Ser Ala Gly Gly Gly Gly Glu Gly Gly
515 520 525

Ser Glu Glu Gly Gly Gly Gly Gly Glu Gly Gly Ser Glu Glu Gly Gly
530 535 540

Gly Gly Ser Glu Glu Gly Gly Gly Gly Gly Glu Gly Gly Ser Glu Glu
545 550 555 560

Gly Gly Gly Gly His His His His His His
565 570

<210> SEQ ID NO 19
<211> LENGTH: 576
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Met Trp Glu Leu Glu Lys Asp Val Tyr Val Val Glu Val Asp Trp Thr
1 5 10 15

Pro Asp Ala Pro Gly Glu Thr Val Asn Leu Thr Cys Asp Thr Pro Glu
20 25 30

Glu Asp Asp Ile Thr Trp Thr Ser Asp Gln Arg His Gly Val Ile Gly
35 40 45

Ser Gly Lys Thr Leu Thr Ile Thr Val Lys Glu Phe Leu Asp Ala Gly
50 55 60

Gln Tyr Thr Cys His Lys Gly Gly Glu Thr Leu Ser His Ser His Leu
65 70 75 80

Leu Leu His Lys Lys Glu Asn Gly Ile Trp Ser Thr Glu Ile Leu Lys
85 90 95

Asn Phe Lys Asn Lys Thr Phe Leu Lys Cys Glu Ala Pro Asn Tyr Ser
100 105 110

Gly Arg Phe Thr Cys Ser Trp Leu Val Gln Arg Asn Met Asp Leu Lys
115 120 125

Phe Asn Ile Lys Ser Ser Ser Ser Ser Pro Asp Ser Arg Ala Val Thr
130 135 140

Cys Gly Met Ala Ser Leu Ser Ala Glu Lys Val Thr Leu Asp Gln Arg
145 150 155 160

Asp Tyr Glu Lys Tyr Ser Val Ser Cys Gln Glu Asp Val Thr Cys Pro
165 170 175

Thr Ala Glu Glu Thr Leu Pro Ile Glu Leu Ala Leu Glu Ala Arg Gln

```
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Glu Gly Gly
        515                 520                 525

Gly Gly Ser Glu Glu Gly Gly Gly Ser Gly Gly Gly Gly Ser Glu Glu
    530                 535                 540

Gly Gly Gly Ser Gly Gly Gly Gly Ser Glu Glu Gly Gly Gly Ser Gly
545                 550                 555                 560

Gly Gly Gly Ser Glu Glu Gly Gly Gly Gly His His His His His His
                565                 570                 575
```

<210> SEQ ID NO 20
<211> LENGTH: 576
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
```

```
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Glu Gly Gly
        515                 520                 525

Gly Gly Ser Glu Glu Gly Gly Gly Glu Gly Gly Gly Gly Ser Glu Glu
    530                 535                 540

Gly Gly Gly Glu Gly Gly Gly Gly Ser Glu Glu Gly Gly Gly Glu Gly
545                 550                 555                 560

Gly Gly Gly Ser Glu Glu Gly Gly Gly Gly His His His His His His
                565                 570                 575


<210> SEQ ID NO 21
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175
```

-continued

```
Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Glu Gly Gly
        515                 520                 525

Gly Gly Ser Glu Glu Gly Gly Gly Gly Ser Glu Glu Gly Gly Gly Gly
    530                 535                 540

Ser Glu Glu Gly Gly Gly Gly Ser Glu Glu Gly Gly Gly Gly Ser Glu
545                 550                 555                 560

Glu Gly Gly Gly Gly Ser Glu Glu Gly Gly Gly Gly His His His His
                565                 570                 575

His His
```

<210> SEQ ID NO 22

<211> LENGTH: 592
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Gly Gly Gly Ser Gly Gly
305                 310                 315                 320

Gly Gly Ser Gly Gly Gly Gly Ser Arg Val Ile Pro Val Ser Gly Pro
                325                 330                 335

Ala Arg Cys Leu Ser Gln Ser Arg Asn Leu Leu Lys Thr Thr Asp Asp
            340                 345                 350

Met Val Lys Thr Ala Arg Glu Lys Leu Lys His Tyr Ser Cys Thr Ala
        355                 360                 365

Glu Asp Ile Asp His Glu Asp Ile Thr Arg Asp Gln Thr Ser Thr Leu
```

```
    370                 375                 380

Lys Thr Cys Leu Pro Leu Glu Leu His Lys Asn Glu Ser Cys Leu Ala
385                 390                 395                 400

Thr Arg Glu Thr Ser Ser Thr Thr Arg Gly Ser Cys Leu Pro Pro Gln
                405                 410                 415

Lys Thr Ser Leu Met Met Thr Leu Cys Leu Gly Ser Ile Tyr Glu Asp
            420                 425                 430

Leu Lys Met Tyr Gln Thr Glu Phe Gln Ala Ile Asn Ala Ala Leu Gln
        435                 440                 445

Asn His Asn His Gln Gln Ile Ile Leu Asp Lys Gly Met Leu Val Ala
    450                 455                 460

Ile Asp Glu Leu Met Gln Ser Leu Asn His Asn Gly Glu Thr Leu Arg
465                 470                 475                 480

Gln Lys Pro Pro Val Gly Glu Ala Asp Pro Tyr Arg Val Lys Met Lys
                485                 490                 495

Leu Cys Ile Leu Leu His Ala Phe Ser Thr Arg Val Val Thr Ile Asn
            500                 505                 510

Arg Val Met Gly Tyr Leu Ser Ser Ala Gly Gly Gly Gly Glu Gly Gly
        515                 520                 525

Gly Gly Ser Glu Glu Gly Gly Gly Gly Ser Glu Glu Gly Gly Gly Gly
    530                 535                 540

Ser Glu Glu Gly Gly Gly Gly Ser Glu Glu Gly Gly Gly Gly Ser Glu
545                 550                 555                 560

Glu Gly Gly Gly Gly Ser Glu Glu Gly Gly Gly Gly Ser Glu Glu Gly
                565                 570                 575

Gly Gly Gly Ser Glu Glu Gly Gly Gly Gly His His His His His His
            580                 585                 590


<210> SEQ ID NO 23
<211> LENGTH: 306
<212> TYPE: PRT
<213> ORGANISM: Homo sapiens

<400> SEQUENCE: 23

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160
```

```
Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 24
<211> LENGTH: 197
<212> TYPE: PRT
<213> ORGANISM: Homo sapiens

<400> SEQUENCE: 24

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195


<210> SEQ ID NO 25
```

<211> LENGTH: 518
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
```

```
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser
        515


<210> SEQ ID NO 26
<211> LENGTH: 529
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205
```

```
Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser His His His His His
        515                 520                 525

His
```

<210> SEQ ID NO 27
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30
```

```
Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
```

```
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Phe Gln Ser Glu Glu
        515                 520                 525

Gln Gln Gly Gly Gly Ser Gly Gly Ser Glu Glu Gly Gly Met Glu Ser
    530                 535                 540

Glu Glu Ser Asn Gly Gly Gly Ser Gly Gly Ser Glu Glu Gly Gly Gly
545                 550                 555                 560

Gly Ser His His His His His His
                565


<210> SEQ ID NO 28
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240
```

```
Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Ser Glu Glu Ser Glu Glu Ser Glu Glu Gly Gly Gly Gly Ser
    530                 535                 540

His His His His His His
545                 550
```

<210> SEQ ID NO 29
<211> LENGTH: 562
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45
```

```
Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460
```

```
Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser His His His His
545                 550                 555                 560

His His


<210> SEQ ID NO 30
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255
```

```
Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Glu Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser Glu Glu Gly Gly
545                 550                 555                 560

Gly Gly Ser Glu Glu Gly Gly Gly Gly Ser Glu Glu Gly Gly Gly Gly
                565                 570                 575

Ser Glu Glu Gly Gly Gly Gly Ser
            580
```

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 32
<211> LENGTH: 604
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

```
Met Tyr Arg Met Gln Leu Leu Ser Cys Ile Ala Leu Ser Leu Ala Leu
1               5                   10                  15

Val Thr Asn Ser Ile Trp Glu Leu Lys Lys Asp Val Tyr Val Val Glu
            20                  25                  30

Leu Asp Trp Tyr Pro Asp Ala Pro Gly Glu Met Val Val Leu Thr Cys
        35                  40                  45

Asp Thr Pro Glu Glu Asp Gly Ile Thr Trp Thr Leu Asp Gln Ser Ser
    50                  55                  60

Glu Val Leu Gly Ser Gly Lys Thr Leu Thr Ile Gln Val Lys Glu Phe
65                  70                  75                  80

Gly Asp Ala Gly Gln Tyr Thr Cys His Lys Gly Gly Glu Val Leu Ser
                85                  90                  95

His Ser Leu Leu Leu Leu His Lys Lys Glu Asp Gly Ile Trp Ser Thr
            100                 105                 110

Asp Ile Leu Lys Asp Gln Lys Glu Pro Lys Asn Lys Thr Phe Leu Arg
        115                 120                 125

Cys Glu Ala Lys Asn Tyr Ser Gly Arg Phe Thr Cys Trp Trp Leu Thr
    130                 135                 140

Thr Ile Ser Thr Asp Leu Thr Phe Ser Val Lys Ser Ser Arg Gly Ser
145                 150                 155                 160

Ser Asp Pro Gln Gly Val Thr Cys Gly Ala Ala Thr Leu Ser Ala Glu
                165                 170                 175

Arg Val Arg Gly Asp Asn Lys Glu Tyr Glu Tyr Ser Val Glu Cys Gln
            180                 185                 190

Glu Asp Ser Ala Cys Pro Ala Ala Glu Glu Ser Leu Pro Ile Glu Val
        195                 200                 205

Met Val Asp Ala Val His Lys Leu Lys Tyr Glu Asn Tyr Thr Ser Ser
    210                 215                 220

Phe Phe Ile Arg Asp Ile Ile Lys Pro Asp Pro Pro Lys Asn Leu Gln
225                 230                 235                 240

Leu Lys Pro Leu Lys Asn Ser Arg Gln Val Glu Val Ser Trp Glu Tyr
                245                 250                 255

Pro Asp Thr Trp Ser Thr Pro His Ser Tyr Phe Ser Leu Thr Phe Cys
            260                 265                 270

Val Gln Val Gln Gly Lys Ser Lys Arg Glu Lys Lys Asp Arg Val Phe
        275                 280                 285

Thr Asp Lys Thr Ser Ala Thr Val Ile Cys Arg Lys Asn Ala Ser Ile
    290                 295                 300

Ser Val Arg Ala Gln Asp Arg Tyr Tyr Ser Ser Ser Trp Ser Glu Trp
305                 310                 315                 320

Ala Ser Val Pro Cys Ser Gly Gly Gly Gly Ser Gly Gly Gly Gly Ser
                325                 330                 335

Gly Gly Gly Gly Ser Arg Asn Leu Pro Val Ala Thr Pro Asp Pro Gly
            340                 345                 350

Met Phe Pro Cys Leu His His Ser Gln Asn Leu Leu Arg Ala Val Ser
```

```
        355                 360                 365

Asn Met Leu Gln Lys Ala Arg Gln Thr Leu Glu Phe Tyr Pro Cys Thr
    370                 375                 380

Ser Glu Glu Ile Asp His Glu Asp Ile Thr Lys Asp Lys Thr Ser Thr
385                 390                 395                 400

Val Glu Ala Cys Leu Pro Leu Glu Leu Thr Lys Asn Glu Ser Cys Leu
                405                 410                 415

Asn Ser Arg Glu Thr Ser Phe Ile Thr Asn Gly Ser Cys Leu Ala Ser
            420                 425                 430

Arg Lys Thr Ser Phe Met Met Ala Leu Cys Leu Ser Ser Ile Tyr Glu
        435                 440                 445

Asp Leu Lys Met Tyr Gln Val Glu Phe Lys Thr Met Asn Ala Lys Leu
    450                 455                 460

Leu Met Asp Pro Lys Arg Gln Ile Phe Leu Asp Gln Asn Met Leu Ala
465                 470                 475                 480

Val Ile Asp Glu Leu Met Gln Ala Leu Asn Phe Asn Ser Glu Thr Val
                485                 490                 495

Pro Gln Lys Ser Ser Leu Glu Glu Pro Asp Phe Tyr Lys Thr Lys Ile
            500                 505                 510

Lys Leu Cys Ile Leu Leu His Ala Phe Arg Ile Arg Ala Val Thr Ile
        515                 520                 525

Asp Arg Val Met Ser Tyr Leu Asn Ala Ser Gly Gly Gly Gly Glu Gly
    530                 535                 540

Gly Gly Gly Ser Glu Glu Gly Gly Gly Gly Ser Glu Glu Gly Gly Gly
545                 550                 555                 560

Gly Ser Glu Glu Gly Gly Gly Gly Ser Glu Glu Gly Gly Gly Gly Ser
                565                 570                 575

Glu Glu Gly Gly Gly Gly Ser Glu Glu Gly Gly Gly Gly Ser Glu Glu
            580                 585                 590

Gly Gly Gly Gly Ser Glu Glu Gly Gly Gly Gly Ser
        595                 600


<210> SEQ ID NO 33
<211> LENGTH: 562
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110
```

```
Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Phe Gln Ser Glu Glu
        515                 520                 525

Gln Gln Gly Gly Gly Ser Gly Gly Ser Glu Glu Gly Gly Met Glu Ser
```

```
    530                 535                 540

Glu Glu Ser Asn Gly Gly Gly Ser Gly Gly Ser Glu Glu Gly Gly Gly
545                 550                 555                 560

Gly Ser


<210> SEQ ID NO 34
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Tyr Arg Met Gln Leu Leu Ser Cys Ile Ala Leu Ser Leu Ala Leu
1               5                   10                  15

Val Thr Asn Ser Ile Trp Glu Leu Lys Lys Asp Val Tyr Val Val Glu
            20                  25                  30

Leu Asp Trp Tyr Pro Asp Ala Pro Gly Glu Met Val Val Leu Thr Cys
        35                  40                  45

Asp Thr Pro Glu Glu Asp Gly Ile Thr Trp Thr Leu Asp Gln Ser Ser
    50                  55                  60

Glu Val Leu Gly Ser Gly Lys Thr Leu Thr Ile Gln Val Lys Glu Phe
65                  70                  75                  80

Gly Asp Ala Gly Gln Tyr Thr Cys His Lys Gly Gly Glu Val Leu Ser
                85                  90                  95

His Ser Leu Leu Leu Leu His Lys Lys Glu Asp Gly Ile Trp Ser Thr
            100                 105                 110

Asp Ile Leu Lys Asp Gln Lys Glu Pro Lys Asn Lys Thr Phe Leu Arg
        115                 120                 125

Cys Glu Ala Lys Asn Tyr Ser Gly Arg Phe Thr Cys Trp Trp Leu Thr
    130                 135                 140

Thr Ile Ser Thr Asp Leu Thr Phe Ser Val Lys Ser Ser Arg Gly Ser
145                 150                 155                 160

Ser Asp Pro Gln Gly Val Thr Cys Gly Ala Ala Thr Leu Ser Ala Glu
                165                 170                 175

Arg Val Arg Gly Asp Asn Lys Glu Tyr Glu Tyr Ser Val Glu Cys Gln
            180                 185                 190

Glu Asp Ser Ala Cys Pro Ala Ala Glu Glu Ser Leu Pro Ile Glu Val
        195                 200                 205

Met Val Asp Ala Val His Lys Leu Lys Tyr Glu Asn Tyr Thr Ser Ser
    210                 215                 220

Phe Phe Ile Arg Asp Ile Ile Lys Pro Asp Pro Pro Lys Asn Leu Gln
225                 230                 235                 240

Leu Lys Pro Leu Lys Asn Ser Arg Gln Val Glu Val Ser Trp Glu Tyr
                245                 250                 255

Pro Asp Thr Trp Ser Thr Pro His Ser Tyr Phe Ser Leu Thr Phe Cys
            260                 265                 270

Val Gln Val Gln Gly Lys Ser Lys Arg Glu Lys Lys Asp Arg Val Phe
        275                 280                 285

Thr Asp Lys Thr Ser Ala Thr Val Ile Cys Arg Lys Asn Ala Ser Ile
    290                 295                 300

Ser Val Arg Ala Gln Asp Arg Tyr Tyr Ser Ser Ser Trp Ser Glu Trp
305                 310                 315                 320

Ala Ser Val Pro Cys Ser Gly Gly Gly Gly Ser Gly Gly Gly Gly Ser
```

```
                325                 330                 335

Gly Gly Gly Gly Ser Arg Asn Leu Pro Val Ala Thr Pro Asp Pro Gly
            340                 345                 350

Met Phe Pro Cys Leu His His Ser Gln Asn Leu Leu Arg Ala Val Ser
        355                 360                 365

Asn Met Leu Gln Lys Ala Arg Gln Thr Leu Glu Phe Tyr Pro Cys Thr
    370                 375                 380

Ser Glu Glu Ile Asp His Glu Asp Ile Thr Lys Asp Lys Thr Ser Thr
385                 390                 395                 400

Val Glu Ala Cys Leu Pro Leu Glu Leu Thr Lys Asn Glu Ser Cys Leu
                405                 410                 415

Asn Ser Arg Glu Thr Ser Phe Ile Thr Asn Gly Ser Cys Leu Ala Ser
            420                 425                 430

Arg Lys Thr Ser Phe Met Met Ala Leu Cys Leu Ser Ser Ile Tyr Glu
        435                 440                 445

Asp Leu Lys Met Tyr Gln Val Glu Phe Lys Thr Met Asn Ala Lys Leu
    450                 455                 460

Leu Met Asp Pro Lys Arg Gln Ile Phe Leu Asp Gln Asn Met Leu Ala
465                 470                 475                 480

Val Ile Asp Glu Leu Met Gln Ala Leu Asn Phe Asn Ser Glu Thr Val
                485                 490                 495

Pro Gln Lys Ser Ser Leu Glu Glu Pro Asp Phe Tyr Lys Thr Lys Ile
            500                 505                 510

Lys Leu Cys Ile Leu Leu His Ala Phe Arg Ile Arg Ala Val Thr Ile
        515                 520                 525

Asp Arg Val Met Ser Tyr Leu Asn Ala Ser Gly Gly Gly Gly Ser Phe
    530                 535                 540

Gln Ser Glu Glu Gln Gln Gly Gly Gly Ser Gly Gly Ser Glu Glu Gly
545                 550                 555                 560

Gly Met Glu Ser Glu Glu Ser Asn Gly Gly Gly Ser Gly Gly Ser Glu
                565                 570                 575

Glu Gly Gly Gly Gly Ser
            580
```

<210> SEQ ID NO 35
<211> LENGTH: 544
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95
```

-continued

```
Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
```

```
        515                 520                 525

Glu Glu Ser Glu Glu Ser Glu Glu Ser Glu Glu Gly Gly Gly Gly Ser
    530                 535                 540


<210> SEQ ID NO 36
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335
```

```
Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser
545                 550                 555
```

<210> SEQ ID NO 37
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140
```

```
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Gly Gly Gly Gly Ser Gly Gly Gly Gly Ser Glu Glu Gly Gly Gly Gly
    530                 535                 540

Ser Glu Glu Gly Gly Gly Gly Ser Glu Glu Gly Gly Gly Gly Ser Glu
545                 550                 555                 560
```

Glu Gly Gly Gly Gly Ser
565

<210> SEQ ID NO 38
<211> LENGTH: 570
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala
180 185 190

Val His Lys Leu Lys Tyr Glu Asn Tyr Thr Ser Ser Phe Phe Ile Arg
195 200 205

Asp Ile Ile Lys Pro Asp Pro Pro Lys Asn Leu Gln Leu Lys Pro Leu
210 215 220

Lys Asn Ser Arg Gln Val Glu Val Ser Trp Glu Tyr Pro Asp Thr Trp
225 230 235 240

Ser Thr Pro His Ser Tyr Phe Ser Leu Thr Phe Cys Val Gln Val Gln
245 250 255

Gly Lys Ser Lys Arg Glu Lys Lys Asp Arg Val Phe Thr Asp Lys Thr
260 265 270

Ser Ala Thr Val Ile Cys Arg Lys Asn Ala Ser Ile Ser Val Arg Ala
275 280 285

Gln Asp Arg Tyr Tyr Ser Ser Trp Ser Glu Trp Ala Ser Val Pro
290 295 300

Cys Ser Gly Gly Gly Gly Ser Gly Gly Gly Gly Ser Gly Gly Gly Gly
305 310 315 320

Ser Arg Asn Leu Pro Val Ala Thr Pro Asp Pro Gly Met Phe Pro Cys
325 330 335

Leu His His Ser Gln Asn Leu Leu Arg Ala Val Ser Asn Met Leu Gln
340 345 350

```
Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser Glu Glu Gly Gly
545                 550                 555                 560

Gly Gly Ser Glu Glu Gly Gly Gly Gly Ser
                565                 570


<210> SEQ ID NO 39
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
```

-continued

```
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser Glu Glu Gly Gly
545                 550                 555                 560
```

```
Gly Gly Ser Glu Glu Gly Gly Gly Gly Ser Glu Glu Gly Gly Gly Gly
                565                 570                 575

Ser Glu Glu Gly Gly Gly Gly Ser
            580


<210> SEQ ID NO 40
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
```

```
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Ser Glu Glu Ser Glu Glu Ser Glu Glu Ser Glu Glu Ser Glu
    530                 535                 540

Glu Gly Gly Gly Gly Ser
545                 550
```

<210> SEQ ID NO 41
<211> LENGTH: 556
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125
```

```
Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Ser Glu Glu Ser Glu Glu Ser Glu Glu Ser Glu Glu Ser Glu
    530                 535                 540

Glu Ser Glu Glu Ser Glu Glu Gly Gly Gly Gly Ser
```

545 550 555

<210> SEQ ID NO 42
<211> LENGTH: 556
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350
```

```
Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Glu Gly Gly Gly Ser Glu Glu Glu Gly Gly Gly Ser Glu Glu
    530                 535                 540

Glu Gly Gly Gly Ser Glu Glu Glu Gly Gly Gly Ser
545                 550                 555


<210> SEQ ID NO 43
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160
```

```
Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Gly Gly Ser
        515                 520                 525

Glu Glu Ala Gly Gly Gly Ser Glu Glu Ala Gly Gly Gly Ser Glu Glu
    530                 535                 540

Ala Gly Gly Gly Ser Glu Glu Ala Gly Gly Gly Ser
545                 550                 555
```

<210> SEQ ID NO 44
<211> LENGTH: 556

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380
```

Leu Pro Leu Glu Leu Thr Lys Asn Glu Ser Cys Leu Asn Ser Arg Glu
385 390 395 400

Thr Ser Phe Ile Thr Asn Gly Ser Cys Leu Ala Ser Arg Lys Thr Ser
405 410 415

Phe Met Met Ala Leu Cys Leu Ser Ser Ile Tyr Glu Asp Leu Lys Met
420 425 430

Tyr Gln Val Glu Phe Lys Thr Met Asn Ala Lys Leu Leu Met Asp Pro
435 440 445

Lys Arg Gln Ile Phe Leu Asp Gln Asn Met Leu Ala Val Ile Asp Glu
450 455 460

Leu Met Gln Ala Leu Asn Phe Asn Ser Glu Thr Val Pro Gln Lys Ser
465 470 475 480

Ser Leu Glu Glu Pro Asp Phe Tyr Lys Thr Lys Ile Lys Leu Cys Ile
485 490 495

Leu Leu His Ala Phe Arg Ile Arg Ala Val Thr Ile Asp Arg Val Met
500 505 510

Ser Tyr Leu Asn Ala Ser Gly Gly Gly Gly Ser Gly Gly Gly Gly Ser
515 520 525

Glu Glu Gln Gly Gly Gly Ser Glu Glu Gln Gly Gly Gly Ser Glu Glu
530 535 540

Gln Gly Gly Gly Ser Glu Glu Gln Gly Gly Gly Ser
545 550 555

<210> SEQ ID NO 45
<211> LENGTH: 562
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala

```
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Ser Gly Gly Ser Glu Glu
        515                 520                 525

Gly Gly Gly Gly Gly Ser Gly Gly Ser Glu Glu Gly Gly Gly Gly Ser
    530                 535                 540

Glu Glu Gly Gly Gly Gly Gly Ser Gly Gly Ser Glu Glu Gly Gly Gly
545                 550                 555                 560

Gly Ser
```

<210> SEQ ID NO 46
<211> LENGTH: 562
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 46

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala
180 185 190

Val His Lys Leu Lys Tyr Glu Asn Tyr Thr Ser Ser Phe Phe Ile Arg
195 200 205

Asp Ile Ile Lys Pro Asp Pro Pro Lys Asn Leu Gln Leu Lys Pro Leu
210 215 220

Lys Asn Ser Arg Gln Val Glu Val Ser Trp Glu Tyr Pro Asp Thr Trp
225 230 235 240

Ser Thr Pro His Ser Tyr Phe Ser Leu Thr Phe Cys Val Gln Val Gln
245 250 255

Gly Lys Ser Lys Arg Glu Lys Lys Asp Arg Val Phe Thr Asp Lys Thr
260 265 270

Ser Ala Thr Val Ile Cys Arg Lys Asn Ala Ser Ile Ser Val Arg Ala
275 280 285

Gln Asp Arg Tyr Tyr Ser Ser Ser Trp Ser Glu Trp Ala Ser Val Pro
290 295 300

Cys Ser Gly Gly Gly Gly Ser Gly Gly Gly Gly Ser Gly Gly Gly Gly
305 310 315 320

Ser Arg Asn Leu Pro Val Ala Thr Pro Asp Pro Gly Met Phe Pro Cys
325 330 335

Leu His His Ser Gln Asn Leu Leu Arg Ala Val Ser Asn Met Leu Gln
340 345 350

Lys Ala Arg Gln Thr Leu Glu Phe Tyr Pro Cys Thr Ser Glu Glu Ile
355 360 365

Asp His Glu Asp Ile Thr Lys Asp Lys Thr Ser Thr Val Glu Ala Cys
370 375 380

Leu Pro Leu Glu Leu Thr Lys Asn Glu Ser Cys Leu Asn Ser Arg Glu
385 390 395 400

Thr Ser Phe Ile Thr Asn Gly Ser Cys Leu Ala Ser Arg Lys Thr Ser
405 410 415

Phe Met Met Ala Leu Cys Leu Ser Ser Ile Tyr Glu Asp Leu Lys Met
420 425 430

Tyr Gln Val Glu Phe Lys Thr Met Asn Ala Lys Leu Leu Met Asp Pro
435 440 445

Lys Arg Gln Ile Phe Leu Asp Gln Asn Met Leu Ala Val Ile Asp Glu
450 455 460

Leu Met Gln Ala Leu Asn Phe Asn Ser Glu Thr Val Pro Gln Lys Ser
465 470 475 480

Ser Leu Glu Glu Pro Asp Phe Tyr Lys Thr Lys Ile Lys Leu Cys Ile
485 490 495

Leu Leu His Ala Phe Arg Ile Arg Ala Val Thr Ile Asp Arg Val Met
500 505 510

Ser Tyr Leu Asn Ala Ser Gly Gly Gly Gly Glu Gly Gly Ser Glu Glu
515 520 525

Gly Gly Gly Gly Gly Glu Gly Gly Ser Glu Glu Gly Gly Gly Gly Ser
530 535 540

Glu Glu Gly Gly Gly Gly Gly Glu Gly Gly Ser Glu Glu Gly Gly Gly
545 550 555 560

Gly Ser

<210> SEQ ID NO 47
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 47

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala
180 185 190

```
Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Glu Gly Gly Gly Gly Ser
        515                 520                 525

Glu Glu Gly Gly Gly Ser Gly Gly Gly Gly Ser Glu Glu Gly Gly Gly
    530                 535                 540

Ser Gly Gly Gly Gly Ser Glu Glu Gly Gly Gly Ser Gly Gly Gly Gly
545                 550                 555                 560

Ser Glu Glu Gly Gly Gly Gly Ser
                565
```

<210> SEQ ID NO 48
<211> LENGTH: 568
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 48

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400
```

Thr Ser Phe Ile Thr Asn Gly Ser Cys Leu Ala Ser Arg Lys Thr Ser
405 410 415

Phe Met Met Ala Leu Cys Leu Ser Ser Ile Tyr Glu Asp Leu Lys Met
420 425 430

Tyr Gln Val Glu Phe Lys Thr Met Asn Ala Lys Leu Leu Met Asp Pro
435 440 445

Lys Arg Gln Ile Phe Leu Asp Gln Asn Met Leu Ala Val Ile Asp Glu
450 455 460

Leu Met Gln Ala Leu Asn Phe Asn Ser Glu Thr Val Pro Gln Lys Ser
465 470 475 480

Ser Leu Glu Glu Pro Asp Phe Tyr Lys Thr Lys Ile Lys Leu Cys Ile
485 490 495

Leu Leu His Ala Phe Arg Ile Arg Ala Val Thr Ile Asp Arg Val Met
500 505 510

Ser Tyr Leu Asn Ala Ser Gly Gly Gly Gly Glu Gly Gly Gly Gly Ser
515 520 525

Glu Glu Gly Gly Gly Glu Gly Gly Gly Gly Ser Glu Glu Gly Gly Gly
530 535 540

Glu Gly Gly Gly Gly Ser Glu Glu Gly Gly Gly Glu Gly Gly Gly Gly
545 550 555 560

Ser Glu Glu Gly Gly Gly Gly Ser
565

<210> SEQ ID NO 49
<211> LENGTH: 556
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala

```
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Glu Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser
545                 550                 555
```

<210> SEQ ID NO 50
<211> LENGTH: 570
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
```

```
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Gly Gly Gly Gly Glu Gly Gly Gly Gly Ser
        515                 520                 525

Glu Glu Gly Gly Gly Gly Ser Glu Glu Gly Gly Gly Gly Ser Glu Glu
    530                 535                 540

Gly Gly Gly Gly Ser Glu Glu Gly Gly Gly Gly Ser Glu Glu Gly Gly
545                 550                 555                 560

Gly Gly Ser Glu Glu Gly Gly Gly Gly Ser
                565                 570


<210> SEQ ID NO 51
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

atgtgggaac tcgaaaagga tgtgtacgtg gtggaagtcg actggactcc tgatgccccg     60

ggagagacag tgaacctgac ctgtgacact cccgaagagg acgacattac ttggaccagc    120

gatcagcggc acggcgtgat cggatccggc aaaaccctga ccatcaccgt gaaagaattc    180

cttgacgcgg gacagtacac ttgccacaag ggcggcgaaa ccctcagcca ttcccacctt    240

ttgctccaca agaaggaaaa cggaatctgg tccaccgaaa ttctgaagaa cttcaagaac    300

aagaccttcc tgaagtgcga ggcgcccaac tactcgggaa ggttcacatg ctcctggctg    360

gtgcagagga acatggatct gaagttcaac atcaagagct cctcctcctc cccggattca    420

agagccgtga cttgcgggat ggcatccctg agcgccgaga aagtcactct ggaccagaga    480

gactacgaga agtactccgt gtcgtgccag gaggacgtga cctgtcctac cgccgaagag    540

actctgccca ttgagctggc tctggaagcc cgccagcaga acaaatacga aaactactcc    600

acgtcattct ttatccggga catcatcaag cccgaccctc ctaagaacct ccagatgaag    660

cccctcaaga acagccaggt cgaggtgtcc tgggaatacc cggactcctg gagcacccca    720

cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aaggggggcaa cgtctgcgtg caagcccaag accgctacta caactcctcc    900

tgctccaaat gggcatgcgt gccgtgtaga gtgcggtccg gtggtggagg atccggaggg    960

ggtggatcag gggggaggcgg atctagggtc attccggtgt ccggtcctgc tcgctgcctg   1020

agtcagtccc ggaatctgct taagactact gacgatatgg tcaagactgc ccgcgagaag   1080
```

```
ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc ccccgcaaaa gacctccctg   1260

atgatgactc tctgtctggg aagcatctac gaagatctga agatgtatca gaccgaattc   1320

caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500

ctgcatgcct tttcgacccg ggtggtcacc atcaacagag tgatgggata cctgagctca   1560

gctggcggtg gtggatctca ccaccatcac catcat                              1596
```

```
<210> SEQ ID NO 52
<211> LENGTH: 1713
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

atgtgggaac tcgaaaagga tgtgtacgtg gtggaagtcg actggactcc tgatgccccg     60

ggagagacag tgaacctgac ctgtgacact cccgaagagg acgacattac ttggaccagc    120

gatcagcggc acggcgtgat cggatccggc aaaaccctga ccatcaccgt gaaagaattc    180

cttgacgcgg gacagtacac ttgccacaag ggcggcgaaa ccctcagcca ttcccacctt    240

ttgctccaca agaaggaaaa cggaatctgg tccaccgaaa ttctgaagaa cttcaagaac    300

aagaccttcc tgaagtgcga ggcgcccaac tactcgggaa ggttcacatg ctcctggctg    360

gtgcagagga acatggatct gaagttcaac atcaagagct cctcctcctc cccggattca    420

agagccgtga cttgcgggat ggcatccctg agcgccgaga aagtcactct ggaccagaga    480

gactacgaga agtactccgt gtcgtgccag gaggacgtga cctgtcctac cgccgaagag    540

actctgccca ttgagctggc tctggaagcc cgccagcaga acaaatacga aaactactcc    600

acgtcattct ttatccggga catcatcaag cccgaccctc ctaagaacct ccagatgaag    660

cccctcaaga acagccaggt cgaggtgtcc tgggaatacc cggactcctg gagcacccca    720

cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aggggggcaa cgtctgcgtg caagcccaag accgctacta caactcctcc    900

tgctccaaat gggcatgcgt gccgtgtaga gtgcggtccg gtggtggagg atccggaggg    960

ggtggatcag gggaggcgg atctagggtc attccggtgt ccggtcctgc tcgctgcctg   1020

agtcagtccc ggaatctgct taagactact gacgatatgg tcaagactgc ccgcgagaag   1080

ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc ccccgcaaaa gacctccctg   1260

atgatgactc tctgtctggg aagcatctac gaagatctga agatgtatca gaccgaattc   1320

caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500
```

```
ctgcatgcct tttcgacccg ggtggtcacc atcaacagag tgatgggata cctgagctca   1560

gctgggggcg gaggctcctt ccaaagcgaa gaacagcagg gagggggctc cggaggtagc   1620

gaagagggag gcatggagag cgaggaaagc aatggaggcg gatcaggcgg atccgaagaa   1680

ggcggtggtg gatctcacca ccatcaccat cat                                1713
```

<210> SEQ ID NO 53
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
atgtgggaac tcgaaaagga tgtgtacgtg gtggaagtcg actggactcc tgatgccccg     60

ggagagacag tgaacctgac ctgtgacact cccgaagagg acgacattac ttggaccagc    120

gatcagcggc acggcgtgat cggatccggc aaaaccctga ccatcaccgt gaaagaattc    180

cttgacgcgg gacagtacac ttgccacaag ggcggcgaaa ccctcagcca ttcccacctt    240

ttgctccaca agaaggaaaa cggaatctgg tccaccgaaa ttctgaagaa cttcaagaac    300

aagaccttcc tgaagtgcga ggcgcccaac tactcgggaa ggttcacatg ctcctggctg    360

gtgcagagga acatggatct gaagttcaac atcaagagct cctcctcctc cccggattca    420

agagccgtga cttgcgggat ggcatccctg agcgccgaga aagtcactct ggaccagaga    480

gactacgaga agtactccgt gtcgtgccag gaggacgtga cctgtcctac cgccgaagag    540

actctgccca ttgagctggc tctggaagcc cgccagcaga acaaatacga aaactactcc    600

acgtcattct ttatccggga catcatcaag cccgaccctc ctaagaacct ccagatgaag    660

cccctcaaga acagccaggt cgaggtgtcc tgggaatacc cggactcctg gagcacccca    720

cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aagggggcaa cgtctgcgtg caagcccaag accgctacta caactcctcc    900

tgctccaaat gggcatgcgt gccgtgtaga gtgcggtccg gtggtggagg atccggaggg    960

ggtggatcag gggaggcgg atctagggtc attccggtgt ccggtcctgc tcgctgcctg   1020

agtcagtccc ggaatctgct taagactact gacgatatgg tcaagactgc ccgcgagaag   1080

ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc cccgcaaaa gacctccctg   1260

atgatgactc tctgtctggg aagcatctac gaagatctga agatgtatca gaccgaattc   1320

caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500

ctgcatgcct tttcgacccg ggtggtcacc atcaacagag tgatgggata cctgagctca   1560

gctggaggcg gaggctcagg aggtggcggc agcgaggaga gcgaagaatc cgaggagtcc   1620

gaggaaggcg gtggtggatc tcaccaccat caccatcat                          1659
```

<210> SEQ ID NO 54
<211> LENGTH: 1695
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 54
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aggggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc ccccgcaaaa gacctccctg 1260
atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggcggag ggggctcagg aggaggcgga agcgaagagg ggggtggtgg atccgaggag 1620
ggaggaggag gctcggaaga gggaggcgga ggatcggagg agggcggtgg tggatctcac 1680
caccatcacc atcat 1695

<210> SEQ ID NO 55
<211> LENGTH: 1725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgtgggagc tggagaagga tgtgtacgtg gtggaggtgg actggacccc tgacgctcct 60
ggagaaaccg tgaacttgac gtgcgacacc cctgaggaag atgacatcac ctggacctcc 120

-continued

```
gaccaaagac acggcgtgat cggctccgga aagaccctga ccatcaccgt gaaggagttc     180
ctggatgccg ggcagtacac ttgccacaag gggggcgaaa cgctgtccca ctcccatctg     240
ctgctgcaca agaaagaaaa cgggatctgg tccaccgaga ttctcaagaa cttcaagaac     300
aagaccttcc ttaagtgcga ggcccccaac tactccggcc gcttcacttg ctcctggctg     360
gtgcagcgca acatggacct gaagttcaat atcaagtcat cctcctcgtc gcctgattcg     420
agagcagtca cttgcgggat ggcgtccctg agcgctgaaa aggtcaccct ggatcagcgg     480
gactacgaga agtactccgt gtcctgccaa gaggacgtga cctgtccgac cgccgaagaa     540
actttgccca tcgaattggc cctcgaagcc aggcagcaga ataagtacga gaactactcc     600
acttcgttct tcattcggga tatcatcaag ccggacccac cgaagaacct ccagatgaag     660
cccctcaaga acagccaggt cgaagtgtcg tgggagtacc cggacagctg gagcacccca     720
catagctact tctcactgaa attcttcgtg cggatccagc gcaagaagga gaagatgaag     780
gaaaccgaag aagggtgcaa ccagaagggc gccttcttgg tggaaaagac cagcaccgag     840
gtgcagtgca aaggcggcaa cgtctgcgtg caagcccagg atagatacta caactcctcg     900
tgctccaaat gggcatgcgt gccatgtaga gtgcgctccg gtggtggagg atcaggcggt     960
ggaggctcag gaggaggggg atcgagggtc attccggtgt ccggtcctgc ccgatgcctg    1020
tcacaatccc ggaaccttct caagactacc gacgacatgg tcaagaccgc tcgggagaaa    1080
ctgaagcact actcctgcac cgccgaggac atcgaccacg aagatattac tcgggatcaa    1140
acttccactc tcaaaacttg cctcccgctc gaactccaca agaacgagtc ctgcttagcg    1200
accagggaaa ctagctccac aacgcggggg tcatgtctgc caccccaaaa gacctccctc    1260
atgatgaccc tgtgccttgg ctccatctat gaggacctga agatgtatca gaccgaattt    1320
caggccatca acgcggcact gcagaaccac aaccatcagc agattatcct ggataagggg    1380
atgctggtcg caatcgacga gctcatgcag tccctgaacc acaatgggga aactctgagg    1440
cagaagcccc ctgtgggaga agcggatccc taccgcgtga agatgaagct atgtatcctg    1500
ctgcatgcct tttccacccg ggtcgtgact atcaatcgcg tgatgggcta ccttagctca    1560
gcgggtggag gaggcagtgg aggcggtgga agcggaggag gaggaagcgg tggagggggt    1620
tccgaggaag gagggggcgg atctgaggaa ggcggaggag gctcagaaga gggtggaggc    1680
ggatccgaag agggaggcgg aggttcgcac catcaccacc accac                    1725
```

<210> SEQ ID NO 56
<211> LENGTH: 1737
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
atgtgggaac tcgaaaagga tgtgtacgtg gtggaagtcg actggactcc tgatgccccg      60
ggagagacag tgaacctgac ctgtgacact cccgaagagg acgacattac ttggaccagc     120
gatcagcggc acggcgtgat cggatccggc aaaaccctga ccatcaccgt gaaagaattc     180
cttgacgcgg gacagtacac ttgccacaag ggcggcgaaa ccctcagcca ttcccacctt     240
ttgctccaca agaaggaaaa cggaatctgg tccaccgaaa ttctgaagaa cttcaagaac     300
aagaccttcc tgaagtgcga ggcgcccaac tactcgggaa ggttcacatg ctcctggctg     360
gtgcagagga acatggatct gaagttcaac atcaagagct cctcctcctc cccggattca     420
```

agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aggggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc cccgcaaaa gacctccctg 1260 atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggcggtg gtggatccgg gggtggaggt tccgaggagg gtggaggagg cagcgaagag 1620
ggcggaggag gatcggaaga gggaggaggc ggaagcgaag aagggggtgg cggatcagag 1680
gagggagggg gaggttcgga agaaggagga gggggatcgc atcatcacca ccaccac 1737

<210> SEQ ID NO 57
<211> LENGTH: 1779
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720

```
cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aagggggcaa cgtctgcgtg caagcccaag accgctacta caactcctcc    900

tgctccaaat gggcatgcgt gccgtgtaga gtgcggtccg gtggtggagg atccggaggg    960

ggtggatcag gggaggcgg atctagggtc attccggtgt ccggtcctgc tcgctgcctg   1020

agtcagtccc ggaatctgct taagactact gacgatatgg tcaagactgc ccgcgagaag   1080

ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc cccgcaaaa gacctccctg   1260

atgatgactc tctgtctggg aagcatctac gaagatctga agatgtatca gaccgaattc   1320

caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500

ctgcatgcct ttcgacccg ggtggtcacc atcaacagag tgatgggata cctgagctca   1560

gctggaggcg gtggatcggg aggaggggga tcggaagaag gggcggaggg ttcagaggaa   1620

ggaggtggcg gatccgagga agggggagga ggctctgagg agggtggtgg cggaagcgaa   1680

gagggaggcg gaggatccga agagggtggc gggggatcag aggagggagg gggaggatca   1740

gaagagggcg gtggtggatc gcaccatcat caccaccac                          1779
```

```
<210> SEQ ID NO 58
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

atgtgggaac tcgaaaagga tgtgtacgtg gtggaagtcg actggactcc tgatgccccg     60

ggagagacag tgaacctgac ctgtgacact cccgaagagg acgacattac ttggaccagc    120

gatcagcggc acggcgtgat cggatccggc aaaaccctga ccatcaccgt gaaagaattc    180

cttgacgcgg gacagtacac ttgccacaag ggcggcgaaa ccctcagcca ttcccacctt    240

ttgctccaca agaaggaaaa cggaatctgg tccaccgaaa ttctgaagaa cttcaagaac    300

aagaccttcc tgaagtgcga ggcgcccaac tactcgggaa ggttcacatg ctcctggctg    360

gtgcagagga acatggatct gaagttcaac atcaagagct cctcctcctc cccggattca    420

agagccgtga cttgcgggat ggcatccctg agcgccgaga aagtcactct ggaccagaga    480

gactacgaga agtactccgt gtcgtgccag gaggacgtga cctgtcctac cgccgaagag    540

actctgccca ttgagctggc tctggaagcc cgccagcaga acaaatacga aaactactcc    600

acgtcattct ttatccggga catcatcaag cccgaccctc ctaagaacct ccagatgaag    660

cccctcaaga acagccaggt cgaggtgtcc tgggaatacc cggactcctg gagcacccca    720

cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aagggggcaa cgtctgcgtg caagcccaag accgctacta caactcctcc    900

tgctccaaat gggcatgcgt gccgtgtaga gtgcggtccg gtggtggagg atccggaggg    960
```

ggtggatcag ggggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc cccgcaaaa gacctccctg 1260 atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggaggcg gtggctctgg tggcggagga tccgaggaat cggaagagtc cgaagagtcg 1620
gaggaaagcg aagagtcaga agaaggggc ggaggttcac accaccacca tcatcac 1677

<210> SEQ ID NO 59
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aggggggcaa cgtctgcgtg caagcccaag accgctacta caactcctcc 900
tgctccaaat gggcatgcgt gccgtgtaga gtgcggtccg gtggtggagg atccggaggg 960
ggtggatcag ggggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc cccgcaaaa gacctccctg 1260 atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctgggggtg gaggttcggg tggcggagga tccgaggaat cggaagagtc cgaagagtcg 1620
gaagaatccg aggaaagcga agagtcagag gaatctgagg agggtggtgg cggaagccat 1680
catcaccacc accac 1695

<210> SEQ ID NO 60
<211> LENGTH: 1695
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aagggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc ccccgcaaaa gacctccctg 1260
atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggaggcg gaggatcggg agggggagga tccgaggaag aagggggtgg cagcgaagaa 1620
gagggaggag ggtctgaaga ggagggcggt ggctcagagg aagagggtgg cggttcgcac 1680
catcaccacc accat 1695

<210> SEQ ID NO 61
<211> LENGTH: 1695
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aggggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcggg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc ccccgcaaaa gacctccctg 1260
atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggaggag gggatccgg tggaggcggt tccgaggaag caggcggtgg atcggaagag 1620
gctgggggtg gaagcgaaga ggccggtggc ggatcagagg aggctggcgg aggatcgcac 1680
caccatcacc accat 1695

<210> SEQ ID NO 62
<211> LENGTH: 1695
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62

```
atgtgggaac tcgaaaagga tgtgtacgtg gtggaagtcg actggactcc tgatgccccg      60
ggagagacag tgaacctgac ctgtgacact cccgaagagg acgacattac ttggaccagc     120
gatcagcggc acggcgtgat cggatccggc aaaaccctga ccatcaccgt gaaagaattc     180
cttgacgcgg gacagtacac ttgccacaag ggcggcgaaa ccctcagcca ttcccacctt     240
ttgctccaca agaaggaaaa cggaatctgg tccaccgaaa ttctgaagaa cttcaagaac     300
aagaccttcc tgaagtgcga ggcgcccaac tactcgggaa ggttcacatg ctcctggctg     360
gtgcagagga acatggatct gaagttcaac atcaagagct cctcctcctc cccggattca     420
agagccgtga cttgcgggat ggcatccctg agcgccgaga aagtcactct ggaccagaga     480
gactacgaga agtactccgt gtcgtgccag gaggacgtga cctgtcctac cgccgaagag     540
actctgccca ttgagctggc tctggaagcc cgccagcaga acaaatacga aaactactcc     600
acgtcattct ttatccggga catcatcaag cccgaccctc ctaagaacct ccagatgaag     660
cccctcaaga acagccaggt cgaggtgtcc tgggaatacc cggactcctg gagcacccca     720
cactcctact tctcgctgaa gtttttcgtg cggatccagc ggaagaaaga gaagatgaaa     780
gagactgaag aggggtgcaa ccagaagggc gctttcctgg tggaaaagac ctcgaccgaa     840
gtgcagtgca aaggggggcaa cgtctgcgtg caagcccaag accgctacta caactcctcc     900
tgctccaaat gggcatgcgt gccgtgtaga gtgcggtccg gtggtggagg atccggaggg     960
ggtggatcag gggaggcgg atctagggtc attccggtgt ccggtcctgc tcgctgcctg    1020
agtcagtccc ggaatctgct taagactact gacgatatgg tcaagactgc ccgcgagaag    1080
ctgaagcact actcctgcac cgccgaggac attgaccacg aagatatcac ccgggaccaa    1140
accagcaccc tcaagacttg cctgccactt gaactgcaca agaacgagag ctgcctggca    1200
accagagaaa ccagctcaac cacacgcgga tcatgtctgc ccccgcaaaa gacctccctg    1260
atgatgactc tctgtctggg aagcatctac gaagatctga agatgtatca gaccgaattc    1320
caggccatca acgcggcgct gcagaaccac aatcatcagc agattatcct ggataagggc    1380
atgctggtcg ccatcgacga gctgatgcag tccttgaatc acaacggcga aacgctccgc    1440
caaaagccgc cagtgggcga agcggaccct tatcgcgtga agatgaagct ctgcatcctg    1500
ctgcatgcct tttcgacccg ggtggtcacc atcaacagag tgatgggata cctgagctca    1560
gctggaggcg gtggatcggg aggtggtggc agcgaagaac agggtggagg gtctgaggaa    1620
cagggcggag gatccgagga gcaagggggt ggctcggaag aacaaggagg agggtcgcac    1680
catcatcacc accac                                                    1695
```

<210> SEQ ID NO 63
<211> LENGTH: 1710
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63

```
atgtgggaac tcgaaaagga tgtgtacgtg gtggaagtcg actggactcc tgatgccccg      60
ggagagacag tgaacctgac ctgtgacact cccgaagagg acgacattac ttggaccagc     120
```

gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aagggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc ccccgcaaaa gacctccctg 1260
atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggcggag gggctcagg aggatccgag gaagggggcg gcggcggatc aggcggctcc 1620
gaagagggcg gaggcggaag cgaagagggt ggcggcggag ggtccggcgg ttccgaggag 1680
ggtggaggcg gccaccacca tcaccaccac 1710

<210> SEQ ID NO 64
<211> LENGTH: 1710
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aaggggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc cccgcaaaa gacctccctg 1260 atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct ttcgacccg ggtggtcacc atcaacagag tgatgggata cctgagctca 1560
gctggcggag gggcgaggg aggttccgaa gaagggggag ggggcggaga gggaggatcc 1620
gaggaaggcg gtggcggatc ggaagaaggt ggcggcggtg gagaaggggg ctcggaagag 1680
ggcggcggag gccaccacca tcaccaccac 1710

<210> SEQ ID NO 65
<211> LENGTH: 1728
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aagggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020
agtcagtccc ggaatctgct taagactact gacgatatgg tcaagactgc ccgcgagaag 1080
ctgaagcact actcctgcac cgccgaggac attgaccacg aagatatcac ccgggaccaa 1140
accagcaccc tcaagacttg cctgccactt gaactgcaca agaacgagag ctgcctggca 1200
accagagaaa ccagctcaac cacacgcgga tcatgtctgc ccccgcaaaa gacctccctg 1260
atgatgactc tctgtctggg aagcatctac gaagatctga agatgtatca gaccgaattc 1320
caggccatca acgcggcgct gcagaaccac aatcatcagc agattatcct ggataagggc 1380
atgctggtcg ccatcgacga gctgatgcag tccttgaatc acaacggcga aacgctccgc 1440
caaaagccgc cagtgggcga agcggaccct tatcgcgtga agatgaagct ctgcatcctg 1500
ctgcatgcct tttcgacccg ggtggtcacc atcaacagag tgatgggata cctgagctca 1560
gctggcggag ggggcgaagg gggcggcgga tcggaagagg gcggcggctc cggaggcgga 1620
ggatcggagg agggaggggg aagcggtgga gggggatctg aggaaggcgg cggaagcgga 1680
gggggcggat ccgaggaggg cggtggcgga caccaccacc atcaccac 1728

<210> SEQ ID NO 66
<211> LENGTH: 1728
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66
atgtgggaac tcgaaaagga tgtgtacgtg gtggaagtcg actggactcc tgatgccccg 60
ggagagacag tgaacctgac ctgtgacact cccgaagagg acgacattac ttggaccagc 120
gatcagcggc acggcgtgat cggatccggc aaaaccctga ccatcaccgt gaaagaattc 180
cttgacgcgg gacagtacac ttgccacaag ggcggcgaaa ccctcagcca ttcccacctt 240
ttgctccaca agaaggaaaa cggaatctgg tccaccgaaa ttctgaagaa cttcaagaac 300
aagaccttcc tgaagtgcga ggcgcccaac tactcgggaa ggttcacatg ctcctggctg 360
gtgcagagga acatggatct gaagttcaac atcaagagct cctcctcctc cccggattca 420
agagccgtga cttgcgggat ggcatccctg agcgccgaga aagtcactct ggaccagaga 480
gactacgaga agtactccgt gtcgtgccag gaggacgtga cctgtcctac cgccgaagag 540
actctgccca ttgagctggc tctggaagcc cgccagcaga acaaatacga aaactactcc 600
acgtcattct ttatccggga catcatcaag cccgaccctc ctaagaacct ccagatgaag 660
cccctcaaga acagccaggt cgaggtgtcc tgggaatacc cggactcctg gagcacccca 720
cactcctact tctcgctgaa gtttttcgtg cggatccagc ggaagaaaga gaagatgaaa 780
gagactgaag aggggtgcaa ccagaagggc gctttcctgg tggaaaagac ctcgaccgaa 840
gtgcagtgca aagggggcaa cgtctgcgtg caagcccaag accgctacta caactcctcc 900
tgctccaaat gggcatgcgt gccgtgtaga gtgcggtccg gtggtggagg atccggaggg 960
ggtggatcag gggaggcgg atctagggtc attccggtgt ccggtcctgc tcgctgcctg 1020

```
agtcagtccc ggaatctgct taagactact gacgatatgg tcaagactgc ccgcgagaag   1080

ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc ccccgcaaaa gacctccctg   1260

atgatgactc tctgtctggg aagcatctac gaagatctga agatgtatca gaccgaattc   1320

caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500

ctgcatgcct tttcgacccg ggtggtcacc atcaacagag tgatgggata cctgagctca   1560

gctggcggag ggggcgaagg cggtggcggt tccgaggagg gcggaggaga agggggaggg   1620

ggttcagagg agggaggtgg agagggtggc ggcggcagcg aagaaggcgg aggcgaagga   1680

ggtggcggca gcgaggaagg aggagggggc caccatcacc accaccat                1728
```

<210> SEQ ID NO 67
<211> LENGTH: 1734
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
atgtgggaac tcgaaaagga tgtgtacgtg gtggaagtcg actggactcc tgatgccccg     60

ggagagacag tgaacctgac ctgtgacact cccgaagagg acgacattac ttggaccagc    120

gatcagcggc acggcgtgat cggatccggc aaaaccctga ccatcaccgt gaaagaattc    180

cttgacgcgg gacagtacac ttgccacaag ggcggcgaaa ccctcagcca ttcccacctt    240

ttgctccaca agaaggaaaa cggaatctgg tccaccgaaa ttctgaagaa cttcaagaac    300

aagaccttcc tgaagtgcga ggcgcccaac tactcgggaa ggttcacatg ctcctggctg    360

gtgcagagga acatggatct gaagttcaac atcaagagct cctcctcctc cccggattca    420

agagccgtga cttgcgggat ggcatccctg agcgccgaga aagtcactct ggaccagaga    480

gactacgaga agtactccgt gtcgtgccag gaggacgtga cctgtcctac cgccgaagag    540

actctgccca ttgagctggc tctggaagcc cgccagcaga acaaatacga aaactactcc    600

acgtcattct ttatccggga catcatcaag cccgaccctc ctaagaacct ccagatgaag    660

cccctcaaga acagccaggt cgaggtgtcc tgggaatacc cggactcctg gagcacccca    720

cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aagggggcaa cgtctgcgtg caagcccaag accgctacta caactcctcc    900

tgctccaaat gggcatgcgt gccgtgtaga gtgcggtccg gtggtggagg atccggaggg    960

ggtggatcag gggaggcgg atctagggtc attccggtgt ccggtcctgc tcgctgcctg    1020

agtcagtccc ggaatctgct taagactact gacgatatgg tcaagactgc ccgcgagaag   1080

ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc ccccgcaaaa gacctccctg   1260

atgatgactc tctgtctggg aagcatctac gaagatctga agatgtatca gaccgaattc   1320
```

```
caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500

ctgcatgcct tttcgacccg ggtggtcacc atcaacagag tgatgggata cctgagctca   1560

gctggaggcg gtggagaggg cggtggcgga tcggaagaag gaggtggcgg atccgaggaa   1620

gggggaggag gctctgagga gggtggtggc ggaagcgaag agggaggcgg aggatccgaa   1680

gagggtggcg gggatcaga ggagggaggg ggaggacatc accaccacca tcat          1734
```

```
<210> SEQ ID NO 68
<211> LENGTH: 1776
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

atgtgggaac tcgaaaagga tgtgtacgtg gtggaagtcg actggactcc tgatgccccg     60

ggagagacag tgaacctgac ctgtgacact cccgaagagg acgacattac ttggaccagc    120

gatcagcggc acggcgtgat cggatccggc aaaaccctga ccatcaccgt gaaagaattc    180

cttgacgcgg gacagtacac ttgccacaag ggcggcgaaa ccctcagcca ttcccacctt    240

ttgctccaca agaaggaaaa cggaatctgg tccaccgaaa ttctgaagaa cttcaagaac    300

aagaccttcc tgaagtgcga ggcgcccaac tactcgggaa ggttcacatg ctcctggctg    360

gtgcagagga acatggatct gaagttcaac atcaagagct cctcctcctc cccggattca    420

agagccgtga cttgcgggat ggcatccctg agcgccgaga aagtcactct ggaccagaga    480

gactacgaga agtactccgt gtcgtgccag gaggacgtga cctgtcctac cgccgaagag    540

actctgccca ttgagctggc tctggaagcc cgccagcaga acaaatacga aaactactcc    600

acgtcattct ttatccggga catcatcaag cccgaccctc ctaagaacct ccagatgaag    660

cccctcaaga acagccaggt cgaggtgtcc tgggaatacc cggactcctg gagcacccca    720

cactcctact tctcgctgaa gtttttcgtg cggatccagc ggaagaaaga gaagatgaaa    780

gagactgaag aggggtgcaa ccagaagggc gctttcctgg tggaaaagac ctcgaccgaa    840

gtgcagtgca aggggggcaa cgtctgcgtg caagcccaag accgctacta caactcctcc    900

tgctccaaat gggcatgcgt gccgtgtaga gtgcggtccg gtggtggagg atccggaggg    960

ggtggatcag gggaggcgg atctagggtc attccggtgt ccggtcctgc tcgctgcctg   1020

agtcagtccc ggaatctgct taagactact gacgatatgg tcaagactgc ccgcgagaag   1080

ctgaagcact actcctgcac cgccgaggac attgaccacg aagatatcac ccgggaccaa   1140

accagcaccc tcaagacttg cctgccactt gaactgcaca agaacgagag ctgcctggca   1200

accagagaaa ccagctcaac cacacgcgga tcatgtctgc ccccgcaaaa gacctccctg   1260

atgatgactc tctgtctggg aagcatctac gaagatctga agatgtatca gaccgaattc   1320

caggccatca acgcggcgct gcagaaccac aatcatcagc agattatcct ggataagggc   1380

atgctggtcg ccatcgacga gctgatgcag tccttgaatc acaacggcga aacgctccgc   1440

caaaagccgc cagtgggcga agcggaccct tatcgcgtga agatgaagct ctgcatcctg   1500

ctgcatgcct tttcgacccg ggtggtcacc atcaacagag tgatgggata cctgagctca   1560

gctggaggcg gtggagaggg tggaggcggt tccgaagaag gggcggagg ttcagaggaa    1620
```

ggaggtggcg gatccgagga agggggagga ggctctgagg agggtggtgg cggaagcgaa 1680
gagggaggcg gaggatccga agagggtggc gggggatcag aggagggagg gggaggatca 1740
gaagagggcg gtggtggaca ccaccaccat catcac 1776

<210> SEQ ID NO 69
<211> LENGTH: 1587
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 69
atctgggagc tgaagaagga cgtctatgtg gtggaacttg actggtaccc ggatgcccct 60
ggagaaatgg tcgtgctgac gtgcgacacc cccgaagagg acggcattac ttggaccctg 120
gaccagtcct ccgaagtgct cgggagcgga aagaccctga ccatccaagt caaggaattc 180
ggcgatgccg gacagtacac ctgtcacaag ggcggagaag tgctgagcca ctccctgctg 240
ctgctgcaca agaaggaaga tggcatctgg tccaccgaca tcctgaaaga ccagaaggag 300
ccgaagaaca agactttcct ccgctgcgaa gccaagaact actccggccg gtttacttgt 360
tggtggctga ccaccatatc aacggatctc accttctccg tgaaatcgtc ccggggaagc 420
tcggaccccc aaggagtgac ttgcggggca gcgaccttgt ccgccgaacg cgtcagaggg 480
gacaacaagg aatacgagta ctccgtggag tgccaagagg actccgcatg tccggctgct 540
gaagagtcgc tgccgattga ggtcatggtg gacgccgtgc acaagctgaa atacgagaat 600
tacacctcct ccttcttcat ccgggacatc attaagcccg accctcctaa gaacctccag 660
ctgaagcctc tgaagaactc ccgccaagtg gaagtgtcct gggagtaccc cgacacttgg 720
tccacccccc attcgtattt ctcactgact ttctgcgtcc aagtgcaggg gaaatccaag 780
agagagaaga aagaccgggt gttcactgat aagactagcg cgaccgtgat ctgtagaaag 840
aacgcgtcta tttccgtgcg cgcccaagat cgctactact cctcctcgtg gtccgaatgg 900
gcctcagtgc catgtagcgg tggtggcgga tccggtggag gcggatcggg tggaggggga 960
tcccggaacc tcccggtggc cactcctgac cctggaatgt tcccgtgcct gcaccatagc 1020
cagaatctgc tgagggccgt gtcgaatatg ttacagaaag ctcggcagac cctcgagttt 1080 taccccctgca cctcggaaga gatcgatcac gaggacatca ctaaggacaa gacctccaca 1140
gtggaagcgt gcctgccact cgaactgacc aagaacgaat cctgcctgaa ctcccgggaa 1200
acctcgttca tcactaacgg ctcttgcttg gcgtcgcgca agacctcatt catgatggcc 1260
ctttgcctct catccatcta cgaagatctg aaaatgtacc aggtcgagtt caagaccatg 1320
aacgctaagt tgctgatgga tccaaagcgc cagattttcc tggaccagaa catgctggcc 1380
gtgatcgacg agctcatgca ggccttgaac tttaacagcg aaaccgtgcc gcagaagagt 1440
agcctcgagg aacccgactt ctacaagact aagattaagc tgtgcattct cctgcacgcc 1500
ttccggatta gggccgtcac catcgaccgc gtcatgtcat acctgaacgc atccggtggc 1560
ggtggaagcc accatcacca ccaccat 1587

<210> SEQ ID NO 70
<211> LENGTH: 1704
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
atctgggagc tgaagaagga cgtctatgtg gtggaacttg actggtaccc ggatgcccct 60
ggagaaatgg tcgtgctgac gtgcgacacc cccgaagagg acggcattac ttggaccctg 120
gaccagtcct ccgaagtgct cgggagcgga aagaccctga ccatccaagt caaggaattc 180
ggcgatgccg gacagtacac ctgtcacaag ggcggagaag tgctgagcca ctccctgctg 240
ctgctgcaca agaaggaaga tggcatctgg tccaccgaca tcctgaaaga ccagaaggag 300
ccgaagaaca agactttcct ccgctgcgaa gccaagaact actccggccg gtttacttgt 360
tggtggctga ccaccatatc aacggatctc accttctccg tgaaatcgtc ccggggaagc 420
tcggaccccc aaggagtgac ttgcggggca gcgaccttgt ccgccgaacg cgtcagaggg 480
gacaacaagg aatacgagta ctccgtggag tgccaagagg actccgcatg tccggctgct 540
gaagagtcgc tgccgattga ggtcatggtg gacgccgtgc acaagctgaa atacgagaat 600
tacacctcct ccttcttcat ccgggacatc attaagcccg accctcctaa gaacctccag 660
ctgaagcctc tgaagaactc ccgccaagtg gaagtgtcct gggagtaccc cgacacttgg 720
tccacccccc attcgtattt ctcactgact ttctgcgtcc aagtgcaggg gaaatccaag 780
agagagaaga aagaccgggt gttcactgat aagactagcg cgaccgtgat ctgtagaaag 840
aacgcgtcta tttccgtgcg cgcccaagat cgctactact cctcctcgtg gtccgaatgg 900
gcctcagtgc catgtagcgg tggtggcgga tccggtggag gcggatcggg tggagggga 960 tcccggaacc tcccggtggc cactcctgac cctggaatgt tcccgtgcct gcaccatagc 1020
cagaatctgc tgagggccgt gtcgaatatg ttacagaaag ctcggcagac cctcgagttt 1080 taccccctgca cctcggaaga gatcgatcac gaggacatca ctaaggacaa gacctccaca 1140
gtggaagcgt gcctgccact cgaactgacc aagaacgaat cctgcctgaa ctcccgggaa 1200
acctcgttca tcactaacgg ctcttgcttg gcgtcgcgca agacctcatt catgatggcc 1260
ctttgcctct catccatcta cgaagatctg aaaatgtacc aggtcgagtt caagaccatg 1320
aacgctaagt tgctgatgga tccaaagcgc cagattttcc tggaccagaa catgctggcc 1380
gtgatcgacg agctcatgca ggccttgaac tttaacagcg aaaccgtgcc gcagaagagt 1440
agcctcgagg aacccgactt ctacaagact aagattaagc tgtgcattct cctgcacgcc 1500
ttccggatta gggccgtcac catcgaccgc gtcatgtcat acctgaacgc atccgggggt 1560
ggaggaagct tccaatcgga ggagcagcag ggaggaggat cgggcggatc cgaggaaggc 1620
ggaatggaga gcgaagaaag caacggcggt ggttccggag gatccgaaga gggtggcggt 1680
ggaagccacc atcaccacca ccat 1704

<210> SEQ ID NO 71
<211> LENGTH: 1650
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
atctgggagc tgaagaagga cgtctatgtg gtggaacttg actggtaccc ggatgcccct 60
ggagaaatgg tcgtgctgac gtgcgacacc cccgaagagg acggcattac ttggaccctg 120
gaccagtcct ccgaagtgct cgggagcgga aagaccctga ccatccaagt caaggaattc 180
ggcgatgccg gacagtacac ctgtcacaag ggcggagaag tgctgagcca ctccctgctg 240

```
ctgctgcaca agaaggaaga tggcatctgg tccaccgaca tcctgaaaga ccagaaggag    300

ccgaagaaca agactttcct ccgctgcgaa gccaagaact actccggccg gtttacttgt    360

tggtggctga ccaccatatc aacggatctc accttctccg tgaaatcgtc ccggggaagc    420

tcggaccccc aaggagtgac ttgcggggca gcgaccttgt ccgccgaacg cgtcagaggg    480

gacaacaagg aatacgagta ctccgtggag tgccaagagg actccgcatg tccggctgct    540

gaagagtcgc tgccgattga ggtcatggtg gacgccgtgc acaagctgaa atacgagaat    600

tacacctcct ccttcttcat ccgggacatc attaagcccg accctcctaa gaacctccag    660

ctgaagcctc tgaagaactc ccgccaagtg gaagtgtcct gggagtaccc cgacacttgg    720

tccacccccc attcgtattt ctcactgact ttctgcgtcc aagtgcaggg gaaatccaag    780

agagagaaga aagaccgggt gttcactgat aagactagcg cgaccgtgat ctgtagaaag    840

aacgcgtcta tttccgtgcg cgcccaagat cgctactact cctcctcgtg gtccgaatgg    900

gcctcagtgc catgtagcgg tggtggcgga tccggtggag gcggatcggg tggaggggga    960

tcccggaacc tcccggtggc cactcctgac cctggaatgt tcccgtgcct gcaccatagc   1020

cagaatctgc tgagggccgt gtcgaatatg ttacagaaag ctcggcagac cctcgagttt   1080

taccccctgca cctcggaaga gatcgatcac gaggacatca ctaaggacaa gacctccaca   1140

gtggaagcgt gcctgccact cgaactgacc aagaacgaat cctgcctgaa ctcccgggaa   1200

acctcgttca tcactaacgg ctcttgcttg gcgtcgcgca agacctcatt catgatggcc   1260

ctttgcctct catccatcta cgaagatctg aaaatgtacc aggtcgagtt caagaccatg   1320

aacgctaagt tgctgatgga tccaaagcgc cagattttcc tggaccagaa catgctggcc   1380

gtgatcgacg agctcatgca ggccttgaac tttaacagcg aaaccgtgcc gcagaagagt   1440

agcctcgagg aacccgactt ctacaagact aagattaagc tgtgcattct cctgcacgcc   1500

ttccggatta gggccgtcac catcgaccgc gtcatgtcat acctgaacgc atccggaggc   1560

ggagggtcgg ggggcggggg atccgaagag tccgaagaat ccgaggaatc cgaagaaggt   1620

ggcggtggaa gccaccatca ccaccaccat                                    1650
```

<210> SEQ ID NO 72
<211> LENGTH: 1686
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
atctgggagc tgaagaagga cgtctatgtg gtggaacttg actggtaccc ggatgcccct     60

ggagaaatgg tcgtgctgac gtgcgacacc cccgaagagg acggcattac ttggaccctg    120

gaccagtcct ccgaagtgct cgggagcgga aagaccctga ccatccaagt caaggaattc    180

ggcgatgccg gacagtacac ctgtcacaag ggcggagaag tgctgagcca ctccctgctg    240

ctgctgcaca agaaggaaga tggcatctgg tccaccgaca tcctgaaaga ccagaaggag    300

ccgaagaaca agactttcct ccgctgcgaa gccaagaact actccggccg gtttacttgt    360

tggtggctga ccaccatatc aacggatctc accttctccg tgaaatcgtc ccggggaagc    420

tcggaccccc aaggagtgac ttgcggggca gcgaccttgt ccgccgaacg cgtcagaggg    480

gacaacaagg aatacgagta ctccgtggag tgccaagagg actccgcatg tccggctgct    540

gaagagtcgc tgccgattga ggtcatggtg gacgccgtgc acaagctgaa atacgagaat    600
```

```
tacacctcct ccttcttcat ccgggacatc attaagcccg accctcctaa gaacctccag    660

ctgaagcctc tgaagaactc ccgccaagtg gaagtgtcct gggagtaccc cgacacttgg    720

tccacccccc attcgtattt ctcactgact ttctgcgtcc aagtgcaggg gaaatccaag    780

agagagaaga aagaccgggt gttcactgat aagactagcg cgaccgtgat ctgtagaaag    840

aacgcgtcta tttccgtgcg cgcccaagat cgctactact cctcctcgtg gtccgaatgg    900

gcctcagtgc catgtagcgg tggtggcgga tccggtggag gcggatcggg tggaggggga    960

tcccggaacc tcccggtggc cactcctgac cctggaatgt tcccgtgcct gcaccatagc   1020

cagaatctgc tgagggccgt gtcgaatatg ttacagaaag ctcggcagac cctcgagttt   1080

taccccctgca cctcggaaga gatcgatcac gaggacatca ctaaggacaa gacctccaca   1140

gtggaagcgt gcctgccact cgaactgacc aagaacgaat cctgcctgaa ctcccgggaa   1200

acctcgttca tcactaacgg ctcttgcttg gcgtcgcgca agacctcatt catgatggcc   1260

ctttgcctct catccatcta cgaagatctg aaaatgtacc aggtcgagtt caagaccatg   1320

aacgctaagt tgctgatgga tccaaagcgc cagattttcc tggaccagaa catgctggcc   1380

gtgatcgacg agctcatgca ggccttgaac tttaacagcg aaaccgtgcc gcagaagagt   1440

agcctcgagg aacccgactt ctacaagact aagattaagc tgtgcattct cctgcacgcc   1500

ttccggatta gggccgtcac catcgaccgc gtcatgtcat acctgaacgc atccggggga   1560

ggaggatcgg gaggtggtgg cagcgaagag ggcggagggg gttcagagga aggcggtgga   1620

gggtccgaag agggtggtgg tgggtccgag gagggtggcg gtggaagcca ccatcaccac   1680

caccat                                                              1686
```

<210> SEQ ID NO 73
<211> LENGTH: 1686
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73

```
atctgggagc tgaagaagga cgtctatgtg gtggaacttg actggtaccc ggatgcccct     60

ggagaaatgg tcgtgctgac gtgcgacacc cccgaagagg acggcattac ttggaccctg    120

gaccagtcct ccgaagtgct cgggagcgga aagaccctga ccatccaagt caaggaattc    180

ggcgatgccg gacagtacac ctgtcacaag ggcggagaag tgctgagcca ctccctgctg    240

ctgctgcaca agaaggaaga tggcatctgg tccaccgaca tcctgaaaga ccagaaggag    300

ccgaagaaca agactttcct ccgctgcgaa gccaagaact actccggccg gtttacttgt    360

tggtggctga ccaccatatc aacggatctc accttctccg tgaaatcgtc ccggggaagc    420

tcggaccccc aaggagtgac ttgcggggca gcgaccttgt ccgccgaacg cgtcagaggg    480

gacaacaagg aatacgagta ctccgtggag tgccaagagg actccgcatg tccggctgct    540

gaagagtcgc tgccgattga ggtcatggtg gacgccgtgc acaagctgaa atacgagaat    600

tacacctcct ccttcttcat ccgggacatc attaagcccg accctcctaa gaacctccag    660

ctgaagcctc tgaagaactc ccgccaagtg gaagtgtcct gggagtaccc cgacacttgg    720

tccacccccc attcgtattt ctcactgact ttctgcgtcc aagtgcaggg gaaatccaag    780

agagagaaga aagaccgggt gttcactgat aagactagcg cgaccgtgat ctgtagaaag    840

aacgcgtcta tttccgtgcg cgcccaagat cgctactact cctcctcgtg gtccgaatgg    900
```

-continued gcctcagtgc catgtagcgg tggtggcgga tccggtggag gcggatcggg tggaggggga 960
tcccggaacc tcccggtggc cactcctgac cctggaatgt tcccgtgcct gcaccatagc 1020
cagaatctgc tgagggccgt gtcgaatatg ttacagaaag ctcggcagac cctcgagttt 1080 taccccctgca cctcggaaga gatcgatcac gaggacatca ctaaggacaa gacctccaca 1140
gtggaagcgt gcctgccact cgaactgacc aagaacgaat cctgcctgaa ctcccgggaa 1200
acctcgttca tcactaacgg ctcttgcttg gcgtcgcgca agacctcatt catgatggcc 1260
ctttgcctct catccatcta cgaagatctg aaaatgtacc aggtcgagtt caagaccatg 1320
aacgctaagt tgctgatgga tccaaagcgc cagattttcc tggaccagaa catgctggcc 1380
gtgatcgacg agctcatgca ggccttgaac tttaacagcg aaaccgtgcc gcagaagagt 1440
agcctcgagg aacccgactt ctacaagact aagattaagc tgtgcattct cctgcacgcc 1500
ttccggatta gggccgtcac catcgaccgc gtcatgtcat acctgaacgc atccggggga 1560
ggaggatcgg gaggtggtgg cagcgaagag ggcggagggg gttcagagga aggcggtgga 1620
gggtccgaag agggtggtgg tgggtccgag gagggtggcg gtggaagcca ccatcaccac 1680
caccat 1686

<210> SEQ ID NO 74
<211> LENGTH: 1752
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 74
atctgggaac tgaagaagga cgtctacgtg gtggaactgg attggtaccc agacgcccct 60
ggagaaatgg tggtgctcac ctgtgatacc cccgaagagg acgggattac ttggaccctg 120
gatcagtcat ccgaagtgct gggatccgga aagaccctga cgatccaggt caaggaattc 180
ggggacgcgg gacagtacac ttgccataag ggcggcgaag tgctgtccca ctccttgctc 240
ctgctccaca agaaagaaga tggaatttgg agcaccgaca tcctgaagga ccagaaagag 300
ccgaagaaca agaccttcct gcgctgcgag gccaagaact acagcggacg ctttacctgt 360
tggtggctga ccactatctc caccgacctg accttctcgg tcaagtcctc gcgcgggagc 420
agcgatcctc agggagtgac ttgcggtgcc gcgactctgt cggccgaaag ggtccggggc 480
gacaacaagg agtacgagta ctcagtcgag tgccaggagg acagcgcatg tccggccgct 540
gaggaatccc tgcctattga agtcatggtg gacgccgtcc acaagctgaa atacgagaac 600
tacacctcct ctttctttat ccgggatatc atcaagcccg acccgcctaa gaaccttcaa 660
ctgaagccac tgaagaacag cagacaagtg gaggtgtcct gggagtaccc ggatacttgg 720
tccactccgc actcctattt ctcgctcacc ttctgcgtcc aagtgcaggg aaagtcgaaa 780
cgggagaaga aggacagagt gttcactgac aagaccagcg caactgtgat ctgtcggaag 840
aacgcctcca tttccgtgcg cgcccaggac cggtactatt cctcatcctg gtcggagtgg 900
gcctcagtgc cctgcagcgg cgggggcggt tcgggtggtg gcggcagcgg gggcggaggg 960
tcccggaatc tgccggtggc gacgcccgac cccggaatgt tcccgtgcct gcaccatagc 1020
cagaacttgc tccgcgcggt gtctaacatg ctgcagaagg cccggcagac cctggaattc 1080 taccccctgca ctagtgaaga gatcgaccat gaagatatta ccaaagacaa gacttccacc 1140
gtggaagcgt gcctcccact ggaactgacc aagaatgagt cctgcctgaa ttcaagggaa 1200
acttcgttca ttaccaacgg ttcctgcctg gcctcgagaa agacctcctt catgatggct 1260
ctctgcctct cctcaatcta cgaagatctc aaaatgtacc aagtggagtt caagaccatg 1320
aacgctaagc tgctgatgga cccgaagcgg cagattttcc tcgaccaaaa catgttggcc 1380
gtgatcgacg agttgatgca ggcccttaac ttcaactccg aaacagtgcc tcagaagtcg 1440
agcctcgagg aacccgactt ctacaagact aagatcaagc tgtgcatcct gctgcacgca 1500
tttcgaattc gggccgtgac catcgaccgc gtgatgagct acctgaacgc atccgggggc 1560
ggcggggaag gaggaggcgg ctcagaggag ggaggaggag gcagcgagga aggaggcgga 1620
ggaagcgaag aaggaggggg aggctcagaa gagggagggg gtggatccga ggaaggcgga 1680
ggaggatccg aagagggcgg tggtggatcg gaggaagggg gaggcggttc tgaggagggt 1740
ggaggaggct cc 1752

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
atgtatagaa tgcagcttct gtcctgtatc gccctctccc tcgcccttgt gaccaactcc 60

<210> SEQ ID NO 76
<211> LENGTH: 1812
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76
atgtatagaa tgcagcttct gtcctgtatc gccctctccc tcgcccttgt gaccaactcc 60
atctgggaac tgaagaagga cgtctacgtg gtggaactgg attggtaccc agacgcccct 120
ggagaaatgg tggtgctcac ctgtgatacc cccgaagagg acgggattac ttggaccctg 180
gatcagtcat ccgaagtgct gggatccgga aagaccctga cgatccaggt caaggaattc 240
ggggacgcgg gacagtacac ttgccataag ggcggcgaag tgctgtccca ctccttgctc 300
ctgctccaca agaaagaaga tggaatttgg agcaccgaca tcctgaagga ccagaaagag 360
ccgaagaaca agaccttcct gcgctgcgag gccaagaact acagcggacg ctttacctgt 420
tggtggctga ccactatctc caccgacctg accttctcgg tcaagtcctc gcgcgggagc 480
agcgatcctc agggagtgac ttgcggtgcc gcgactctgt cggccgaaag ggtccggggc 540
gacaacaagg agtacgagta ctcagtcgag tgccaggagg acagcgcatg tccggccgct 600
gaggaatccc tgcctattga agtcatggtg gacgccgtcc acaagctgaa atacgagaac 660
tacacctcct ctttctttat ccgggatatc atcaagcccg acccgcctaa gaaccttcaa 720
ctgaagccac tgaagaacag cagacaagtg gaggtgtcct gggagtaccc ggatacttgg 780
tccactccgc actcctattt ctcgctcacc ttctgcgtcc aagtgcaggg aaagtcgaaa 840
cgggagaaga aggacagagt gttcactgac aagaccagcg caactgtgat ctgtcggaag 900
aacgcctcca tttccgtgcg cgcccaggac cggtactatt cctcatcctg gtcggagtgg 960
gcctcagtgc cctgcagcgg cgggggcggt tcgggtggtg gcggcagcgg gggcggaggg 1020

```
tcccggaatc tgccggtggc gacgcccgac cccggaatgt tcccgtgcct gcaccatagc   1080

cagaacttgc tccgcgcggt gtctaacatg ctgcagaagg cccggcagac cctggaattc   1140

taccccctgca ctagtgaaga gatcgaccat gaagatatta ccaaagacaa gacttccacc   1200

gtggaagcgt gcctcccact ggaactgacc aagaatgagt cctgcctgaa ttcaagggaa   1260

acttcgttca ttaccaacgg ttcctgcctg gcctcgagaa agacctcctt catgatggct   1320

ctctgcctct cctcaatcta cgaagatctc aaaatgtacc aagtggagtt caagaccatg   1380

aacgctaagc tgctgatgga cccgaagcgg cagattttcc tcgaccaaaa catgttggcc   1440

gtgatcgacg agttgatgca ggcccttaac ttcaactccg aaacagtgcc tcagaagtcg   1500

agcctcgagg aacccgactt ctacaagact aagatcaagc tgtgcatcct gctgcacgca   1560

tttcgaattc gggccgtgac catcgaccgc gtgatgagct acctgaacgc atccgggggc   1620

ggcggggaag gaggaggcgg ctcagaggag ggaggaggag gcagcgagga aggaggcgga   1680

ggaagcgaag aaggaggggg aggctcagaa gagggagggg gtggatccga ggaaggcgga   1740

ggaggatccg aagagggcgg tggtggatcg gaggaagggg gaggcggttc tgaggagggt   1800

ggaggaggct cc                                                       1812
```

<210> SEQ ID NO 77
<211> LENGTH: 1686
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
atctgggaac tgaagaagga cgtctacgtg gtggaactgg attggtaccc agacgcccct     60

ggagaaatgg tggtgctcac ctgtgatacc cccgaagagg acgggattac ttggaccctg    120

gatcagtcat ccgaagtgct gggatccgga aagaccctga cgatccaggt caaggaattc    180

ggggacgcgg gacagtacac ttgccataag ggcggcgaag tgctgtccca ctccttgctc    240

ctgctccaca agaaagaaga tggaatttgg agcaccgaca tcctgaagga ccagaaagag    300

ccgaagaaca agaccttcct gcgctgcgag gccaagaact acagcggacg ctttacctgt    360

tggtggctga ccactatctc caccgacctg accttctcgg tcaagtcctc gcgcgggagc    420

agcgatcctc agggagtgac ttgcggtgcc gcgactctgt cggccgaaag ggtccggggc    480

gacaacaagg agtacgagta ctcagtcgag tgccaggagg acagcgcatg tccggccgct    540

gaggaatccc tgcctattga agtcatggtg gacgccgtcc acaagctgaa atacgagaac    600

tacacctcct ctttctttat ccgggatatc atcaagcccg acccgcctaa gaaccttcaa    660

ctgaagccac tgaagaacag cagacaagtg gaggtgtcct gggagtaccc ggatacttgg    720

tccactccgc actcctattt ctcgctcacc ttctgcgtcc aagtgcaggg aaagtcgaaa    780

cgggagaaga aggacagagt gttcactgac aagaccagcg caactgtgat ctgtcggaag    840

aacgcctcca tttccgtgcg cgcccaggac cggtactatt cctcatcctg gtcggagtgg    900

gcctcagtgc cctgcagcgg cgggggcggt tcgggtggtg gcggcagcgg gggcggaggg    960

tcccggaatc tgccggtggc gacgcccgac cccggaatgt tcccgtgcct gcaccatagc   1020

cagaacttgc tccgcgcggt gtctaacatg ctgcagaagg cccggcagac cctggaattc   1080

taccccctgca ctagtgaaga gatcgaccat gaagatatta ccaaagacaa gacttccacc   1140

gtggaagcgt gcctcccact ggaactgacc aagaatgagt cctgcctgaa ttcaagggaa   1200
```

acttcgttca ttaccaacgg ttcctgcctg gcctcgagaa agacctcctt catgatggct 1260
ctctgcctct cctcaatcta cgaagatctc aaaatgtacc aagtggagtt caagaccatg 1320
aacgctaagc tgctgatgga cccgaagcgg cagattttcc tcgaccaaaa catgttggcc 1380
gtgatcgacg agttgatgca ggcccttaac ttcaactccg aaacagtgcc tcagaagtcg 1440
agcctcgagg aacccgactt ctacaagact aagatcaagc tgtgcatcct gctgcacgca 1500
tttcgaattc gggccgtgac catcgaccgc gtgatgagct acctgaacgc atccgggggc 1560
ggcgggagct tccagtccga ggaacaacag ggagggggct ccggcggatc agaggaggga 1620
ggcatggaat cagaagagag caacggcggc ggttccggag gatcggaaga gggcggcggc 1680
ggatcg 1686

<210> SEQ ID NO 78
<211> LENGTH: 1746
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78
atgtatagaa tgcagcttct gtcctgtatc gccctctccc tcgcccttgt gaccaactcc 60
atctgggaac tgaagaagga cgtctacgtg gtggaactgg attggtaccc agacgcccct 120
ggagaaatgg tggtgctcac ctgtgatacc cccgaagagg acgggattac ttggaccctg 180
gatcagtcat ccgaagtgct gggatccgga aagaccctga cgatccaggt caaggaattc 240
ggggacgcgg gacagtacac ttgccataag ggcggcgaag tgctgtccca ctccttgctc 300
ctgctccaca agaaagaaga tggaatttgg agcaccgaca tcctgaagga ccagaaagag 360
ccgaagaaca agaccttcct gcgctgcgag gccaagaact acagcggacg ctttacctgt 420
tggtggctga ccactatctc caccgacctg accttctcgg tcaagtcctc gcgcgggagc 480
agcgatcctc agggagtgac ttgcggtgcc gcgactctgt cggccgaaag ggtccggggc 540
gacaacaagg agtacgagta ctcagtcgag tgccaggagg acagcgcatg tccggccgct 600
gaggaatccc tgcctattga agtcatggtg gacgccgtcc acaagctgaa atacgagaac 660
tacacctcct ctttctttat ccgggatatc atcaagcccg acccgcctaa gaaccttcaa 720
ctgaagccac tgaagaacag cagacaagtg gaggtgtcct gggagtaccc ggatacttgg 780
tccactccgc actcctattt ctcgctcacc ttctgcgtcc aagtgcaggg aaagtcgaaa 840
cgggagaaga aggacagagt gttcactgac aagaccagcg caactgtgat ctgtcggaag 900
aacgcctcca tttccgtgcg cgcccaggac cggtactatt cctcatcctg gtcggagtgg 960
gcctcagtgc cctgcagcgg cgggggcggt tcgggtggtg gcggcagcgg gggcggaggg 1020
tcccggaatc tgccggtggc gacgcccgac ccccggaatgt tcccgtgcct gcaccatagc 1080
cagaacttgc tccgcgcggt gtctaacatg ctgcagaagg cccggcagac cctggaattc 1140 taccccctgca ctagtgaaga gatcgaccat gaagatatta ccaaagacaa gacttccacc 1200
gtggaagcgt gcctcccact ggaactgacc aagaatgagt cctgcctgaa ttcaagggaa 1260
acttcgttca ttaccaacgg ttcctgcctg gcctcgagaa agacctcctt catgatggct 1320
ctctgcctct cctcaatcta cgaagatctc aaaatgtacc aagtggagtt caagaccatg 1380
aacgctaagc tgctgatgga cccgaagcgg cagattttcc tcgaccaaaa catgttggcc 1440
gtgatcgacg agttgatgca ggcccttaac ttcaactccg aaacagtgcc tcagaagtcg 1500

```
agcctcgagg aacccgactt ctacaagact aagatcaagc tgtgcatcct gctgcacgca   1560

tttcgaattc gggccgtgac catcgaccgc gtgatgagct acctgaacgc atccgggggc   1620

ggcgggagct tccagtccga ggaacaacag ggagggggct ccggcggatc agaggaggga   1680

ggcatggaat cagaagagag caacggcggc ggttccggag gatcggaaga gggcggcggc   1740

ggatcg                                                              1746


<210> SEQ ID NO 79
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Lys Met Met Leu Val Arg Arg Phe Arg Val Leu Ile Leu Met Val
1               5                   10                  15

Phe Leu Val Ala Cys Ala Leu His Ile Ala Leu Asp Leu Leu Pro Arg
            20                  25                  30

Leu Glu Arg Arg Gly Ala Arg Pro Ser Gly Glu Pro Gly Cys Ser Cys
        35                  40                  45

Ala Gln Pro Ala Ala Glu Val Ala Ala Pro Gly Trp Ala Gln Val Arg
    50                  55                  60

Gly Arg Pro Gly Glu Pro Pro Ala Ala Ser Ser Ala Ala Gly Asp Ala
65                  70                  75                  80

Gly Trp Pro Asn Lys His Thr Leu Arg Ile Leu Gln Asp Phe Ser Ser
                85                  90                  95

Asp Pro Ser Ser Asn Leu Ser Ser His Ser Leu Glu Lys Leu Pro Pro
            100                 105                 110

Ala Ala Glu Pro Ala Glu Arg Ala Leu Arg Gly Arg Asp Pro Gly Ala
        115                 120                 125

Leu Arg Pro His Asp Pro Ala His Arg Pro Leu Leu Arg Asp Pro Gly
    130                 135                 140

Pro Arg Arg Ser Glu Ser Pro Pro Gly Pro Gly Gly Asp Ala Ser Leu
145                 150                 155                 160

Leu Ala Arg Leu Phe Glu His Pro Leu Tyr Arg Val Ala Val Pro Pro
                165                 170                 175

Leu Thr Glu Glu Asp Val Leu Phe Asn Val Asn Ser Asp Thr Arg Leu
            180                 185                 190

Ser Pro Lys Ala Ala Glu Asn Pro Asp Trp Pro His Ala Gly Ala Glu
        195                 200                 205

Gly Ala Glu Phe Leu Ser Pro Gly Glu Ala Ala Val Asp Ser Tyr Pro
    210                 215                 220

Asn Trp Leu Lys Phe His Ile Gly Ile Asn Arg Tyr Glu Leu Tyr Ser
225                 230                 235                 240

Arg His Asn Pro Ala Ile Glu Ala Leu Leu His Asp Leu Ser Ser Gln
                245                 250                 255

Arg Ile Thr Ser Val Ala Met Lys Ser Gly Gly Thr Gln Leu Lys Leu
            260                 265                 270

Ile Met Thr Phe Gln Asn Tyr Gly Gln Ala Leu Phe Lys Pro Met Lys
        275                 280                 285

Gln Thr Arg Glu Gln Glu Thr Pro Pro Asp Phe Phe Tyr Phe Ser Asp
    290                 295                 300

Tyr Glu Arg His Asn Ala Glu Ile Ala Ala Phe His Leu Asp Arg Ile
```

```
305                 310                 315                 320

Leu Asp Phe Arg Arg Val Pro Pro Val Ala Gly Arg Met Val Asn Met
                325                 330                 335

Thr Lys Glu Ile Arg Asp Val Thr Arg Asp Lys Lys Leu Trp Arg Thr
            340                 345                 350

Phe Phe Ile Ser Pro Ala Asn Asn Ile Cys Phe Tyr Gly Glu Cys Ser
        355                 360                 365

Tyr Tyr Cys Ser Thr Glu His Ala Leu Cys Gly Lys Pro Asp Gln Ile
    370                 375                 380

Glu Gly Ser Leu Ala Ala Phe Leu Pro Asp Leu Ser Leu Ala Lys Arg
385                 390                 395                 400

Lys Thr Trp Arg Asn Pro Trp Arg Arg Ser Tyr His Lys Arg Lys Lys
                405                 410                 415

Ala Glu Trp Glu Val Asp Pro Asp Tyr Cys Glu Glu Val Lys Gln Thr
            420                 425                 430

Pro Pro Tyr Asp Ser Ser His Arg Ile Leu Asp Val Met Asp Met Thr
        435                 440                 445

Ile Phe Asp Phe Leu Met Gly Asn Met Asp Arg His His Tyr Glu Thr
    450                 455                 460

Phe Glu Lys Phe Gly Asn Glu Thr Phe Ile Ile His Leu Asp Asn Gly
465                 470                 475                 480

Arg Gly Phe Gly Lys Tyr Ser His Asp Glu Leu Ser Ile Leu Val Pro
                485                 490                 495

Leu Gln Gln Cys Cys Arg Ile Arg Lys Ser Thr Tyr Leu Arg Leu Gln
            500                 505                 510

Leu Leu Ala Lys Glu Glu Tyr Lys Leu Ser Leu Leu Met Ala Glu Ser
        515                 520                 525

Leu Arg Gly Asp Gln Val Ala Pro Val Leu Tyr Gln Pro His Leu Glu
    530                 535                 540

Ala Leu Asp Arg Arg Leu Arg Val Val Leu Lys Ala Val Arg Asp Cys
545                 550                 555                 560

Val Glu Arg Asn Gly Leu His Ser Val Val Asp Asp Asp Leu Asp Thr
                565                 570                 575

Glu His Arg Ala Ala Ser Ala Arg Gly Gly Gly Ser Lys Asp Glu Leu
            580                 585                 590


<210> SEQ ID NO 80
<211> LENGTH: 1752
<212> TYPE: DNA
<213> ORGANISM: Homo sapiens

<400> SEQUENCE: 80

atgaagatga tgcttgttcg aagattccgg gtcctgattc tgatggtatt cctcgtcgca      60

tgcgccctgc acatcgcctt ggacctcctc cctcggctgg aacgcagagg agcacggcct     120

tccggagaac cgggctgctc gtgtgcacaa ccagccgccg aagtcgctgc ccctggatgg     180

gctcaagtca gaggacggcc tggagaaccc ccggcagctt cctccgcggc tggagatgcg     240

ggatggccca acaagcacac cctccggatc ctgcaggact tctcctccga cccctcctcg     300

aatctgagct cccactccct cgaaaagctg cctcctgctg ccgagccagc tgaacgggcc     360

ctgaggggta gagatcccgg tgcactcagg ccacatgacc ctgcgcaccg acctctgttg     420

agagatccgg gtcctcggag gtctgaatca ccgccaggtc ctggtggcga tgcgtccctt     480

cttgcgcgct tgttcgagca cccgctgtac cgggtggcag tgcctcccct caccgaggaa     540
```

```
gatgtgctgt tcaacgtgaa cagcgatacc cgcctgagcc cgaaagccgc cgagaatccc    600

gactggcctc atgccggagc cgaaggagcc gagttcctga gccctggaga agcggccgtg    660

gattcgtacc cgaactggct aaagttccat atcggcatca accgctacga gctctactcg    720

aggcataacc cggccattga ggccctgctg cacgacctca gcagccaacg gatcactagc    780

gtggccatga agtccggggg cactcagctg aagttgatca tgacctttca gaactacggc    840

caggccctgt ttaagcccat gaagcagacc cgggagcagg aaacaccgcc ggactttttc    900

tacttctcgg actacgaacg ccacaacgcc gagattgccg ccttccacct ggatcgcatc    960

ctggatttca gacgggtgcc acctgtggcg ggacgcatgg tcaatatgac caaagaaatc   1020

cgcgacgtca ctcgcgacaa gaagctctgg cggacgttct tcatttcccc ggccaacaac   1080

atctgcttct acggggagtg ctcatactac tgctccaccg agcatgccct ttgcggaaag   1140

cccgaccaga tcgaagggtc cctggcagcc ttccttcccg acctgagcct ggcgaagcgc   1200

aagacttgga gaaacccatg gcgccgctca taccacaagc ggaagaaggc ggagtgggag   1260

gtggaccccg actactgcga ggaagtcaag cagaccccccc cctacgactc ctcccaccgg   1320

attctggacg tgatggacat gactattttc gatttcctca tgggcaacat ggaccggcac   1380

cactatgaaa ccttcgaaaa gttcgggaac gagactttca ttattcacct ggacaacggc   1440

cggggattcg gaaagtacag ccacgacgaa ctctccatcc tggtgccgct gcagcagtgt   1500

tgccggatcc gcaagtccac gtacctgaga ctgcagctgt tggccaaaga ggagtataag   1560

ctgtcgctcc tgatggccga atccctccgc ggcgatcaag tcgcccccggt gctgtaccag   1620

ccgcatctcg aggccctgga caggagactg cgcgtggtgc tcaaagctgt gcgggattgt   1680

gtggaacgga acggcctgca ttctgtggtg gacgacgacc tggacaccga acacagagcc   1740

gcatccgcta gg                                                       1752
```

<210> SEQ ID NO 81
<211> LENGTH: 1776
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
atgaagatga tgcttgttcg aagattccgg gtcctgattc tgatggtatt cctcgtcgca     60

tgcgccctgc acatcgcctt ggacctcctc cctcggctgg aacgcagagg agcacggcct    120

tccggagaac cgggctgctc gtgtgcacaa ccagccgccg aagtcgctgc ccctggatgg    180

gctcaagtca gaggacggcc tggagaaccc ccggcagctt cctccgcggc tggagatgcg    240

ggatggccca acaagcacac cctccggatc ctgcaggact tctcctccga cccctcctcg    300

aatctgagct cccactccct cgaaaagctg cctcctgctg ccgagccagc tgaacgggcc    360

ctgaggggta gagatcccgg tgcactcagg ccacatgacc ctgcgcaccg acctctgttg    420

agagatccgg gtcctcggag gtctgaatca ccgccaggtc ctggtggcga tgcgtccctt    480

cttgcgcgct tgttcgagca cccgctgtac cgggtggcag tgcctcccct caccgaggaa    540

gatgtgctgt tcaacgtgaa cagcgatacc cgcctgagcc cgaaagccgc cgagaatccc    600

gactggcctc atgccggagc cgaaggagcc gagttcctga gccctggaga agcggccgtg    660

gattcgtacc cgaactggct aaagttccat atcggcatca accgctacga gctctactcg    720

aggcataacc cggccattga ggccctgctg cacgacctca gcagccaacg gatcactagc    780
```

```
gtggccatga agtccggggg cactcagctg aagttgatca tgacctttca gaactacggc    840

caggccctgt ttaagcccat gaagcagacc cgggagcagg aaacaccgcc ggactttttc    900

tacttctcgg actacgaacg ccacaacgcc gagattgccg ccttccacct ggatcgcatc    960

ctggatttca gacgggtgcc acctgtggcg ggacgcatgg tcaatatgac caaagaaatc   1020

cgcgacgtca ctcgcgacaa gaagctctgg cggacgttct tcatttcccc ggccaacaac   1080

atctgcttct acggggagtg ctcatactac tgctccaccg agcatgccct ttgcggaaag   1140

cccgaccaga tcgaagggtc cctggcagcc ttccttcccg acctgagcct ggcgaagcgc   1200

aagacttgga gaaacccatg gcgccgctca taccacaagc ggaagaaggc ggagtgggag   1260

gtggaccccg actactgcga ggaagtcaag cagaccccc cctacgactc ctcccaccgg   1320

attctggacg tgatggacat gactattttc gatttcctca tgggcaacat ggaccggcac   1380

cactatgaaa ccttcgaaaa gttcgggaac gagactttca ttattcacct ggacaacggc   1440

cggggattcg gaaagtacag ccacgacgaa ctctccatcc tggtgccgct gcagcagtgt   1500

tgccggatcc gcaagtccac gtacctgaga ctgcagctgt tggccaaaga ggagtataag   1560

ctgtcgctcc tgatggccga atccctccgc ggcgatcaag tcgccccggt gctgtaccag   1620

ccgcatctcg aggccctgga caggagactg cgcgtggtgc tcaaagctgt gcgggattgt   1680

gtggaacgga acggcctgca ttctgtggtg gacgacgacc tggacaccga acacagagcc   1740

gcatccgcta ggggtggagg gtccaaagat gagctg                             1776
```

<210> SEQ ID NO 82
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Gly Gly Gly Gly Ser Gly Gly Gly Gly Ser Glu Glu Gly Gly Gly Gly
1               5                   10                  15

Ser Glu Glu Gly Gly Gly Gly Ser Glu Glu Gly Gly Gly Gly Ser Glu
            20                  25                  30

Glu Gly Gly Gly Gly Ser
        35
```

<210> SEQ ID NO 83
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Gly Gly Gly Gly Ser Gly Gly Gly Gly Ser Glu Glu Gly Gly Gly Gly
1               5                   10                  15

Ser Glu Glu Gly Gly Gly Gly Ser Glu Glu Gly Gly Gly Gly Ser Glu
            20                  25                  30

Glu Gly Gly Gly Gly Ser Glu Glu Gly Gly Gly Gly Ser Glu Glu Gly
        35                  40                  45

Gly Gly Gly Ser
    50
```

<210> SEQ ID NO 84

```
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Gly Gly Gly Ser Gly Gly Gly Gly Ser Glu Glu Gly Gly Gly Gly
1               5                   10                  15

Ser Glu Glu Gly Gly Gly Gly Ser Glu Glu Gly Gly Gly Gly Ser Glu
            20                  25                  30

Glu Gly Gly Gly Gly Ser Glu Glu Gly Gly Gly Gly Ser Glu Glu Gly
        35                  40                  45

Gly Gly Gly Ser Glu Glu Gly Gly Gly Gly Ser Glu Glu Gly Gly Gly
    50                  55                  60

Gly Ser
65


<210> SEQ ID NO 85
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Gly Gly Gly Ser Gly Gly Gly Gly Ser Glu Glu Ser Glu Glu Ser
1               5                   10                  15

Glu Glu Ser Glu Glu Ser Glu Glu Ser Glu Glu Gly Gly Gly Gly Ser
            20                  25                  30


<210> SEQ ID NO 86
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Gly Gly Gly Ser Gly Gly Gly Gly Ser Glu Glu Ser Glu Glu Ser
1               5                   10                  15

Glu Glu Ser Glu Glu Ser Glu Glu Ser Glu Glu Ser Glu Glu Ser Glu
            20                  25                  30

Glu Gly Gly Gly Gly Ser
        35


<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Gly Gly Gly Ser Gly Gly Gly Gly Ser Glu Glu Glu Gly Gly Gly
1               5                   10                  15

Ser Glu Glu Glu Gly Gly Gly Ser Glu Glu Glu Gly Gly Gly Ser Glu
            20                  25                  30

Glu Glu Gly Gly Gly Ser
```

35

<210> SEQ ID NO 88
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 88

Gly Gly Gly Gly Ser Gly Gly Gly Gly Ser Glu Glu Ala Gly Gly Gly
1 5 10 15

Ser Glu Glu Ala Gly Gly Gly Ser Glu Glu Ala Gly Gly Gly Ser Glu
20 25 30

Glu Ala Gly Gly Gly Ser
35

<210> SEQ ID NO 89
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

Gly Gly Gly Gly Ser Gly Gly Gly Gly Ser Glu Glu Gln Gly Gly Gly
1 5 10 15

Ser Glu Glu Gln Gly Gly Gly Ser Glu Glu Gln Gly Gly Gly Ser Glu
20 25 30

Glu Gln Gly Gly Gly Ser
35

<210> SEQ ID NO 90
<211> LENGTH: 44
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

Gly Gly Gly Gly Ser Phe Gln Ser Glu Glu Gln Gln Gly Gly Gly Ser
1 5 10 15

Gly Gly Ser Glu Glu Gly Gly Met Glu Ser Glu Glu Ser Asn Gly Gly
20 25 30

Gly Ser Gly Gly Ser Glu Glu Gly Gly Gly Gly Ser
35 40

<210> SEQ ID NO 91
<211> LENGTH: 43
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 91

Gly Gly Gly Gly Ser Gly Gly Ser Glu Glu Gly Gly Gly Gly Gly Ser
1 5 10 15

Gly Gly Ser Glu Glu Gly Gly Gly Gly Ser Glu Glu Gly Gly Gly Gly
20 25 30

```
Gly Ser Gly Gly Ser Glu Glu Gly Gly Gly Gly
        35                  40


<210> SEQ ID NO 92
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Gly Gly Gly Glu Gly Gly Ser Glu Glu Gly Gly Gly Gly Gly Glu
1               5                   10                  15

Gly Gly Ser Glu Glu Gly Gly Gly Gly Ser Glu Glu Gly Gly Gly Gly
            20                  25                  30

Gly Glu Gly Gly Ser Glu Glu Gly Gly Gly Gly
        35                  40


<210> SEQ ID NO 93
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Gly Gly Gly Glu Gly Gly Gly Gly Ser Glu Glu Gly Gly Gly Ser
1               5                   10                  15

Gly Gly Gly Gly Ser Glu Glu Gly Gly Gly Ser Gly Gly Gly Gly Ser
            20                  25                  30

Glu Glu Gly Gly Gly Ser Gly Gly Gly Gly Ser Glu Glu Gly Gly Gly
        35                  40                  45

Gly


<210> SEQ ID NO 94
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Gly Gly Gly Glu Gly Gly Gly Gly Ser Glu Glu Gly Gly Gly Glu
1               5                   10                  15

Gly Gly Gly Gly Ser Glu Glu Gly Gly Gly Glu Gly Gly Gly Gly Ser
            20                  25                  30

Glu Glu Gly Gly Gly Glu Gly Gly Gly Gly Ser Glu Glu Gly Gly Gly
        35                  40                  45

Gly


<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Gly Gly Gly Glu Gly Gly Gly Gly Ser Glu Glu Gly Gly Gly Gly
```

1 5 10 15

Ser Glu Glu Gly Gly Gly Gly Ser Glu Glu Gly Gly Gly Gly Ser Glu
20 25 30

Glu Gly Gly Gly Gly
35

<210> SEQ ID NO 96
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Gly Gly Gly Gly Glu Gly Gly Gly Gly Ser Glu Glu Gly Gly Gly Gly
1 5 10 15

Ser Glu Glu Gly Gly Gly Gly Ser Glu Glu Gly Gly Gly Gly Ser Glu
20 25 30

Glu Gly Gly Gly Gly Ser Glu Glu Gly Gly Gly Gly Ser Glu Glu Gly
35 40 45

Gly Gly Gly
50

<210> SEQ ID NO 97
<211> LENGTH: 65
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Gly Gly Gly Gly Glu Gly Gly Gly Gly Ser Glu Glu Gly Gly Gly Gly
1 5 10 15

Ser Glu Glu Gly Gly Gly Gly Ser Glu Glu Gly Gly Gly Gly Ser Glu
20 25 30

Glu Gly Gly Gly Gly Ser Glu Glu Gly Gly Gly Gly Ser Glu Glu Gly
35 40 45

Gly Gly Gly Ser Glu Glu Gly Gly Gly Gly Ser Glu Glu Gly Gly Gly
50 55 60

Gly
65

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 98

His His His His His His
1 5

<210> SEQ ID NO 99
<211> LENGTH: 584
<212> TYPE: PRT
<213> ORGANISM: Homo sapiens

<400> SEQUENCE: 99

```
Met Lys Met Met Leu Val Arg Arg Phe Arg Val Leu Ile Leu Met Val
1               5                   10                  15

Phe Leu Val Ala Cys Ala Leu His Ile Ala Leu Asp Leu Leu Pro Arg
            20                  25                  30

Leu Glu Arg Arg Gly Ala Arg Pro Ser Gly Glu Pro Gly Cys Ser Cys
        35                  40                  45

Ala Gln Pro Ala Ala Glu Val Ala Ala Pro Gly Trp Ala Gln Val Arg
    50                  55                  60

Gly Arg Pro Gly Glu Pro Pro Ala Ala Ser Ser Ala Ala Gly Asp Ala
65                  70                  75                  80

Gly Trp Pro Asn Lys His Thr Leu Arg Ile Leu Gln Asp Phe Ser Ser
                85                  90                  95

Asp Pro Ser Ser Asn Leu Ser Ser His Ser Leu Glu Lys Leu Pro Pro
            100                 105                 110

Ala Ala Glu Pro Ala Glu Arg Ala Leu Arg Gly Arg Asp Pro Gly Ala
        115                 120                 125

Leu Arg Pro His Asp Pro Ala His Arg Pro Leu Leu Arg Asp Pro Gly
    130                 135                 140

Pro Arg Arg Ser Glu Ser Pro Pro Gly Pro Gly Gly Asp Ala Ser Leu
145                 150                 155                 160

Leu Ala Arg Leu Phe Glu His Pro Leu Tyr Arg Val Ala Val Pro Pro
                165                 170                 175

Leu Thr Glu Glu Asp Val Leu Phe Asn Val Asn Ser Asp Thr Arg Leu
            180                 185                 190

Ser Pro Lys Ala Ala Glu Asn Pro Asp Trp Pro His Ala Gly Ala Glu
        195                 200                 205

Gly Ala Glu Phe Leu Ser Pro Gly Glu Ala Ala Val Asp Ser Tyr Pro
    210                 215                 220

Asn Trp Leu Lys Phe His Ile Gly Ile Asn Arg Tyr Glu Leu Tyr Ser
225                 230                 235                 240

Arg His Asn Pro Ala Ile Glu Ala Leu Leu His Asp Leu Ser Ser Gln
                245                 250                 255

Arg Ile Thr Ser Val Ala Met Lys Ser Gly Gly Thr Gln Leu Lys Leu
            260                 265                 270

Ile Met Thr Phe Gln Asn Tyr Gly Gln Ala Leu Phe Lys Pro Met Lys
        275                 280                 285

Gln Thr Arg Glu Gln Glu Thr Pro Pro Asp Phe Phe Tyr Phe Ser Asp
    290                 295                 300

Tyr Glu Arg His Asn Ala Glu Ile Ala Ala Phe His Leu Asp Arg Ile
305                 310                 315                 320

Leu Asp Phe Arg Arg Val Pro Pro Val Ala Gly Arg Met Val Asn Met
                325                 330                 335

Thr Lys Glu Ile Arg Asp Val Thr Arg Asp Lys Lys Leu Trp Arg Thr
            340                 345                 350

Phe Phe Ile Ser Pro Ala Asn Asn Ile Cys Phe Tyr Gly Glu Cys Ser
        355                 360                 365

Tyr Tyr Cys Ser Thr Glu His Ala Leu Cys Gly Lys Pro Asp Gln Ile
    370                 375                 380

Glu Gly Ser Leu Ala Ala Phe Leu Pro Asp Leu Ser Leu Ala Lys Arg
385                 390                 395                 400

Lys Thr Trp Arg Asn Pro Trp Arg Arg Ser Tyr His Lys Arg Lys Lys
                405                 410                 415

Ala Glu Trp Glu Val Asp Pro Asp Tyr Cys Glu Glu Val Lys Gln Thr
```

```
            420                 425                 430

Pro Pro Tyr Asp Ser Ser His Arg Ile Leu Asp Val Met Asp Met Thr
        435                 440                 445

Ile Phe Asp Phe Leu Met Gly Asn Met Asp Arg His His Tyr Glu Thr
    450                 455                 460

Phe Glu Lys Phe Gly Asn Glu Thr Phe Ile Ile His Leu Asp Asn Gly
465                 470                 475                 480

Arg Gly Phe Gly Lys Tyr Ser His Asp Glu Leu Ser Ile Leu Val Pro
                485                 490                 495

Leu Gln Gln Cys Cys Arg Ile Arg Lys Ser Thr Tyr Leu Arg Leu Gln
            500                 505                 510

Leu Leu Ala Lys Glu Glu Tyr Lys Leu Ser Leu Leu Met Ala Glu Ser
        515                 520                 525

Leu Arg Gly Asp Gln Val Ala Pro Val Leu Tyr Gln Pro His Leu Glu
    530                 535                 540

Ala Leu Asp Arg Arg Leu Arg Val Val Leu Lys Ala Val Arg Asp Cys
545                 550                 555                 560

Val Glu Arg Asn Gly Leu His Ser Val Val Asp Asp Asp Leu Asp Thr
                565                 570                 575

Glu His Arg Ala Ala Ser Ala Arg
            580


<210> SEQ ID NO 100
<211> LENGTH: 307
<212> TYPE: PRT
<213> ORGANISM: Canis sp.

<400> SEQUENCE: 100

Ile Trp Glu Leu Glu Lys Asp Val Tyr Val Val Glu Leu Asp Trp His
1               5                   10                  15

Pro Asp Ala Pro Gly Glu Met Val Val Leu Thr Cys His Thr Pro Glu
            20                  25                  30

Glu Asp Asp Ile Thr Trp Thr Ser Ala Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
                165                 170                 175

Ala Cys Pro Ser Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205
```

```
Arg Asp Ile Ile Lys Pro Asp Pro Pro Thr Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Val Gln Ala
                245                 250                 255

Gln Gly Lys Asn Asn Arg Glu Lys Lys Asp Arg Leu Cys Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asp Trp Ala Ser Val
    290                 295                 300

Ser Cys Ser
305


<210> SEQ ID NO 101
<211> LENGTH: 197
<212> TYPE: PRT
<213> ORGANISM: Canis sp.

<400> SEQUENCE: 101

Arg Ser Leu Pro Thr Ala Ser Pro Ser Pro Gly Ile Phe Gln Cys Leu
1               5                   10                  15

Asn His Ser Gln Asn Leu Leu Arg Ala Val Ser Asn Thr Leu Gln Lys
            20                  25                  30

Ala Arg Gln Thr Leu Glu Leu Tyr Ser Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Met Asn Glu Ser Cys Leu Ala Ser Arg Glu Ile
65                  70                  75                  80

Ser Leu Ile Thr Asn Gly Ser Cys Leu Ala Ser Gly Lys Ala Ser Phe
                85                  90                  95

Met Thr Val Leu Cys Leu Ser Ser Ile Tyr Glu Asp Leu Lys Met Tyr
            100                 105                 110

Gln Met Glu Phe Lys Ala Met Asn Ala Lys Leu Leu Met Asp Pro Lys
        115                 120                 125

Arg Gln Ile Phe Leu Asp Gln Asn Met Leu Thr Ala Ile Asp Glu Leu
    130                 135                 140

Leu Gln Ala Leu Asn Phe Asn Ser Val Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Met Met Ser
            180                 185                 190

Tyr Leu Asn Ser Ser
        195


<210> SEQ ID NO 102
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102
```

-continued

```
Ile Trp Glu Leu Glu Lys Asp Val Tyr Val Val Glu Leu Asp Trp His
1               5                   10                  15

Pro Asp Ala Pro Gly Glu Met Val Val Leu Thr Cys His Thr Pro Glu
            20                  25                  30

Glu Asp Asp Ile Thr Trp Thr Ser Ala Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
                165                 170                 175

Ala Cys Pro Ser Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Thr Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Val Gln Ala
                245                 250                 255

Gln Gly Lys Asn Asn Arg Glu Lys Lys Asp Arg Leu Cys Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asp Trp Ala Ser Val
    290                 295                 300

Ser Cys Ser Gly Gly Gly Gly Ser Gly Gly Gly Gly Ser Gly Gly Gly
305                 310                 315                 320

Gly Ser Arg Ser Leu Pro Thr Ala Ser Pro Ser Pro Gly Ile Phe Gln
                325                 330                 335

Cys Leu Asn His Ser Gln Asn Leu Leu Arg Ala Val Ser Asn Thr Leu
            340                 345                 350

Gln Lys Ala Arg Gln Thr Leu Glu Leu Tyr Ser Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Met Asn Glu Ser Cys Leu Ala Ser Arg
385                 390                 395                 400

Glu Ile Ser Leu Ile Thr Asn Gly Ser Cys Leu Ala Ser Gly Lys Ala
                405                 410                 415

Ser Phe Met Thr Val Leu Cys Leu Ser Ser Ile Tyr Glu Asp Leu Lys
```

```
            420                 425                 430

Met Tyr Gln Met Glu Phe Lys Ala Met Asn Ala Lys Leu Leu Met Asp
        435                 440                 445

Pro Lys Arg Gln Ile Phe Leu Asp Gln Asn Met Leu Thr Ala Ile Asp
    450                 455                 460

Glu Leu Leu Gln Ala Leu Asn Phe Asn Ser Val Thr Val Pro Gln Lys
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asp Arg Met
            500                 505                 510

Met Ser Tyr Leu Asn Ser Ser
        515


<210> SEQ ID NO 103
<211> LENGTH: 590
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ile Trp Glu Leu Glu Lys Asp Val Tyr Val Val Glu Leu Asp Trp His
1               5                   10                  15

Pro Asp Ala Pro Gly Glu Met Val Val Leu Thr Cys His Thr Pro Glu
            20                  25                  30

Glu Asp Asp Ile Thr Trp Thr Ser Ala Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
                165                 170                 175

Ala Cys Pro Ser Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Thr Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Val Gln Ala
                245                 250                 255
```

```
Gln Gly Lys Asn Asn Arg Glu Lys Lys Asp Arg Leu Cys Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asp Trp Ala Ser Val
    290                 295                 300

Ser Cys Ser Gly Gly Gly Gly Ser Gly Gly Gly Gly Ser Gly Gly Gly
305                 310                 315                 320

Gly Ser Arg Ser Leu Pro Thr Ala Ser Pro Ser Pro Gly Ile Phe Gln
                325                 330                 335

Cys Leu Asn His Ser Gln Asn Leu Leu Arg Ala Val Ser Asn Thr Leu
            340                 345                 350

Gln Lys Ala Arg Gln Thr Leu Glu Leu Tyr Ser Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Met Asn Glu Ser Cys Leu Ala Ser Arg
385                 390                 395                 400

Glu Ile Ser Leu Ile Thr Asn Gly Ser Cys Leu Ala Ser Gly Lys Ala
                405                 410                 415

Ser Phe Met Thr Val Leu Cys Leu Ser Ser Ile Tyr Glu Asp Leu Lys
            420                 425                 430

Met Tyr Gln Met Glu Phe Lys Ala Met Asn Ala Lys Leu Leu Met Asp
        435                 440                 445

Pro Lys Arg Gln Ile Phe Leu Asp Gln Asn Met Leu Thr Ala Ile Asp
    450                 455                 460

Glu Leu Leu Gln Ala Leu Asn Phe Asn Ser Val Thr Val Pro Gln Lys
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asp Arg Met
            500                 505                 510

Met Ser Tyr Leu Asn Ser Ser Gly Gly Gly Gly Glu Gly Gly Gly Gly
        515                 520                 525

Ser Glu Glu Gly Gly Gly Gly Ser Glu Glu Gly Gly Gly Gly Ser Glu
    530                 535                 540

Glu Gly Gly Gly Gly Ser Glu Glu Gly Gly Gly Gly Ser Glu Glu Gly
545                 550                 555                 560

Gly Gly Gly Ser Glu Glu Gly Gly Gly Gly Ser Glu Glu Gly Gly Gly
                565                 570                 575

Gly Ser Glu Glu Gly Gly Gly Gly His His His His His His
            580                 585                 590
```

<210> SEQ ID NO 104
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Met Tyr Arg Met Gln Leu Leu Ser Cys Ile Ala Leu Ser Leu Ala Leu
1               5                   10                  15

Val Thr Asn Ser Ile Trp Glu Leu Glu Lys Asp Val Tyr Val Val Glu
            20                  25                  30
```

```
Leu Asp Trp His Pro Asp Ala Pro Gly Glu Met Val Val Leu Thr Cys
        35                  40                  45

His Thr Pro Glu Glu Asp Asp Ile Thr Trp Thr Ser Ala Gln Ser Ser
    50                  55                  60

Glu Val Leu Gly Ser Gly Lys Thr Leu Thr Ile Gln Val Lys Glu Phe
65                  70                  75                  80

Gly Asp Ala Gly Gln Tyr Thr Cys His Lys Gly Gly Lys Val Leu Ser
                85                  90                  95

Arg Ser Leu Leu Leu Ile His Lys Lys Glu Asp Gly Ile Trp Ser Thr
            100                 105                 110

Asp Ile Leu Lys Glu Gln Lys Glu Ser Lys Asn Lys Ile Phe Leu Lys
        115                 120                 125

Cys Glu Ala Lys Asn Tyr Ser Gly Arg Phe Thr Cys Trp Trp Leu Thr
    130                 135                 140

Ala Ile Ser Thr Asp Leu Lys Phe Ser Val Lys Ser Ser Arg Gly Phe
145                 150                 155                 160

Ser Asp Pro Gln Gly Val Thr Cys Gly Ala Val Thr Leu Ser Ala Glu
                165                 170                 175

Arg Val Arg Val Asp Asn Arg Asp Tyr Lys Lys Tyr Thr Val Glu Cys
            180                 185                 190

Gln Glu Gly Ser Ala Cys Pro Ser Ala Glu Glu Ser Leu Pro Ile Glu
        195                 200                 205

Val Val Val Asp Ala Ile His Lys Leu Lys Tyr Glu Asn Tyr Thr Ser
    210                 215                 220

Ser Phe Phe Ile Arg Asp Ile Ile Lys Pro Asp Pro Pro Thr Asn Leu
225                 230                 235                 240

Gln Leu Lys Pro Leu Lys Asn Ser Arg His Val Glu Val Ser Trp Glu
                245                 250                 255

Tyr Pro Asp Thr Trp Ser Thr Pro His Ser Tyr Phe Ser Leu Thr Phe
            260                 265                 270

Cys Val Gln Ala Gln Gly Lys Asn Asn Arg Glu Lys Lys Asp Arg Leu
        275                 280                 285

Cys Val Asp Lys Thr Ser Ala Lys Val Val Cys His Lys Asp Ala Lys
    290                 295                 300

Ile Arg Val Gln Ala Arg Asp Arg Tyr Tyr Ser Ser Ser Trp Ser Asp
305                 310                 315                 320

Trp Ala Ser Val Ser Cys Ser Gly Gly Gly Gly Ser Gly Gly Gly Gly
                325                 330                 335

Ser Gly Gly Gly Gly Ser Arg Ser Leu Pro Thr Ala Ser Pro Ser Pro
            340                 345                 350

Gly Ile Phe Gln Cys Leu Asn His Ser Gln Asn Leu Leu Arg Ala Val
        355                 360                 365

Ser Asn Thr Leu Gln Lys Ala Arg Gln Thr Leu Glu Leu Tyr Ser Cys
    370                 375                 380

Thr Ser Glu Glu Ile Asp His Glu Asp Ile Thr Lys Asp Lys Thr Ser
385                 390                 395                 400

Thr Val Glu Ala Cys Leu Pro Leu Glu Leu Thr Met Asn Glu Ser Cys
                405                 410                 415

Leu Ala Ser Arg Glu Ile Ser Leu Ile Thr Asn Gly Ser Cys Leu Ala
            420                 425                 430

Ser Gly Lys Ala Ser Phe Met Thr Val Leu Cys Leu Ser Ser Ile Tyr
        435                 440                 445
```

```
Glu Asp Leu Lys Met Tyr Gln Met Glu Phe Lys Ala Met Asn Ala Lys
    450                 455                 460

Leu Leu Met Asp Pro Lys Arg Gln Ile Phe Leu Asp Gln Asn Met Leu
465                 470                 475                 480

Thr Ala Ile Asp Glu Leu Leu Gln Ala Leu Asn Phe Asn Ser Val Thr
                485                 490                 495

Val Pro Gln Lys Ser Ser Leu Glu Glu Pro Asp Phe Tyr Lys Thr Lys
            500                 505                 510

Ile Lys Leu Cys Ile Leu Leu His Ala Phe Arg Ile Arg Ala Val Thr
        515                 520                 525

Ile Asp Arg Met Met Ser Tyr Leu Asn Ser Ser Gly Gly Gly Gly Glu
    530                 535                 540

Gly Gly Gly Gly Ser Glu Glu Gly Gly Gly Gly Ser Glu Glu Gly Gly
545                 550                 555                 560

Gly Gly Ser Glu Glu Gly Gly Gly Gly Ser Glu Glu Gly Gly Gly Gly
                565                 570                 575

Ser Glu Glu Gly Gly Gly Gly Ser Glu Glu Gly Gly Gly Gly Ser Glu
            580                 585                 590

Glu Gly Gly Gly Gly Ser Glu Glu Gly Gly Gly Gly His His His His
        595                 600                 605

His His
    610


<210> SEQ ID NO 105
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ile Trp Glu Leu Glu Lys Asp Val Tyr Val Val Glu Leu Asp Trp His
1               5                   10                  15

Pro Asp Ala Pro Gly Glu Met Val Val Leu Thr Cys His Thr Pro Glu
            20                  25                  30

Glu Asp Asp Ile Thr Trp Thr Ser Ala Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
                165                 170                 175

Ala Cys Pro Ser Ala Glu Glu Ser Leu Pro Ile Glu Val Val Val Asp
            180                 185                 190
```

```
Ala Ile His Lys Leu Lys Tyr Glu Asn Tyr Thr Ser Ser Phe Phe Ile
        195                 200                 205

Arg Asp Ile Ile Lys Pro Asp Pro Pro Thr Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Val Gln Ala
                245                 250                 255

Gln Gly Lys Asn Asn Arg Glu Lys Lys Asp Arg Leu Cys Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asp Trp Ala Ser Val
    290                 295                 300

Ser Cys Ser Gly Gly Gly Gly Ser Gly Gly Gly Gly Ser Gly Gly Gly
305                 310                 315                 320

Gly Ser Arg Ser Leu Pro Thr Ala Ser Pro Ser Pro Gly Ile Phe Gln
                325                 330                 335

Cys Leu Asn His Ser Gln Asn Leu Leu Arg Ala Val Ser Asn Thr Leu
            340                 345                 350

Gln Lys Ala Arg Gln Thr Leu Glu Leu Tyr Ser Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Met Asn Glu Ser Cys Leu Ala Ser Arg
385                 390                 395                 400

Glu Ile Ser Leu Ile Thr Asn Gly Ser Cys Leu Ala Ser Gly Lys Ala
                405                 410                 415

Ser Phe Met Thr Val Leu Cys Leu Ser Ser Ile Tyr Glu Asp Leu Lys
            420                 425                 430

Met Tyr Gln Met Glu Phe Lys Ala Met Asn Ala Lys Leu Leu Met Asp
        435                 440                 445

Pro Lys Arg Gln Ile Phe Leu Asp Gln Asn Met Leu Thr Ala Ile Asp
    450                 455                 460

Glu Leu Leu Gln Ala Leu Asn Phe Asn Ser Val Thr Val Pro Gln Lys
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asp Arg Met
            500                 505                 510

Met Ser Tyr Leu Asn Ser Ser Gly Gly Gly Gly Glu Gly Gly Gly Gly
        515                 520                 525

Ser Glu Glu Gly Gly Gly Gly Ser Glu Glu Gly Gly Gly Gly Ser Glu
    530                 535                 540

Glu Gly Gly Gly Gly Ser Glu Glu Gly Gly Gly Gly Ser Glu Glu Gly
545                 550                 555                 560

Gly Gly Gly Ser Glu Glu Gly Gly Gly Gly Ser Glu Glu Gly Gly Gly
                565                 570                 575

Gly Ser Glu Glu Gly Gly Gly Gly Ser
            580                 585
```

<210> SEQ ID NO 106
<211> LENGTH: 307

<212> TYPE: PRT
<213> ORGANISM: Felis sp.

<400> SEQUENCE: 106

```
Ile Trp Glu Leu Glu Lys Asn Val Tyr Val Val Glu Leu Asp Trp His
1               5                   10                  15

Pro Asp Ala Pro Gly Glu Met Val Val Leu Thr Cys Asn Thr Pro Glu
            20                  25                  30

Glu Asp Asp Ile Thr Trp Thr Ser Asp Gln Ser Ser Glu Val Leu Gly
        35                  40                  45

Ser Gly Lys Thr Leu Thr Ile Gln Val Lys Glu Phe Ala Asp Ala Gly
    50                  55                  60

Gln Tyr Thr Cys His Lys Gly Gly Glu Val Leu Ser His Ser Phe Leu
65                  70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Thr Val Lys Ser Ser Arg Gly Ser Ser Asp Pro Gln
    130                 135                 140

Gly Val Thr Cys Gly Ala Ala Thr Leu Ser Ala Glu Lys Val Arg Val
145                 150                 155                 160

Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
    290                 295                 300

Ser Cys Ser
305
```

<210> SEQ ID NO 107
<211> LENGTH: 197
<212> TYPE: PRT
<213> ORGANISM: Felis sp.

<400> SEQUENCE: 107

```
Arg Asn Leu Pro Thr Pro Thr Pro Ser Pro Gly Met Phe Gln Cys Leu
1               5                   10                  15

Asn His Ser Gln Thr Leu Leu Arg Ala Ile Ser Asn Thr Leu Gln Lys
            20                  25                  30
```

```
Ala Arg Gln Thr Leu Glu Phe Tyr Ser Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Met Asn Glu Ser Cys Leu Ala Ser Arg Glu Ile
65                  70                  75                  80

Ser Leu Ile Thr Asn Gly Ser Cys Leu Ala Ser Arg Lys Thr Ser Phe
                85                  90                  95

Met Thr Thr Leu Cys Leu Ser Ser Ile Tyr Glu Asp Leu Lys Met Tyr
            100                 105                 110

Gln Val Glu Phe Lys Ala Met Asn Ala Lys Leu Leu Met Asp Pro Lys
        115                 120                 125

Arg Gln Ile Phe Leu Asp Gln Asn Met Leu Thr Ala Ile Asp Glu Leu
    130                 135                 140

Leu Gln Ala Leu Asn Val Asn Ser Val Thr Val Pro Gln Asn Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asn Arg Met Met Ser
            180                 185                 190

Tyr Leu Asn Ser Ser
        195
```

<210> SEQ ID NO 108
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Ile Trp Glu Leu Glu Lys Asn Val Tyr Val Val Glu Leu Asp Trp His
1               5                   10                  15

Pro Asp Ala Pro Gly Glu Met Val Val Leu Thr Cys Asn Thr Pro Glu
            20                  25                  30

Glu Asp Asp Ile Thr Trp Thr Ser Asp Gln Ser Ser Glu Val Leu Gly
        35                  40                  45

Ser Gly Lys Thr Leu Thr Ile Gln Val Lys Glu Phe Ala Asp Ala Gly
    50                  55                  60

Gln Tyr Thr Cys His Lys Gly Gly Glu Val Leu Ser His Ser Phe Leu
65                  70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Thr Val Lys Ser Ser Arg Gly Ser Ser Asp Pro Gln
    130                 135                 140

Gly Val Thr Cys Gly Ala Ala Thr Leu Ser Ala Glu Lys Val Arg Val
145                 150                 155                 160

Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190
```

```
Ala Ile His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
    290                 295                 300

Ser Cys Ser Gly Gly Gly Gly Ser Gly Gly Gly Gly Ser Gly Gly Gly
305                 310                 315                 320

Gly Ser Arg Asn Leu Pro Thr Pro Thr Pro Ser Pro Gly Met Phe Gln
                325                 330                 335

Cys Leu Asn His Ser Gln Thr Leu Leu Arg Ala Ile Ser Asn Thr Leu
            340                 345                 350

Gln Lys Ala Arg Gln Thr Leu Glu Phe Tyr Ser Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Met Asn Glu Ser Cys Leu Ala Ser Arg
385                 390                 395                 400

Glu Ile Ser Leu Ile Thr Asn Gly Ser Cys Leu Ala Ser Arg Lys Thr
                405                 410                 415

Ser Phe Met Thr Thr Leu Cys Leu Ser Ser Ile Tyr Glu Asp Leu Lys
            420                 425                 430

Met Tyr Gln Val Glu Phe Lys Ala Met Asn Ala Lys Leu Leu Met Asp
        435                 440                 445

Pro Lys Arg Gln Ile Phe Leu Asp Gln Asn Met Leu Thr Ala Ile Asp
    450                 455                 460

Glu Leu Leu Gln Ala Leu Asn Val Asn Ser Val Thr Val Pro Gln Asn
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asn Arg Met
            500                 505                 510

Met Ser Tyr Leu Asn Ser Ser
        515


<210> SEQ ID NO 109
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ile Trp Glu Leu Glu Lys Asn Val Tyr Val Val Glu Leu Asp Trp His
1               5                   10                  15

Pro Asp Ala Pro Gly Glu Met Val Val Leu Thr Cys Asn Thr Pro Glu
```

```
            20                  25                  30

Glu Asp Asp Ile Thr Trp Thr Ser Asp Gln Ser Ser Glu Val Leu Gly
        35                  40                  45

Ser Gly Lys Thr Leu Thr Ile Gln Val Lys Glu Phe Ala Asp Ala Gly
    50                  55                  60

Gln Tyr Thr Cys His Lys Gly Gly Glu Val Leu Ser His Ser Phe Leu
65                  70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Thr Val Lys Ser Ser Arg Gly Ser Ser Asp Pro Gln
    130                 135                 140

Gly Val Thr Cys Gly Ala Ala Thr Leu Ser Ala Glu Lys Val Arg Val
145                 150                 155                 160

Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
    290                 295                 300

Ser Cys Ser Gly Gly Gly Gly Ser Gly Gly Gly Gly Ser Gly Gly Gly
305                 310                 315                 320

Gly Ser Arg Asn Leu Pro Thr Pro Thr Pro Ser Pro Gly Met Phe Gln
                325                 330                 335

Cys Leu Asn His Ser Gln Thr Leu Leu Arg Ala Ile Ser Asn Thr Leu
            340                 345                 350

Gln Lys Ala Arg Gln Thr Leu Glu Phe Tyr Ser Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Met Asn Glu Ser Cys Leu Ala Ser Arg
385                 390                 395                 400

Glu Ile Ser Leu Ile Thr Asn Gly Ser Cys Leu Ala Ser Arg Lys Thr
                405                 410                 415

Ser Phe Met Thr Thr Leu Cys Leu Ser Ser Ile Tyr Glu Asp Leu Lys
            420                 425                 430

Met Tyr Gln Val Glu Phe Lys Ala Met Asn Ala Lys Leu Leu Met Asp
        435                 440                 445
```

```
Pro Lys Arg Gln Ile Phe Leu Asp Gln Asn Met Leu Thr Ala Ile Asp
    450                 455                 460

Glu Leu Leu Gln Ala Leu Asn Val Asn Ser Val Thr Val Pro Gln Asn
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asn Arg Met
            500                 505                 510

Met Ser Tyr Leu Asn Ser Ser Gly Gly Gly Gly Glu Gly Gly Gly Gly
        515                 520                 525

Ser Glu Glu Gly Gly Gly Gly Ser Glu Glu Gly Gly Gly Gly Ser Glu
    530                 535                 540

Glu Gly Gly Gly Gly Ser Glu Glu Gly Gly Gly Gly Ser Glu Glu Gly
545                 550                 555                 560

Gly Gly Gly Ser Glu Glu Gly Gly Gly Gly Ser Glu Glu Gly Gly Gly
                565                 570                 575

Gly Ser Glu Glu Gly Gly Gly Gly Ser
            580                 585


<210> SEQ ID NO 110
<211> LENGTH: 302
<212> TYPE: PRT
<213> ORGANISM: Sus sp.

<400> SEQUENCE: 110

Ile Trp Glu Leu Glu Lys Asn Val Tyr Val Val Glu Leu Asp Trp Tyr
1               5                   10                  15

Pro Asn Ala Pro Gly Glu Met Val Val Leu Thr Cys Asn Thr Pro Glu
            20                  25                  30

Glu Asp Gly Ile Thr Trp Thr Ser Asp Gln Ser Ser Glu Val Leu Gly
        35                  40                  45

Thr Gly Lys Thr Leu Thr Ile His Val Lys Glu Phe Gly Asp Ala Gly
    50                  55                  60

Gln Tyr Thr Cys Arg Lys Gly Gly Ala Val Leu Ser Gln Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Ser Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Thr Asp Pro Arg
    130                 135                 140

Gly Val Thr Cys Gly Thr Ala Thr Leu Ser Glu Asp Leu Gly Glu Tyr
145                 150                 155                 160

Lys Lys Tyr Arg Val Glu Cys Gln Glu Gly Ser Ala Cys Pro Ala Ala
                165                 170                 175

Glu Glu Ser Leu Pro Ile Glu Val Val Leu Glu Ala Val His Lys Leu
            180                 185                 190

Lys Tyr Glu Asn Tyr Thr Ser Ser Phe Phe Ile Arg Asp Ile Ile Lys
        195                 200                 205

Pro Asp Pro Pro Lys Asn Leu Gln Leu Asn Pro Leu Lys Asn Ser Arg
    210                 215                 220

His Val Glu Ile Ser Trp Glu Tyr Pro Asp Thr Trp Ser Thr Pro His
```

```
225                 230                 235                 240

Ser Tyr Phe Ser Leu Met Phe Gly Val Gln Val Gln Gly Lys Asn Lys
                245                 250                 255

Arg Glu Lys Lys Asp Lys Leu Phe Thr Asp Gln Ile Ser Ala Lys Val
            260                 265                 270

Thr Cys His Lys Asp Ala Asn Ile Arg Val Gln Ala Arg Asp Arg Tyr
        275                 280                 285

Tyr Ser Ser Ser Trp Ser Glu Trp Ala Ser Val Ser Cys Asn
    290                 295                 300


<210> SEQ ID NO 111
<211> LENGTH: 197
<212> TYPE: PRT
<213> ORGANISM: Sus sp.

<400> SEQUENCE: 111

Arg Ser Leu Pro Ala Thr Thr Ala Gly Pro Gly Met Phe Lys Cys Leu
1               5                   10                  15

Asn His Ser Gln Asn Leu Leu Lys Ala Val Ser Asn Thr Leu Gln Lys
            20                  25                  30

Ala Lys Gln Thr Leu Glu Phe Tyr Ser Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Ala Thr Asn Glu Ser Cys Leu Ala Ala Arg Glu Thr
65                  70                  75                  80

Ser Leu Ile Thr Asn Gly Asn Cys Leu Thr Ser Gly Lys Thr Ser Phe
                85                  90                  95

Met Thr Thr Leu Cys Leu Ser Ser Ile Tyr Glu Asp Leu Lys Met Tyr
            100                 105                 110

His Val Glu Phe Gln Ala Met Asn Ala Lys Leu Leu Met Asp Pro Lys
        115                 120                 125

Arg Gln Ile Phe Leu Asp Gln Asn Met Leu Thr Ala Ile Thr Glu Leu
    130                 135                 140

Met Gln Ala Leu Asn Phe Asn Ser Glu Thr Val Pro Gln Lys Pro Ser
145                 150                 155                 160

Leu Glu Glu Leu Asp Phe Tyr Lys Thr Lys Ile Lys Leu Cys Ile Leu
                165                 170                 175

Leu His Ala Phe Arg Ile Arg Ala Val Thr Ile Asp Arg Met Met Ser
            180                 185                 190

Tyr Leu Asn Ser Ser
        195


<210> SEQ ID NO 112
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Trp Glu Leu Glu Lys Asn Val Tyr Val Val Glu Leu Asp Trp Tyr
1               5                   10                  15

Pro Asn Ala Pro Gly Glu Met Val Val Leu Thr Cys Asn Thr Pro Glu
            20                  25                  30

Glu Asp Gly Ile Thr Trp Thr Ser Asp Gln Ser Ser Glu Val Leu Gly
```

```
        35                  40                  45

Thr Gly Lys Thr Leu Thr Ile His Val Lys Glu Phe Gly Asp Ala Gly
    50                  55                  60

Gln Tyr Thr Cys Arg Lys Gly Gly Ala Val Leu Ser Gln Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Ser Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Thr Asp Pro Arg
    130                 135                 140

Gly Val Thr Cys Gly Thr Ala Thr Leu Ser Glu Asp Leu Gly Glu Tyr
145                 150                 155                 160

Lys Lys Tyr Arg Val Glu Cys Gln Glu Gly Ser Ala Cys Pro Ala Ala
                165                 170                 175

Glu Glu Ser Leu Pro Ile Glu Val Val Leu Glu Ala Val His Lys Leu
            180                 185                 190

Lys Tyr Glu Asn Tyr Thr Ser Ser Phe Phe Ile Arg Asp Ile Ile Lys
        195                 200                 205

Pro Asp Pro Pro Lys Asn Leu Gln Leu Asn Pro Leu Lys Asn Ser Arg
    210                 215                 220

His Val Glu Ile Ser Trp Glu Tyr Pro Asp Thr Trp Ser Thr Pro His
225                 230                 235                 240

Ser Tyr Phe Ser Leu Met Phe Gly Val Gln Val Gln Gly Lys Asn Lys
                245                 250                 255

Arg Glu Lys Lys Asp Lys Leu Phe Thr Asp Gln Ile Ser Ala Lys Val
            260                 265                 270

Thr Cys His Lys Asp Ala Asn Ile Arg Val Gln Ala Arg Asp Arg Tyr
        275                 280                 285

Tyr Ser Ser Ser Trp Ser Glu Trp Ala Ser Val Ser Cys Asn Gly Gly
    290                 295                 300

Gly Gly Ser Gly Gly Gly Gly Ser Gly Gly Gly Gly Ser Arg Ser Leu
305                 310                 315                 320

Pro Ala Thr Thr Ala Gly Pro Gly Met Phe Lys Cys Leu Asn His Ser
                325                 330                 335

Gln Asn Leu Leu Lys Ala Val Ser Asn Thr Leu Gln Lys Ala Lys Gln
            340                 345                 350

Thr Leu Glu Phe Tyr Ser Cys Thr Ser Glu Glu Ile Asp His Glu Asp
        355                 360                 365

Ile Thr Lys Asp Lys Thr Ser Thr Val Glu Ala Cys Leu Pro Leu Glu
    370                 375                 380

Leu Ala Thr Asn Glu Ser Cys Leu Ala Ala Arg Glu Thr Ser Leu Ile
385                 390                 395                 400

Thr Asn Gly Asn Cys Leu Thr Ser Gly Lys Thr Ser Phe Met Thr Thr
                405                 410                 415

Leu Cys Leu Ser Ser Ile Tyr Glu Asp Leu Lys Met Tyr His Val Glu
            420                 425                 430

Phe Gln Ala Met Asn Ala Lys Leu Leu Met Asp Pro Lys Arg Gln Ile
        435                 440                 445

Phe Leu Asp Gln Asn Met Leu Thr Ala Ile Thr Glu Leu Met Gln Ala
    450                 455                 460
```

Leu Asn Phe Asn Ser Glu Thr Val Pro Gln Lys Pro Ser Leu Glu Glu
465 470 475 480

Leu Asp Phe Tyr Lys Thr Lys Ile Lys Leu Cys Ile Leu Leu His Ala
485 490 495

Phe Arg Ile Arg Ala Val Thr Ile Asp Arg Met Met Ser Tyr Leu Asn
500 505 510

Ser Ser

<210> SEQ ID NO 113
<211> LENGTH: 580
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Ile Trp Glu Leu Glu Lys Asn Val Tyr Val Val Glu Leu Asp Trp Tyr
1 5 10 15

Pro Asn Ala Pro Gly Glu Met Val Val Leu Thr Cys Asn Thr Pro Glu
20 25 30

Glu Asp Gly Ile Thr Trp Thr Ser Asp Gln Ser Ser Glu Val Leu Gly
35 40 45

Thr Gly Lys Thr Leu Thr Ile His Val Lys Glu Phe Gly Asp Ala Gly
50 55 60

Gln Tyr Thr Cys Arg Lys Gly Gly Ala Val Leu Ser Gln Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Ser Phe Leu Lys Cys Glu Ala Lys
100 105 110

Asn Tyr Ser Gly Arg Phe Thr Cys Trp Trp Leu Thr Ala Ile Ser Thr
115 120 125

Asp Leu Lys Phe Ser Val Lys Ser Ser Arg Gly Ser Thr Asp Pro Arg
130 135 140

Gly Val Thr Cys Gly Thr Ala Thr Leu Ser Glu Asp Leu Gly Glu Tyr
145 150 155 160

Lys Lys Tyr Arg Val Glu Cys Gln Glu Gly Ser Ala Cys Pro Ala Ala
165 170 175

Glu Glu Ser Leu Pro Ile Glu Val Val Leu Glu Ala Val His Lys Leu
180 185 190

Lys Tyr Glu Asn Tyr Thr Ser Ser Phe Phe Ile Arg Asp Ile Ile Lys
195 200 205

Pro Asp Pro Pro Lys Asn Leu Gln Leu Asn Pro Leu Lys Asn Ser Arg
210 215 220

His Val Glu Ile Ser Trp Glu Tyr Pro Asp Thr Trp Ser Thr Pro His
225 230 235 240

Ser Tyr Phe Ser Leu Met Phe Gly Val Gln Val Gln Gly Lys Asn Lys
245 250 255

Arg Glu Lys Lys Asp Lys Leu Phe Thr Asp Gln Ile Ser Ala Lys Val
260 265 270

Thr Cys His Lys Asp Ala Asn Ile Arg Val Gln Ala Arg Asp Arg Tyr
275 280 285

Tyr Ser Ser Ser Trp Ser Glu Trp Ala Ser Val Ser Cys Asn Gly Gly
290 295 300

Gly Gly Ser Gly Gly Gly Gly Ser Gly Gly Gly Gly Ser Arg Ser Leu
305 310 315 320

Pro Ala Thr Thr Ala Gly Pro Gly Met Phe Lys Cys Leu Asn His Ser
325 330 335

Gln Asn Leu Leu Lys Ala Val Ser Asn Thr Leu Gln Lys Ala Lys Gln
340 345 350

Thr Leu Glu Phe Tyr Ser Cys Thr Ser Glu Glu Ile Asp His Glu Asp
355 360 365

Ile Thr Lys Asp Lys Thr Ser Thr Val Glu Ala Cys Leu Pro Leu Glu
370 375 380

Leu Ala Thr Asn Glu Ser Cys Leu Ala Ala Arg Glu Thr Ser Leu Ile
385 390 395 400

Thr Asn Gly Asn Cys Leu Thr Ser Gly Lys Thr Ser Phe Met Thr Thr
405 410 415

Leu Cys Leu Ser Ser Ile Tyr Glu Asp Leu Lys Met Tyr His Val Glu
420 425 430

Phe Gln Ala Met Asn Ala Lys Leu Leu Met Asp Pro Lys Arg Gln Ile
435 440 445

Phe Leu Asp Gln Asn Met Leu Thr Ala Ile Thr Glu Leu Met Gln Ala
450 455 460

Leu Asn Phe Asn Ser Glu Thr Val Pro Gln Lys Pro Ser Leu Glu Glu
465 470 475 480

Leu Asp Phe Tyr Lys Thr Lys Ile Lys Leu Cys Ile Leu Leu His Ala
485 490 495

Phe Arg Ile Arg Ala Val Thr Ile Asp Arg Met Met Ser Tyr Leu Asn
500 505 510

Ser Ser Gly Gly Gly Gly Glu Gly Gly Gly Gly Ser Glu Glu Gly Gly
515 520 525

Gly Gly Ser Glu Glu Gly Gly Gly Gly Ser Glu Glu Gly Gly Gly Gly
530 535 540

Ser Glu Glu Gly Gly Gly Gly Ser Glu Glu Gly Gly Gly Gly Ser Glu
545 550 555 560

Glu Gly Gly Gly Gly Ser Glu Glu Gly Gly Gly Gly Ser Glu Glu Gly
565 570 575

Gly Gly Gly Ser
580

<210> SEQ ID NO 114
<211> LENGTH: 307
<212> TYPE: PRT
<213> ORGANISM: Equus sp.

<400> SEQUENCE: 114

Ile Trp Glu Leu Glu Lys Asp Val Tyr Val Val Glu Leu Asp Trp Tyr
1 5 10 15

Pro Asp Ala Pro Gly Glu Met Val Val Leu Thr Cys Asn Thr Pro Glu
20 25 30

Glu Glu Gly Ile Thr Trp Thr Ser Ala Gln Ser Asn Glu Val Leu Gly
35 40 45

Ser Gly Lys Thr Leu Thr Ile Gln Val Lys Glu Phe Gly Asp Ala Gly
50 55 60

Trp Tyr Thr Cys His Lys Gly Gly Glu Val Leu Ser His Ser His Leu
65 70 75 80

Leu Leu His Lys Lys Glu Asp Gly Ile Trp Ser Thr Asp Ile Leu Lys

```
                85                  90                  95

Asp Gln Lys Glu Ser Lys Asn Lys Thr Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Ser Asp Pro Arg
    130                 135                 140

Gly Val Thr Cys Gly Ala Ala Thr Leu Ser Ala Glu Arg Val Ser Val
145                 150                 155                 160

Asp Asp Arg Glu Tyr Lys Lys Tyr Thr Val Glu Cys Gln Glu Gly Ser
                165                 170                 175

Ala Cys Pro Ala Ala Glu Glu Ser Leu Pro Ile Glu Ile Val Val Asp
            180                 185                 190

Ala Val His Lys Leu Lys Tyr Glu Asn Tyr Thr Ser Gly Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg Gln Val Glu Val Ser Trp Glu Tyr Pro Glu Thr
225                 230                 235                 240

Trp Ser Thr Pro His Ser Tyr Phe Ser Leu Thr Phe Ser Ile Gln Val
                245                 250                 255

Gln Gly Lys Asn Lys Lys Glu Arg Lys Asp Arg Leu Phe Met Asp Glu
            260                 265                 270

Thr Ser Ala Thr Val Thr Cys His Lys Asp Gly Gln Ile Arg Val Gln
        275                 280                 285

Ala Arg Asp Arg Tyr Tyr Ser Ser Ser Trp Ser Glu Trp Ala Ser Val
    290                 295                 300

Ser Cys Ser
305


<210> SEQ ID NO 115
<211> LENGTH: 197
<212> TYPE: PRT
<213> ORGANISM: Equus sp.

<400> SEQUENCE: 115

Arg Asn Leu Pro Thr Ala Thr Pro Gly Pro Gly Met Phe Gln Cys Leu
1               5                   10                  15

Asn His Ser Gln Asn Leu Leu Arg Thr Val Ser Asn Thr Leu Gln Lys
            20                  25                  30

Ala Arg Gln Thr Leu Glu Phe Tyr Ser Cys Thr Ser Glu Glu Ile Asp
        35                  40                  45

His Glu Asp Ile Thr Lys Asp Lys Ser Ser Thr Val Ala Ala Cys Leu
    50                  55                  60

Pro Leu Glu Leu Ala Pro Asn Glu Ser Cys Leu Ala Ser Arg Glu Ile
65                  70                  75                  80

Ser Phe Ile Thr Asn Gly Ser Cys Leu Thr Pro Gly Lys Ala Ser Ser
                85                  90                  95

Met Met Thr Leu Cys Leu Ser Ser Ile Tyr Glu Asp Leu Lys Met Tyr
            100                 105                 110

Gln Val Glu Phe Lys Ala Met Asn Ala Lys Leu Leu Ile Asp Pro Gln
        115                 120                 125

Arg Gln Ile Phe Leu Asp Glu Asn Met Leu Thr Ala Ile Asp Lys Leu
    130                 135                 140
```

```
Met Gln Ala Leu Asn Phe Asn Ser Glu Thr Val Pro Gln Lys Pro Ser
145                 150                 155                 160

Leu Glu Gly Leu Asp Phe Tyr Lys Thr Lys Val Lys Leu Cys Ile Leu
                165                 170                 175

Leu His Ala Phe Arg Ile Arg Ala Val Thr Ile Asn Arg Met Met Gly
            180                 185                 190

Tyr Leu Asn Ala Ser
        195


<210> SEQ ID NO 116
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Trp Glu Leu Glu Lys Asp Val Tyr Val Val Glu Leu Asp Trp Tyr
1               5                   10                  15

Pro Asp Ala Pro Gly Glu Met Val Val Leu Thr Cys Asn Thr Pro Glu
            20                  25                  30

Glu Glu Gly Ile Thr Trp Thr Ser Ala Gln Ser Asn Glu Val Leu Gly
        35                  40                  45

Ser Gly Lys Thr Leu Thr Ile Gln Val Lys Glu Phe Gly Asp Ala Gly
    50                  55                  60

Trp Tyr Thr Cys His Lys Gly Gly Glu Val Leu Ser His Ser His Leu
65                  70                  75                  80

Leu Leu His Lys Lys Glu Asp Gly Ile Trp Ser Thr Asp Ile Leu Lys
                85                  90                  95

Asp Gln Lys Glu Ser Lys Asn Lys Thr Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Ser Asp Pro Arg
    130                 135                 140

Gly Val Thr Cys Gly Ala Ala Thr Leu Ser Ala Glu Arg Val Ser Val
145                 150                 155                 160

Asp Asp Arg Glu Tyr Lys Lys Tyr Thr Val Glu Cys Gln Glu Gly Ser
                165                 170                 175

Ala Cys Pro Ala Ala Glu Glu Ser Leu Pro Ile Glu Ile Val Val Asp
            180                 185                 190

Ala Val His Lys Leu Lys Tyr Glu Asn Tyr Thr Ser Gly Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg Gln Val Glu Val Ser Trp Glu Tyr Pro Glu Thr
225                 230                 235                 240

Trp Ser Thr Pro His Ser Tyr Phe Ser Leu Thr Phe Ser Ile Gln Val
                245                 250                 255

Gln Gly Lys Asn Lys Lys Glu Arg Lys Asp Arg Leu Phe Met Asp Glu
            260                 265                 270

Thr Ser Ala Thr Val Thr Cys His Lys Asp Gly Gln Ile Arg Val Gln
        275                 280                 285

Ala Arg Asp Arg Tyr Tyr Ser Ser Ser Trp Ser Glu Trp Ala Ser Val
    290                 295                 300
```

```
Ser Cys Ser Gly Gly Gly Gly Ser Gly Gly Gly Gly Ser Gly Gly Gly
305                 310                 315                 320

Gly Ser Arg Asn Leu Pro Thr Ala Thr Pro Gly Pro Gly Met Phe Gln
                325                 330                 335

Cys Leu Asn His Ser Gln Asn Leu Leu Arg Thr Val Ser Asn Thr Leu
            340                 345                 350

Gln Lys Ala Arg Gln Thr Leu Glu Phe Tyr Ser Cys Thr Ser Glu Glu
        355                 360                 365

Ile Asp His Glu Asp Ile Thr Lys Asp Lys Ser Ser Thr Val Ala Ala
    370                 375                 380

Cys Leu Pro Leu Glu Leu Ala Pro Asn Glu Ser Cys Leu Ala Ser Arg
385                 390                 395                 400

Glu Ile Ser Phe Ile Thr Asn Gly Ser Cys Leu Thr Pro Gly Lys Ala
                405                 410                 415

Ser Ser Met Met Thr Leu Cys Leu Ser Ser Ile Tyr Glu Asp Leu Lys
            420                 425                 430

Met Tyr Gln Val Glu Phe Lys Ala Met Asn Ala Lys Leu Leu Ile Asp
        435                 440                 445

Pro Gln Arg Gln Ile Phe Leu Asp Glu Asn Met Leu Thr Ala Ile Asp
    450                 455                 460

Lys Leu Met Gln Ala Leu Asn Phe Asn Ser Glu Thr Val Pro Gln Lys
465                 470                 475                 480

Pro Ser Leu Glu Gly Leu Asp Phe Tyr Lys Thr Lys Val Lys Leu Cys
                485                 490                 495

Ile Leu Leu His Ala Phe Arg Ile Arg Ala Val Thr Ile Asn Arg Met
            500                 505                 510

Met Gly Tyr Leu Asn Ala Ser
        515


<210> SEQ ID NO 117
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ile Trp Glu Leu Glu Lys Asp Val Tyr Val Val Glu Leu Asp Trp Tyr
1               5                   10                  15

Pro Asp Ala Pro Gly Glu Met Val Val Leu Thr Cys Asn Thr Pro Glu
            20                  25                  30

Glu Glu Gly Ile Thr Trp Thr Ser Ala Gln Ser Asn Glu Val Leu Gly
        35                  40                  45

Ser Gly Lys Thr Leu Thr Ile Gln Val Lys Glu Phe Gly Asp Ala Gly
    50                  55                  60

Trp Tyr Thr Cys His Lys Gly Gly Glu Val Leu Ser His Ser His Leu
65                  70                  75                  80

Leu Leu His Lys Lys Glu Asp Gly Ile Trp Ser Thr Asp Ile Leu Lys
                85                  90                  95

Asp Gln Lys Glu Ser Lys Asn Lys Thr Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Ser Asp Pro Arg
```

```
    130                 135                 140

Gly Val Thr Cys Gly Ala Ala Thr Leu Ser Ala Glu Arg Val Ser Val
145                 150                 155                 160

Asp Asp Arg Glu Tyr Lys Lys Tyr Thr Val Glu Cys Gln Glu Gly Ser
                165                 170                 175

Ala Cys Pro Ala Ala Glu Glu Ser Leu Pro Ile Glu Ile Val Val Asp
            180                 185                 190

Ala Val His Lys Leu Lys Tyr Glu Asn Tyr Thr Ser Gly Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg Gln Val Glu Val Ser Trp Glu Tyr Pro Glu Thr
225                 230                 235                 240

Trp Ser Thr Pro His Ser Tyr Phe Ser Leu Thr Phe Ser Ile Gln Val
                245                 250                 255

Gln Gly Lys Asn Lys Lys Glu Arg Lys Asp Arg Leu Phe Met Asp Glu
            260                 265                 270

Thr Ser Ala Thr Val Thr Cys His Lys Asp Gly Gln Ile Arg Val Gln
        275                 280                 285

Ala Arg Asp Arg Tyr Tyr Ser Ser Ser Trp Ser Glu Trp Ala Ser Val
    290                 295                 300

Ser Cys Ser Gly Gly Gly Gly Ser Gly Gly Gly Gly Ser Gly Gly Gly
305                 310                 315                 320

Gly Ser Arg Asn Leu Pro Thr Ala Thr Pro Gly Pro Gly Met Phe Gln
                325                 330                 335

Cys Leu Asn His Ser Gln Asn Leu Leu Arg Thr Val Ser Asn Thr Leu
            340                 345                 350

Gln Lys Ala Arg Gln Thr Leu Glu Phe Tyr Ser Cys Thr Ser Glu Glu
        355                 360                 365

Ile Asp His Glu Asp Ile Thr Lys Asp Lys Ser Ser Thr Val Ala Ala
    370                 375                 380

Cys Leu Pro Leu Glu Leu Ala Pro Asn Glu Ser Cys Leu Ala Ser Arg
385                 390                 395                 400

Glu Ile Ser Phe Ile Thr Asn Gly Ser Cys Leu Thr Pro Gly Lys Ala
                405                 410                 415

Ser Ser Met Met Thr Leu Cys Leu Ser Ser Ile Tyr Glu Asp Leu Lys
            420                 425                 430

Met Tyr Gln Val Glu Phe Lys Ala Met Asn Ala Lys Leu Leu Ile Asp
        435                 440                 445

Pro Gln Arg Gln Ile Phe Leu Asp Glu Asn Met Leu Thr Ala Ile Asp
    450                 455                 460

Lys Leu Met Gln Ala Leu Asn Phe Asn Ser Glu Thr Val Pro Gln Lys
465                 470                 475                 480

Pro Ser Leu Glu Gly Leu Asp Phe Tyr Lys Thr Lys Val Lys Leu Cys
                485                 490                 495

Ile Leu Leu His Ala Phe Arg Ile Arg Ala Val Thr Ile Asn Arg Met
            500                 505                 510

Met Gly Tyr Leu Asn Ala Ser Gly Gly Gly Gly Glu Gly Gly Gly Gly
        515                 520                 525

Ser Glu Glu Gly Gly Gly Gly Ser Glu Glu Gly Gly Gly Gly Ser Glu
    530                 535                 540

Glu Gly Gly Gly Gly Ser Glu Glu Gly Gly Gly Gly Ser Glu Glu Gly
545                 550                 555                 560
```

Gly Gly Gly Ser Glu Glu Gly Gly Gly Gly Ser Glu Glu Gly Gly Gly
565 570 575

Gly Ser Glu Glu Gly Gly Gly Gly Ser
580 585

<210> SEQ ID NO 118
<211> LENGTH: 1770
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118
atctgggaac tggagaagga tgtgtacgtg gtcgagctcg attggcatcc tgatgcgcct 60
ggcgaaatgg tggtgctgac ttgccacact cccgaggagg acgacattac ctggacctcg 120
gcccagtcct ccgaagtcct gggaagcggg aaaactctga caattcaggt caaagagttc 180
ggcgacgcag gacagtacac ctgtcacaag ggtggaaagg tcctgagcag atcgctgttg 240
ctgatccaca agaaggaaga tggcatctgg tccacggaca tcctgaagga gcagaaggaa 300
tccaagaaca agatctttct taagtgcgaa gccaagaact actcgggccg gttcacctgt 360
tggtggctta ctgccatatc aaccgacctg aagttttccg tgaaatcgag ccgcggcttc 420
tcggaccctc aaggagtgac ttgcggagcc gtgaccctct ccgccgagag agtgcgggtc 480
gacaaccggg actacaagaa gtacaccgtg gagtgccagg aaggatccgc ctgtccaagc 540
gccgaggaaa gcctgccgat tgaggtggtc gtcgatgcca tccacaagct gaaatacgag 600
aattacactt cgtccttctt catccgggac atcatcaagc ccgatccgcc aaccaacttg 660
caactcaagc cgctgaagaa ttcgcgccac gtggaggtgt cctgggagta ccccgatacg 720
tggtccaccc cgcatagcta tttctccctc actttctgcg tgcaagccca gggaaagaac 780
aaccgcgaga agaaggaccg gctgtgcgtg gataagacca gcgcgaaagt ggtctgccac 840
aaggacgcga agatcagagt gcaggctcgg gacagatatt acagcagctc ctggtccgac 900
tgggcctccg tgtcctgttc cggcggagga ggatccggag gagggggttc cggtggaggc 960
ggttcgaggt ccctgcctac tgctagccct tcccccggga ttttccagtg cctgaaccac 1020
tcccagaact tgctgagggc cgtgtccaac acccttcaaa aggctcggca gaccctggaa 1080
ctgtactcct gcacttccga ggaaattgac cacgaagata tcaccaagga caagacttcc 1140
accgtggagg cctgtctgcc cctggaactt actatgaacg agtcatgcct cgcaagccgc 1200
gagattagcc tgattaccaa cggctcctgc ctggcttcgg ggaaggcgtc gttcatgacc 1260
gtgctctgcc tgtcaagcat ctacgaggac ctgaaaatgt accagatgga attcaaggcc 1320
atgaacgcca agctcctgat ggacccgaag aggcagatct tcctggacca aaacatgctg 1380
actgccattg acgaactgct tcaggcactc aacttcaact ctgtgaccgt gccgcagaag 1440
tcatcgttgg aggaaccaga tttctacaag accaagatta agctttgcat tctcctccat 1500
gcgtttcgca tccgcgccgt gaccatcgac aggatgatgt cctacctgaa ttcaagcgga 1560
ggaggcggag aaggaggcgg tggaagcgaa gagggcggtg gaggcagtga agaaggaggg 1620
ggcggatctg aagaaggggg cggtggatca gaagagggag ggggaggctc agaggaagga 1680
ggtggcggtt ccgaggaagg gggtggcgga tcagaggagg gaggcggagg atcggaggaa 1740
ggcggaggtg gacaccacca ccatcatcac 1770

<210> SEQ ID NO 119
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Gly Gly Gly Ser Gly Gly Gly Gly Ser Glu Glu Ser Glu Glu Ser
1               5                   10                  15

Glu Glu Ser Glu Glu Gly Gly Gly Gly Ser
            20                  25
```

<210> SEQ ID NO 120
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Gly Gly Gly Gly Ser Gly Gly Gly Gly Ser Gly Gly Gly Gly Ser Gly
1               5                   10                  15

Gly Gly Gly Ser Glu Glu Gly Gly Gly Gly Ser Glu Glu Gly Gly Gly
            20                  25                  30

Gly Ser Glu Glu Gly Gly Gly Gly Ser Glu Glu Gly Gly Gly Gly Ser
        35                  40                  45
```

<210> SEQ ID NO 121
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Gly Gly Gly Gly Ser Phe Gln Ser Glu Glu Gln Gln Gly Gly Gly Ser
1               5                   10                  15

Gly Gly Ser Glu Glu Gly Gly Met Glu Ser Glu Glu Ser Asn Gly Gly
            20                  25                  30

Gly Ser Gly Gly Ser Glu Glu Gly Gly Gly Gly Ser His His His His
        35                  40                  45

His His
    50
```

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Gly Gly Gly Gly Glu Gly Gly Gly Gly
1               5
```

<210> SEQ ID NO 123
<211> LENGTH: 9
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 123

Gly Gly Gly Gly Ser Gly Gly Gly Gly
1 5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 124

Ser Xaa Gln Xaa Xaa Asp Glu Glu
1 5

<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Ser Glu Glu Glu
1

<210> SEQ ID NO 126
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Ser Glu Glu Ala
1

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Ser Glu Glu Gln
1

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Gly Gly Gly Ser Gly Gly Gly Gly
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Gly Gly Gly Glu Gly Gly Gly Gly
1               5

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Gly Gly Gly Gly
1

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Gly Gly Gly Gly Ser
1               5

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Gly Gly Gly Gly His His His His His His
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Gly Gly Gly Gly Ser His His His His His His
1               5                   10

<210> SEQ ID NO 134

<211> LENGTH: 50
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: SITE
<222> LOCATION: (1)..(50)
<223> OTHER INFORMATION: This sequence may encompass 1-10 "Gly Gly Gly
Gly Ser" repeating units

<400> SEQUENCE: 134

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

```
Gly Gly Gly Gly Ser Gly Gly Gly Gly Ser
1               5                   10
```

<210> SEQ ID NO 136
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 137
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 138

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 139
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 139

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser
35

<210> SEQ ID NO 140
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 140

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser
35 40

<210> SEQ ID NO 141
<211> LENGTH: 45
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser
35 40 45

<210> SEQ ID NO 142
<211> LENGTH: 50
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 142

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Gly Ser Lys Asp Glu Leu
1               5


<210> SEQ ID NO 144
<211> LENGTH: 4
<212> TYPE: PRT
<213> ORGANISM: Unknown
<220> FEATURE:
<223> OTHER INFORMATION: Description of Unknown: "KDEL" motif
      peptide sequence

<400> SEQUENCE: 144

Lys Asp Glu Leu
1
```

FUSION POLYPEPTIDES COMPRISING INTERLEUKIN 12 AND A METAL-HYDROXIDE BINDING POLYPEPTIDE

CROSS REFERENCE TO RELATED APPLICATIONS

This application claims priority to and the benefit of U.S. Provisional Patent Application No. 63/184,620, filed May 5, 2021, the entirety of which is incorporated herein by reference.

SEQUENCE LISTING

The instant application contains a Sequence Listing which has been submitted electronically as a .txt file named "2013762-0012_SL.txt". The .txt file was created on Jul. 8, 2022 and is 394,949 bytes in size. The entire contents of the Sequence Listing are herein incorporated by reference.

BACKGROUND

Immunomodulatory polypeptides engineered to conjugate with metal hydroxides (e.g., aluminum hydroxide) can show increased anti-tumor efficacy when delivered by intratumoral injection relative to unconjugated immunomodulatory polypeptides.

SUMMARY

Various immunomodulatory polypeptides, such as certain cytokines, immune checkpoint modulators, etc., have shown significant promise in the treatment of cancer, but significant challenges remain, including dose-limiting toxicities that have been reported for many of the potent cytokines. See, for example, Milling et al., *Adv. Drug. Deliv. Rec.* 114:79, 2017). Recent work, as described for example, in International Patent Application, WO2020263399 (the "Fusion Protein Filing") has described a particularly interesting approach for addressing such toxicity and/or otherwise improving therapeutic usefulness: fusing the relevant immunomodulatory polypeptide with another polypeptide characterized by an ability to complex with metal hydroxides. Without wishing to be bound by any particular theory, it is proposed that the metal hydroxide can act as a particulate scaffold able to persist at the site of injection for extended periods of time (e.g., days to weeks), and that such complexation (i.e., conjugation of the fusion polypeptide with the metal hydroxide) retains the fusion polypeptide (including its immunomodulatory polypeptide moiety) at the injection site (e.g., intratumoral injection). Accordingly, the immunomodulatory polypeptide persists within the tumor microenvironment enhancing efficacy and systemic exposure is limited, reducing toxicity.

The Fusion Protein Filing specifically demonstrated that polypeptides amenable to phosphorylation can adsorb to alum much more strongly when in their phosphorylated form (i.e., where phosphate groups have replaced hydroxyl groups). Various alum-binding peptides ("ABPs") were developed that included phosphorylation sites for the Fam20C kinase and that could be fused with other polypeptides (e.g., immunomodulatory polypeptides). Fusion polypeptides were generated, in which an alum-binding polypeptide was linked to the N- or C-terminus of an immunomodulatory polypeptide, typically by way of a linker. The extent of phosphorylation of these fusion polypeptides was assessed when expressed alone or in combination with Fam20C kinase, and the phosphorylated polypeptides were characterized for their absorption to and release from alum in the presence of serum. Moreover, intratumoral persistence of fusion polypeptides complexed with alum was determined after intratumoral injection.

Fusion polypeptides with greater phosphorylation tended to be retained longer on alum in serum conditions. Of the ABPs analyzed, the polypeptide, GGGGSFQSE-EQQGGGSGGSEEGGMESEESNGGGSGG-SEEGGGGSHHHHHH, referred to as ABP10, demonstrated the highest phosphorylation, with an increase of phosphorylation of approximately 4- to 6-fold when the protein was expressed with a wild-type (WT) kinase (e.g., WT Fam20C kinase), compared to when the protein was expressed with a mutant kinase (e.g., mutant Fam20C kinase). ABP10 consists of four SXE motifs, a prevalent phosphorylation site motif, separated by short spacer sequences. The Fusion Protein Filing demonstrated that immunomodulatory polypeptides (e.g., interleukin-2 and interleukin-12) linked to ABP10 showed improved survival in a mouse model of melanoma compared to the immunomodulatory polypeptides without ABP10.

We have surprisingly found that improved metal-hydroxide binding polypeptides, and improved fusion polypeptides including them, can be developed. Among other things, we have developed metal-hydroxide binding polypeptides characterized by enhanced metal hydroxide (e.g., alum) retention relative to an appropriate reference (e.g., to ABP10). Alternatively or additionally, provided metal-hydroxide binding polypeptides are characterized by improved efficacy, as compared to an appropriate reference (e.g., to ABP10), when administered to a subject with a tumor.

Among other things, the present disclosure provides particularly useful fusion polypeptides (FIG. 1). Furthermore, the present disclosure demonstrates effectiveness of the fusion polypeptides in treating a subject with a tumor; in some embodiments, effectiveness is demonstrated as monotherapy. Alternatively or additionally, in some embodiments, effectiveness is demonstrated in combination, for example, with immune-modulator therapy, chemotherapeutic agent, or surgical resection.

Among other things, the present disclosure provides certain technologies for production of provided fusion polypeptides and/or compositions that comprise them. In some embodiments, provided technologies achieve reproducible production of fusion peptide preparations, including specifically phosphorylated preparations. In some embodiments, provided technologies may include, for example, expression, purification, and/or analytical technologies. Moreover, the present disclosure provides desirable preparations of provided fusion polypeptides, including in some embodiments phosphorylated preparations and/or in some embodiments, preparations of fusion polypeptides (e.g., phosphorylated fusion polypeptides) complexed with a metal hydroxide.

Thus, among other things, the present disclosure identifies the source of a problem with certain metal-hydroxide binding polypeptides and/or fusion polypeptides that include them. For example, the present disclosure appreciates that manufacturing challenges can be associated with certain such polypeptides and/or fusions. Without wishing to be bound by any particular theory, the present disclosure notes that secondary phosphorylation on the polypeptide may contribute to and/or be responsible for certain such manufacturing challenges. Among other things, the present disclosure provides metal-hydroxide-binding polypeptides, and fusion polypeptides that include them, which demonstrate high levels of adsorption to metal hydroxides and also desirable manufacturing characteristics (e.g., one or more of reproducibility, consistency, reduced immunogenicity, etc.).

In one aspect, the present disclosure provides fusion polypeptides comprising: (a) an immunomodulatory polypeptide that comprises an immune agonist moiety; and (b) a metal-hydroxide binding polypeptide whose amino acid sequence includes a plurality of phosphorylation sites, so that it can adopt phosphorylated and unphosphorylated forms. In some embodiments, the fusion polypeptides, when exposed to a metal-hydroxide forms a complex therewith. In some embodiments, the metal hydroxide is aluminum hydroxide. In some embodiments, the complex forms more readily when the metal-hydroxide-binding polypeptide is in a phosphorylated form than when it is in an unphosphorylated form.

In some embodiments, one or more of the phosphorylation sites is targeted by a Fam20C kinase. In some embodiments, the phosphorylation site is or comprises an S-X-E motif. In some embodiments, the plurality of phosphorylation sites comprises more than 4 S-X-E motifs. In some embodiments, the plurality of phosphorylation sites comprises 8 S-X-E motifs.

In some embodiments, at least two adjacent S-X-E motifs are separated by a spacer. In some embodiments, the spacer comprises at least one glycine residue. In some embodiments, the spacer comprises a plurality of glycine residues. In some embodiments, the spacer comprises at least four glycine residues. In some embodiments, the spacer has a sequence that comprises four glycine residues. In some embodiments, each SXE motif is separated from each adjacent S-X-E motif by a spacer.

In one aspect, the present disclosure provides method of treating a subject with a tumor, the method comprising a step of: treating the subject with a complex comprising: (a) fusion polypeptide comprising: (i) an immunomodulatory polypeptide that comprises an immune agonist moiety; and (ii) a metal-hydroxide binding peptide; and, (b) a metal hydroxide. In some embodiments, (a) and (b) are formulated together. In some embodiments, (a) and (b) are mixed prior to administration.

In some embodiments, the complex is administered by intratumoral injection. In some embodiments, the complex is administered by peritumoral injection. In some embodiments, the complex is administered to a tumor-draining lymph node or lymph nodes.

In some embodiments, the complex is administered in combination with a second therapeutic. In some embodiments, the second therapeutic is radiation. In some embodiments, the second therapeutic is surgical tumor resection. In some embodiments, the fusion polypeptide is administered prior to surgical tumor resection. In some embodiments, the second therapeutic is a chemotherapy. In some embodiments, the second therapeutic is an anti-tumor antibody. In some embodiments, the second therapeutic is a targeted therapy (e.g., BRAF inhibitor, MEK inhibitor, etc.). In some embodiments, the second therapeutic is an immune modulator. In some embodiments, the immune modulator is a checkpoint inhibitor. In some embodiments, the checkpoint inhibitor is an antibody or a functional fragment thereof. In some embodiments, the antibody targets one or more of PD-1, PD-L1, CTLA-4, TIM3, TIGIT, and LAG3. In some embodiments, the antibody targets PD-1. In some embodiments, the antibody is a tumor-targeting CD3 bispecific antibody. In some embodiments, the immune modulator is a cell therapy. In some embodiments, the cell therapy is selected from the group consisting of: CAR-T cells, ex-vivo expanded TILs, and NK cells.

In one aspect, the present disclosure provides methods of treating a subject with a tumor comprising administering a fusion polypeptide comprising: (a) an immunomodulatory polypeptide that comprises an immune agonist moiety; and (b) a metal-hydroxide binding peptide, wherein the fusion polypeptide is formulated with a metal hydroxide; and wherein the subject has received or is receiving therapy with at least one additional therapeutic. In some embodiments, the fusion polypeptide and metal-hydroxide are formulated together, forming a complex. In some embodiments, the fusion polypeptide and metal-hydroxide are mixed prior to administration.

In some embodiments, the fusion polypeptide is administered by intratumoral injection. In some embodiments, the fusion polypeptide is administered by peritumoral injection. In some embodiments, the fusion polypeptide is administered to a tumor-draining lymph node or lymph nodes.

In some embodiments, the at least one additional therapeutic is radiation. In some embodiments, the at least one additional therapeutic is surgical tumor resection. In some embodiments, the fusion polypeptide is administered prior to surgical tumor resection. In some embodiments, the at least one additional therapeutic is a chemotherapy. In some embodiments, the at least one additional therapeutic is an anti-tumor antibody. In some embodiments, the second therapeutic is an immune modulator. In some embodiments, the immune modulator is a checkpoint inhibitor. In some embodiments, a checkpoint inhibitor inhibits MEK. In some embodiments, the checkpoint inhibitor is an antibody or a functional fragment thereof. In some embodiments, the antibody targets one or more of PD-1, PD-L1, CTLA-4, TIM3, TIGIT, and LAG3. In some embodiments, the antibody targets PD-1. In some embodiments, the antibody is a tumor-targeting CD3 bispecific antibody. In some embodiments, the immune modulator is a cell therapy. In some embodiments, the cell therapy is selected from the group consisting of: CAR-T cells, ex-vivo expanded TILs, and NK cells.

In some embodiments, the immune agonist moiety of a fusion polypeptide disclosed herein comprises a first moiety or a functional fragment thereof. In some embodiments, the functional fragment is signaling competent. In some embodiments, the first moiety comprises an IL12 moiety or a functional fragment thereof. In some embodiments, the IL12 moiety comprises IL12B or a functional fragment thereof.

In some embodiments, the immune agonist moiety of a fusion polypeptide disclosed herein comprises a first and a second moiety or a functional fragment thereof. In some embodiments, the first moiety comprises an IL12 moiety or a functional fragment thereof. In some embodiments, the IL12 moiety comprises IL12B or a functional fragment thereof. In some embodiments, the second moiety comprises an IL12 moiety or a functional fragment thereof. In some embodiments, the second IL12 moiety comprises IL12A or a functional fragment thereof. In some embodiments, the first and second moieties or functional fragments thereof are linked via a first linker. In some embodiments, the first linker comprises a polypeptide. In some embodiments, the polypeptide comprises a $(G_4S)_3$ linker.

In some embodiments, an immunomodulatory polypeptide of a fusion polypeptide disclosed herein and a metal-hydroxide binding polypeptide are linked via a second linker. In some embodiments, the second linker comprises a polypeptide. In some embodiments, the polypeptide comprises the amino acid sequence, GGGGEGGGG. In some embodiments, the polypeptide comprises the amino acid sequence, GGGGSGGGG. In some embodiments, the metal-hydroxide binding polypeptide is linked directly to the c-terminus of the immunomodulatory polypeptide. In some embodiments, the metal-hydroxide binding polypeptide is linked via a second linker to the c-terminus of the immunomodulatory polypeptide.

In some embodiments, the present disclosure provides a method of manufacturing a phosphorylated form of fusion polypeptides disclosed herein by contacting the fusion polypeptide with a kinase. In some embodiments, contacting comprises co-expressing the fusion polypeptide and a kinase. In some embodiments, the fusion polypeptide and kinase are co-expressed at a ratio of 2:1 to 100:1. In some embodiments, the ratio is 4:1. In some embodiments, the 4:1 ratio is achieved using two separate plasmids to express the fusion polypeptide and the kinase. In some embodiments, the two separate plasmids comprise promoters of differing strength to produce the ratio of 4:1. In some embodiments, the ratio is 8:1. In some embodiments, the 8:1 ratio is achieved using a single vector with two promoters to express the fusion polypeptide and the kinase. In some embodiments, the kinase is Fam20C.

In some embodiments, the step of co-expressing comprises expressing from promoters established to direct expression at the ratio. In some embodiments, the step of co-expressing comprises expressing from a bi-cistronic construct.

In some embodiments, the method further comprises a step of purifying the phosphorylated form. In some embodiments, the step of purifying comprises affinity chromatography.

In some embodiments, the fusion polypeptide is exposed to a metal-hydroxide to form a complex therewith. In some embodiments, the complex is prepared prior to administering to a subject. In some embodiments, a fusion polypeptide of the present disclosure is manufactured by contacting a phosphorylated form of a fusion polypeptide with a metal hydroxide.

In some embodiments, a complex comprises a fusion polypeptide of the present disclosure and a metal hydroxide. In some embodiments, the complex comprises an average of 2-8 phosphates per fusion polypeptide. In some embodiments, the complex is characterized as having greater than 95% metal hydroxide retention. In some embodiments, the complex comprises a ratio of 1:1 to 1:20 by mass of fusion polypeptide to metal hydroxide, e.g., as defined by metal mass. In some embodiments, the ratio is 1:5 to 1:20 by mass of fusion polypeptide to metal hydroxide, e.g., as defined by metal mass. In some embodiments, the ratio is 1:10 by mass of fusion polypeptide to metal hydroxide, e.g., as defined by metal mass. In some embodiments, the ratio is 1:5 by mass of fusion polypeptide to metal hydroxide, e.g., as defined by metal mass.

In some embodiments, the present disclosure provides a pharmaceutical composition comprising a fusion polypeptide as disclosed herein. In some embodiments, a pharmaceutical composition is formulated as a fusion polypeptide metal-hydroxide complex.

In some embodiments, the present disclosure provides methods of characterizing a preparation of a fusion polypeptide of the present disclosure by assessing degree of phosphorylation. In some embodiments, the degree of phosphorylation is assessed by determining the number of phosphates per protein. In some embodiments, the number of phosphates per protein is determined using a colorimetric assay. In some embodiments, the colorimetric assay is a malachite green assay.

In some embodiments, the present disclosure provides methods of characterizing a preparation of a fusion polypeptide of the present disclosure by assessing heterogeneity of the preparation. In some embodiments, heterogeneity of the preparation is assessed using analytical ion exchange.

In some embodiments, the present disclosure provides methods of characterizing a preparation of a fusion polypeptide of the present disclosure by assessing retention of the fusion polypeptide on the metal hydroxide. In some embodiments, retention is assessed using an in vitro retention assay.

In some embodiments, the present disclosure provides methods of characterizing a fusion polypeptide of the present disclosure by assessing signaling activity of the fusion polypeptide. In some embodiments, the signaling activity is assessed in vitro. In some embodiments, in vitro assessment utilizes a reporter assay.

In some embodiments, the present disclosure provides methods of characterizing a fusion polypeptide of the present disclosure by assessing purity of the preparation.

In some embodiments, the present disclosure provides methods of characterizing a fusion polypeptide of the present disclosure by assessing phosphate content. In some embodiments, assessing phosphate content comprises use of a malachite green assay. In some embodiments, assessing phosphate content comprises use of a high performance liquid chromatography assay. In some embodiments, high performance liquid chromatography assay utilizes a SAX-10 column.

In some embodiments, the present disclosure provides methods of characterizing a fusion polypeptide of the present disclosure by assessing potency of the preparation. In some embodiments, potency is characterized by assessing immune moiety signaling. In some embodiments, immune moiety signaling is determined using a reporter assay. In some embodiments, potency is characterized by assessing IL12 signaling. In some embodiments, IL12 signaling is determined using a reporter assay.

In some embodiments, the present disclosure provides methods of characterizing a complex as disclosed herein comprising assessing retention of a fusion polypeptide of the present disclosure to the metal hydroxide. In some embodiments, assessing retention comprises use of a metal hydroxide retention assay.

In some embodiments, the present disclosure provides a method of characterizing a pharmaceutical composition as described herein comprising assessing one or more of: (a) the purity of the preparation; (b) phosphate content; (c) potency of the pharmaceutical composition; (d) retention of the fusion polypeptide to the metal hydroxide; (e) efficacy of treating a subject having a tumor; and (0 combination with a second therapeutic agent

BRIEF DESCRIPTION OF THE DRAWING

FIGS. 3A-C provide assessment of phosphorylation levels using a malachite green assay for exemplary human and mouse IL-12 constructs with various metal-hydroxide binding polypeptides (e.g., alum binding polypeptides). FIG. 3A shows an exemplary graph illustrating that hIL12-ABP and mIL12-ABP polypeptides co-expressed with Fam20C (denoted as "-K") had significantly higher phosphate levels compared to polypeptides without Fam20C co-expression or wild-type hIL12 or mIL12 lacking the ABP co-expressed with Fam20C. FIG. 3B shows an exemplary graph illustrating results from mouse IL12-ABP variants that were expressed at 1 L scale in transient HEK with Fam20C co-expression and purified by sequential Ni-NTA and SEC chromatography. In the malachite green assay, mIL12-ABP10 again had the highest phosphorylation followed in order by ABP20-G4-G520, ABP20-G4, and ABP20. FIG. 3C provides exemplary metal-hydroxide binding polypeptide sequences.

FIG. 4A shows an exemplary graph of tumor volume in mice treated with vehicle or PD-1 only. FIG. 4B shows an exemplary graph of tumor volume in mice treated with vehicle or an mIL12 and PD-1 combination treatment. FIG. 4C shows an exemplary graph of tumor volume in mice treated with vehicle or an mIL12/alum and PD-1 combination treatment. FIG. 4D shows an exemplary graph of tumor volume in mice treated with vehicle or an mIL12-ABP10-k/alum and PD-1 combination treatment. FIG. 4E shows an exemplary graph of tumor volume in mice treated with vehicle or an mIL12-ABP20-K/alum and PD-1 combination treatment. FIG. 4F shows an exemplary graph of tumor volume in mice treated with vehicle or an mIL12-ABP20-G4-K/alum and PD-1 combination treatment. FIG. 4G shows an exemplary graph of tumor volume in mice treated with vehicle or an mIL12-ABP20-G4-G520-K/alum and PD-1 combination treatment.

FIG. 5 shows exemplary ABP sequences.

FIG. 7A shows results for mIL12-ABP10. FIG. 7B shows results for mIL12-ABP20-G4-6x-GE. FIG. 7C shows results for mIL12-ABP20-G4-8x-GE.

FIGS. 10A-10C provide exemplary assessment of enriched pools of fusion polypeptide. Enriched pools of mIL12-ABP10 (FIG. 10A) and mIL12-ABP20-G4-8x-GE (FIG. 10B) after preparative anion exchange chromatography were compared to the original material by analytical ion exchange chromatography. Elution times for (mIL12-ABP10) and (mIL12-ABP20-G4-8x-GE) are summarized in (FIG. 10C).

FIG. 11A shows ion-exchange enriched mIL12-ABP10 and mIL12-ABP20-G4-8x-GE assessed in an alum retention assay along with a sample of mIL12-ABP20-G4-8x-GE prior to ion-exchange polishing. Polypeptides were complexed with a 10-fold mass excess of aluminum hydroxide as defined by metal mass then diluted in elution buffer containing 5 mM phosphate and 20% mouse serum for 24 hours before quantifying free polypeptide in the supernatant. Ion exchange purified mIL12-ABP20-G4-8x-GE had the highest retention with 89% bound to alum at 24 hours compared to 86% for mIL12-ABP10 and 78% for the non-ion exchanged material demonstrating that the low phosphate fractions elute off the alum faster. FIG. 11B shows that samples were bound to a 10-fold mass excess of aluminum hydroxide as defined by metal mass then eluted with 5 mM phosphate and 20% mouse serum for up to 48 hours. Ion exchange purified mIL12-ABP20-G4-8x-GE again had the highest retention with 82% bound to alum at 48 hours compared to 78% for mIL12-ABP10 and 17% for unmodified mIL12.

FIG. 12A shows that mIL12-ABP10 was active in the assay with an EC50 value of 3.6 ng/mL compared to control, mIL12, with an EC50 value of 3.5 ng/mL. When bound to alum the EC50 values shifted ~2-4 fold with EC50 values of 8 ng/mL for mIL12-ABP10. FIG. 12B shows that mIL12-ABP20-G4-8x-GE was active in the assay with an EC50 value of 5.4 ng/mL, identical to control, mIL12, with an EC50 value of 5.4 ng/mL. When bound to alum the EC50 values shifted ~2-4 fold with EC50 value of 22 ng/mL for mIL12-ABP20-G4-8x-GE.

FIG. 14A shows an exemplary graph illustrating that a single intratumoral injection of 5 μg of either mIL12-ABP or mIL12-ABP20-G4-8x-GE fusion polypeptides complexed with 50 μg alum on Day 6 post tumor inoculation led to increased survival compared to vehicle treated animals. FIGS. 14B and 14C show exemplary graphs illustrating that a single intratumoral injection of 5 μg of either mIL12-ABP or mIL12-ABP20-G4-8x-GE fusion polypeptides complexed with 50 μg alum on Day 6 post tumor inoculation led to significant tumor delays and regressions compared to vehicle treated mice. Complete responses with no measurable tumor were observed in 4/10 mice treated with mIL12-ABP10+alum and 5/10 mice treated with mIL12-ABP20-G4-8x-GE+alum.

FIG. 15A shows an exemplary graph of percent survival over time. FIG. 15B shows an exemplary graph of tumor volume over time in animals treated with mIL12-ABP10-K/alum compared to vehicle. FIG. 15C shows an exemplary graph of tumor volume over time in animals treated with mIL12-ABP20-G4-8x-GE/alum compared to vehicle. FIG. 15D shows an exemplary graph of tumor volume over time in animals treated with mIL12-ABP10-K/alum and anti-PD-1 antibody compared to treatment with anti-PD-1 antibody alone. FIG. 15E shows an exemplary graph of tumor volume over time in animals treated with mIL12-ABP20-G4-8x-GE-K/alum and anti-PD-1 antibody compared to treatment with anti-PD-1 antibody alone.

FIG. 16A shows an exemplary graph illustrating that mIL12-ABP20-G4-8x-GE/alum treatment led to growth delay of the primary tumor compared to vehicle treatment. FIG. 16B shows an exemplary graph illustrating results from animals that were sacrificed on Day 28 and metastases were counted in the lung. 10/10 vehicle treated mice had at least one lung metastasis, while 6/10 of the mice in the mIL12-ABP20-G4-8x-GE/alum treated mice were metastases-free.

FIG. 17A and FIG. 17B provide exemplary results from purification of fusion polypeptide metal-hydroxide complex, mIL12-ABP20-G4-8x-GE to isolate fractions with different phosphorylation levels. FIG. 17A show exemplary results for a fusion polypeptide that was purified by Ni-NTA chromatography and size exclusion chromatography, then run on a HiTrap Q Sepharose anion exchange column with a linear salt elution gradient. FIG. 17B shows exemplary results from when individual elution fractions were collected and phosphate levels were measured by malachite green assay. Average phosphate levels per fraction ranged from 2 to 7 phosphate groups per fusion polypeptide. No Fam20C was utilized as a negative control. A pool of fractions 112-118 was utilized as a positive control.

In FIG. 18A free protein in supernatant over time quantified by ELISA was compared to theoretical concentration of 12,500 ng/mL if all protein was eluted.

FIG. 18B shows exemplary results illustrating that fraction 110 with 2.4 phosphates per polypeptide had <50% polypeptide retained on alum at 24 hours and fraction 111 with 3.7 phosphates per polypeptide had ~80% polypeptide retained on alum. Fractions 112 and 113 with 4.6 and 5.8 phosphates per polypeptide respectively were highly retained with >95% bound to alum at 24 hours. Fractions 114-117 with >6 phosphates per polypeptide had no measurable free polypeptide eluting off alum in the assay.

FIG. 19A and FIG. 19B illustrate that fractions 110 and 112 had similar peak activity levels with or without alum and 2-3 fold shifts in EC50 when bound to alum. FIG. 19C and FIG. 19D illustrate that fractions 114 and 117 had reduced peak activity when complexed with alum.

FIG. 20 summarizes phosphorylation levels, alum retention, and signaling competency of individual fractions of exemplary fusion polypeptide, mIL12-ABP20-G4-8x.

FIG. 21A shows an exemplary graph illustrating that human IL12-ABP20-G4-8x-GE is active in the HEK-Blue-IL12 assay with an EC50 of 3.6 ng/mL alone or 8.2 ng/mL when complexed with aluminum hydroxide. FIG. 21B shows an exemplary graph illustrating that, following incubation of the polypeptide/alum complex in elution buffer containing 1 mM phosphate and 20% mouse serum, the supernatant EC50 shifts>300-fold suggesting minimal polypeptide elution after 24 hours, while the pellet maintained activity with a 5×EC50 shift. FIG. 21C shows an exemplary graph illustrating that in a separate alum retention assay, hIL12 or hIL12-ABP was bound to a 10-fold mass excess of aluminum hydroxide as defined by metal mass then diluted in elution buffer containing 1 mM phosphate and 20% mouse serum with free polypeptide detected by ELISA. Approximately 80% of the hIL12-ABP20-G4-8x-GE was retained on the alum at 24 hours compared to 0% for unmodified IL12.

FIG. 22 presents exemplary results of an assessment of an exemplary human IL12-ABP20-G4-8x-GE protein. Human IL12-ABP20-G4-8x-GE was separated by anion exchange chromatography and selected purification fractions were assessed for numbers of phosphate per protein using a malachite green assay, IL12 signaling potency using the HEK-Blue-IL12 assay, and aluminum hydroxide binding using an alum retention assay.

FIG. 25 presents results of assessment of an exemplary canine-IL12-ABP20-G4-8x-GE. Canine-IL12-ABP20-G4-8x-GE was co-transfected in suspension HEK-293 cells with a human Fam20C-KDEL plasmid at a 4:1 mass ratio. Supernatants were harvested and canine-IL12-ABP20-G4-8x-GE was purified. Selected purification fractions were assessed for numbers of phosphate per protein using a malachite green assay, IL12 signaling potency using the HEK-Blue-IL12 assay, and aluminum hydroxide binding using an alum retention assay.

DEFINITIONS

Figure 1:
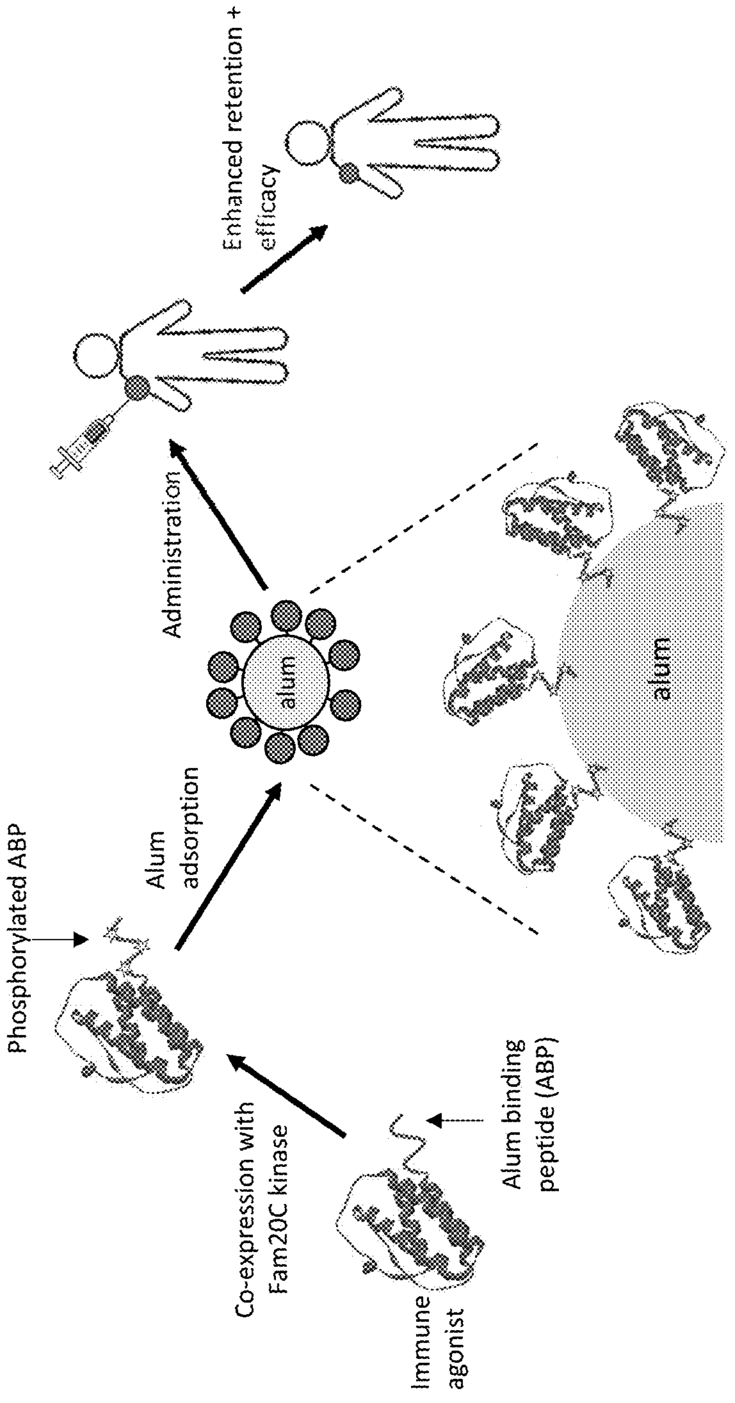
FIG. 1 provides an exemplary schematic of fusion polypeptide metal-hydroxide complexes of the present disclosure. Fusion polypeptide metal-hydroxide complexes can be administered to a subject and result in enhanced retention and/or efficacy compared to an appropriate reference standard.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be systemic or local. In some embodiments, administration may be enteral or parenteral. In some embodiments, administration may be by injection (e.g., intramuscular, intratumoral, intravenous, or subcutaneous injection). In some embodiments, injection may involve bolus injection, drip, perfusion, or infusion. In many embodiments, administration in accordance with the present disclosure is by intratumoral injection.

Affinity: As is known in the art, "affinity" is a measure of the tightness with which two or more binding partners associate with one another. Those skilled in the art are aware of a variety of assays that can be used to assess affinity, and will furthermore be aware of appropriate controls for such assays. In some embodiments, affinity is assessed in a quantitative assay. In some embodiments, affinity is assessed over a plurality of concentrations (e.g., of one binding partner at a time). In some embodiments, affinity is assessed in the presence of one or more potential competitor entities (e.g., that might be present in a relevant—e.g., physiological—setting). In some embodiments, affinity is assessed relative to a reference (e.g., that has a known affinity above a particular threshold [a "positive control" reference] or that has a known affinity below a particular threshold [a "negative control" reference"]. In some embodiments, affinity may be assessed relative to a contemporaneous reference; in some embodiments, affinity may be assessed relative to a historical reference. Typically, when affinity is assessed relative to a reference, it is assessed under comparable conditions.

Agent: In general, the term "agent", as used herein, is used to refer to an entity (e.g., for example, a lipid, metal, nucleic acid, polypeptide, polysaccharide, small molecule, etc, or complex, combination, mixture or system [e.g., cell, tissue, organism] thereof), or phenomenon (e.g., heat, electric current or field, magnetic force or field, etc). In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them.

Agonist: Those skilled in the art will appreciate that the term "agonist" may be used to refer to an agent, condition, or event whose presence, level, degree, type, or form correlates with increased level or activity of another agent (i.e., the agonized agent or the target agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Amino acid: in its broadest sense, as used herein, the term "amino acid" refers to a compound and/or substance that can be, is, or has been incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Animal: as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a horse, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)— an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies, alternative scaffolds or antibody mimetics (e.g., anticalins, FN3 monobodies, DARPins, Affibodies, Affilins, Affimers, Affitins, Alphabodies, Avimers, Fynomers, Im7, VLR, VNAR, Trimab, CrossMab, Trident); nanobodies, binanobodies, F(ab')2, Fab', di-sdFv, single domain antibodies, trifunctional antibodies, diabodies, and minibodies. etc. In some embodiments, relevant formats may be or include: Adnectins®; Affibodies®; Affilins®; Anticalins®; Avimers®; BiTE®s; cameloid antibodies; Centyrins®; ankyrin repeat proteins or DARPINs®; dual-affinity re-targeting (DART) agents; Fynomers®; shark single domain antibodies such as IgNAR; immune mobilixing monoclonal T cell receptors against cancer (ImmTACs); KALBITOR®s; MicroProteins; Nanobodies® minibodies; masked antibodies (e.g., Probodies®); Small Modular ImmunoPharmaceuticals ("SMIPs™"); single chain or Tandem diabodies (TandAb®); TCR-like antibodies; Trans-bodies®; TrimerX®; VHHs. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.])

Antibody fragment: As used herein, an "antibody fragment" refers to a portion of an antibody or antibody agent as described herein, and typically refers to a portion that includes an antigen-binding portion or variable region thereof. An antibody fragment may be produced by any means. For example, in some embodiments, an antibody fragment may be enzymatically or chemically produced by fragmentation of an intact antibody or antibody agent. Alternatively, in some embodiments, an antibody fragment may be recombinantly produced (i.e., by expression of an engineered nucleic acid sequence. In some embodiments, an antibody fragment may be wholly or partially synthetically produced. In some embodiments, an antibody fragment (particularly an antigen-binding antibody fragment) may have a length of at least about 50, 60, 70, 80, 90, 100, 110, 120, 130, 140, 150, 160, 170, 180, 190 amino acids or more, in some embodiments at least about 200 amino acids.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently, electrostatically, or otherwise associated with a carrier entity and/or in a biological system or cell). Binding between two entities may be considered "specific" if, under the conditions assessed, the relevant entities are more likely to associate with one another than with other available binding partners.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-SME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent may be one described as utilized in an antibody-drug conjugate as described or discussed in one or more of Govindan et al, TheScientificWorldJOURNAL 10:2070, 2010, -2089). In some embodiments, a chemotherapeutic agent may be or comprise one or more of farnesyl-thiosalicylic acid (FTS), 4-(4-Chloro-2-methylphenoxy)-N-hydroxybutanamide (CMH), estradiol (E2), tetramethoxystilbene (TMS), δ-tocatrienol, salinomycin, or curcumin Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Epitope: as used herein, the term "epitope" refers to a moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, etc); (3) translation of an RNA into a polypeptide or protein; and/or (4) post-translational modification of a polypeptide or protein.

Functional: As used herein, the term "functional" is used to refer to a form or fragment of an entity that exhibits a particular property and/or activity.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the fragment.

Gene: As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., cell-type-specific expression, inducible expression, etc.).

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Genome: As used herein, the term "genome" refers to the total genetic information carried by an individual organism or cell, represented by the complete DNA sequences of its chromosomes.

Host cell: as used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO Kl, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes.

Human: In some embodiments, a human is an embryo, a fetus, an infant, a child, a teenager, an adult, or a senior citizen.

"Improved," "increased" or "reduced": As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Linker: as used herein, is used to refer to that portion of a multi-element agent that connects different elements to one another. For example, those of ordinary skill in the art appreciate that a polypeptide whose structure includes two or more functional or organizational moieties or domains often includes a stretch of amino acids between such moieties or domains that links them to one another. In some embodiments, a polypeptide comprising a linker element has an overall structure of the general form S1-L-S2, wherein S1 and S2 may be the same or different and represent two moieties or domains associated with one another by the linker. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger et al., *Proc. Natl. Acad. Sci. USA* 90:6444, 1993; Poljak et al. *Structure* 2:1121, 1994).

Modulator: The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level Moiety: Those skilled in the art will appreciate that a "moiety" is a defined chemical group or entity with a particular structure and/or or activity, as described herein. Typically, a "moiety" is part of, less than the entirety of, a molecule or entity.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Operably linked: as used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for a particular route of administration, e.g., as described herein.

Pharmaceutically acceptable: As used herein, the phrase "pharmaceutically acceptable" is used to refer to an agent or entity that, within the scope of sound medical judgment, is suitable for use in contact with tissues of human beings and/or animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Polypeptide: As used herein refers to a polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Predetermined: By predetermined is meant deliberately selected, for example as opposed to randomly occurring or achieved.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

Reference standard: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Specific: The term "specific", when used herein with reference to an agent having an activity, is understood by those skilled in the art to mean that the agent discriminates between potential target entities or states. For example, an in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

Specificity: As is known in the art, "specificity" is a measure of the ability of a particular ligand to distinguish its binding partner from other potential binding partners.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Transformation: as used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Treatment: As used herein, the term "treatment" (also "treat" or "treating") refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. Thus, in some embodiments, treatment may be prophylactic; in some embodiments, treatment may be therapeutic.

Tumor: As used herein, the term "tumor" refers to an abnormal growth of cells or tissue. In some embodiments, a tumor may comprise cells that are precancerous (e.g., benign), malignant, pre-metastatic, metastatic, and/or non-metastatic. In some embodiments, a tumor is associated with, or is a manifestation of, a cancer. In some embodiments, a tumor may be a disperse tumor or a liquid tumor. In some embodiments, a tumor may be a solid tumor.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residues as compared to a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition or deletion, and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature. In some embodiments, a reference polypeptide or nucleic acid is a human polypeptide or nucleic acid.

Vector: as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Wild-type: As used herein, the term "wild-type" has its art-understood meaning and refers to a form of an entity (e.g., a polypeptide or nucleic acid) that has a structure and/or activity as found in nature in a "normal" (as contrasted with mutant, diseased, altered) state or context. In some embodiments, more than one "wild type" form of a particular polypeptide or nucleic acid may exist in nature, for example as "alleles" of a particular gene or normal variants of a particular polypeptide. In some embodiments, that form (or those forms) of a particular polypeptide or nucleic acid that is most commonly observed in a population (e.g., in a human population) is the "wild type" form.

DETAILED DESCRIPTION OF CERTAIN EMBODIMENTS

Fusion Polypeptide-Metal Hydroxide Complexes

Figure 2:
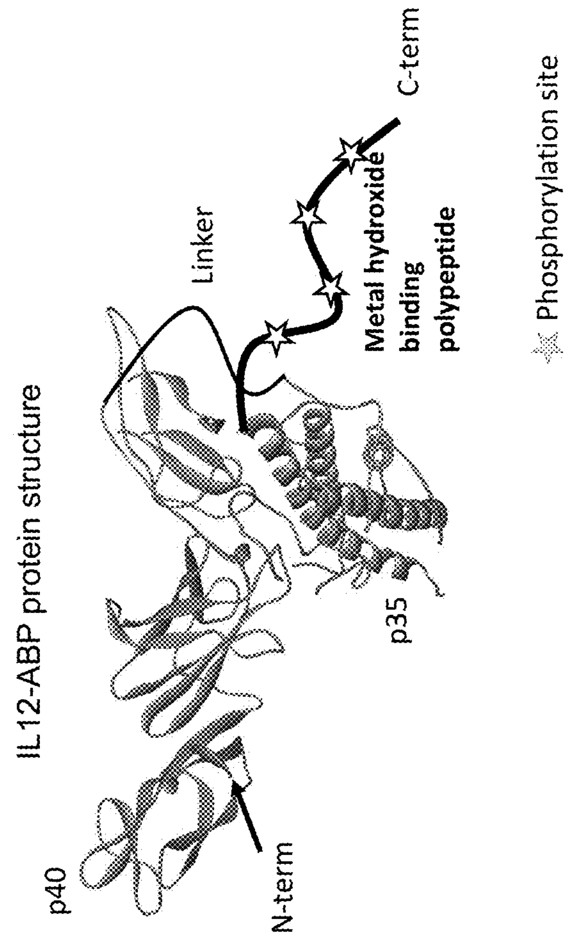
FIG. 2 provides a diagram of an exemplary fusion polypeptide of the present disclosure comprising a first (p40) and second (p35) IL12 immune agonist moieties and a metal-hydroxide binding polypeptide with a plurality of phosphorylation sites.

Immune-modulating therapeutic approaches can be useful in treating a variety of disease states, including cancer. Established immune-modulating therapeutic approaches include, but are not limited to, monoclonal antibodies, T cell therapy, immune checkpoint modulators, and immunomodulatory polypeptides. The present disclosure provides technologies that, among other things, include fusion polypeptides comprising an immunomodulatory polypeptide and a metal-hydroxide-binding polypeptide, as well as technologies to produce and/or utilize such fusion polypeptides (for example, FIG. 2). In some embodiments, provided fusion polypeptides utilize a metal-hydroxide-binding polypeptide that adopts at least first and second states, one of which shows materially higher metal-hydroxide binding (e.g., when included in a fusion polypeptide as described herein) than the other. In some embodiments, such first and second states differ from one another by substitution of one or more hydroxyl moieties (e.g., by phosphorylation).

In some embodiments, provided fusion polypeptides display one or more improved structural or functional characteristics relative to a reference polypeptide as described in the Fusion Protein Filing; in some such embodiments, the reference polypeptide includes ABP10.

Among other things, the present disclosure provides a surprising discovery that improved (e.g., relative to a reference described in the Fusion Protein Filing, which reference may be or comprise ABP10) metal-hydroxide binding polypeptides can be developed. For example, in some embodiments, the present disclosure provides metal-hydroxide binding polypeptides characterized by enhanced metal hydroxide (e.g., alum) conjugation (e.g., enhanced rate and/or extent of association and/or decreased rate and/or extent of release) relative to such appropriate reference (e.g., alone and/or when included in a fusion polypeptide, for example as described and/or exemplified herein). Alternatively or additionally, in some embodiments, provided metal-hydroxide binding polypeptides are characterized by improved intratumoral retention (e.g., after intratumoral injection) efficacy, as compared to such appropriate reference (e.g., alone and/or when included in a fusion polypeptide, for example as described and/or exemplified herein).

In some embodiments, a fusion polypeptide in accordance with the present disclosure is characterized by improved tumor retention and/or efficacy as compared with an appropriate comparable reference fusion polypeptide that includes ABP10.

In some embodiments, the present disclosure provides technologies for developing, providing, and/or utilizing improved metal-hydroxide binding polypeptides and/or fusion polypeptides that include them; in some embodiments, improvement comprises and/or involves optimizing phosphate content (e.g., of a metal-hydroxide-binding polypeptide and/or of a fusion polypeptide that comprises it).

Among other things, the present disclosure surprisingly teaches that certain metal-hydroxide-binding polypeptides, and/or one or more fusion polypeptides that include them, are characterized by one or more in improved manufacturing features (e.g., are amenable to more facile and/or reproducible manufacturing).

Among other things, the present disclosure provides particularly useful fusion polypeptides. Furthermore, the present disclosure demonstrates effectiveness of provided fusion polypeptides in treating a subject with a tumor. Still further, the present disclosure surprisingly teaches that, in some embodiments, a particular fusion polypeptide is useful as a monotherapy and/or that, in some embodiments, a particular fusion polypeptide is particularly useful in combination therapy (e.g., in combination with an immune modulator such as an immune checkpoint inhibitor such as, for example, an anti-PD-1 agent such as an anti-PD-1 antibody.

Alternatively or additionally, in some embodiments, the present disclosure provides certain technologies for production and/or characterization of provided fusion polypeptides, compositions that comprise them, and/or components within them (e.g., immunomodulatory polypeptides, metal-hydroxide-binding polypeptides, linkers, etc).

In some embodiments, provided technologies achieve reproducible production of fusion peptide preparations, specifically including phosphorylated preparations and/or metal-hydroxide-complexed preparations. In some embodiments, provided technologies may include, for example, expression, purification, and/or analytical technologies. Moreover, in some embodiments, the present disclosure provides desirable preparations of provided fusion polypeptides, including in some embodiments phosphorylated preparations and/or in some embodiments, preparations of fusion polypeptides (e.g., phosphorylated fusion polypeptides) complexed with a metal hydroxide.

Table 1 provides exemplary amino acid sequences of polypeptides described herein.

TABLE 1

Exemplary Amino Acid Sequences

| SEQ ID NO: | Polypeptide | Sequence |
|---|---|---|
| 1 | Mouse IL12B | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRS |
| 2 | Mouse IL12A | RVIPVSGPARCLSQSRNLLKTTDDMVKTAREKLKHYSCTAED<br>IDHEDITRDQTSTLKTCLPLELHKNESCLATRETSSTTRGSCLP<br>PQKTSLMMTLCLGSIYEDLKMYQTEFQAINAALQNHNHQQII<br>LDKGMLVAIDELMQSLNHNGETLRQKPPVGEADPYRVKMKL<br>CILLHAFSTRVVTINRVMGYLSSA |
| 3 | (G4S)3 Linker | GGGGSGGGGSGGGGS |
| 4 | Mouse IL12 (IL12B-linker-IL12A) | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSA |
| 5 | mIL12-His (no ABP) | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSAGGGGSHHHHHH |
| 6 | mIL12-ABP10 | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSAGGGGSFQSEEQQGGGSGGSEEGGMES<br>EESNGGGSGGSEEGGGGSHHHHHH |
| 7 | mIL12-ABP20 | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS |

TABLE 1-continued

| SEQ ID NO: | Polypeptide | Sequence |
|---|---|---|
| Exemplary Amino Acid Sequences | | |
| | | TRVVTINRVMGYLSSAGGGGSGGGGSEESEESEESEEGGGGS<br>HHHHHH |
| 8 | mIL12-ABP20-G4 | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSAGGGGSGGGGSEEGGGGSEEGGGGSE<br>EGGGGSEEGGGGSHHHHHH |
| 9 | mIL12-ABP20-G4-GS20 | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSAGGGGSGGGGSGGGGSGGGGSEEGGG<br>GSEEGGGGSEEGGGGSEEGGGGSHHHHHH |
| 10 | mIL12-ABP20-G4-6x | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSAGGGGSGGGGSEEGGGGSEEGGGGSE<br>EGGGGSEEGGGGSEEGGGGSEEGGGGSHHHHHH |
| 11 | mIL12-ABP20-G4-8x | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM<br>MTLCLGSIYEDLKMYQTEFQAINAALQNHNHQQIILDKGMLV<br>AIDELMQSLNHNGETLRQKPPVGEADPYRVKMKLCILLHAFS<br>TRVVTINRVMGYLSSAGGGGSGGGGSEEGGGGSEEGGGGSE<br>EGGGGSEEGGGGSEEGGGGSEEGGGGSEEGGGGSEEGGGGS<br>HHHHHH |
| 12 | mIL12-ABP20-6x | MWELEKDVYVVEVDWTPDAPGETVNLTCDTPEEDDITWTSD<br>QRHGVIGSGKTLTITVKEFLDAGQYTCHKGGETLSHSHLLLH<br>KKENGIWSTEILKNFKNKTFLKCEAPNYSGRFTCSWLVQRNM<br>DLKFNIKSSSSSPDSRAVTCGMASLSAEKVTLDQRDYEKYSVS<br>CQEDVTCPTAEETLPIELALEARQQNKYENYSTSFFIRDIIKPDP<br>PKNLQMKPLKNSQVEVSWEYPDSWSTPHSYFSLKFFVRIQRK<br>KEKMKETEEGCNQKGAFLVEKTSTEVQCKGGNVCVQAQDR<br>YYNSSCSKWACVPCRVRSGGGGSGGGGSGGGGSRVIPVSGP<br>ARCLSQSRNLLKTTDDMVKTAREKLKHYSCTAEDIDHEDITR<br>DQTSTLKTCLPLELHKNESCLATRETSSTTRGSCLPPQKTSLM |

TABLE 1-continued

| Exemplary Amino Acid Sequences | | |
|---|---|---|
| SEQ ID NO: | Polypeptide | Sequence |
| | | MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGSGGGGSEESEESEESEESEESEE GGGGSHHHHHH |
| 13 | mIL12-ABP20-8x | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGSGGGGSEESEESEESEESEESEE SEESEEGGGGSHHHHHH |
| 14 | mIL12-ABP20-G4-SEEE | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGSGGGGSEEEGGGSEEEGGGSEE EGGGSEEEGGGSHHHHHH |
| 15 | mIL12-ABP20-G4-SEEA | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGSGGGGSEEAGGGSEEAGGGSE EAGGGSEEAGGGSHHHHHH |
| 16 | mIL12-ABP20-G4-SEEQ | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGSGGGGSEEQGGGSEEQGGGSE EQGGGSEEQGGGSHHHHHH |
| 17 | mIL12-ABP10-GS | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR |

TABLE 1-continued

Exemplary Amino Acid Sequences

| SEQ ID NO: | Polypeptide | Sequence |
|---|---|---|
| | | DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGSGGSEEGGGGGSGGSEEGGGG SEEGGGGGSGGSEEGGGGHHHHHH |
| 18 | mIL12-ABP10-GE | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGEGGSEEGGGGGEGGSEEGGGG SEEGGGGGEGGSEEGGGGHHHHHH |
| 19 | mIL12-ABP20-G8-GS | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGEGGGGSEEGGGSGGGGSEEGG GSGGGGSEEGGGSGGGGSEEGGGGHHHHHH |
| 20 | mIL12-ABP20-G8-GE | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGEGGGGSEEGGGEGGGGSEEGG GEGGGGSEEGGGEGGGGSEEGGGGHHHHHH |
| 21 | mIL12-ABP20-G4-6x-GE | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGEGGGGSEEGGGGSEEGGGGSE EGGGGSEEGGGGSEEGGGGSEEGGGGHHHHHH |
| 22 | mIL12-ABP20-G4-8x-GE | MWELEKDVYVVEVDWTPDAPGETVNLTCDTPEEDDITWTSD QRHGVIGSGKTLTITVKEFLDAGQYTCHKGGETLSHSHLLLH KKENGIWSTEILKNFKNKTFLKCEAPNYSGRFTCSWLVQRNM DLKFNIKSSSSSPDSRAVTCGMASLSAEKVTLDQRDYEKYSVS CQEDVTCPTAEETLPIELALEARQQNKYENYSTSFFIRDIIKPDP PKNLQMKPLKNSQVEVSWEYPDSWSTPHSYFSLKFFVRIQRK KEKMKETEEGCNQKGAFLVEKTSTEVQCKGGNVCVQAQDR YYNSSCSKWACVPCRVRSGGGGSGGGGSGGGGSRVIPVSGP |

TABLE 1-continued

| Exemplary Amino Acid Sequences | | |
|---|---|---|
| SEQ ID NO: | Polypeptide | Sequence |
| | | ARCLSQSRNLLKTTDDMVKTAREKLKHYSCTAEDIDHEDITR DQTSTLKTCLPLELHKNESCLATRETSSTTRGSCLPPQKTSLM MTLCLGSIYEDLKMYQTEFQAINAALQNHNHQQIILDKGMLV AIDELMQSLNHNGETLRQKPPVGEADPYRVKMKLCILLHAFS TRVVTINRVMGYLSSAGGGGEGGGGSEEGGGGSEEGGGGSE EGGGGSEEGGGGSEEGGGGSEEGGGGSEEGGGGSEEGGGGH HHHHH |
| 23 | Human IL12B | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCS |
| 24 | Human IL12A | RNLPVATPDPGMFPCLHHSQNLLRAVSNMLQKARQTLEFYPC TSEEIDHEDITKDKTSTVEACLPLELTKNESCLNSRETSFITNGS CLASRKTSFMMALCLSSIYEDLKMYQVEFKTMNAKLLMDPK RQIFLDQNMLAVIDELMQALNFNSETVPQKSSLEEPDFYKTKI KLCILLHAFRIRAVTIDRVMSYLNAS |
| 25 | Human IL12 (IL12B-linker-IL12A) | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNAS |
| 26 | hIL12-His (no ABP) | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSHHHHHH |
| 27 | hL12-ABP10-His | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSFQSEEQQGGGSGGSEEGGMESEESNGG GSGGSEEGGGGSHHHHHH |
| 28 | hL12-ABP20-His | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL |

TABLE 1-continued

| SEQ ID NO: | Polypeptide | Sequence |
|---|---|---|
| | Exemplary Amino Acid Sequences | |
| | | HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEESEESEESEEGGGGSHHHHHH |
| 29 | hIL12-ABP20-G4-His | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEGGGGSEEGGGGSEEGGGGSE EGGGGSHHHHHH |
| 30 | hL12-ABP20-G4-8x-GE (mature polypeptide) | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGEGGGGSEEGGGGSEEGGGGSEEGGGGSE EGGGGSEEGGGGSEEGGGGSEEGGGGSEEGGGGS |
| 31 | Signal polypeptide | MYRMQLLSCIALSLALVTNS |
| 32 | hL12-ABP20-G4-8x-GE w/ signal polypeptide | MYRMQLLSCIALSLALVTNSIWELKKDVYVVELDWYPDAPG EMVVLTCDTPEEDGITWTLDQSSEVLGSGKTLTIQVKEFGDA GQYTCHKGGEVLSHSLLLLHKKEDGIWSTDILKDQKEPKNKT FLRCEAKNYSGRFTCWWLTTISTDLTFSVKSSRGSSDPQGVTC GAATLSAERVRGDNKEYEYSVECQEDSACPAAEESLPIEVMV DAVHKLKYENYTSSFFIRDIIKPDPPKNLQLKPLKNSRQVEVS WEYPDTWSTPHSYFSLTFCVQVQGKSKREKKDRVFTDKTSAT VICRKNASISVRAQDRYYSSSWSEWASVPCSGGGGSGGGGSG GGGSRNLPVATPDPGMFPCLHHSQNLLRAVSNMLQKARQTL EFYPCTSEEIDHEDITKDKTSTVEACLPLELTKNESCLNSRETS FITNGSCLASRKTSFMMALCLSSIYEDLKMYQVEFKTMNAKL LMDPKRQIFLDQNMLAVIDELMQALNFNSETVPQKSSLEEPD FYKTKIKLCILLHAFRIRAVTIDRVMSYLNASGGGGEGGGGSE EGGGGSEEGGGGSEEGGGGSEEGGGGSEEGGGGSEEGGGGS EEGGGGSEEGGGGS |
| 33 | hIL12-ABP10 (mature polypeptide) | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSFQSEEQQGGGSGGSEEGGMESEESNGG GSGGSEEGGGGS |
| 34 | hIL12-ABP10 w/ signal polypeptide | MYRMQLLSCIALSLALVTNSIWELKKDVYVVELDWYPDAPG EMVVLTCDTPEEDGITWTLDQSSEVLGSGKTLTIQVKEFGDA GQYTCHKGGEVLSHSLLLLHKKEDGIWSTDILKDQKEPKNKT FLRCEAKNYSGRFTCWWLTTISTDLTFSVKSSRGSSDPQGVTC |

TABLE 1-continued

Exemplary Amino Acid Sequences

| SEQ ID NO: | Polypeptide | Sequence |
|---|---|---|
| | | GAATLSAERVRGDNKEYEYSVECQEDSACPAAEESLPIEVMV DAVHKLKYENYTSSFFIRDIIKPDPPKNLQLKPLKNSRQVEVS WEYPDTWSTPHSYFSLTFCVQVQGKSKREKKDRVFTDKTSAT VICRKNASISVRAQDRYYSSSWSEWASVPCSGGGGSGGGGSG GGGSRNLPVATPDPGMFPCLHHSQNLLRAVSNMLQKARQTL EFYPCTSEEIDHEDITKDKTSTVEACLPLELTKNESCLNSRETS FITNGSCLASRKTSFMMALCLSSIYEDLKMYQVEFKTMNAKL LMDPKRQIFLDQNMLAVIDELMQALNFNSETVPQKSSLEEPD FYKTKIKLCILLHAFRIRAVTIDRVMSYLNASGGGGSFQSEEQ QGGGSGGSEEGGMESEESNGGGSGGSEEGGGGS |
| 35 | hIL12-ABP20 | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEESEESEESEEGGGGS |
| 36 | hIL12-ABP20-G4 | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEGGGGSEEGGGGSEEGGGGSE EGGGGS |
| 37 | hL12-ABP20-G4-GS20 | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSGGGGSGGGGSEEGGGGSEEGG GGSEEGGGGSEEGGGGS |
| 38 | hL12-ABP20-G4-6x | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEGGGGSEEGGGGSEEGGGGSE EGGGGSEEGGGGSEEGGGGS |
| 39 | hIL12-ABP20-G4-8x | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS |

TABLE 1-continued

| SEQ ID NO: | Polypeptide | Sequence |
|---|---|---|
| | | Exemplary Amino Acid Sequences |
| | | VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEGGGGSEEGGGGSEEGGGGSE EGGGGSEEGGGGSEEGGGGSEEGGGGSEEGGGGS |
| 40 | hL12-ABP20-6x | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEESEESEESEESEESEEGGGGS |
| 41 | hL12-ABP20-8x | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEESEESEESEESEESEESEESEEG GGGS |
| 42 | hL12-ABP20-G4-SEEE | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEEGGGSEEEGGGSEEEGGGSEE EGGGS |
| 43 | hIL12-ABP20-G4-SEEA | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEAGGGSEEAGGGSEEAGGGSE EAGGGS |
| 44 | hL12-ABP20-G4-SEEQ | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS |

TABLE 1-continued

| Exemplary Amino Acid Sequences | | |
|---|---|---|
| SEQ ID NO: | Polypeptide | Sequence |
| | | VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGGGSEEQGGGSEEQGGGSEEQGGGSE EQGGGS |
| 45 | hL12-ABP10-GS | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGSGGSEEGGGGGSGGSEEGGGGSEEGGGG GSGGSEEGGGGS |
| 46 | hIL12-ABP10-GE | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGEGGSEEGGGGGEGGSEEGGGGSEEGGGG GEGGSEEGGGGS |
| 47 | hL12-ABP20-G8-GS | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGEGGGGSEEGGGSGGGGSEEGGGSGGGGS EEGGGSGGGGSEEGGGGS |
| 48 | hL12-ABP20-G8-GE | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGEGGGGSEEGGGEGGGGSEEGGGEGGGG SEEGGGEGGGGSEEGGGGS |
| 49 | hL12-ABP20-G4-GE | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT |

TABLE 1-continued

Exemplary Amino Acid Sequences

| SEQ ID NO: | Polypeptide | Sequence |
|---|---|---|
| | | ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGEGGGGSEEGGGGSEEGGGGSEEGGGGSE EGGGGS |
| 50 | hL12-ABP20-G4-6x-GE | IWELKKDVYVVELDWYPDAPGEMVVLTCDTPEEDGITWTLD QSSEVLGSGKTLTIQVKEFGDAGQYTCHKGGEVLSHSLLLLH KKEDGIWSTDILKDQKEPKNKTFLRCEAKNYSGRFTCWWLTT ISTDLTFSVKSSRGSSDPQGVTCGAATLSAERVRGDNKEYEYS VECQEDSACPAAEESLPIEVMVDAVHKLKYENYTSSFFIRDIIK PDPPKNLQLKPLKNSRQVEVSWEYPDTWSTPHSYFSLTFCVQ VQGKSKREKKDRVFTDKTSATVICRKNASISVRAQDRYYSSS WSEWASVPCSGGGGSGGGGSGGGGSRNLPVATPDPGMFPCL HHSQNLLRAVSNMLQKARQTLEFYPCTSEEIDHEDITKDKTST VEACLPLELTKNESCLNSRETSFITNGSCLASRKTSFMMALCL SSIYEDLKMYQVEFKTMNAKLLMDPKRQIFLDQNMLAVIDEL MQALNFNSETVPQKSSLEEPDFYKTKIKLCILLHAFRIRAVTID RVMSYLNASGGGGEGGGGSEEGGGGSEEGGGGSEEGGGGSE EGGGGSEEGGGGSEEGGGGS |
| 82 | ABP20-G4 | GGGGSGGGGSEEGGGGSEEGGGGSEEGGGGSEEGGGGS |
| 83 | ABP20-G4-6x | GGGGSGGGGSEEGGGGSEEGGGGSEEGGGGSEEGGGGSEEG GGGSEEGGGGS |
| 84 | ABP20-G4-8x | GGGGSGGGGSEEGGGGSEEGGGGSEEGGGGSEEGGGGSEEG GGGSEEGGGGSEEGGGGSEEGGGGS |
| 85 | ABP20-6x | GGGGSGGGGSEESEESEESEESEESEEGGGGS |
| 86 | ABP20-8x | GGGGSGGGGSEESEESEESEESEESEESEESEEGGGGS |
| 87 | ABP20-G4-SEEE | GGGGSGGGGSEEEGGGSEEEGGGSEEEGGGSEEEGGGS |
| 88 | ABP20-G4-SEEA | GGGGSGGGGSEEAGGGSEEAGGGSEEAGGGSEEAGGGS |
| 89 | ABP20-G4-SEEQ | GGGGSGGGGSEEQGGGSEEQGGGSEEQGGGSEEQGGGS |
| 90 | ABP10 | GGGGSFQSEEQQGGGSGGSEEGGMESEESNGGGSGGSEEGG GGS |
| 91 | ABP10-GS | GGGGSGGSEEGGGGGSGGSEEGGGGSEEGGGGGSGGSEEGG GG |
| 92 | ABP10-GE | GGGGEGGSEEGGGGGEGGSEEGGGGSEEGGGGGEGGSEEGG GG |
| 93 | ABP20-G8-GS | GGGGEGGGGSEEGGGSGGGGSEEGGGSGGGGSEEGGGSGGG GSEEGGGG |
| 94 | ABP20-G8-GE | GGGGEGGGGSEEGGGEGGGGSEEGGGEGGGGSEEGGGEGG GGSEEGGGG |
| 95 | ABP20-G4-GE | GGGGEGGGGSEEGGGGSEEGGGGSEEGGGGSEEGGGG |
| 96 | ABP20-G4-6x-GE | GGGGEGGGGSEEGGGGSEEGGGGSEEGGGGSEEGGGGSEEG GGGSEEGGGG |
| 97 | ABP20-G4-8x-GE | GGGGEGGGGSEEGGGGSEEGGGGSEEGGGGSEEGGGGSEEG GGGSEEGGGGSEEGGGGSEEGGGG |
| 98 | His | HHHHHH |

TABLE 1-continued

Exemplary Amino Acid Sequences

| SEQ ID NO: | Polypeptide | Sequence |
|---|---|---|
| 100 | Canine IL12B | IWELEKDVYVVELDWHPDAPGEMVVLTCHTPEEDDITWTSA<br>QSSEVLGSGKTLTIQVKEFGDAGQYTCHKGGKVLSRSLLLIHK<br>KEDGIWSTDILKEQKESKNKIFLKCEAKNYSGRFTCWWLTAIS<br>TDLKFSVKSSRGFSDPQGVTCGAVTLSAERVRVDNRDYKKYT<br>VECQEGSACPSAEESLPIEVVVDAIHKLKYENYTSSFFIRDIIKP<br>DPPTNLQLKPLKNSRHVEVSWEYPDTWSTPHSYFSLTFCVQA<br>QGKNNREKKDRLCVDKTSAKVVCHKDAKIRVQARDRYYSSS<br>WSDWASVSCS |
| 101 | Canine IL12A | RSLPTASPSPGIFQCLNHSQNLLRAVSNTLQKARQTLELYSCTS<br>EEIDHEDITKDKTSTVEACLPLELTMNESCLASREISLITNGSCL<br>ASGKASFMTVLCLSSIYEDLKMYQMEFKAMNAKLLMDPKRQ<br>IFLDQNMLTAIDELLQALNFNSVTVPQKSSLEEPDFYKTKIKLC<br>ILLHAFRIRAVTIDRMMSYLNSS |
| 102 | Canine IL12 (IL12B-linker-IL12A) | IWELEKDVYVVELDWHPDAPGEMVVLTCHTPEEDDITWTSA<br>QSSEVLGSGKTLTIQVKEFGDAGQYTCHKGGKVLSRSLLLIHK<br>KEDGIWSTDILKEQKESKNKIFLKCEAKNYSGRFTCWWLTAIS<br>TDLKFSVKSSRGFSDPQGVTCGAVTLSAERVRVDNRDYKKYT<br>VECQEGSACPSAEESLPIEVVVDAIHKLKYENYTSSFFIRDIIKP<br>DPPTNLQLKPLKNSRHVEVSWEYPDTWSTPHSYFSLTFCVQA<br>QGKNNREKKDRLCVDKTSAKVVCHKDAKIRVQARDRYYSSS<br>WSDWASVSCSGGGGSGGGGSGGGGSRSLPTASPSPGIFQCLN<br>HSQNLLRAVSNTLQKARQTLELYSCTSEEIDHEDITKDKTSTV<br>EACLPLELTMNESCLASREISLITNGSCLASGKASFMTVLCLSS<br>IYEDLKMYQMEFKAMNAKLLMDPKRQIFLDQNMLTAIDELL<br>QALNFNSVTVPQKSSLEEPDFYKTKIKLCILLHAFRIRAVTIDR<br>MMSYLNSS |
| 103 | Canine IL12-ABP20-G4-8x-GE-His (mature protein) | IWELEKDVYVVELDWHPDAPGEMVVLTCHTPEEDDITWTSA<br>QSSEVLGSGKTLTIQVKEFGDAGQYTCHKGGKVLSRSLLLIHK<br>KEDGIWSTDILKEQKESKNKIFLKCEAKNYSGRFTCWWLTAIS<br>TDLKFSVKSSRGFSDPQGVTCGAVTLSAERVRVDNRDYKKYT<br>VECQEGSACPSAEESLPIEVVVDAIHKLKYENYTSSFFIRDIIKP<br>DPPTNLQLKPLKNSRHVEVSWEYPDTWSTPHSYFSLTFCVQA<br>QGKNNREKKDRLCVDKTSAKVVCHKDAKIRVQARDRYYSSS<br>WSDWASVSCSGGGGSGGGGSGGGGSRSLPTASPSPGIFQCLN<br>HSQNLLRAVSNTLQKARQTLELYSCTSEEIDHEDITKDKTSTV<br>EACLPLELTMNESCLASREISLITNGSCLASGKASFMTVLCLSS<br>IYEDLKMYQMEFKAMNAKLLMDPKRQIFLDQNMLTAIDELL<br>QALNFNSVTVPQKSSLEEPDFYKTKIKLCILLHAFRIRAVTIDR<br>MMSYLNSSGGGGEGGGGSEEGGGGSEEGGGGSEEGGGGSEE<br>GGGGSEEGGGGSEEGGGGSEEGGGGSEEGGGGHHHHHH |
| 104 | Canine IL12-ABP20-G4-8x-GE-His (w/ signal peptide) | MYRMQLLSCIALSLALVTNSIWELEKDVYVVELDWHPDAPG<br>EMVVLTCHTPEEDDITWTSAQSSEVLGSGKTLTIQVKEFGDA<br>GQYTCHKGGKVLSRSLLLIHKKEDGIWSTDILKEQKESKNKIF<br>LKCEAKNYSGRFTCWWLTAISTDLKFSVKSSRGFSDPQGVTC<br>GAVTLSAERVRVDNRDYKKYTVECQEGSACPSAEESLPIEVV<br>VDAIHKLKYENYTSSFFIRDIIKPDPPTNLQLKPLKNSRHVEVS<br>WEYPDTWSTPHSYFSLTFCVQAQGKNNREKKDRLCVDKTSA<br>KVVCHKDAKIRVQARDRYYSSSWSDWASVSCSGGGGSGGG<br>GSGGGGSRSLPTASPSPGIFQCLNHSQNLLRAVSNTLQKARQT<br>LELYSCTSEEIDHEDITKDKTSTVEACLPLELTMNESCLASREI<br>SLITNGSCLASGKASFMTVLCLSSIYEDLKMYQMEFKAMNAK<br>LLMDPKRQIFLDQNMLTAIDELLQALNFNSVTVPQKSSLEEPD<br>FYKTKIKLCILLHAFRIRAVTIDRMMSYLNSSGGGGEGGGGSE<br>EGGGGSEEGGGGSEEGGGGSEEGGGGSEEGGGGSEEGGGGS<br>EEGGGGSEEGGGGHHHHHH |
| 105 | Canine IL12-ABP20-G4-8x-GE (Untagged, mature protein) | IWELEKDVYVVELDWHPDAPGEMVVLTCHTPEEDDITWTSA<br>QSSEVLGSGKTLTIQVKEFGDAGQYTCHKGGKVLSRSLLLIHK<br>KEDGIWSTDILKEQKESKNKIFLKCEAKNYSGRFTCWWLTAIS<br>TDLKFSVKSSRGFSDPQGVTCGAVTLSAERVRVDNRDYKKYT<br>VECQEGSACPSAEESLPIEVVVDAIHKLKYENYTSSFFIRDIIKP<br>DPPTNLQLKPLKNSRHVEVSWEYPDTWSTPHSYFSLTFCVQA<br>QGKNNREKKDRLCVDKTSAKVVCHKDAKIRVQARDRYYSSS<br>WSDWASVSCSGGGGSGGGGSGGGGSRSLPTASPSPGIFQCLN<br>HSQNLLRAVSNTLQKARQTLELYSCTSEEIDHEDITKDKTSTV<br>EACLPLELTMNESCLASREISLITNGSCLASGKASFMTVLCLSS<br>IYEDLKMYQMEFKAMNAKLLMDPKRQIFLDQNMLTAIDELL<br>QALNFNSVTVPQKSSLEEPDFYKTKIKLCILLHAFRIRAVTIDR<br>MMSYLNSSGGGGEGGGGSEEGGGGSEEGGGGSEEGGGGSEE<br>GGGGSEEGGGGSEEGGGGSEEGGGGSEEGGGGS |

TABLE 1-continued

| Exemplary Amino Acid Sequences | | |
|---|---|---|
| SEQ ID NO: | Polypeptide | Sequence |
| 106 | Feline IL12B | IWELEKNVYVVELDWHPDAPGEMVVLTCNTPEEDDITWTSD QSSEVLGSGKTLTIQVKEFADAGQYTCHKGGEVLSHSFLLIHK KEDGIWSTDILREQKESKNKIFLKCEAKNYSGRFTCWWLTAIS TDLKFTVKSSRGSSDPQGVTCGAATLSAEKVRVDNRDYKKY TVECQEGSACPAAEESLPIEVVVDAIHKLKYENYTSSFFIRDIIK PDPPKNLQLKPLKNSRHVEVSWEYPDTWSTPHSYFSLTFGVQ VQGKNNREKKDRLSVDKTSAKVVCHKDAKIRVQARDRYYSS SWSNWASVSCS |
| 107 | Feline IL12A | RNLPTPTPSPGMFQCLNHSQTLLRAISNTLQKARQTLEFYSCT SEEIDHEDITKDKTSTVEACLPLELTMNESCLASREISLITNGSC LASRKTSFMTTLCLSSIYEDLKMYQVEFKAMNAKLLMDPKR QIFLDQNMLTAIDELLQALNVNSVTVPQNSSLEEPDFYKTKIK LCILLHAFRIRAVTINRMMSYLNSS |
| 108 | Feline IL12 (IL12B-linker-IL12A) | IWELEKNVYVVELDWHPDAPGEMVVLTCNTPEEDDITWTSD QSSEVLGSGKTLTIQVKEFADAGQYTCHKGGEVLSHSFLLIHK KEDGIWSTDILREQKESKNKIFLKCEAKNYSGRFTCWWLTAIS TDLKFTVKSSRGSSDPQGVTCGAATLSAEKVRVDNRDYKKY TVECQEGSACPAAEESLPIEVVVDAIHKLKYENYTSSFFIRDIIK PDPPKNLQLKPLKNSRHVEVSWEYPDTWSTPHSYFSLTFGVQ VQGKNNREKKDRLSVDKTSAKVVCHKDAKIRVQARDRYYSS SWSNWASVSCSGGGGSGGGGSGGGGSRNLPTPTPSPGMFQC LNHSQTLLRAISNTLQKARQTLEFYSCTSEEIDHEDITKDKTST VEACLPLELTMNESCLASREISLITNGSCLASRKTSFMTTLCLS SIYEDLKMYQVEFKAMNAKLLMDPKRQIFLDQNMLTAIDELL QALNVNSVTVPQNSSLEEPDFYKTKIKLCILLHAFRIRAVTINR MMSYLNSS |
| 109 | Feline IL12-ABP20-G4-8x-GE (Untagged, mature protein) | IWELEKNVYVVELDWHPDAPGEMVVLTCNTPEEDDITWTSD QSSEVLGSGKTLTIQVKEFADAGQYTCHKGGEVLSHSFLLIHK KEDGIWSTDILREQKESKNKIFLKCEAKNYSGRFTCWWLTAIS TDLKFTVKSSRGSSDPQGVTCGAATLSAEKVRVDNRDYKKY TVECQEGSACPAAEESLPIEVVVDAIHKLKYENYTSSFFIRDIIK PDPPKNLQLKPLKNSRHVEVSWEYPDTWSTPHSYFSLTFGVQ VQGKNNREKKDRLSVDKTSAKVVCHKDAKIRVQARDRYYSS SWSNWASVSCSGGGGSGGGGSGGGGSRNLPTPTPSPGMFQC LNHSQTLLRAISNTLQKARQTLEFYSCTSEEIDHEDITKDKTST VEACLPLELTMNESCLASREISLITNGSCLASRKTSFMTTLCLS SIYEDLKMYQVEFKAMNAKLLMDPKRQIFLDQNMLTAIDELL QALNVNSVTVPQNSSLEEPDFYKTKIKLCILLHAFRIRAVTINR MMSYLNSSGGGGEGGGGSEEGGGGSEEGGGGSEEGGGGSEE GGGGSEEGGGGSEEGGGGSEEGGGGSEEGGGGS |
| 110 | Porcine IL12B | IWELEKNVYVVELDWYPNAPGEMVVLTCNTPEEDGITWTSD QSSEVLGTGKTLTIHVKEFGDAGQYTCRKGGAVLSQSLLLLH KKEDGIWSTDILKDQKEPKNKSFLKCEAKNYSGRFTCWWLT AISTDLKFSVKSSRGSTDPRGVTCGTATLSEDLGEYKKYRVEC QEGSACPAAEESLPIEVVLEAVHKLKYENYTSSFFIRDIIKPDPP KNLQLNPLKNSRHVEISWEYPDTWSTPHSYFSLMFGVQVQGK NKREKKDKLFTDQISAKVTCHKDANIRVQARDRYYSSSWSE WASVSCN |
| 111 | Porcine IL12A | RSLPATTAGPGMFKCLNHSQNLLKAVSNTLQKAKQTLEFYSC TSEEIDHEDITKDKTSTVEACLPLELATNESCLAARETSLITNG NCLTSGKTSFMTTLCLSSIYEDLKMYHVEFQAMNAKLLMDP KRQIFLDQNMLTAITELMQALNFNSETVPQKPSLEELDFYKTK IKLCILLHAFRIRAVTIDRMMSYLNSS |
| 112 | Porcine IL12 (IL12B-linker-IL12A) | IWELEKNVYVVELDWYPNAPGEMVVLTCNTPEEDGITWTSD QSSEVLGTGKTLTIHVKEFGDAGQYTCRKGGAVLSQSLLLLH KKEDGIWSTDILKDQKEPKNKSFLKCEAKNYSGRFTCWWLT AISTDLKFSVKSSRGSTDPRGVTCGTATLSEDLGEYKKYRVEC QEGSACPAAEESLPIEVVLEAVHKLKYENYTSSFFIRDIIKPDPP KNLQLNPLKNSRHVEISWEYPDTWSTPHSYFSLMFGVQVQGK NKREKKDKLFTDQISAKVTCHKDANIRVQARDRYYSSSWSE |

TABLE 1-continued

Exemplary Amino Acid Sequences

| SEQ ID NO: | Polypeptide | Sequence |
|---|---|---|
| | | WASVSCNGGGGSGGGGSGGGGSRSLPATTAGPGMFKCLNHS QNLLKAVSNTLQKAKQTLEFYSCTSEEIDHEDITKDKTSTVEA CLPLELATNESCLAARETSLITNGNCLTSGKTSFMTTLCLSSIY EDLKMYHVEFQAMNAKLLMDPKRQIFLDQNMLTAITELMQA LNFNSETVPQKPSLEELDFYKTKIKLCILLHAFRIRAVTIDRMM SYLNSS |
| 113 | Porcine IL12-ABP20-G4-8x-GE (Untagged, mature protein) | IWELEKNVYVVELDWYPNAPGEMVVLTCNTPEEDGITWTSD QSSEVLGTGKTLTIHVKEFGDAGQYTCRKGGAVLSQSLLLLH KKEDGIWSTDILKDQKEPKNKSFLKCEAKNYSGRFTCWWLT AISTDLKFSVKSSRGSTDPRGVTCGTATLSEDLGEYKKYRVEC QEGSACPAAEESLPIEVVLEAVHKLKYENYTSSFFIRDIIKPDPP KNLQLNPLKNSRHVEISWEYPDTWSTPHSYFSLMFGVQVQGK NKREKKDKLFTDQISAKVTCHKDANIRVQARDRYYSSSWSE WASVSCNGGGGSGGGGSGGGGSRSLPATTAGPGMFKCLNHS QNLLKAVSNTLQKAKQTLEFYSCTSEEIDHEDITKDKTSTVEA CLPLELATNESCLAARETSLITNGNCLTSGKTSFMTTLCLSSIY EDLKMYHVEFQAMNAKLLMDPKRQIFLDQNMLTAITELMQA LNFNSETVPQKPSLEELDFYKTKIKLCILLHAFRIRAVTIDRMM SYLNSSGGGGEGGGGSEEGGGGSEEGGGGSEEGGGGSEEGG GGSEEGGGGSEEGGGGSEEGGGGSEEGGGGS |
| 114 | Equine IL12B | IWELEKDVYVVELDWYPDAPGEMVVLTCNTPEEEGITWTSA QSNEVLGSGKTLTIQVKEFGDAGWYTCHKGGEVLSHSHLLLH KKEDGIWSTDILKDQKESKNKTFLKCEAKNYSGRFTCWWLT AISTDLKFSVKSSRGSSDPRGVTCGAATLSAERVSVDDREYKK YTVECQEGSACPAAEESLPIEIVVDAVHKLKYENYTSGFFIRDI IKPDPPKNLQLKPLKNSRQVEVSWEYPETWSTPHSYFSLTFSIQ VQGKNKKERKDRLFMDETSATVTCHKDGQIRVQARDRYYSS SWSEWASVSCS |
| 115 | Equine IL12A | RNLPTATPGPGMFQCLNHSQNLLRTVSNTLQKARQTLEFYSC TSEEIDHEDITKDKSSTVAACLPLELAPNESCLASREISFITNGS CLTPGKASSMMTLCLSSIYEDLKMYQVEFKAMNAKLLIDPQR QIFLDENMLTAIDKLMQALNFNSETVPQKPSLEGLDFYKTKV KLCILLHAFRIRAVTINRMMGYLNAS |
| 116 | Equine IL12 (IL12B-linker-IL12A) | IWELEKDVYVVELDWYPDAPGEMVVLTCNTPEEEGITWTSA QSNEVLGSGKTLTIQVKEFGDAGWYTCHKGGEVLSHSHLLLH KKEDGIWSTDILKDQKESKNKTFLKCEAKNYSGRFTCWWLT AISTDLKFSVKSSRGSSDPRGVTCGAATLSAERVSVDDREYKK YTVECQEGSACPAAEESLPIEIVVDAVHKLKYENYTSGFFIRDI IKPDPPKNLQLKPLKNSRQVEVSWEYPETWSTPHSYFSLTFSIQ VQGKNKKERKDRLFMDETSATVTCHKDGQIRVQARDRYYSS SWSEWASVSCSGGGGSGGGGSGGGGSRNLPTATPGPGMFQC LNHSQNLLRTVSNTLQKARQTLEFYSCTSEEIDHEDITKDKSS TVAACLPLELAPNESCLASREISFITNGSCLTPGKASSMMTLCL SSIYEDLKMYQVEFKAMNAKLLIDPQRQIFLDENMLTAIDKL MQALNFNSETVPQKPSLEGLDFYKTKVKLCILLHAFRIRAVTI NRMMGYLNAS |
| 117 | Equine IL12-ABP20-G4-8x-GE (Untagged, mature protein) | IWELEKDVYVVELDWYPDAPGEMVVLTCNTPEEEGITWTSA QSNEVLGSGKTLTIQVKEFGDAGWYTCHKGGEVLSHSHLLLH KKEDGIWSTDILKDQKESKNKTFLKCEAKNYSGRFTCWWLT AISTDLKFSVKSSRGSSDPRGVTCGAATLSAERVSVDDREYKK YTVECQEGSACPAAEESLPIEIVVDAVHKLKYENYTSGFFIRDI IKPDPPKNLQLKPLKNSRQVEVSWEYPETWSTPHSYFSLTFSIQ VQGKNKKERKDRLFMDETSATVTCHKDGQIRVQARDRYYSS SWSEWASVSCSGGGGSGGGGSGGGGSRNLPTATPGPGMFQC LNHSQNLLRTVSNTLQKARQTLEFYSCTSEEIDHEDITKDKSS TVAACLPLELAPNESCLASREISFITNGSCLTPGKASSMMTLCL SSIYEDLKMYQVEFKAMNAKLLIDPQRQIFLDENMLTAIDKL MQALNFNSETVPQKPSLEGLDFYKTKVKLCILLHAFRIRAVTI NRMMGYLNASGGGGEGGGGSEEGGGGSEEGGGGSEEGGGG SEEGGGGSEEGGGGSEEGGGGSEEGGGGSEEGGGGS |

Table 2 provides exemplary nucleotide sequences encoding polypeptides described herein.

TABLE 2

| Exemplary Nucleotide Sequences | | |
|---|---|---|
| SEQ ID NO: | Polypeptide | Sequence |
| 51 | mIL12-His (no ABP) | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGTG GTGGATCTCACCACCATCACCATCAT |
| 52 | mIL12-ABP10 | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA |

TABLE 2-continued

| Exemplary Nucleotide Sequences | | |
|---|---|---|
| SEQ ID NO: | Polypeptide | Sequence |
| | | AACCAGCTCAACCACACGCGGATCATGTCTGCCCCCGCAA<br>AAGACCTCCCTGATGATGACTCTCTGTCTGGGAAGCATCTA<br>CGAAGATCTGAAGATGTATCAGACCGAATTCCAGGCCATC<br>AACGCGGCGCTGCAGAACCACAATCATCAGCAGATTATCC<br>TGGATAAGGGCATGCTGGTCGCCATCGACGAGCTGATGCA<br>GTCCTTGAATCACAACGGCGAAACGCTCCGCCAAAAGCCG<br>CCAGTGGGCGAAGCGGACCCTTATCGCGTGAAGATGAAGC<br>TCTGCATCCTGCTGCATGCCTTTTCGACCCGGGTGGTCACC<br>ATCAACAGAGTGATGGGATACCTGAGCTCAGCTGGGGGCG<br>GAGGCTCCTTCCAAAGCGAAGAACAGCAGGGAGGGGGCTC<br>CGGAGGTAGCGAAGAGGGAGGCATGGAGAGCGAGGAAAG<br>CAATGGAGGCGGATCAGGCGGATCCGAAGAAGGCGGTGGT<br>GGATCTCACCACCATCACCATCAT |
| 53 | mIL12-ABP20 | ATGTGGGAACTCGAAAAGGATGTGTACGTGGTGGAAGTCG<br>ACTGGACTCCTGATGCCCCGGGAGAGACAGTGAACCTGAC<br>CTGTGACACTCCCGAAGAGGACGACATTACTTGGACCAGC<br>GATCAGCGGCACGGCGTGATCGGATCCGGCAAAACCCTGA<br>CCATCACCGTGAAAGAATTCCTTGACGCGGGACAGTACAC<br>TTGCCACAAGGGCGGCGAAACCCTCAGCCATTCCCACCTTT<br>TGCTCCACAAGAAGGAAAACGGAATCTGGTCCACCGAAAT<br>TCTGAAGAACTTCAAGAACAAGACCTTCCTGAAGTGCGAG<br>GCGCCCAACTACTCGGGAAGGTTCACATGCTCCTGGCTGGT<br>GCAGAGGAACATGGATCTGAAGTTCAACATCAAGAGCTCC<br>TCCTCCTCCCCGGATTCAAGAGCCGTGACTTGCGGGATGGC<br>ATCCCTGAGCGCCGAGAAAGTCACTCTGGACCAGAGAGAC<br>TACGAGAAGTACTCCGTGTCGTGCCAGGAGGACGTGACCT<br>GTCCTACCGCCGAAGAGACTCTGCCCATTGAGCTGGCTCTG<br>GAAGCCCGCCAGCAGAACAAATACGAAAACTACTCCACGT<br>CATTCTTTATCCGGGACATCATCAAGCCCGACCCTCCTAAG<br>AACCTCCAGATGAAGCCCCTCAAGAACAGCCAGGTCGAGG<br>TGTCCTGGGAATACCCGGACTCCTGGAGCACCCCACACTCC<br>TACTTCTCGCTGAAGTTTTTCGTGCGGATCCAGCGGAAGAA<br>AGAGAAGATGAAAGAGACTGAAGAGGGGTGCAACCAGAA<br>GGGCGCTTTCCTGGTGGAAAAGACCTCGACCGAAGTGCAG<br>TGCAAAGGGGGCAACGTCTGCGTGCAAGCCCAAGACCGCT<br>ACTACAACTCCTCCTGCTCCAAATGGGCATGCGTGCCGTGT<br>AGAGTGCGGTCCGGTGGTGGAGGATCCGGAGGGGGTGGAT<br>CAGGGGGAGGCGGATCTAGGGTCATTCCGGTGTCCGGTCC<br>TGCTCGCTGCCTGAGTCAGTCCCGGAATCTGCTTAAGACTA<br>CTGACGATATGGTCAAGACTGCCCGCGAGAAGCTGAAGCA<br>CTACTCCTGCACCGCCGAGGACATTGACCACGAAGATATC<br>ACCCGGGACCAAACCAGCACCCTCAAGACTTGCCTGCCAC<br>TTGAACTGCACAAGAACGAGAGCTGCCTGGCAACCAGAGA<br>AACCAGCTCAACCACACGCGGATCATGTCTGCCCCCGCAA<br>AAGACCTCCCTGATGATGACTCTCTGTCTGGGAAGCATCTA<br>CGAAGATCTGAAGATGTATCAGACCGAATTCCAGGCCATC<br>AACGCGGCGCTGCAGAACCACAATCATCAGCAGATTATCC<br>TGGATAAGGGCATGCTGGTCGCCATCGACGAGCTGATGCA<br>GTCCTTGAATCACAACGGCGAAACGCTCCGCCAAAAGCCG<br>CCAGTGGGCGAAGCGGACCCTTATCGCGTGAAGATGAAGC<br>TCTGCATCCTGCTGCATGCCTTTTCGACCCGGGTGGTCACC<br>ATCAACAGAGTGATGGGATACCTGAGCTCAGCTGGAGGCG<br>GAGGCTCAGGAGGTGGCGGCAGCGAGGAGAGCGAAGAAT<br>CCGAGGAGTCCGAGGAAGGCGGTGGTGGATCTCACCACCA<br>TCACCATCAT |
| 54 | mIL12-ABP20-G4 | ATGTGGGAACTCGAAAAGGATGTGTACGTGGTGGAAGTCG<br>ACTGGACTCCTGATGCCCCGGGAGAGACAGTGAACCTGAC<br>CTGTGACACTCCCGAAGAGGACGACATTACTTGGACCAGC<br>GATCAGCGGCACGGCGTGATCGGATCCGGCAAAACCCTGA<br>CCATCACCGTGAAAGAATTCCTTGACGCGGGACAGTACAC<br>TTGCCACAAGGGCGGCGAAACCCTCAGCCATTCCCACCTTT<br>TGCTCCACAAGAAGGAAAACGGAATCTGGTCCACCGAAAT<br>TCTGAAGAACTTCAAGAACAAGACCTTCCTGAAGTGCGAG<br>GCGCCCAACTACTCGGGAAGGTTCACATGCTCCTGGCTGGT<br>GCAGAGGAACATGGATCTGAAGTTCAACATCAAGAGCTCC<br>TCCTCCTCCCCGGATTCAAGAGCCGTGACTTGCGGGATGGC<br>ATCCCTGAGCGCCGAGAAAGTCACTCTGGACCAGAGAGAC<br>TACGAGAAGTACTCCGTGTCGTGCCAGGAGGACGTGACCT<br>GTCCTACCGCCGAAGAGACTCTGCCCATTGAGCTGGCTCTG<br>GAAGCCCGCCAGCAGAACAAATACGAAAACTACTCCACGT<br>CATTCTTTATCCGGGACATCATCAAGCCCGACCCTCCTAAG<br>AACCTCCAGATGAAGCCCCTCAAGAACAGCCAGGTCGAGG |

TABLE 2-continued

Exemplary Nucleotide Sequences

| SEQ ID NO: | Polypeptide | Sequence |
|---|---|---|
| | | TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGAG GGGGCTCAGGAGGAGGCGGAAGCGAAGAGGGGGGTGGTG GATCCGAGGAGGGAGGAGGAGGCTCGGAAGAGGGAGGCG GAGGATCGGAGGAGGGCGGTGGTGGATCTCACCACCATCA CCATCAT |
| 55 | mIL12-ABP20-G4-GS20 | ATGTGGGAGCTGGAGAAGGATGTGTACGTGGTGGAGGTGG ACTGGACCCCTGACGCTCCTGGAGAAACCGTGAACTTGAC GTGCGACACCCCTGAGGAAGATGACATCACCTGGACCTCC GACCAAAGACACGGCGTGATCGGCTCCGGAAAGACCCTGA CCATCACCGTGAAGGAGTTCCTGGATGCCGGGCAGTACAC TTGCCACAAGGGGGGCGAAACGCTGTCCCACTCCCATCTG CTGCTGCACAAGAAAGAAAACGGGATCTGGTCCACCGAGA TTCTCAAGAACTTCAAGAACAAGACCTTCCTTAAGTGCGAG GCCCCCAACTACTCCGGCCGCTTCACTTGCTCCTGGCTGGT GCAGCGCAACATGGACCTGAAGTTCAATATCAAGTCATCC TCCTCGTCGCCTGATTCGAGAGCAGTCACTTGCGGGATGGC GTCCCTGAGCGCTGAAAAGGTCACCCTGGATCAGCGGGAC TACGAGAAGTACTCCGTGTCCTGCCAAGAGGACGTGACCT GTCCGACCGCCGAAGAAACTTTGCCCATCGAATTGGCCCTC GAAGCCAGGCAGCAGAATAAGTACGAGAACTACTCCACTT CGTTCTTCATTCGGGATATCATCAAGCCGGACCCACCGAAG AACCTCCAGATGAAGCCCCTCAAGAACAGCCAGGTCGAAG TGTCGTGGGAGTACCCGGACAGCTGGAGCACCCCACATAG CTACTTCTCACTGAAATTCTTCGTGCGGATCCAGCGCAAGA AGGAGAAGATGAAGGAAACCGAAGAAGGGTGCAACCAGA AGGGCGCCTTCTTGGTGGAAAAGACCAGCACCGAGGTGCA GTGCAAAGGCGGCAACGTCTGCGTGCAAGCCCAGGATAGA TACTACAACTCCTCGTGCTCCAAATGGGCATGCGTGCCATG TAGAGTGCGCTCCGGTGGTGGAGGATCAGGCGGTGGAGGC TCAGGAGGAGGGGGATCGAGGGTCATTCCGGTGTCCGGTC CTGCCCGATGCCTGTCACAATCCCGGAACCTTCTCAAGACT ACCGACGACATGGTCAAGACCGCTCGGGAGAAACTGAAGC ACTACTCCTGCACCGCCGAGGACATCGACCACGAAGATAT TACTCGGGATCAAACTTCCACTCTCAAAACTTGCCTCCCGC TCGAACTCCACAAGAACGAGTCCTGCTTAGCGACCAGGGA AACTAGCTCCACAACGCGGGGGTCATGTCTGCCACCCCAA AAGACCTCCCTCATGATGACCCTGTGCCTTGGCTCCATCTA TGAGGACCTGAAGATGTATCAGACCGAATTTCAGGCCATC AACGCGGCACTGCAGAACCACAACCATCAGCAGATTATCC TGGATAAGGGGATGCTGGTCGCAATCGACGAGCTCATGCA GTCCCTGAACCACAATGGGGAAACTCTGAGGCAGAAGCCC CCTGTGGGAGAAGCGGATCCCTACCGCGTGAAGATGAAGC TATGTATCCTGCTGCATGCCTTTTCCACCCGGGTCGTGACT ATCAATCGCGTGATGGGCTACCTTAGCTCAGCGGGTGGAG GAGGCAGTGGAGGCGGTGGAAGCGGAGGAGGAGGAAGCG GTGGAGGGGGTTCCGAGGAAGGAGGGGGCGGATCTGAGG AAGGCGGAGGAGGCTCAGAAGAGGGTGGAGGCGGATCCG AAGAGGGAGGCGGAGGTTCGCACCATCACCACCACCAC |
| 56 | mIL12-ABP20-G4-6x | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC |

TABLE 2-continued

Exemplary Nucleotide Sequences

| SEQ ID NO: | Polypeptide | Sequence |
|---|---|---|
| | | GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGTG GTGGATCCGGGGGTGGAGGTTCCGAGGAGGGTGGAGGAG GCAGCGAAGAGGGCGGAGGAGGATCGGAAGAGGGAGGAG GCGGAAGCGAAGAAGGGGGTGGCGGATCAGAGGAGGGAG GGGGAGGTTCGGAAGAAGGAGGAGGGGGATCGCATCATC ACCACCACCAC |
| 57 | mIL12-ABP20-G4-8x | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA |

TABLE 2-continued

| Exemplary Nucleotide Sequences | | |
|---|---|---|
| SEQ ID NO: | Polypeptide | Sequence |
| | | CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGAGGCG GTGGATCGGGAGGAGGGGGATCGGAAGAAGGGGGCGGAG GTTCAGAGGAAGGAGGTGGCGGATCCGAGGAAGGGGGAG GAGGCTCTGAGGAGGGTGGTGGCGGAAGCGAAGAGGGAG GCGGAGGATCCGAAGAGGGTGGCGGGGGATCAGAGGAGG GAGGGGGAGGATCAGAAGAGGGCGGTGGTGGATCGCACC ATCATCACCACCAC |
| 58 | mIL12-ABP20-6x | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGAGGCG GTGGCTCTGGTGGCGGAGGATCCGAGGAATCGGAAGAGTC CGAAGAGTCGGAGGAAAGCGAAGAGTCAGAAGAAGGGGG CGGAGGTTCACACCACCACCATCATCAC |
| 59 | mIL12-ABP20-8x | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG |

TABLE 2-continued

Exemplary Nucleotide Sequences

| SEQ ID NO: | Polypeptide | Sequence |
|---|---|---|
| | | TGTCCTGGGAATACCCGGACTCCTGGAGCACCCCACACTCC<br>TACTTCTCGCTGAAGTTTTTCGTGCGGATCCAGCGGAAGAA<br>AGAGAAGATGAAAGAGACTGAAGAGGGGTGCAACCAGAA<br>GGGCGCTTTCCTGGTGGAAAAGACCTCGACCGAAGTGCAG<br>TGCAAAGGGGGCAACGTCTGCGTGCAAGCCCAAGACCGCT<br>ACTACAACTCCTCCTGCTCCAAATGGGCATGCGTGCCGTGT<br>AGAGTGCGGTCCGGTGGTGGAGGATCCGGAGGGGGTGGAT<br>CAGGGGGAGGCGGATCTAGGGTCATTCCGGTGTCCGGTCC<br>TGCTCGCTGCCTGAGTCAGTCCCGGAATCTGCTTAAGACTA<br>CTGACGATATGGTCAAGACTGCCCGCGAGAAGCTGAAGCA<br>CTACTCCTGCACCGCCGAGGACATTGACCACGAAGATATC<br>ACCCGGGACCAAACCAGCACCCTCAAGACTTGCCTGCCAC<br>TTGAACTGCACAAGAACGAGAGCTGCCTGGCAACCAGAGA<br>AACCAGCTCAACCACACGCGGATCATGTCTGCCCCCGCAA<br>AAGACCTCCCTGATGATGACTCTCTGTCTGGGAAGCATCTA<br>CGAAGATCTGAAGATGTATCAGACCGAATTCCAGGCCATC<br>AACGCGGCGCTGCAGAACCACAATCATCAGCAGATTATCC<br>TGGATAAGGGCATGCTGGTCGCCATCGACGAGCTGATGCA<br>GTCCTTGAATCACAACGGCGAAACGCTCCGCCAAAAGCCG<br>CCAGTGGGCGAAGCGGACCCTTATCGCGTGAAGATGAAGC<br>TCTGCATCCTGCTGCATGCCTTTTCGACCCGGGTGGTCACC<br>ATCAACAGAGTGATGGGATACCTGAGCTCAGCTGGGGGTG<br>GAGGTTCGGGTGGCGGAGGATCCGAGGAATCGGAAGAGTC<br>CGAAGAGTCGGAAGAATCCGAGGAAAGCGAAGAGTCAGA<br>GGAATCTGAGGAGGGTGGTGGCGGAAGCCATCATCACCAC<br>CACCAC |
| 60 | mIL12-ABP20-G4-SEEE | ATGTGGGAACTCGAAAAGGATGTGTACGTGGTGGAAGTCG<br>ACTGGACTCCTGATGCCCCGGGAGAGACAGTGAACCTGAC<br>CTGTGACACTCCCGAAGAGGACGACATTACTTGGACCAGC<br>GATCAGCGGCACGGCGTGATCGGATCCGGCAAAACCCTGA<br>CCATCACCGTGAAAGAATTCCTTGACGCGGGACAGTACAC<br>TTGCCACAAGGGCGGCGAAACCCTCAGCCATTCCCACCTTT<br>TGCTCCACAAGAAGGAAAACGGAATCTGGTCCACCGAAAT<br>TCTGAAGAACTTCAAGAACAAGACCTTCCTGAAGTGCGAG<br>GCGCCCAACTACTCGGGAAGGTTCACATGCTCCTGGCTGGT<br>GCAGAGGAACATGGATCTGAAGTTCAACATCAAGAGCTCC<br>TCCTCCTCCCCGGATTCAAGAGCCGTGACTTGCGGGATGGC<br>ATCCCTGAGCGCCGAGAAAGTCACTCTGGACCAGAGAGAC<br>TACGAGAAGTACTCCGTGTCGTGCCAGGAGGACGTGACCT<br>GTCCTACCGCCGAAGAGACTCTGCCCATTGAGCTGGCTCTG<br>GAAGCCCGCCAGCAGAACAAATACGAAAACTACTCCACGT<br>CATTCTTTATCCGGGACATCATCAAGCCCGACCCTCCTAAG<br>AACCTCCAGATGAAGCCCCTCAAGAACAGCCAGGTCGAGG<br>TGTCCTGGGAATACCCGGACTCCTGGAGCACCCCACACTCC<br>TACTTCTCGCTGAAGTTTTTCGTGCGGATCCAGCGGAAGAA<br>AGAGAAGATGAAAGAGACTGAAGAGGGGTGCAACCAGAA<br>GGGCGCTTTCCTGGTGGAAAAGACCTCGACCGAAGTGCAG<br>TGCAAAGGGGGCAACGTCTGCGTGCAAGCCCAAGACCGCT<br>ACTACAACTCCTCCTGCTCCAAATGGGCATGCGTGCCGTGT<br>AGAGTGCGGTCCGGTGGTGGAGGATCCGGAGGGGGTGGAT<br>CAGGGGGAGGCGGATCTAGGGTCATTCCGGTGTCCGGTCC<br>TGCTCGCTGCCTGAGTCAGTCCCGGAATCTGCTTAAGACTA<br>CTGACGATATGGTCAAGACTGCCCGCGAGAAGCTGAAGCA<br>CTACTCCTGCACCGCCGAGGACATTGACCACGAAGATATC<br>ACCCGGGACCAAACCAGCACCCTCAAGACTTGCCTGCCAC<br>TTGAACTGCACAAGAACGAGAGCTGCCTGGCAACCAGAGA<br>AACCAGCTCAACCACACGCGGATCATGTCTGCCCCCGCAA<br>AAGACCTCCCTGATGATGACTCTCTGTCTGGGAAGCATCTA<br>CGAAGATCTGAAGATGTATCAGACCGAATTCCAGGCCATC<br>AACGCGGCGCTGCAGAACCACAATCATCAGCAGATTATCC<br>TGGATAAGGGCATGCTGGTCGCCATCGACGAGCTGATGCA<br>GTCCTTGAATCACAACGGCGAAACGCTCCGCCAAAAGCCG<br>CCAGTGGGCGAAGCGGACCCTTATCGCGTGAAGATGAAGC<br>TCTGCATCCTGCTGCATGCCTTTTCGACCCGGGTGGTCACC<br>ATCAACAGAGTGATGGGATACCTGAGCTCAGCTGGAGGCG<br>GAGGATCGGGAGGGGGAGGATCCGAGGAAGAAGGGGGTG<br>GCAGCGAAGAAGAGGGAGGAGGGTCTGAAGAGGAGGGCG<br>GTGGCTCAGAGGAAGAGGGTGGCGGTTCGCACCATCACCA<br>CCACCAT |
| 61 | mIL12-ABP20-G4-SEEA | ATGTGGGAACTCGAAAAGGATGTGTACGTGGTGGAAGTCG<br>ACTGGACTCCTGATGCCCCGGGAGAGACAGTGAACCTGAC<br>CTGTGACACTCCCGAAGAGGACGACATTACTTGGACCAGC |

TABLE 2-continued

| SEQ ID NO: | Polypeptide | Sequence |
|---|---|---|
| | | GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGAGGAG GGGGATCCGGTGGAGGCGGTTCCGAGGAAGCAGGCGGTGG ATCGGAAGAGGCTGGGGGTGGAAGCGAAGAGGCCGGTGG CGGATCAGAGGAGGCTGGCGGAGGATCGCACCACCATCAC CACCAT |
| 62 | mIL12-ABP20-G4-SEEQ | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC |

TABLE 2-continued

| SEQ ID NO: | Polypeptide | Sequence |
|---|---|---|
| | | AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGAGGCG GTGGATCGGGAGGTGGTGGCAGCGAAGAACAGGGTGGAG GGTCTGAGGAACAGGGCGGAGGATCCGAGGAGCAAGGGG GTGGCTCGGAAGAACAAGGAGGAGGGTCGCACCATCATCA CCACCAC |
| 63 | mIL12-ABP10-GS | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGAG GGGGCTCAGGAGGATCCGAGGAAGGGGGCGGCGGCGGAT CAGGCGGCTCCGAAGAGGGCGGAGGCGGAAGCGAAGAGG GTGGCGGCGGAGGGTCCGGCGGTTCCGAGGAGGGTGGAGG CGGCCACCACCATCACCACCAC |
| 64 | mIL12-ABP10-GE | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA |

TABLE 2-continued

Exemplary Nucleotide Sequences

| SEQ ID NO: | Polypeptide | Sequence |
|---|---|---|
| | | AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGAG GGGGCGAGGGAGGTTCCGAAGAAGGGGGAGGGGGCGGAG AGGGAGGATCCGAGGAAGGCGGTGGCGGATCGGAAGAAG GTGGCGGCGGTGGAGAAGGGGGCTCGGAAGAGGGCGGCG GAGGCCACCACCATCACCACCAC |
| 65 | mIL12-ABP20-G8-GS | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGAG GGGGCGAAGGGGGCGGCGGATCGGAAGAGGGCGGCGGCT CCGGAGGCGGAGGATCGGAGGAGGGAGGGGGAAGCGGTG GAGGGGGATCTGAGGAAGGCGGCGGAAGCGGAGGGGGCG GATCCGAGGAGGGCGGTGGCGGACACCACCACCATCACCA C |
| 66 | mIL12-ABP20-G8-GE | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA |

TABLE 2-continued

| SEQ ID NO: | Polypeptide | Sequence |
|---|---|---|
| | | CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC AACGCGGCGCTGCAGAACCACAATCATCAGCAGATTATCC TGGATAAGGGCATGCTGGTCGCCATCGACGAGCTGATGCA GTCCTTGAATCACAACGGCGAAACGCTCCGCCAAAAGCCG CCAGTGGGCGAAGCGGACCCTTATCGCGTGAAGATGAAGC TCTGCATCCTGCTGCATGCCTTTTCGACCCGGGTGGTCACC ATCAACAGAGTGATGGGATACCTGAGCTCAGCTGGCGGAG GGGGCGAAGGCGGTGGCGGTTCCGAGGAGGGCGGAGGAG AAGGGGGAGGGGGTTCAGAGGAGGGAGGTGGAGAGGGTG GCGGCGGCAGCGAAGAAGGCGGAGGCGAAGGAGGTGGCG GCAGCGAGGAAGGAGGAGGGGGCCACCATCACCACCACC AT |
| 67 | mIL12-ABP20-G4-6x-GE | ATGTGGGAACTCGAAAAGGATGTGTACGTGGTGGAAGTCG ACTGGACTCCTGATGCCCCGGGAGAGACAGTGAACCTGAC CTGTGACACTCCCGAAGAGGACGACATTACTTGGACCAGC GATCAGCGGCACGGCGTGATCGGATCCGGCAAAACCCTGA CCATCACCGTGAAAGAATTCCTTGACGCGGGACAGTACAC TTGCCACAAGGGCGGCGAAACCCTCAGCCATTCCCACCTTT TGCTCCACAAGAAGGAAAACGGAATCTGGTCCACCGAAAT TCTGAAGAACTTCAAGAACAAGACCTTCCTGAAGTGCGAG GCGCCCAACTACTCGGGAAGGTTCACATGCTCCTGGCTGGT GCAGAGGAACATGGATCTGAAGTTCAACATCAAGAGCTCC TCCTCCTCCCCGGATTCAAGAGCCGTGACTTGCGGGATGGC ATCCCTGAGCGCCGAGAAAGTCACTCTGGACCAGAGAGAC TACGAGAAGTACTCCGTGTCGTGCCAGGAGGACGTGACCT GTCCTACCGCCGAAGAGACTCTGCCCATTGAGCTGGCTCTG GAAGCCCGCCAGCAGAACAAATACGAAAACTACTCCACGT CATTCTTTATCCGGGACATCATCAAGCCCGACCCTCCTAAG AACCTCCAGATGAAGCCCCTCAAGAACAGCCAGGTCGAGG TGTCCTGGGAATACCCGGACTCCTGGAGCACCCCACACTCC TACTTCTCGCTGAAGTTTTTCGTGCGGATCCAGCGGAAGAA AGAGAAGATGAAAGAGACTGAAGAGGGGTGCAACCAGAA GGGCGCTTTCCTGGTGGAAAAGACCTCGACCGAAGTGCAG TGCAAAGGGGGCAACGTCTGCGTGCAAGCCCAAGACCGCT ACTACAACTCCTCCTGCTCCAAATGGGCATGCGTGCCGTGT AGAGTGCGGTCCGGTGGTGGAGGATCCGGAGGGGGTGGAT CAGGGGGAGGCGGATCTAGGGTCATTCCGGTGTCCGGTCC TGCTCGCTGCCTGAGTCAGTCCCGGAATCTGCTTAAGACTA CTGACGATATGGTCAAGACTGCCCGCGAGAAGCTGAAGCA CTACTCCTGCACCGCCGAGGACATTGACCACGAAGATATC ACCCGGGACCAAACCAGCACCCTCAAGACTTGCCTGCCAC TTGAACTGCACAAGAACGAGAGCTGCCTGGCAACCAGAGA AACCAGCTCAACCACACGCGGATCATGTCTGCCCCCGCAA AAGACCTCCCTGATGATGACTCTCTGTCTGGGAAGCATCTA CGAAGATCTGAAGATGTATCAGACCGAATTCCAGGCCATC |

TABLE 2-continued

Exemplary Nucleotide Sequences

| SEQ ID NO: | Polypeptide | Sequence |
| --- | --- | --- |
| | | AACGCGGCGCTGCAGAACCACAATCATCAGCAGATTATCC<br>TGGATAAGGGCATGCTGGTCGCCATCGACGAGCTGATGCA<br>GTCCTTGAATCACAACGGCGAAACGCTCCGCCAAAAGCCG<br>CCAGTGGGCGAAGCGGACCCTTATCGCGTGAAGATGAAGC<br>TCTGCATCCTGCTGCATGCCTTTTCGACCCGGGTGGTCACC<br>ATCAACAGAGTGATGGGATACCTGAGCTCAGCTGGAGGCG<br>GTGGAGAGGGCGGTGGCGGATCGGAAGAAGGAGGTGGCG<br>GATCCGAGGAAGGGGGAGGAGGCTCTGAGGAGGGTGGTG<br>GCGGAAGCGAAGAGGGAGGCGGAGGATCCGAAGAGGGTG<br>GCGGGGGATCAGAGGAGGGAGGGGGAGGACATCACCACC<br>ACCATCAT |
| 68 | mIL12-ABP20-G4-8x-GE | ATGTGGGAACTCGAAAAGGATGTGTACGTGGTGGAAGTCG<br>ACTGGACTCCTGATGCCCCGGGAGAGACAGTGAACCTGAC<br>CTGTGACACTCCCGAAGAGGACGACATTACTTGGACCAGC<br>GATCAGCGGCACGGCGTGATCGGATCCGGCAAAACCCTGA<br>CCATCACCGTGAAAGAATTCCTTGACGCGGGACAGTACAC<br>TTGCCACAAGGGCGGCGAAACCCTCAGCCATTCCCACCTTT<br>TGCTCCACAAGAAGGAAAACGGAATCTGGTCCACCGAAAT<br>TCTGAAGAACTTCAAGAACAAGACCTTCCTGAAGTGCGAG<br>GCGCCCAACTACTCGGGAAGGTTCACATGCTCCTGGCTGGT<br>GCAGAGGAACATGGATCTGAAGTTCAACATCAAGAGCTCC<br>TCCTCCTCCCCGGATTCAAGAGCCGTGACTTGCGGGATGGC<br>ATCCCTGAGCGCCGAGAAAGTCACTCTGGACCAGAGAGAC<br>TACGAGAAGTACTCCGTGTCGTGCCAGGAGGACGTGACCT<br>GTCCTACCGCCGAAGAGACTCTGCCCATTGAGCTGGCTCTG<br>GAAGCCCGCCAGCAGAACAAATACGAAAACTACTCCACGT<br>CATTCTTTATCCGGGACATCATCAAGCCCGACCCTCCTAAG<br>AACCTCCAGATGAAGCCCCTCAAGAACAGCCAGGTCGAGG<br>TGTCCTGGGAATACCCGGACTCCTGGAGCACCCCACACTCC<br>TACTTCTCGCTGAAGTTTTTCGTGCGGATCCAGCGGAAGAA<br>AGAGAAGATGAAAGAGACTGAAGAGGGGTGCAACCAGAA<br>GGGCGCTTTCCTGGTGGAAAAGACCTCGACCGAAGTGCAG<br>TGCAAAGGGGGCAACGTCTGCGTGCAAGCCCAAGACCGCT<br>ACTACAACTCCTCCTGCTCCAAATGGGCATGCGTGCCGTGT<br>AGAGTGCGGTCCGGTGGTGGAGGATCCGGAGGGGGTGGAT<br>CAGGGGGAGGCGGATCTAGGGTCATTCCGGTGTCCGGTCC<br>TGCTCGCTGCCTGAGTCAGTCCCGGAATCTGCTTAAGACTA<br>CTGACGATATGGTCAAGACTGCCCGCGAGAAGCTGAAGCA<br>CTACTCCTGCACCGCCGAGGACATTGACCACGAAGATATC<br>ACCCGGGACCAAACCAGCACCCTCAAGACTTGCCTGCCAC<br>TTGAACTGCACAAGAACGAGAGCTGCCTGGCAACCAGAGA<br>AACCAGCTCAACCACACGCGGATCATGTCTGCCCCCGCAA<br>AAGACCTCCCTGATGATGACTCTCTGTCTGGGAAGCATCTA<br>CGAAGATCTGAAGATGTATCAGACCGAATTCCAGGCCATC<br>AACGCGGCGCTGCAGAACCACAATCATCAGCAGATTATCC<br>TGGATAAGGGCATGCTGGTCGCCATCGACGAGCTGATGCA<br>GTCCTTGAATCACAACGGCGAAACGCTCCGCCAAAAGCCG<br>CCAGTGGGCGAAGCGGACCCTTATCGCGTGAAGATGAAGC<br>TCTGCATCCTGCTGCATGCCTTTTCGACCCGGGTGGTCACC<br>ATCAACAGAGTGATGGGATACCTGAGCTCAGCTGGAGGCG<br>GTGGAGAGGGTGGAGGCGGTTCCGAAGAAGGGGGCGGAG<br>GTTCAGAGGAAGGAGGTGGCGGATCCGAGGAAGGGGGAG<br>GAGGCTCTGAGGAGGGTGGTGGCGGAAGCGAAGAGGGAG<br>GCGGAGGATCCGAAGAGGGTGGCGGGGGATCAGAGGAGG<br>GAGGGGGAGGATCAGAAGAGGGCGGTGGTGGACACCACC<br>ACCATCATCAC |
| 69 | hIL12-His (no ABP) | ATCTGGGAGCTGAAGAAGGACGTCTATGTGGTGGAACTTG<br>ACTGGTACCCGGATGCCCCTGGAGAAATGGTCGTGCTGAC<br>GTGCGACACCCCCGAAGAGGACGGCATTACTTGGACCCTG<br>GACCAGTCCTCCGAAGTGCTCGGGAGCGGAAAGACCCTGA<br>CCATCCAAGTCAAGGAATTCGGCGATGCCGGACAGTACAC<br>CTGTCACAAGGGCGGAGAAGTGCTGAGCCACTCCCTGCTG<br>CTGCTGCACAAGAAGGAAGATGGCATCTGGTCCACCGACA<br>TCCTGAAAGACCAGAAGGAGCCGAAGAACAAGACTTTCCT<br>CCGCTGCGAAGCCAAGAACTACTCCGGCCGGTTTACTTGTT<br>GGTGGCTGACCACCATATCAACGGATCTCACCTTCTCCGTG<br>AAATCGTCCCGGGGAAGCTCGGACCCCCAAGGAGTGACTT<br>GCGGGGCAGCGACCTTGTCCGCCGAACGCGTCAGAGGGGA<br>CAACAAGGAATACGAGTACTCCGTGGAGTGCCAAGAGGAC<br>TCCGCATGTCCGGCTGCTGAAGAGTCGCTGCCGATTGAGGT<br>CATGGTGGACGCCGTGCACAAGCTGAAATACGAGAATTAC<br>ACCTCCTCCTTCTTCATCCGGGACATCATTAAGCCCGACCC |

TABLE 2-continued

| Exemplary Nucleotide Sequences | | |
|---|---|---|
| SEQ ID NO: | Polypeptide | Sequence |
| | | TCCTAAGAACCTCCAGCTGAAGCCTCTGAAGAACTCCCGCC AAGTGGAAGTGTCCTGGGAGTACCCCGACACTTGGTCCAC CCCCCATTCGTATTTCTCACTGACTTTCTGCGTCCAAGTGCA GGGGAAATCCAAGAGAGAGAAGAAAGACCGGGTGTTCAC TGATAAGACTAGCGCGACCGTGATCTGTAGAAAGAACGCG TCTATTTCCGTGCGCGCCCAAGATCGCTACTACTCCTCCTC GTGGTCCGAATGGGCCTCAGTGCCATGTAGCGGTGGTGGC GGATCCGGTGGAGGCGGATCGGGTGGAGGGGGATCCCGGA ACCTCCCGGTGGCCACTCCTGACCCTGGAATGTTCCCGTGC CTGCACCATAGCCAGAATCTGCTGAGGGCCGTGTCGAATA TGTTACAGAAAGCTCGGCAGACCCTCGAGTTTTACCCCTGC ACCTCGGAAGAGATCGATCACGAGGACATCACTAAGGACA AGACCTCCACAGTGGAAGCGTGCCTGCCACTCGAACTGAC CAAGAACGAATCCTGCCTGAACTCCCGGGAAACCTCGTTC ATCACTAACGGCTCTTGCTTGGCGTCGCGCAAGACCTCATT CATGATGGCCCTTTGCCTCTCATCCATCTACGAAGATCTGA AAATGTACCAGGTCGAGTTCAAGACCATGAACGCTAAGTT GCTGATGGATCCAAAGCGCCAGATTTTCCTGGACCAGAAC ATGCTGGCCGTGATCGACGAGCTCATGCAGGCCTTGAACTT TAACAGCGAAACCGTGCCGCAGAAGAGTAGCCTCGAGGAA CCCGACTTCTACAAGACTAAGATTAAGCTGTGCATTCTCCT GCACGCCTTCCGGATTAGGGCCGTCACCATCGACCGCGTCA TGTCATACCTGAACGCATCCGGTGGCGGTGGAAGCCACCA TCACCACCACCAT |
| 70 | hIL12-ABP10-His | ATCTGGGAGCTGAAGAAGGACGTCTATGTGGTGGAACTTG ACTGGTACCCGGATGCCCCTGGAGAAATGGTCGTGCTGAC GTGCGACACCCCCGAAGAGGACGGCATTACTTGGACCCTG GACCAGTCCTCCGAAGTGCTCGGGAGCGGAAAGACCCTGA CCATCCAAGTCAAGGAATTCGGCGATGCCGGACAGTACAC CTGTCACAAGGGCGGAGAAGTGCTGAGCCACTCCCTGCTG CTGCTGCACAAGAAGGAAGATGGCATCTGGTCCACCGACA TCCTGAAAGACCAGAAGGAGCCGAAGAACAAGACTTTCCT CCGCTGCGAAGCCAAGAACTACTCCGGCCGGTTTACTTGTT GGTGGCTGACCACCATATCAACGGATCTCACCTTCTCCGTG AAATCGTCCCGGGGAAGCTCGGACCCCCAAGGAGTGACTT GCGGGGCAGCGACCTTGTCCGCCGAACGCGTCAGAGGGGA CAACAAGGAATACGAGTACTCCGTGGAGTGCCAAGAGGAC TCCGCATGTCCGGCTGCTGAAGAGTCGCTGCCGATTGAGGT CATGGTGGACGCCGTGCACAAGCTGAAATACGAGAATTAC ACCTCCTCCTTCTTCATCCGGGACATCATTAAGCCCGACCC TCCTAAGAACCTCCAGCTGAAGCCTCTGAAGAACTCCCGCC AAGTGGAAGTGTCCTGGGAGTACCCCGACACTTGGTCCAC CCCCCATTCGTATTTCTCACTGACTTTCTGCGTCCAAGTGCA GGGGAAATCCAAGAGAGAGAAGAAAGACCGGGTGTTCAC TGATAAGACTAGCGCGACCGTGATCTGTAGAAAGAACGCG TCTATTTCCGTGCGCGCCCAAGATCGCTACTACTCCTCCTC GTGGTCCGAATGGGCCTCAGTGCCATGTAGCGGTGGTGGC GGATCCGGTGGAGGCGGATCGGGTGGAGGGGGATCCCGGA ACCTCCCGGTGGCCACTCCTGACCCTGGAATGTTCCCGTGC CTGCACCATAGCCAGAATCTGCTGAGGGCCGTGTCGAATA TGTTACAGAAAGCTCGGCAGACCCTCGAGTTTTACCCCTGC ACCTCGGAAGAGATCGATCACGAGGACATCACTAAGGACA AGACCTCCACAGTGGAAGCGTGCCTGCCACTCGAACTGAC CAAGAACGAATCCTGCCTGAACTCCCGGGAAACCTCGTTC ATCACTAACGGCTCTTGCTTGGCGTCGCGCAAGACCTCATT CATGATGGCCCTTTGCCTCTCATCCATCTACGAAGATCTGA AAATGTACCAGGTCGAGTTCAAGACCATGAACGCTAAGTT GCTGATGGATCCAAAGCGCCAGATTTTCCTGGACCAGAAC ATGCTGGCCGTGATCGACGAGCTCATGCAGGCCTTGAACTT TAACAGCGAAACCGTGCCGCAGAAGAGTAGCCTCGAGGAA CCCGACTTCTACAAGACTAAGATTAAGCTGTGCATTCTCCT GCACGCCTTCCGGATTAGGGCCGTCACCATCGACCGCGTCA TGTCATACCTGAACGCATCCGGGGGTGGAGGAAGCTTCCA ATCGGAGGAGCAGCAGGGAGGAGGATCGGGCGGATCCGA GGAAGGCGGAATGGAGAGCGAAGAAAGCAACGGCGGTGG TTCCGGAGGATCCGAAGAGGGTGGCGGTGGAAGCCACCAT CACCACCACCAT |
| 71 | hIL12-ABP20-His | ATCTGGGAGCTGAAGAAGGACGTCTATGTGGTGGAACTTG ACTGGTACCCGGATGCCCCTGGAGAAATGGTCGTGCTGAC GTGCGACACCCCCGAAGAGGACGGCATTACTTGGACCCTG GACCAGTCCTCCGAAGTGCTCGGGAGCGGAAAGACCCTGA CCATCCAAGTCAAGGAATTCGGCGATGCCGGACAGTACAC |

TABLE 2-continued

Exemplary Nucleotide Sequences

| SEQ ID NO: | Polypeptide | Sequence |
|---|---|---|
| | | CTGTCACAAGGGCGGAGAAGTGCTGAGCCACTCCCTGCTG CTGCTGCACAAGAAGGAAGATGGCATCTGGTCCACCGACA TCCTGAAAGACCAGAAGGAGCCGAAGAACAAGACTTTCCT CCGCTGCGAAGCCAAGAACTACTCCGGCCGGTTTACTTGTT GGTGGCTGACCACCATATCAACGGATCTCACCTTCTCCGTG AAATCGTCCCGGGGAAGCTCGGACCCCCAAGGAGTGACTT GCGGGGCAGCGACCTTGTCCGCCGAACGCGTCAGAGGGGA CAACAAGGAATACGAGTACTCCGTGGAGTGCCAAGAGGAC TCCGCATGTCCGGCTGCTGAAGAGTCGCTGCCGATTGAGGT CATGGTGGACGCCGTGCACAAGCTGAAATACGAGAATTAC ACCTCCTCCTTCTTCATCCGGGACATCATTAAGCCCGACCC TCCTAAGAACCTCCAGCTGAAGCCTCTGAAGAACTCCCGCC AAGTGGAAGTGTCCTGGGAGTACCCCGACACTTGGTCCAC CCCCCATTCGTATTTCTCACTGACTTTCTGCGTCCAAGTGCA GGGGAAATCCAAGAGAGAGAAGAAAGACCGGGTGTTCAC TGATAAGACTAGCGCGACCGTGATCTGTAGAAAGAACGCG TCTATTTCCGTGCGCGCCCAAGATCGCTACTACTCCTCCTC GTGGTCCGAATGGGCCTCAGTGCCATGTAGCGGTGGTGGC GGATCCGGTGGAGGCGGATCGGGTGGAGGGGGATCCCGGA ACCTCCCGGTGGCCACTCCTGACCCTGGAATGTTCCCGTGC CTGCACCATAGCCAGAATCTGCTGAGGGCCGTGTCGAATA TGTTACAGAAAGCTCGGCAGACCCTCGAGTTTTACCCCTGC ACCTCGGAAGAGATCGATCACGAGGACATCACTAAGGACA AGACCTCCACAGTGGAAGCGTGCCTGCCACTCGAACTGAC CAAGAACGAATCCTGCCTGAACTCCCGGGAAACCTCGTTC ATCACTAACGGCTCTTGCTTGGCGTCGCGCAAGACCTCATT CATGATGGCCCTTTGCCTCTCATCCATCTACGAAGATCTGA AAATGTACCAGGTCGAGTTCAAGACCATGAACGCTAAGTT GCTGATGGATCCAAAGCGCCAGATTTTCCTGGACCAGAAC ATGCTGGCCGTGATCGACGAGCTCATGCAGGCCTTGAACTT TAACAGCGAAACCGTGCCGCAGAAGAGTAGCCTCGAGGAA CCCGACTTCTACAAGACTAAGATTAAGCTGTGCATTCTCCT GCACGCCTTCCGGATTAGGGCCGTCACCATCGACCGCGTCA TGTCATACCTGAACGCATCCGGAGGCGGAGGGTCGGGGGG CGGGGGATCCGAAGAGTCCGAAGAATCCGAGGAATCCGAA GAAGGTGGCGGTGGAAGCCACCATCACCACCACCAT |
| 72 | hL12-ABP20-G4-His | ATCTGGGAGCTGAAGAAGGACGTCTATGTGGTGGAACTTG ACTGGTACCCGGATGCCCCTGGAGAAATGGTCGTGCTGAC GTGCGACACCCCCGAAGAGGACGGCATTACTTGGACCCTG GACCAGTCCTCCGAAGTGCTCGGGAGCGGAAAGACCCTGA CCATCCAAGTCAAGGAATTCGGCGATGCCGGACAGTACAC CTGTCACAAGGGCGGAGAAGTGCTGAGCCACTCCCTGCTG CTGCTGCACAAGAAGGAAGATGGCATCTGGTCCACCGACA TCCTGAAAGACCAGAAGGAGCCGAAGAACAAGACTTTCCT CCGCTGCGAAGCCAAGAACTACTCCGGCCGGTTTACTTGTT GGTGGCTGACCACCATATCAACGGATCTCACCTTCTCCGTG AAATCGTCCCGGGGAAGCTCGGACCCCCAAGGAGTGACTT GCGGGGCAGCGACCTTGTCCGCCGAACGCGTCAGAGGGGA CAACAAGGAATACGAGTACTCCGTGGAGTGCCAAGAGGAC TCCGCATGTCCGGCTGCTGAAGAGTCGCTGCCGATTGAGGT CATGGTGGACGCCGTGCACAAGCTGAAATACGAGAATTAC ACCTCCTCCTTCTTCATCCGGGACATCATTAAGCCCGACCC TCCTAAGAACCTCCAGCTGAAGCCTCTGAAGAACTCCCGCC AAGTGGAAGTGTCCTGGGAGTACCCCGACACTTGGTCCAC CCCCCATTCGTATTTCTCACTGACTTTCTGCGTCCAAGTGCA GGGGAAATCCAAGAGAGAGAAGAAAGACCGGGTGTTCAC TGATAAGACTAGCGCGACCGTGATCTGTAGAAAGAACGCG TCTATTTCCGTGCGCGCCCAAGATCGCTACTACTCCTCCTC GTGGTCCGAATGGGCCTCAGTGCCATGTAGCGGTGGTGGC GGATCCGGTGGAGGCGGATCGGGTGGAGGGGGATCCCGGA ACCTCCCGGTGGCCACTCCTGACCCTGGAATGTTCCCGTGC CTGCACCATAGCCAGAATCTGCTGAGGGCCGTGTCGAATA TGTTACAGAAAGCTCGGCAGACCCTCGAGTTTTACCCCTGC ACCTCGGAAGAGATCGATCACGAGGACATCACTAAGGACA AGACCTCCACAGTGGAAGCGTGCCTGCCACTCGAACTGAC CAAGAACGAATCCTGCCTGAACTCCCGGGAAACCTCGTTC ATCACTAACGGCTCTTGCTTGGCGTCGCGCAAGACCTCATT CATGATGGCCCTTTGCCTCTCATCCATCTACGAAGATCTGA AAATGTACCAGGTCGAGTTCAAGACCATGAACGCTAAGTT GCTGATGGATCCAAAGCGCCAGATTTTCCTGGACCAGAAC ATGCTGGCCGTGATCGACGAGCTCATGCAGGCCTTGAACTT TAACAGCGAAACCGTGCCGCAGAAGAGTAGCCTCGAGGAA CCCGACTTCTACAAGACTAAGATTAAGCTGTGCATTCTCCT |

TABLE 2-continued

Exemplary Nucleotide Sequences

| SEQ ID NO: | Polypeptide | Sequence |
|---|---|---|
| | | GCACGCCTTCCGGATTAGGGCCGTCACCATCGACCGCGTCA |
| | | TGTCATACCTGAACGCATCCGGGGGAGGAGGATCGGGAGG |
| | | TGGTGGCAGCGAAGAGGGCGGAGGGGGTTCAGAGGAAGG |
| | | CGGTGGAGGGTCCGAAGAGGGTGGTGGTGGGTCCGAGGAG |
| | | GGTGGCGGTGGAAGCCACCATCACCACCACCAT |
| 73 | hIL12- | ATCTGGGAGCTGAAGAAGGACGTCTATGTGGTGGAACTTG |
| | ABP20-G4- | ACTGGTACCCGGATGCCCCTGGAGAAATGGTCGTGCTGAC |
| | His | GTGCGACACCCCCGAAGAGGACGGCATTACTTGGACCCTG |
| | | GACCAGTCCTCCGAAGTGCTCGGGAGCGGAAAGACCCTGA |
| | | CCATCCAAGTCAAGGAATTCGGCGATGCCGGACAGTACAC |
| | | CTGTCACAAGGGCGGAGAAGTGCTGAGCCACTCCCTGCTG |
| | | CTGCTGCACAAGAAGGAAGATGGCATCTGGTCCACCGACA |
| | | TCCTGAAAGACCAGAAGGAGCCGAAGAACAAGACTTTCCT |
| | | CCGCTGCGAAGCCAAGAACTACTCCGGCCGGTTTACTTGTT |
| | | GGTGGCTGACCACCATATCAACGGATCTCACCTTCTCCGTG |
| | | AAATCGTCCCGGGGAAGCTCGGACCCCCAAGGAGTGACTT |
| | | GCGGGGCAGCGACCTTGTCCGCCGAACGCGTCAGAGGGGA |
| | | CAACAAGGAATACGAGTACTCCGTGGAGTGCCAAGAGGAC |
| | | TCCGCATGTCCGGCTGCTGAAGAGTCGCTGCCGATTGAGGT |
| | | CATGGTGGACGCCGTGCACAAGCTGAAATACGAGAATTAC |
| | | ACCTCCTCCTTCTTCATCCGGGACATCATTAAGCCCGACCC |
| | | TCCTAAGAACCTCCAGCTGAAGCCTCTGAAGAACTCCCGCC |
| | | AAGTGGAAGTGTCCTGGGAGTACCCCGACACTTGGTCCAC |
| | | CCCCCATTCGTATTTCTCACTGACTTTCTGCGTCCAAGTGCA |
| | | GGGGAAATCCAAGAGAGAGAAGAAAGACCGGGTGTTCAC |
| | | TGATAAGACTAGCGCGACCGTGATCTGTAGAAAGAACGCG |
| | | TCTATTTCCGTGCGCGCCCAAGATCGCTACTACTCCTCCTC |
| | | GTGGTCCGAATGGGCCTCAGTGCCATGTAGCGGTGGTGGC |
| | | GGATCCGGTGGAGGCGGATCGGGTGGAGGGGGATCCCGGA |
| | | ACCTCCCGGTGGCCACTCCTGACCCTGGAATGTTCCCGTGC |
| | | CTGCACCATAGCCAGAATCTGCTGAGGGCCGTGTCGAATA |
| | | TGTTACAGAAAGCTCGGCAGACCCTCGAGTTTTACCCCTGC |
| | | ACCTCGGAAGAGATCGATCACGAGGACATCACTAAGGACA |
| | | AGACCTCCACAGTGGAAGCGTGCCTGCCACTCGAACTGAC |
| | | CAAGAACGAATCCTGCCTGAACTCCCGGGAAACCTCGTTC |
| | | ATCACTAACGGCTCTTGCTTGGCGTCGCGCAAGACCTCATT |
| | | CATGATGGCCCTTTGCCTCTCATCCATCTACGAAGATCTGA |
| | | AAATGTACCAGGTCGAGTTCAAGACCATGAACGCTAAGTT |
| | | GCTGATGGATCCAAAGCGCCAGATTTTCCTGGACCAGAAC |
| | | ATGCTGGCCGTGATCGACGAGCTCATGCAGGCCTTGAACTT |
| | | TAACAGCGAAACCGTGCCGCAGAAGAGTAGCCTCGAGGAA |
| | | CCCGACTTCTACAAGACTAAGATTAAGCTGTGCATTCTCCT |
| | | GCACGCCTTCCGGATTAGGGCCGTCACCATCGACCGCGTCA |
| | | TGTCATACCTGAACGCATCCGGGGGAGGAGGATCGGGAGG |
| | | TGGTGGCAGCGAAGAGGGCGGAGGGGGTTCAGAGGAAGG |
| | | CGGTGGAGGGTCCGAAGAGGGTGGTGGTGGGTCCGAGGAG |
| | | GGTGGCGGTGGAAGCCACCATCACCACCACCAT |
| 74 | hIL12- | ATCTGGGAACTGAAGAAGGACGTCTACGTGGTGGAACTGG |
| | ABP20-G4- | ATTGGTACCCAGACGCCCCTGGAGAAATGGTGGTGCTCAC |
| | 8x-GE | CTGTGATACCCCCGAAGAGGACGGGATTACTTGGACCCTG |
| | (mature | GATCAGTCATCCGAAGTGCTGGGATCCGGAAAGACCCTGA |
| | polypeptide) | CGATCCAGGTCAAGGAATTCGGGGACGCGGGACAGTACAC |
| | | TTGCCATAAGGGCGGCGAAGTGCTGTCCCACTCCTTGCTCC |
| | | TGCTCCACAAGAAAGAAGATGGAATTTGGAGCACCGACAT |
| | | CCTGAAGGACCAGAAAGAGCCGAAGAACAAGACCTTCCTG |
| | | CGCTGCGAGGCCAAGAACTACAGCGGACGCTTTACCTGTT |
| | | GGTGGCTGACCACTATCTCCACCGACCTGACCTTCTCGGTC |
| | | AAGTCCTCGCGCGGGAGCAGCGATCCTCAGGGAGTGACTT |
| | | GCGGTGCCGCGACTCTGTCGGCCGAAAGGGTCCGGGGCGA |
| | | CAACAAGGAGTACGAGTACTCAGTCGAGTGCCAGGAGGAC |
| | | AGCGCATGTCCGGCCGCTGAGGAATCCCTGCCTATTGAAGT |
| | | CATGGTGGACGCCGTCCACAAGCTGAAATACGAGAACTAC |
| | | ACCTCCTCTTTCTTTATCCGGGATATCATCAAGCCCGACCC |
| | | GCCTAAGAACCTTCAACTGAAGCCACTGAAGAACAGCAGA |
| | | CAAGTGGAGGTGTCCTGGGAGTACCCGGATACTTGGTCCA |
| | | CTCCGCACTCCTATTTCTCGCTCACCTTCTGCGTCCAAGTGC |
| | | AGGGAAAGTCGAAACGGGAGAAGAAGGACAGAGTGTTCA |
| | | CTGACAAGACCAGCGCAACTGTGATCTGTCGGAAGAACGC |
| | | CTCCATTTCCGTGCGCGCCCAGGACCGGTACTATTCCTCAT |
| | | CCTGGTCGGAGTGGGCCTCAGTGCCCTGCAGCGGCGGGGG |
| | | CGGTTCGGGTGGTGGCGGCAGCGGGGGCGGAGGGTCCCGG |
| | | AATCTGCCGGTGGCGACGCCCGACCCCGGAATGTTCCCGT |

TABLE 2-continued

| Exemplary Nucleotide Sequences | | |
|---|---|---|
| SEQ ID NO: | Polypeptide | Sequence |
| | | GCCTGCACCATAGCCAGAACTTGCTCCGCGCGGTGTCTAAC<br>ATGCTGCAGAAGGCCCGGCAGACCCTGGAATTCTACCCCT<br>GCACTAGTGAAGAGATCGACCATGAAGATATTACCAAAGA<br>CAAGACTTCCACCGTGGAAGCGTGCCTCCCACTGGAACTG<br>ACCAAGAATGAGTCCTGCCTGAATTCAAGGGAAACTTCGT<br>TCATTACCAACGGTTCCTGCCTGGCCTCGAGAAAGACCTCC<br>TTCATGATGGCTCTCTGCCTCTCCTCAATCTACGAAGATCT<br>CAAAATGTACCAAGTGGAGTTCAAGACCATGAACGCTAAG<br>CTGCTGATGGACCCGAAGCGGCAGATTTTCCTCGACCAAA<br>ACATGTTGGCCGTGATCGACGAGTTGATGCAGGCCCTTAAC<br>TTCAACTCCGAAACAGTGCCTCAGAAGTCGAGCCTCGAGG<br>AACCCGACTTCTACAAGACTAAGATCAAGCTGTGCATCCTG<br>CTGCACGCATTTCGAATTCGGGCCGTGACCATCGACCGCGT<br>GATGAGCTACCTGAACGCATCCGGGGGCGGCGGGGAAGGA<br>GGAGGCGGCTCAGAGGAGGGAGGAGGAGGCAGCGAGGAA<br>GGAGGCGGAGGAAGCGAAGAAGGAGGGGGAGGCTCAGAA<br>GAGGGAGGGGGTGGATCCGAGGAAGGCGGAGGAGGATCC<br>GAAGAGGGCGGTGGTGGATCGGAGGAAGGGGGAGGCGGT<br>TCTGAGGAGGGTGGAGGAGGCTCC |
| 75 | Signal polypeptide | ATGTATAGAATGCAGCTTCTGTCCTGTATCGCCCTCTCCCT<br>CGCCCTTGTGACCAACTCC |
| 76 | hL12-ABP20-G4-8x-GE w/ signal polypeptide | ATGTATAGAATGCAGCTTCTGTCCTGTATCGCCCTCTCCCT<br>CGCCCTTGTGACCAACTCCATCTGGGAACTGAAGAAGGAC<br>GTCTACGTGGTGGAACTGGATTGGTACCCAGACGCCCCTG<br>GAGAAATGGTGGTGCTCACCTGTGATACCCCCGAAGAGGA<br>CGGGATTACTTGGACCCTGGATCAGTCATCCGAAGTGCTGG<br>GATCCGGAAAGACCCTGACGATCCAGGTCAAGGAATTCGG<br>GGACGCGGGACAGTACACTTGCCATAAGGGCGGCGAAGTG<br>CTGTCCCACTCCTTGCTCCTGCTCCACAAGAAAGAAGATGG<br>AATTTGGAGCACCGACATCCTGAAGGACCAGAAAGAGCCG<br>AAGAACAAGACCTTCCTGCGCTGCGAGGCCAAGAACTACA<br>GCGGACGCTTTACCTGTTGGTGGCTGACCACTATCTCCACC<br>GACCTGACCTTCTCGGTCAAGTCCTCGCGCGGGAGCAGCG<br>ATCCTCAGGGAGTGACTTGCGGTGCCGCGACTCTGTCGGCC<br>GAAAGGGTCCGGGGCGACAACAAGGAGTACGAGTACTCA<br>GTCGAGTGCCAGGAGGACAGCGCATGTCCGGCCGCTGAGG<br>AATCCCTGCCTATTGAAGTCATGGTGGACGCCGTCCACAAG<br>CTGAAATACGAGAACTACACCTCCTCTTTCTTTATCCGGGA<br>TATCATCAAGCCCGACCCGCCTAAGAACCTTCAACTGAAG<br>CCACTGAAGAACAGCAGACAAGTGGAGGTGTCCTGGGAGT<br>ACCCGGATACTTGGTCCACTCCGCACTCCTATTTCTCGCTC<br>ACCTTCTGCGTCCAAGTGCAGGGAAAGTCGAAACGGGAGA<br>AGAAGGACAGAGTGTTCACTGACAAGACCAGCGCAACTGT<br>GATCTGTCGGAAGAACGCCTCCATTTCCGTGCGCGCCCAGG<br>ACCGGTACTATTCCTCATCCTGGTCGGAGTGGGCCTCAGTG<br>CCCTGCAGCGGCGGGGGCGGTTCGGGTGGTGGCGGCAGCG<br>GGGGCGGAGGGTCCCGGAATCTGCCGGTGGCGACGCCCGA<br>CCCCGGAATGTTCCCGTGCCTGCACCATAGCCAGAACTTGC<br>TCCGCGCGGTGTCTAACATGCTGCAGAAGGCCCGGCAGAC<br>CCTGGAATTCTACCCCTGCACTAGTGAAGAGATCGACCATG<br>AAGATATTACCAAAGACAAGACTTCCACCGTGGAAGCGTG<br>CCTCCCACTGGAACTGACCAAGAATGAGTCCTGCCTGAATT<br>CAAGGGAAACTTCGTTCATTACCAACGGTTCCTGCCTGGCC<br>TCGAGAAAGACCTCCTTCATGATGGCTCTCTGCCTCTCCTC<br>AATCTACGAAGATCTCAAAATGTACCAAGTGGAGTTCAAG<br>ACCATGAACGCTAAGCTGCTGATGGACCCGAAGCGGCAGA<br>TTTTCCTCGACCAAAACATGTTGGCCGTGATCGACGAGTTG<br>ATGCAGGCCCTTAACTTCAACTCCGAAACAGTGCCTCAGA<br>AGTCGAGCCTCGAGGAACCCGACTTCTACAAGACTAAGAT<br>CAAGCTGTGCATCCTGCTGCACGCATTTCGAATTCGGGCCG<br>TGACCATCGACCGCGTGATGAGCTACCTGAACGCATCCGG<br>GGGCGGCGGGGAAGGAGGAGGCGGCTCAGAGGAGGGAGG<br>AGGAGGCAGCGAGGAAGGAGGCGGAGGAAGCGAAGAAGG<br>AGGGGGAGGCTCAGAAGAGGGAGGGGGTGGATCCGAGGA<br>AGGCGGAGGAGGATCCGAAGAGGGCGGTGGTGGATCGGA<br>GGAAGGGGGAGGCGGTTCTGAGGAGGGTGGAGGAGGCTC<br>C |
| 77 | hL12-ABP10 (mature polypeptide) | ATCTGGGAACTGAAGAAGGACGTCTACGTGGTGGAACTGG<br>ATTGGTACCCAGACGCCCCTGGAGAAATGGTGGTGCTCAC<br>CTGTGATACCCCCGAAGAGGACGGGATTACTTGGACCCTG<br>GATCAGTCATCCGAAGTGCTGGGATCCGGAAAGACCCTGA |

TABLE 2-continued

| Exemplary Nucleotide Sequences | | |
|---|---|---|
| SEQ ID NO: | Polypeptide | Sequence |
| | | CGATCCAGGTCAAGGAATTCGGGGACGCGGGACAGTACAC TTGCCATAAGGGCGGCGAAGTGCTGTCCCACTCCTTGCTCC TGCTCCACAAGAAAGAAGATGGAATTTGGAGCACCGACAT CCTGAAGGACCAGAAAGAGCCGAAGAACAAGACCTTCCTG CGCTGCGAGGCCAAGAACTACAGCGGACGCTTTACCTGTT GGTGGCTGACCACTATCTCCACCGACCTGACCTTCTCGGTC AAGTCCTCGCGCGGGAGCAGCGATCCTCAGGGAGTGACTT GCGGTGCCGCGACTCTGTCGGCCGAAAGGGTCCGGGGCGA CAACAAGGAGTACGAGTACTCAGTCGAGTGCCAGGAGGAC AGCGCATGTCCGGCCGCTGAGGAATCCCTGCCTATTGAAGT CATGGTGGACGCCGTCCACAAGCTGAAATACGAGAACTAC ACCTCCTCTTTCTTTATCCGGGATATCATCAAGCCCGACCC GCCTAAGAACCTTCAACTGAAGCCACTGAAGAACAGCAGA CAAGTGGAGGTGTCCTGGGAGTACCCGGATACTTGGTCCA CTCCGCACTCCTATTTCTCGCTCACCTTCTGCGTCCAAGTGC AGGGAAAGTCGAAACGGGAGAAGAAGGACAGAGTGTTCA CTGACAAGACCAGCGCAACTGTGATCTGTCGGAAGAACGC CTCCATTTCCGTGCGCGCCCAGGACCGGTACTATTCCTCAT CCTGGTCGGAGTGGGCCTCAGTGCCCTGCAGCGGCGGGGG CGGTTCGGGTGGTGGCGGCAGCGGGGGCGGAGGGTCCCGG AATCTGCCGGTGGCGACGCCCGACCCCGGAATGTTCCCGT GCCTGCACCATAGCCAGAACTTGCTCCGCGCGGTGTCTAAC ATGCTGCAGAAGGCCCGGCAGACCCTGGAATTCTACCCCT GCACTAGTGAAGAGATCGACCATGAAGATATTACCAAAGA CAAGACTTCCACCGTGGAAGCGTGCCTCCCACTGGAACTG ACCAAGAATGAGTCCTGCCTGAATTCAAGGGAAACTTCGT TCATTACCAACGGTTCCTGCCTGGCCTCGAGAAAGACCTCC TTCATGATGGCTCTCTGCCTCTCCTCAATCTACGAAGATCT CAAAATGTACCAAGTGGAGTTCAAGACCATGAACGCTAAG CTGCTGATGGACCCGAAGCGGCAGATTTTCCTCGACCAAA ACATGTTGGCCGTGATCGACGAGTTGATGCAGGCCCTTAAC TTCAACTCCGAAACAGTGCCTCAGAAGTCGAGCCTCGAGG AACCCGACTTCTACAAGACTAAGATCAAGCTGTGCATCCTG CTGCACGCATTTCGAATTCGGGCCGTGACCATCGACCGCGT GATGAGCTACCTGAACGCATCCGGGGGCGGCGGGAGCTTC CAGTCCGAGGAACAACAGGGAGGGGGCTCCGGCGGATCA GAGGAGGGAGGCATGGAATCAGAAGAGAGCAACGGCGGC GGTTCCGGAGGATCGGAAGAGGGCGGCGGCGGATCG |
| 78 | hIL12-ABP10 w/ signal polypeptide | ATGTATAGAATGCAGCTTCTGTCCTGTATCGCCCTCTCCCT CGCCCTTGTGACCAACTCCATCTGGGAACTGAAGAAGGAC GTCTACGTGGTGGAACTGGATTGGTACCCAGACGCCCCTG GAGAAATGGTGGTGCTCACCTGTGATACCCCCGAAGAGGA CGGGATTACTTGGACCCTGGATCAGTCATCCGAAGTGCTGG GATCCGGAAAGACCCTGACGATCCAGGTCAAGGAATTCGG GGACGCGGGACAGTACACTTGCCATAAGGGCGGCGAAGTG CTGTCCCACTCCTTGCTCCTGCTCCACAAGAAAGAAGATGG AATTTGGAGCACCGACATCCTGAAGGACCAGAAAGAGCCG AAGAACAAGACCTTCCTGCGCTGCGAGGCCAAGAACTACA GCGGACGCTTTACCTGTTGGTGGCTGACCACTATCTCCACC GACCTGACCTTCTCGGTCAAGTCCTCGCGCGGGAGCAGCG ATCCTCAGGGAGTGACTTGCGGTGCCGCGACTCTGTCGGCC GAAAGGGTCCGGGGCGACAACAAGGAGTACGAGTACTCA GTCGAGTGCCAGGAGGACAGCGCATGTCCGGCCGCTGAGG AATCCCTGCCTATTGAAGTCATGGTGGACGCCGTCCACAAG CTGAAATACGAGAACTACACCTCCTCTTTCTTTATCCGGGA TATCATCAAGCCCGACCCGCCTAAGAACCTTCAACTGAAG CCACTGAAGAACAGCAGACAAGTGGAGGTGTCCTGGGAGT ACCCGGATACTTGGTCCACTCCGCACTCCTATTTCTCGCTC ACCTTCTGCGTCCAAGTGCAGGGAAAGTCGAAACGGGAGA AGAAGGACAGAGTGTTCACTGACAAGACCAGCGCAACTGT GATCTGTCGGAAGAACGCCTCCATTTCCGTGCGCGCCCAGG ACCGGTACTATTCCTCATCCTGGTCGGAGTGGGCCTCAGTG CCCTGCAGCGGCGGGGGCGGTTCGGGTGGTGGCGGCAGCG GGGGCGGAGGGTCCCGGAATCTGCCGGTGGCGACGCCCGA CCCCGGAATGTTCCCGTGCCTGCACCATAGCCAGAACTTGC TCCGCGCGGTGTCTAACATGCTGCAGAAGGCCCGGCAGAC CCTGGAATTCTACCCCTGCACTAGTGAAGAGATCGACCATG AAGATATTACCAAAGACAAGACTTCCACCGTGGAAGCGTG CCTCCCACTGGAACTGACCAAGAATGAGTCCTGCCTGAATT CAAGGGAAACTTCGTTCATTACCAACGGTTCCTGCCTGGCC TCGAGAAAGACCTCCTTCATGATGGCTCTCTGCCTCTCCTC AATCTACGAAGATCTCAAAATGTACCAAGTGGAGTTCAAG ACCATGAACGCTAAGCTGCTGATGGACCCGAAGCGGCAGA |

TABLE 2-continued

Exemplary Nucleotide Sequences

| SEQ ID NO: | Polypeptide | Sequence |
|---|---|---|
| | | TTTTCCTCGACCAAAACATGTTGGCCGTGATCGACGAGTTG<br>ATGCAGGCCCTTAACTTCAACTCCGAAACAGTGCCTCAGA<br>AGTCGAGCCTCGAGGAACCCGACTTCTACAAGACTAAGAT<br>CAAGCTGTGCATCCTGCTGCACGCATTTCGAATTCGGGCCG<br>TGACCATCGACCGCGTGATGAGCTACCTGAACGCATCCGG<br>GGGCGGCGGGAGCTTCCAGTCCGAGGAACAACAGGGAGG<br>GGGCTCCGGCGGATCAGAGGAGGGAGGCATGGAATCAGA<br>AGAGAGCAACGGCGGCGGTTCCGGAGGATCGGAAGAGGG<br>CGGCGGCGGATCG |
| 118 | His-tagged canine IL12-ABP expressed and tested (mature sequence) | ATCTGGGAACTGGAGAAGGATGTGTACGTGGTCGAGCTCG<br>ATTGGCATCCTGATGCGCCTGGCGAAATGGTGGTGCTGACT<br>TGCCACACTCCCGAGGAGGACGACATTACCTGGACCTCGG<br>CCCAGTCCTCCGAAGTCCTGGGAAGCGGGAAAACTCTGAC<br>AATTCAGGTCAAAGAGTTCGGCGACGCAGGACAGTACACC<br>TGTCACAAGGGTGGAAAGGTCCTGAGCAGATCGCTGTTGC<br>TGATCCACAAGAAGGAAGATGGCATCTGGTCCACGGACAT<br>CCTGAAGGAGCAGAAGGAATCCAAGAACAAGATCTTTCTT<br>AAGTGCGAAGCCAAGAACTACTCGGGCCGGTTCACCTGTT<br>GGTGGCTTACTGCCATATCAACCGACCTGAAGTTTTCCGTG<br>AAATCGAGCCGCGGCTTCTCGGACCCTCAAGGAGTGACTT<br>GCGGAGCCGTGACCCTCTCCGCCGAGAGAGTGCGGGTCGA<br>CAACCGGGACTACAAGAAGTACACCGTGGAGTGCCAGGAA<br>GGATCCGCCTGTCCAAGCGCCGAGGAAAGCCTGCCGATTG<br>AGGTGGTCGTCGATGCCATCCACAAGCTGAAATACGAGAA<br>TTACACTTCGTCCTTCTTCATCCGGGACATCATCAAGCCCG<br>ATCCGCCAACCAACTTGCAACTCAAGCCGCTGAAGAATTC<br>GCGCCACGTGGAGGTGTCCTGGGAGTACCCCGATACGTGG<br>TCCACCCCGCATAGCTATTTCTCCCTCACTTTCTGCGTGCAA<br>GCCCAGGGAAAGAACAACCGCGAGAAGAAGGACCGGCTG<br>TGCGTGGATAAGACCAGCGCGAAAGTGGTCTGCCACAAGG<br>ACGCGAAGATCAGAGTGCAGGCTCGGGACAGATATTACAG<br>CAGCTCCTGGTCCGACTGGGCCTCCGTGTCCTGTTCCGGCG<br>GAGGAGGATCCGGAGGAGGGGGTTCCGGTGGAGGCGGTTC<br>GAGGTCCCTGCCTACTGCTAGCCCTTCCCCCGGGATTTTCC<br>AGTGCCTGAACCACTCCCAGAACTTGCTGAGGGCCGTGTCC<br>AACACCCTTCAAAAGGCTCGGCAGACCCTGGAACTGTACT<br>CCTGCACTTCCGAGGAAATTGACCACGAAGATATCACCAA<br>GGACAAGACTTCCACCGTGGAGGCCTGTCTGCCCCTGGAA<br>CTTACTATGAACGAGTCATGCCTCGCAAGCCGCGAGATTA<br>GCCTGATTACCAACGGCTCCTGCCTGGCTTCGGGGAAGGC<br>GTCGTTCATGACCGTGCTCTGCCTGTCAAGCATCTACGAGG<br>ACCTGAAAATGTACCAGATGGAATTCAAGGCCATGAACGC<br>CAAGCTCCTGATGGACCCGAAGAGGCAGATCTTCCTGGAC<br>CAAAACATGCTGACTGCCATTGACGAACTGCTTCAGGCACT<br>CAACTTCAACTCTGTGACCGTGCCGCAGAAGTCATCGTTGG<br>AGGAACCAGATTTCTACAAGACCAAGATTAAGCTTTGCATT<br>CTCCTCCATGCGTTTCGCATCCGCGCCGTGACCATCGACAG<br>GATGATGTCCTACCTGAATTCAAGCGGAGGAGGCGGAGAA<br>GGAGGCGGTGGAAGCGAAGAGGGCGGTGGAGGCAGTGAA<br>GAAGGAGGGGGCGGATCTGAAGAAGGGGGCGGTGGATCA<br>GAAGAGGGAGGGGGAGGCTCAGAGGAAGGAGGTGGCGGT<br>TCCGAGGAAGGGGGTGGCGGATCAGAGGAGGGAGGCGGA<br>GGATCGGAGGAAGGCGGAGGTGGACACCACCACCATCATC<br>AC |

Fusion Polypeptides

Immunomodulatory Polypeptide

Fusion polypeptides of the present disclosure comprise at least one immunomodulatory polypeptide.

In some embodiments, an immunomodulatory polypeptide is or comprises at least one immune agonist moiety. In some embodiments, an immune agonist moiety is or comprises a functional fragment of a parent (e.g., a wild type) polypeptide; for example, in some embodiments, an immunomodulatory polypeptide is or comprises a functional fragment that is a signaling competent fragment. In some embodiments, an immunomodulatory polypeptide comprises one, two, three, four, five, or six immune agonist moieties.

In some embodiments, a fusion polypeptide comprises two or more immunomodulatory polypeptides (e.g., two or more immune agonist moieties). In some such embodiments, a fusion polypeptide comprises two or more immunomodulatory polypeptides that are the same; in some such embodiments, all immunomodulatory polypeptides in a fusion polypeptide in accordance with the present disclosure are the same. In some such embodiments, a fusion polypeptide comprises two or more immunomodulatory polypeptides that at are different from one another.

Thus, in some embodiments, an immunomodulatory polypeptide may include more than one immune agonist moiety which, in various embodiments, may be the same or different. In some such embodiments, two or more such immune agonist moieties are the same; in some embodiments, all such immune agonist moieties are the same. In some embodiments, an immunomodulatory polypeptide includes two or more immune agonist moieties that differ from one another; in some embodiments, no two such immune agonist moieties are the same.

In some embodiments, a fusion polypeptide comprises two or more immunomodulatory polypeptides (e.g., two or more immune agonist moieties) that include at least two subtypes of immunomodulatory polypeptides (e.g., immune agonist moieties)—for example so that the fusion polypeptide includes at least two of a first subtype and at least two of a second subtype. In some such embodiments, a subset of the same immunomodulatory polypeptides (e.g., immune agonist moieties) equals 1 immunomodulatory polypeptide out of 2 total moieties in the fusion polypeptide, 2 immunomodulatory polypeptides out of 2 total, 1 immunomodulatory polypeptides out of 3, 2 immunomodulatory polypeptides out of 3 total, or 3 immunomodulatory polypeptides out of 3. In some such embodiments, a subset of different immunomodulatory polypeptides equals 1 immune immunomodulatory polypeptides out of 2 total, 2 immunomodulatory polypeptides out of 2 total, 1 immunomodulatory polypeptides out of 3 total, 2 immunomodulatory polypeptides out of 3 total, or 3 immunomodulatory polypeptides out of 3 total.

In some embodiments, an immunomodulatory polypeptide (e.g., an immune agonist moiety) activates or inhibits activity of a cell of the immune system (e.g., is signaling competent). In some embodiments, an immunomodulatory polypeptide (e.g., an immune agonist moiety) is assessed, for example as part of a fusion polypeptide, e.g., as described herein.

For example, in some embodiments, signal competency is characterized in that, when assessed for binding to a particular binding partner, an immune agonist moiety or moieties or functional fragments thereof displays binding comparable to that of a reference standard (e.g., a wild-type polypeptide). For example, in some embodiments, signal competency is characterized in that, when assessed for a biological effect, e.g., in vitro or in vivo, an immune agonist moiety or moieties or functional fragments thereof displays said biological effect comparable to that of a reference standard (e.g., a wild-type polypeptide).

For example, in some embodiments, an immunomodulatory polypeptide (e.g., an immune agonist moiety) is an immune response stimulatory moiety. In some embodiments, a response stimulatory moiety is, for example, but without limitation, a cytokine, a chemokine, an agonistic antibody, an immune checkpoint inhibitor, or a combination thereof.

IL-12

In some embodiments, an immunomodulatory polypeptide comprises an interleukin-12 (IL-12) immunomodulatory polypeptide (e.g., an IL-12 immune agonist moiety).

IL-12 is a pro-inflammatory cytokine that plays an important role in innate and adaptive immunity. Wild type IL-12 is a heterodimeric protein comprising two subunits, p35 (IL-12A; GenBenk GeneID: 3592) and p40 (IL-12B; GenBank GeneID: 3593), connected by disulfide bonds. Binding of IL-12 to the IL-12 receptor complex (IL-12Rβ1/IL-12Rβ2) on T cells and Natural Killer (NK) cells leads to signaling via signal transducer and activator of transcription 4 (STAT4) and subsequent interferon γ (IFN-γ) production and secretion.

IL-12 subunits, IL-12A and IL-12B, can also form heterodimers with other IL-12 family members. For example, IL-12A may also dimerize with Epstein-Barr virus induced gene 3 (EBI3) to form IL-12 family member, IL-35 and IL-12B may dimerize with a p19 monomer, to form IL-12 family member, IL23.

IL-12 plays important roles in the innate and adaptive immune response, and dysregulation of IL-12 has been implicated in a number of disease states. Exemplary such disease states include, but are not limited to, inflammatory bowel disease, psoriasis, diabetes mellitus, multiple sclerosis, rheumatoid arthritis, cancer, lupus erythematosus, primarily biliary cholangitis and Sjögren's syndrome (Ullich et al. *EXCL1 journal* vol. 19 1563-1589. 11 Dec. 2020). Use of IL-12 as a therapeutic modality has been studied extensively, including for treatment of tumors (Nastala C L et al. J Immol. 1994 Aug. 15; Lasek et al. *Cancer immunology immunotherapy: CII* vol. 63; 5 (2014): 419-35).

In some embodiments, an immunomodulatory polypeptide disclosed herein is or comprises an IL-12 immune agonist moiety. In some embodiments, an immunomodulatory polypeptide disclosed herein comprises a plurality of IL-12 immune agonist moieties. In some embodiments, an immunomodulatory polypeptide disclosed herein comprises exactly two IL-12 immune agonist moieties. In some embodiments, two or more IL-12 moieties of a plurality of (e.g., two) IL-12 moieties are the same moiety. In some such embodiments, a plurality (e.g., two) IL-12 moieties are different moieties. In some such embodiments, an IL-12 moiety comprises an IL-12A polypeptide or functional fragment thereof. In some embodiments, an IL-12 moiety comprises an IL-12B polypeptide or functional fragment thereof.

In some embodiments, an IL-12B immune agonist moiety is located N-terminal to an IL-12A immune agonist moiety in an immunomodulatory polypeptide. In some embodiments, an IL-12A immune agonist moiety is located N-terminal to an IL-12B immune agonist moiety in an immunomodulatory polypeptide.

In some embodiments, an immunomodulatory polypeptide comprising a plurality (e.g., two) IL-12 moieties (e.g., IL-12A and/or IL-12B) are linked directly. In some embodiments, an immunomodulatory polypeptide comprising a plurality (e.g., two) IL-12 moieties (e.g., IL-12A and/or IL-12B) are linked via a first linker. Non-limiting examples of linkers are discussed elsewhere herein.

In some embodiments, an immunomodulatory polypeptide disclosed herein comprises an IL-12A and/or IL-12B immune agonist moiety comprising a variant. In some embodiments, an IL-12A and/or IL-12B immune agonist moiety variant comprises a substitution, deletion, addition, and/or insertion of relative to a wild-type IL-12A or IL-12B polynucleotide or amino acid sequence. In some embodiments, an IL-12A and/or IL-12B immune agonist moiety comprises a plurality of variants. In some embodiments, a plurality of variants comprises one or more of a substitution, deletion, addition, and/or insertion relative to a wild-type IL-12A or IL-12B. In some embodiments, a variant comprises a substitute that does not change the amino acid sequence relative to a wild-type IL-12A or IL-12B.

In some embodiments, an IL12 variant comprises a S43X mutation relative to SEQ ID NO: 25, wherein X is any amino acid other than S. In some embodiments, an IL12 variant comprises a S154X mutation relative to SEQ ID NO: 25, wherein X is any amino acid other than S. In some embodiments, an IL12 variant comprises a S168X mutation relative to SEQ ID NO: 25, wherein X is any amino acid other than S. In some embodiments, an IL12 variant comprises a S227X mutation relative to SEQ ID NO: 25, wherein X is any amino acid other than S. In some embodiments, an IL12 variant comprises a S233X mutation relative to SEQ ID NO: 25, wherein X is any amino acid other than S. In some embodiments, an IL12 variant comprises a T364X mutation relative to SEQ ID NO: 25, wherein X is any amino acid other than T. In some embodiments, an IL12 variant comprises a S365X mutation relative to SEQ ID NO: 25, wherein X is any amino acid other than S. In some embodiments, an IL12 variant comprises a S398X mutation relative to SEQ ID NO: 25, wherein X is any amino acid other than S. In some embodiments, an IL12 variant comprises a S365X mutation relative to SEQ ID NO: 25, wherein X is any amino acid other than S. In some embodiments, an IL12 variant comprises a S480X mutation relative to SEQ ID NO: 25, wherein X is any amino acid other than S. In some embodiments, an IL12 variant comprises a S481X mutation relative to SEQ ID NO: 25, wherein X is any amino acid other than S. In some embodiments, an IL12 variant comprises a S365X and S481X mutation relative to SEQ ID NO: 25, wherein X is any amino acid other than S. In some embodiments, an IL12 variant comprises a S365X, S398X, and S481X mutation relative to SEQ ID NO: 25, wherein X is any amino acid other than S. In some embodiments, an IL12 variant comprises any combination of variants, including, for example, those disclosed herein.

In some embodiments, an immunomodulatory polypeptide disclosed herein comprises an IL-12A and/or IL-12B immune agonist moiety that is a functional fragment thereof (e.g., a signaling competent fragment). In some embodiments, an immunomodulatory polypeptide comprises a functional IL-12A fragment. In some embodiments, an immunomodulatory polypeptide comprises a functional IL-12B fragment. In some embodiments, an immunomodulatory polypeptide comprises a full length IL-12A and a functional IL-12B fragment. In some embodiments, an immunomodulatory polypeptide comprises a full length IL-12B and a functional IL-12A fragment.

In some embodiments, a IL-12A or IL-12B fragment comprises or consists of at least 5%, 10,%, 15%, 20%, 25%, 30%, 35%, 40%, 45%, 50%, 55%, 60%, 65%, 70%, 75%, 80%, 85%, 90%, 95%, 99% or more of the monomeric units (e.g., residues) as found in wild-type IL-12A or IL-12B.

Metal-Hydroxide Binding Polypeptide

The Fusion Protein Filing has taught that hydroxyl replacement (e.g., with phosphate groups) can increase a polypeptide's adsorption via ligand exchange with a metal hydroxide (e.g., aluminum hydroxide), and furthermore can improve tumor retention and anti-tumor efficacy of such polypeptide (e.g., specifically of a fusion polypeptide comprising an immunomodulatory polypeptide and a metal-hydroxide-binding polypeptide in which such hydroxyl replacement has occurred.

As discussed above, metal-hydroxide- (e.g., alum-) binding polypeptides were developed that could be fused to an immunomodulatory polypeptide to allow strong binding to aluminum hydroxide. Various immunomodulatory polypeptides fused to ABPs were assessed. It was determined that the ABPs adsorbed to alum in serum and could be used to retain proteins and peptides in tumors. Additionally, polypeptides with greater phosphorylation tended to be retained on alum for much longer in serum conditions. Of the ABPs analyzed, the polypeptide, GGGGSFQSEEQQGGGSGG-SEEGGMESEESNGGGSGGSEEGGGGSHHHHHH, referred to as ABP10, demonstrated the highest phosphorylation with an increase of phosphorylation of 4-6-fold when the protein was expressed with a wild-type (WT) kinase (e.g., WT Fam20C kinase), compared to when the protein was expressed with a mutant kinase (e.g., mutant Fam20C kinase). ABP10 consists of four SXE motifs, a prevalent phosphorylation site motif, separated by short spacer sequences. It was demonstrated immunomodulatory polypeptides (e.g., interleukin-2 and interleukin-12) linked to ABP10 showed improved survival in a mouse model of melanoma compared to the immunomodulatory polypeptides without ABP10.

We have surprisingly found that improved metal-hydroxide binding polypeptides can be developed. Among other things, we have developed metal-hydroxide binding polypeptides characterized by enhanced metal hydroxide (e.g., alum) retention relative to an appropriate reference (e.g., to ABP10). Alternatively or additionally, provided metal-hydroxide binding polypeptides are characterized by improved efficacy, as compared to an appropriate reference (e.g., to ABP10), when administered to a subject with a tumor.

Thus, among other things, the present disclosure identifies the source of a problem with certain metal-hydroxide binding polypeptides and/or fusion polypeptides that include them. For example, the present disclosure appreciates that manufacturing challenges can be associated with certain such polypeptides and/or fusions. Without wishing to be bound by any particular theory, the present disclosure notes that secondary phosphorylation on the polypeptide may contribute to and/or be responsible for certain such manufacturing challenges. Among other things, the present disclosure provides metal-hydroxide-binding polypeptides, and fusion polypeptides that include them, which demonstrate high levels of adsorption to metal hydroxides and also desirable manufacturing characteristics (e.g., one or more of reproducibility, consistency, production of a homogeneously-phosphorylated preparation, etc.).

In some embodiments, a metal-hydroxide binding polypeptide comprises an amino acid sequence that includes a plurality of phosphorylation sites, so that it can adopt phosphorylated and unphosphorylated forms. In some embodiments, a metal-hydroxide binding polypeptide comprises at least one kinase target motif. A target kinase motif comprises an amino acid that is phosphorylated by a kinase. Amino acids that are typically phosphorylated include a hydroxyl, such as serine (Ser, S), threonine (Thr, T), and tyrosine (Tyr, Y) residues. A kinase motif refers to the amino acid sequence immediately N- and/or C-terminal to the amino acid residue capable of being phosphorylated. Without wishing to be bound by any one theory, many kinases comprise structural features that confer specificity such that the kinase phosphorylates a particular amino acid (e.g., serine, threonine, or tyrosine) of a particular kinase target motif.

Kinase target motifs recognized are highly diverse depending on the particular type of kinase. In some embodiments, the present disclosure provides metal-hydroxide binding polypeptides comprising one or more kinase target motifs of a secretory pathway kinase. The secretory pathway, which is the pathway by which a cell secretes proteins and/or other biomolecules into the extracellular space, refers to the endoplasmic reticulum (ER), Golgi apparatus (Golgi), cell membrane, and lysosomal storage compartments as well as the vesicles that travel between them. Secretory pathway kinases are localized throughout the secretory pathway (e.g., at the ER, Golgi, etc.) and function to phosphorylate proteins destined for secretion (Sreelatha et al. Biochimica et biophysica acta vol. 1854,10 Pt B (2015): 1687-93).

In some embodiments, a relevant kinase is a naturally occurring secretory pathway kinase (e.g., is endogenously targeted to the secretory pathway to function). In some embodiments, a secretory pathway kinase comprises a signal sequence that targets the kinase to the secretory pathway. Naturally-occurring human secretory pathway kinases include, for example, four-jointed box kinase 1, Fam20A, Fam20B, Fam20C, vertebrate lonesome kinase (VLK), SGK196, and Fam69A, Fam69B, and Fam69C.

In some embodiments, a relevant kinase is a non-naturally occurring secretory pathway kinase. In some embodiments, a non-naturally occurring kinase is produced by linking a secretory signal peptide to a kinase endogenously localized to a non-secretory pathway cellular compartment.

In some embodiments, a kinase target motif is a target kinase motif of a secretory pathway kinase. In some embodiments, a secretory pathway kinase target kinase motif comprises an S-X-E motif. For example, Fam20C phosphorylates serine and has been shown to phosphorylate kinase targets motif comprising the amino acid sequence Ser-X-Glu (e.g., S-X-E), Ser-X-pSer (e.g., S-X-pS), and Ser-X-Gln-X-X-Asp-Glu-Glu (S-X-Q-X-X-D-E-E) wherein X is any amino acid, and pS is phosphorylated serine (Mercier, et al (1981) Biochimie, 63: 1-17; Mercier et al (1971) Eur J. Biochem. 23:41-51; Lasa-Benito (1996) FEES Lett. 382: 149; Brunati, et al (2000) 3:765, Tagliabracci, et al (2015) Cell 161:1619-1632; Tagliabracci, et al (2012) Science 336:1150-1153). In some embodiments, a target kinase motif comprises the amino acid sequence SEEE. In some embodiments, a target kinase motif comprises the amino acid sequence SEEA. In some embodiments, a target kinase motif comprises the amino acid sequence SEEQ. In some embodiments, a target kinase motif comprises the amino acid sequence SEE.

In some embodiments, a metal-hydroxide binding polypeptide comprises at least one, two, three, four, five, six, seven, eight, nine, ten, eleven, or twelve target kinase motifs. In some embodiments, a metal-hydroxide binding polypeptide comprises at least one, two, three, four, five, six, seven, eight, nine, ten, eleven, or twelve S-X-E motifs. In some embodiments, a metal-hydroxide binding polypeptide comprises more than four S-X-E motifs. In some embodiments, a metal-hydroxide binding polypeptide comprises eight S-X-E motifs. In some embodiments, the number of target kinase motifs (e.g., S-X-E motifs) contributes to the number of phosphorylated residues on a metal-hydroxide binding polypeptide.

In some embodiments, a metal-hydroxide binding polypeptide is a metal-hydroxide binding polypeptide whose amino acid sequence includes a plurality of phosphorylation sites. In some embodiments, a plurality of phosphorylation sites comprises at least one, two, three, four, five, six, seven, eight, nine, ten, eleven, or twelve target kinase motifs. In some embodiments, a plurality of phosphorylation sites comprises at least one, two, three, four, five, six, seven, eight, nine, ten, eleven, or twelve S-X-E motifs. In some embodiments, a plurality of phosphorylation sites comprises more than four S-X-E motifs. In some embodiments, a plurality of phosphorylation sites comprises more than eight S-X-E motifs. In some embodiments, the number of target kinase motifs (e.g., S-X-E motifs) contributes to the number of phosphorylated residues on a metal-hydroxide binding polypeptide.

In some embodiments, the at least one, two, three, four, five, six, seven, eight, nine, ten, eleven, or twelve target kinase motifs (e.g., S-X-E motifs) are directly adjacent (e.g., linked) to the next target kinase (e.g., S-X-E motif). In some embodiments, the at least one, two, three, four, five, six, seven, eight, nine, ten, eleven, or twelve target kinase motifs (e.g., S-X-E motifs) are separated (e.g., linked) to the next target kinase motif (e.g., S-X-E motif) by a spacer. In some embodiments, the spacer comprises at least one glycine residue. In some embodiments, the spacer comprises a plurality of glycine residues. In some embodiments, the spacer comprises three glycine residues. In some embodiments, the spacer comprises at least four glycine residues. In some embodiments, the spacer has a sequence that comprises four glycine residues. In some embodiments, the spacer has an amino acid sequence comprising GGGSGGGG. In some embodiments, the spacer has an amino acid sequence comprising GGGEGGGG.

In some embodiments, a metal-hydroxide binding polypeptide comprises four S-X-E motifs and three spacers comprising four glycine residues. In some embodiments, a metal-hydroxide binding polypeptide comprises six S-X-E motifs and five spacers comprising four glycine residues. In some embodiments, a metal-hydroxide binding polypeptide comprises eight S-X-E motifs and seven spacers comprising four glycine residues. In some embodiments, a metal-hydroxide binding polypeptide comprises four motifs with the amino acid sequence, SEEE, and three spacers comprising three glycine residues. In some embodiments, a metal-hydroxide binding polypeptide comprises four motifs with the amino acid sequence, SEEA, and three spacers comprising three glycine residues. In some embodiments, a metal-hydroxide binding polypeptide comprises four motifs with the amino acid sequence, SEEQ, and three spacers comprising three glycine residues. In some embodiments, a metal-hydroxide binding polypeptide comprises four motifs with the amino acid sequence, SEE, and three spacers comprising the amino acid sequence, GGGSGGGG. In some embodiments, a metal-hydroxide binding polypeptide comprises four motifs with the amino acid sequence, SEE, and three spacers comprising the amino acid sequence, GGGEGGGG.

In some embodiments, a metal-hydroxide binding polypeptide comprises six S-X-E motifs, wherein each S-X-E motif is directly adjacent to the next S-X-E motif. In some embodiments, a metal-hydroxide binding polypeptide comprises eight S-X-E motifs, wherein each S-X-E motif is directly adjacent to the next S-X-E motif.

In some embodiments, a metal-hydroxide binding polypeptide comprise an ending sequence (e.g., an amino acid sequence at the c-terminus of the fusion polypeptide. In some embodiments, an ending sequence comprises a plurality of amino acid residues. In some embodiments, a plurality of amino acid residues comprises GGGG. In some such embodiments, an ending sequence comprises the amino acid sequence GGGGS. In some such embodiments, an ending sequence comprises the amino acid sequence GGGGHHHHHH In some such embodiments, an ending sequence comprises the amino acid sequence GGGGSHHHHHH. In some embodiments, an ending sequence comprises an optional tag, as discussed elsewhere herein.

Among other things, the present disclosure identifies the source of a problem with certain metal-hydroxide binding polypeptides and/or fusion polypeptides that include them. Among other things, the present disclosure provides metal-hydroxide-binding polypeptides, and fusion polypeptides that include them, which demonstrate high levels of adsorption to metal hydroxides and also desirable manufacturing characteristics (e.g., one or more of reproducibility, consistency, production of a homogeneously-phosphorylated fusion polypeptide, etc.). For example, in some embodiments, an optimal number of kinase target motifs (e.g., phosphorylation sites) are utilized. In some embodiments, for example, spacing of kinase target motifs (e.g., phosphorylation sites) is or has been optimized.

In some embodiments, a desired (e.g., optimal) number of kinase target motifs and/or spacing of kinase motifs may be determined based on one or more of, for example, desired phosphate content to achieve strong metal-hydroxide retention and/or avoidance of one or more manufacturing challenges (e.g., which the present disclosure appreciates may be associated with highly phosphorylated elements). In some embodiments, a desired (e.g., optimal) number and/or spacing of kinase motifs results in an exposure of the polypeptide to the kinase to achieve a desired level of fusion polypeptide phosphorylation. In some embodiments, improved fusion polypeptides as described herein, results in one or more of improved reproducibility, consistency, and/or production of a homogenously-phosphorylated fusion polypeptide. For example, in some embodiments, provided technologies achieve reproducible manufacturing of comparable preparations (e.g., preparations that are consistently within established parameters) of fusion polypeptides (e.g., phosphorylated fusion polypeptides) and/or complexes as described herein. For example, in some embodiments, provided technologies achieve reduced immunogenicity compared to an appropriate reference standard (e.g., fusion polypeptides comprising ABP-10). Without wishing to be bound by any one theory, reduced immunogenicity is achieved by removing hydrophobic amino acids, thus, reducing binding to major histocompatibility complex.

Linkers

In some embodiments, fusion polypeptides as described herein may include one or more linkers or spacers.

For example, in some embodiments, fusion polypeptides comprise an immunomodulatory polypeptide comprising a first and a second immune agonist moiety. In some embodiments, a first and a second immune agonist moiety are linked via a first linker.

In some embodiments, fusion polypeptides of the present disclosure comprise an immunomodulatory polypeptide and a metal-hydroxide binding polypeptide. In some embodiments, an immunomodulatory polypeptide and a metal-hydroxide binding polypeptide are linked via a second linker.

In some embodiments, a first linker and/or a second linker is a polypeptide linker. In some embodiments, a polypeptide linker is synthetic. For example, a synthetic polypeptide linker may comprise non-naturally occurring polypeptides which are modified forms of naturally occurring polypeptides.

In some embodiments, polypeptide linkers of the present disclosure are at least one amino acid in length and can be any suitable number of amino acids. In some embodiments, a polypeptide linker is 1, 2, 3, 4, 5, 6, 7, 8, 9, 10, 11, 12, 13, 14, 15, 16, 17, 18, 19, 20, 25, 30, 35, 40, 45, or 50 amino acids in length.

In some embodiments, a first linker comprises a polypeptide linker. In some embodiments, a first linker comprises or consists of a Glycine-Serine (Gly-Ser or G-S linker). A Gly-Ser linker is a polypeptide linker that consists of glycine and serine residues. In some embodiments, a Gly-Ser linker comprises an amino acid sequence of $(Gly_4Ser)_n$, wherein n is a positive integer (e.g., 1, 2, 3, 4, 5, 6, 7, 8, 9, or 10). In some embodiments, a Gly-Ser linker is $(Gly_4Ser)_1$. In some embodiments, a Gly-Ser linker is $(Gly_4Ser)_2$. In some embodiments, a Gly-Ser linker is $(Gly_4Ser)_3$. In some embodiments, a Gly-Ser linker is $(Gly_4Ser)_4$. In some embodiments, a Gly-Ser linker is $(Gly_4Ser)_5$. In some embodiments, a Gly-Ser linker is $(Gly_4Ser)_6$. In some embodiments, a Gly-Ser linker is $(Gly_4Ser)_7$. In some embodiments, a Gly-Ser linker is $(Gly_4Ser)_8$. In some embodiments, a Gly-Ser linker is $(Gly_4Ser)_9$. In some embodiments, a Gly-Ser linker is $(Gly_4Ser)_{10}$.

In some embodiments, a second linker comprises a polypeptide linker. In some embodiments, a second linker comprises a plurality of glycine residues. In some embodiments, a second linker comprises a polypeptide linker with the amino acid sequence, GGGGSGGGG. In some embodiments, a second linker comprises a polypeptide linker with the amino acid sequence, GGGGEGGGG.

Variants

In some embodiments, an immunomodulatory polypeptide or a metal-hydroxide-binding polypeptide utilized in accordance with the present disclosure is a variant of a relevant reference polypeptide (e.g., a wild type polypeptide or functional portion thereof).

In some embodiments, a variant shows at least 70% identity to its reference polypeptide. In some such embodiments, a variant shows at least 70%, 75%, 80%, 85%, 90%, 91%, 92%, 93%, 94%, 95%, 96%, 97%, 98%, 99% or higher identity to its references polypeptide In some embodiments, a variant comprises one or more conservative or otherwise non-disruptive modifications (e.g., substitutions, deletions or additions) relative to its reference. In some embodiments, a variant is free of any disruptive modifications (e.g., substitutions, deletions or additions) so that an immunomodulatory polypeptide maintains one or more functional characteristics of the reference. In some embodiments, maintains means an immunomodulatory polypeptide display comparable activity (e.g., signaling competency or binding) compared to an appropriate reference standard (e.g., a wild-type immunomodulatory polypeptide). For example, in some such embodiments, an immunomodulatory polypeptide maintains at least about 70%, 75%, 80%, 85%, 90%, 91%, 92%, 93%, 94%, 95%, 96%, 97%, 98%, 99% or higher activity compared to an appropriate reference standard (e.g., a wild-type immunomodulatory polypeptide).

Metal Hydroxides

In some embodiments, the present disclosure provides fusion polypeptides comprising an immunomodulatory polypeptide and a metal-hydroxide binding polypeptides, wherein the fusion polypeptide, when exposed to a metal-hydroxide forms a complex therewith. A complex is formed via adsorption of the fusion polypeptide to a metal-hydroxide. Without wishing to be bound by any one theory, it is hypothesized adsorption of a fusion polypeptide to a metal hydroxide occurs by ligand exchange. Ligand exchange, for example, is a substitution or exchange of a surface hydroxyl by another ligand. In some embodiments, substitution or exchange of a surface hydroxyl occurs by a hydroxyl-replacement group (e.g., a phosphate group).

In some embodiments, a metal-hydroxide is a substance that includes at least one hydroxyl group bound to a metal. In accordance with the present disclosure, in some embodiments, a metal-hydroxide can adsorb fusion polypeptides comprising a hydroxyl-replacement moiety. In some embodiments, a hydroxyl-replacement moiety is a phosphate group.

In some embodiments, a metal-hydroxide is selected based on its inherent qualities or characteristics. In some embodiments, a metal-hydroxide is selected due to its biocompatibility for use in a subject (e.g., a mammal, e.g., a human). In some embodiments, a metal-hydroxide is aluminum hydroxide (e.g., alum). In some embodiments, a metal-hydroxide is iron-hydroxide. A skilled artisan will recognize any number of metal-hydroxide may be successfully utilized in accordance with the present disclosure.

Tags

In some embodiments, a fusion polypeptide of the present disclosure comprises an immunomodulatory polypeptide that comprises an immune agonist moiety and a metal-hydroxide binding polypeptide whose amino acid sequence includes a plurality of phosphorylation sites, so that it can adopt phosphorylated and unphosphorylated forms. In some embodiments, a fusion polypeptide of the present disclosure comprises an ending sequence. In some embodiments, an ending sequences comprises a tag. A tag, as used herein, is an amino acid sequence that, when detected and/or measured in a particular sample, indicates that the protein to which it was linked is present in the sample and can provide a quantitative measurement thereof. A variety of tags known in the art may be used in accordance with the present disclosure. For example, in some embodiments, a tag comprises a FLAG tag, a polyhistidine tag, a V5 tag, a MBP tag.

In some embodiments, a tag is inserted at the N- or C-terminus of the fusion polypeptide to minimize interference with fusion polypeptide function. In some embodiments, the tags are be placed internally in-frame within the fusion polypeptide sequence without affecting functionality. Preferred locations for the tag may be determined in part based on available empirical data (e.g., from affinity tag or other fusion polypeptide experiments such as polyhistidine, FLAG tag, MBP tag, etc.), three dimensional structures of the fusion polypeptide or similar polypeptides and/or in vivo or in vitro expression experiments.

In some embodiments, a tag can also contain a short sequence motif, such as an affinity tag or chromatography tag to allow for partial or complete purification from a complex mixture or preparation. In some embodiments, the peptide tags can be designed to allow inclusion of a fixed number (e.g., one, two, three, or more) of a set of preselected (e.g., one, two, three, or more) amino acids.

Production of Fusion Polypeptide Metal-Hydroxide Complexes

In one aspect of the present disclosure, fusion polypeptide-metal hydroxide complexes described herein are produced by (1) making a fusion polypeptide; (2) phosphorylating a fusion polypeptide; and (3) contacting a fusion polypeptide with metal hydroxide.

Production of Fusion Polypeptides

In some embodiments, fusion polypeptides described herein are made in host cells using techniques for exogenous expression. Methods of exogenously expressing polypeptides are well known in the art and the skilled artisan would recognize a variety of techniques could be successfully utilized.

Recombinant polynucleotides (e.g., DNA or RNA) encoding for fusion polypeptides of the present disclosure may be prepared by a variety of methods available. For example, sequences encoding for fusion polypeptides may be excised from DNA using restriction enzymes, may be amplified from plasmids or genomic polynucleotide sequences using, for example, polymerase chain reaction, or may be synthesized using chemical synthesis techniques. In some embodiments, a combination of known methods is utilized to prepare a recombinant polynucleotide encoding for fusion polypeptides of the present disclosure.

Recombinant polynucleotides encoding fusion polypeptides of the present disclosure may be cloned into a vector capable of expressing a fusion polypeptide. Cloning may be carried out according to a variety of methods available (e.g., Gibson assembly, restriction digest and ligation, etc.). In some embodiments, a vector is a viral vector. In some embodiments, a vector is a non-viral vector. In some embodiments, a vector is a plasmid.

In some embodiments, a vector capable of expression comprises a recombinant polynucleotide that encodes a fusion polypeptide of the present disclosure operatively linked to a sequence or sequences that control expression (e.g., promoters, start signals, stop signals, polyadenylation signals, activators, repressors, etc.). In some embodiments, a sequence or sequences that control expression are selected to achieve a desired level of expression. In some embodiments, more than one sequence that controls expression (e.g., promoters) are utilized. In some embodiments, more than one sequence that controls expression (e.g., promoters) are utilized to achieve a desired level of expression of a plurality of recombinant polynucleotides that encode a plurality polypeptides. In some embodiments, a plurality of recombinant polypeptides are expressed from the same vector (e.g., a bi-cistronic vector, a tri-cistronic vector, multi-cistronic). In some embodiments, a plurality of recombinant polypeptides are expressed, each of which is expressed from a separate vector.

In some embodiments, a vector capable of expression comprising a recombinant polynucleotide encoding a fusion polypeptide of the present disclosure is used to express a fusion polypeptide in a host cell. A host cell may be selected from a variety of the available and known host cells (e.g., Human Embryonic Kidney (HEK) cells, suspension HEK293 cells, Chinese Hamster Ovary cells) suitable expressing fusion polypeptides disclosed herein.

A variety of methods are available to introduce a vector into host cells. In some embodiments, a vector may be introduced into host cells using transfection. In some embodiments, transfection is completed, for example, using calcium phosphate transfection, lipofection, or polyethylenimine-mediated transfection. In some embodiments, a vector may be introduced into a host cell using transduction.

In some embodiments, a transformed host cells are cultured following introduction of a vector into a host cell to allow for expression of said recombinant polynucleotides. In some embodiments, a transformed host cells are cultured for at least 12 hours, 16 hours, 20 hours, 24 hours, 28 hours, 32 hours, 36 hours 40 hours, 44 hours, 48 hours, 52 hours, 56 hours, 60 hours, 64 hours, 68 hours, 72 hours or longer. Transformed host cells are cultured in growth conditions (e.g., temperature, carbon-dioxide levels, growth medium) in accordance with the requirements of a host cell selected. A skilled artisan would recognize culture conditions for host cells selected are well known in the art.

Phosphorylating Fusion Polypeptides

In some embodiments, fusion polypeptides described herein are phosphorylated by contacting a fusion polypeptide with a kinase. In some embodiments, a fusion polypeptide is contacted with a kinase by co-expressing a fusion polypeptide in a host cell with a kinase. In some embodiments, co-expression is achieved by introducing two vectors, one comprising a recombinant polynucleotide encoding a fusion polypeptide and one comprising a recombinant polynucleotide encoding a kinase, into a host cell. In some embodiments, co-expression is achieved by introducing a single, multi-cistronic (e.g., bi-cistronic) vector that comprises a plurality of recombinant polynucleotides. In some embodiments, a recombinant polynucleotides encode a fusion polypeptide and a recombinant polynucleotide encoding a kinase. In some embodiments, a transformed host cell is cultured following introduction of a vector into a host cell. Without wishing to be bound by any one theory, upon co-expression of a fusion polypeptide and a kinase in a host cell, a kinase can contact a fusion polypeptide, phosphorylating it.

In some embodiments, co-expression is achieved by introducing two vectors, one comprising a recombinant polynucleotide encoding a fusion polypeptide and one comprising a recombinant polynucleotide encoding a kinase, into a host cell. In some embodiments, two vectors are introduced at a ratio of vector encoding fusion polypeptide to vector encoding a kinase introduced into a host cell optimized to achieve a desired, relative level of expression of fusion polypeptide to kinase. In some embodiments, a ratio of vector encoding fusion polypeptide to vector encoding a kinase is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

In some embodiments, co-expression is achieved by introducing one vector comprising both a recombinant polynucleotide encoding a fusion polypeptide and a recombinant polypeptide encoding a kinase (e.g., a bi-cistronic vector) into a host cell. In some embodiments, a recombinant polynucleotide encoding a fusion polypeptide and a recombinant polynucleotide encoding a kinase are operatively linked to a sequence or sequences that control expression (e.g., promoters, start signals, stop signals, polyadenylation signals, activators, repressors, etc.). In some embodiments, a sequence or sequences that control expression are selected to achieve a desired level of expression. In some embodiments, multiple sequences that control expression (e.g., promoters) are utilized to achieve a desired ratio of expression of fusion polypeptide to kinase. In some embodiments, a ratio is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

Exemplary nucleotide and amino acid sequences of Fam20C kinases include those described in Table 3.

TABLE 3

Exemplary nucleotide and amino acid sequences of Fam20C kinases

| SEQ ID NO: | Fam20C | Sequence |
|---|---|---|
| 99 | hFam20C (w/ signal polypeptide) | MKMMLVRRFRVLILMVFLVACALHIALDLLPRLERRGARPSG<br>EPGCSCAQPAAEVAAPGWAQVRGRPGEPPAASSAAGDAGWPN<br>KHTLRILQDFSSDPSSNLSSHSLEKLPPAAEPAERALRGRDP<br>GALRPHDPAHRPLLRDPGPRRSESPPGPGGDASLLARLFEHP<br>LYRVAVPPLTEEDVLFNVNSDTRLSPKAAENPDWPHAGAEGA<br>EFLSPGEAAVDSYPNWLKFHIGINRYELYSRHNPAIEALLHD<br>LSSQRITSVAMKSGGTQLKLIMTFQNYGQALFKPMKQTREQE<br>TPPDFFYFSDYERHNAEIAAFHLDRILDFRRVPPVAGRMVNM<br>TKEIRDVTRDKKLWRTFFISPANNICFYGECSYYCSTEHALC<br>GKPDQIEGSLAAFLPDLSLAKRKTWRNPWRRSYHKRKKAEWE<br>VDPDYCEEVKQTPPYDSSHRILDVMDMTIFDFLMGNMDRHHY<br>ETFEKFGNETFIIHLDNGRGFGKYSHDELSILVPLQQCCRIR<br>KSTYLRLQLLAKEEYKLSLLMAESLRGDQVAPVLYQPHLEAL<br>DRRLRVVLKAVRDCVERNGLHSVVDDDLDTEHRAASAR |
| 79 | hFam20C-KDEL (w/ signal polypeptide) | MKMMLVRRFRVLILMVFLVACALHIALDLLPRLERRGARPSG<br>EPGCSCAQPAAEVAAPGWAQVRGRPGEPPAASSAAGDAGWPN<br>KHTLRILQDFSSDPSSNLSSHSLEKLPPAAEPAERALRGRDP<br>GALRPHDPAHRPLLRDPGPRRSESPPGPGGDASLLARLFEHP<br>LYRVAVPPLTEEDVLFNVNSDTRLSPKAAENPDWPHAGAEGA<br>EFLSPGEAAVDSYPNWLKFHIGINRYELYSRHNPAIEALLHD<br>LSSQRITSVAMKSGGTQLKLIMTFQNYGQALFKPMKQTREQE<br>TPPDFFYFSDYERHNAEIAAFHLDRILDFRRVPPVAGRMVNM<br>TKEIRDVTRDKKLWRTFFISPANNICFYGECSYYCSTEHALC<br>GKPDQIEGSLAAFLPDLSLAKRKTWRNPWRRSYHKRKKAEWE<br>VDPDYCEEVKQTPPYDSSHRILDVMDMTIFDFLMGNMDRHHY<br>ETFEKFGNETFIIHLDNGRGFGKYSHDELSILVPLQQCCRIR<br>KSTYLRLQLLAKEEYKLSLLMAESLRGDQVAPVLYQPHLEAL<br>DRRLRVVLKAVRDCVERNGLHSVVDDDLDTEHRAASARGGGS<br>KDEL |
| 80 | hFam20C (w/ signal polypeptide) | ATGAAGATGATGCTTGTTCGAAGATTCCGGGTCCTGATTCTG<br>ATGGTATTCCTCGTCGCATGCGCCCTGCACATCGCCTTGGAC<br>CTCCTCCCTCGGCTGGAACGCAGAGGAGCACGGCCTTCCGGA<br>GAACCGGGCTGCTCGTGTGCACAACCAGCCGCCGAAGTCGCT<br>GCCCCTGGATGGGCTCAAGTCAGAGGACGGCCTGGAGAACCC<br>CCGGCAGCTTCCTCCGCGGCTGGAGATGCGGGATGGCCCAAC<br>AAGCACACCCTCCGGATCCTGCAGGACTTCTCCTCCGACCCC<br>TCCTCGAATCTGAGCTCCCACTCCCTCGAAAAGCTGCCTCCT<br>GCTGCCGAGCCAGCTGAACGGGCCCTGAGGGGTAGAGATCCC<br>GGTGCACTCAGGCCACATGACCCTGCGCACCGACCTCTGTTG<br>AGAGATCCGGGTCCTCGGAGGTCTGAATCACCGCCAGGTCCT<br>GGTGGCGATGCGTCCCTTCTTGCGCGCTTGTTCGAGCACCCG<br>CTGTACCGGGTGGCAGTGCCTCCCCTCACCGAGGAAGATGTG<br>CTGTTCAACGTGAACAGCGATACCCGCCTGAGCCCGAAAGCC<br>GCCGAGAATCCCGACTGGCCTCATGCCGGAGCCGAAGGAGCC<br>GAGTTCCTGAGCCCTGGAGAAGCGGCCGTGGATTCGTACCCG<br>AACTGGCTAAAGTTCCATATCGGCATCAACCGCTACGAGCTC<br>TACTCGAGGCATAACCCGGCCATTGAGGCCCTGCTGCACGAC<br>CTCAGCAGCCAACGGATCACTAGCGTGGCCATGAAGTCCGGG<br>GGCACTCAGCTGAAGTTGATCATGACCTTTCAGAACTACGGC |

TABLE 3-continued

Exemplary nucleotide and amino acid sequences of Fam20C kinases

| SEQ ID NO: | Fam20C | Sequence |
|---|---|---|
| | | CAGGCCCTGTTTAAGCCCATGAAGCAGACCCGGGAGCAGGAA ACACCGCCGGACTTTTTCTACTTCTCGGACTACGAACGCCAC AACGCCGAGATTGCCGCCTTCCACCTGGATCGCATCCTGGAT TTCAGACGGGTGCCACCTGTGGCGGGACGCATGGTCAATATG ACCAAAGAAATCCGCGACGTCACTCGCGACAAGAAGCTCTGG CGGACGTTCTTCATTTCCCCGGCCAACAACATCTGCTTCTAC GGGGAGTGCTCATACTACTGCTCCACCGAGCATGCCCTTTGC GGAAAGCCCGACCAGATCGAAGGGTCCCTGGCAGCCTTCCTT CCCGACCTGAGCCTGGCGAAGCGCAAGACTTGGAGAAACCCA TGGCGCCGCTCATACCACAAGCGGAAGAAGGCGGAGTGGGAG GTGGACCCCGACTACTGCGAGGAAGTCAAGCAGACCCCCCCC TACGACTCCTCCCACCGGATTCTGGACGTGATGGACATGACT ATTTTCGATTTCCTCATGGGCAACATGGACCGGCACCACTAT GAAACCTTCGAAAAGTTCGGGAACGAGACTTTCATTATTCAC CTGGACAACGGCCGGGGATTCGGAAAGTACAGCCACGACGAA CTCTCCATCCTGGTGCCGCTGCAGCAGTGTTGCCGGATCCGC AAGTCCACGTACCTGAGACTGCAGCTGTTGGCCAAAGAGGAG TATAAGCTGTCGCTCCTGATGGCCGAATCCCTCCGCGGCGAT CAAGTCGCCCCGGTGCTGTACCAGCCGCATCTCGAGGCCCTG GACAGGAGACTGCGCGTGGTGCTCAAAGCTGTGCGGGATTGT GTGGAACGGAACGGCCTGCATTCTGTGGTGGACGACGACCTG GACACCGAACACAGAGCCGCATCCGCTAGG |
| 81 | hFam20C-KDEL (w/ signal polypeptide) | ATGAAGATGATGCTTGTTCGAAGATTCCGGGTCCTGATTCTG ATGGTATTCCTCGTCGCATGCGCCCTGCACATCGCCTTGGAC CTCCTCCCTCGGCTGGAACGCAGAGGAGCACGGCCTTCCGGA GAACCGGGCTGCTCGTGTGCACAACCAGCCGCCGAAGTCGCT GCCCCTGGATGGGCTCAAGTCAGAGGACGGCCTGGAGAACCC CCGGCAGCTTCCTCCGCGGCTGGAGATGCGGGATGGCCCAAC AAGCACACCCTCCGGATCCTGCAGGACTTCTCCTCCGACCCC TCCTCGAATCTGAGCTCCCACTCCCTCGAAAAGCTGCCTCCT GCTGCCGAGCCAGCTGAACGGGCCCTGAGGGGTAGAGATCCC GGTGCACTCAGGCCACATGACCCTGCGCACCGACCTCTGTTG AGAGATCCGGGTCCTCGGAGGTCTGAATCACCGCCAGGTCCT GGTGGCGATGCGTCCCTTCTTGCGCGCTTGTTCGAGCACCCG CTGTACCGGGTGGCAGTGCCTCCCCTCACCGAGGAAGATGTG CTGTTCAACGTGAACAGCGATACCCGCCTGAGCCCGAAAGCC GCCGAGAATCCCGACTGGCCTCATGCCGGAGCCGAAGGAGCC GAGTTCCTGAGCCCTGGAGAAGCGGCCGTGGATTCGTACCCG AACTGGCTAAAGTTCCATATCGGCATCAACCGCTACGAGCTC TACTCGAGGCATAACCCGGCCATTGAGGCCCTGCTGCACGAC CTCAGCAGCCAACGGATCACTAGCGTGGCCATGAAGTCCGGG GGCACTCAGCTGAAGTTGATCATGACCTTTCAGAACTACGGC CAGGCCCTGTTTAAGCCCATGAAGCAGACCCGGGAGCAGGAA ACACCGCCGGACTTTTTCTACTTCTCGGACTACGAACGCCAC AACGCCGAGATTGCCGCCTTCCACCTGGATCGCATCCTGGAT TTCAGACGGGTGCCACCTGTGGCGGGACGCATGGTCAATATG ACCAAAGAAATCCGCGACGTCACTCGCGACAAGAAGCTCTGG CGGACGTTCTTCATTTCCCCGGCCAACAACATCTGCTTCTAC GGGGAGTGCTCATACTACTGCTCCACCGAGCATGCCCTTTGC GGAAAGCCCGACCAGATCGAAGGGTCCCTGGCAGCCTTCCTT CCCGACCTGAGCCTGGCGAAGCGCAAGACTTGGAGAAACCCA TGGCGCCGCTCATACCACAAGCGGAAGAAGGCGGAGTGGGAG GTGGACCCCGACTACTGCGAGGAAGTCAAGCAGACCCCCCCC TACGACTCCTCCCACCGGATTCTGGACGTGATGGACATGACT ATTTTCGATTTCCTCATGGGCAACATGGACCGGCACCACTAT GAAACCTTCGAAAAGTTCGGGAACGAGACTTTCATTATTCAC CTGGACAACGGCCGGGGATTCGGAAAGTACAGCCACGACGAA CTCTCCATCCTGGTGCCGCTGCAGCAGTGTTGCCGGATCCGC AAGTCCACGTACCTGAGACTGCAGCTGTTGGCCAAAGAGGAG TATAAGCTGTCGCTCCTGATGGCCGAATCCCTCCGCGGCGAT CAAGTCGCCCCGGTGCTGTACCAGCCGCATCTCGAGGCCCTG GACAGGAGACTGCGCGTGGTGCTCAAAGCTGTGCGGGATTGT GTGGAACGGAACGGCCTGCATTCTGTGGTGGACGACGACCTG GACACCGAACACAGAGCCGCATCCGCTAGGGGTGGAGGGTCC AAAGATGAGCTG |

Complex Formation

In some embodiments, a fusion polypeptide described herein, when exposed to a metal-hydroxide (e.g., aluminum hydroxide) forms a complex therewith. In some embodiments, fusion polypeptides comprise hydroxyl replacement groups (e.g., phosphate groups) for adsorption via ligand exchange with a metal hydroxide. In some embodiments, a fusion polypeptide can, via electrostatic interactions, form a complex with a metal hydroxide.

In some embodiments, a fusion polypeptide metal-hydroxide complex of the present disclosure is formed by mixing. In some embodiments, mixing occurs in a buffer (e.g., a tris-buffered saline buffer). In some such embodiments, a buffer does not contain phosphate. In some such embodiments, a buffer does not contain a substance or substances that solubilize a metal-hydroxide (e.g., citric acid, malic acid, or lactic acid). Without wishing to be bound by any one theory, buffers that contain phosphate compete with, and can hinder, complex formation. In some embodiments, mixing occurs for a duration of time at a particular temperature. In some such embodiments, a duration of time is 5 minutes, 10 minutes, 15 minutes, 20 minutes, 25 minutes, 30 minutes, 35 minutes, 40 minutes, or 45 minutes. In some such embodiments, a particular temperature is approximately 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., or 35° C.

Purification

Commonly aberrant products (e.g., residual protein, host cell contaminants, etc.) are removed from fusion polypeptide preparations. A variety of purification technologies are available and known to the skilled artisan.

In some embodiments, a fusion polypeptide can be purified by a chromatography method. In some embodiments, such a chromatography purification method can be performed with a chromatography method known in the art, including, but not limited to, high-performance liquid chromatography, size exclusion chromatography, ion exchange chromatography, wherein components of a mixture travel through a stationary phase at different speeds, resulting in separation from one another. It will be apparent to a skilled artisan a variety of solid substrates may be used (e.g., beads, particles, microspheres, resins, etc.). For example, in some embodiments, a solid substrate has properties such that, in accordance with the present disclosure, permits a different retention time for a fusion polypeptide relative to any other undesirable components in the preparation of fusion polypeptide.

In some embodiments, a fusion polypeptide can be purified by an affinity-based purification method. In some embodiments, such an affinity-based purification method may be performed with a solid substrate known in the art. A wide variety of substrates could be utilized, such as, for example, membranes, polymeric beads, magnetic beads, or composites. For example, in some embodiments, a solid substrate (e.g., polymeric beads or particles) coated or pre-charged with a substance or composition (e.g., nickel ions) that has a high binding affinity for a fusion polypeptides can be useful in accordance with the present disclosure such that a fusion polypeptide will bind to a solid substrate, while any other undesirable components present in a preparation will remain in solution. In some embodiments, a fusion polypeptide may be eluted from a solid substrate. In some embodiments, elution may be carried out using specific elution. For example, in some embodiments specific elution is completed by challenging a polypeptide-substrate complex by an agent or agents that will compete for complexation with either a substrate or a polypeptide, releasing a polypeptide into solution. In some embodiments, elution may be carried out using non-specific elution. For example, in some embodiments, non-specific elution is completed by manipulating solvent or buffer conditions (e.g., increasing concentration of a buffer, e.g., an imidazole buffer) to reduce the associate rate constant, resulting in dissociation of the polypeptide from the substrate.

Characterization

Among other things, in some embodiments, the present disclosure provides technologies for characterizing fusion polypeptides (e.g., phosphorylated or unphosphorylated preparations thereof) and/or of complexes comprising such fusion polypeptides and metal hydroxides. In characterization is performed during and/or following production process. In some embodiments, a particular preparation process may be modified or terminated in light of a characterization (e.g., if a particular preparation fails to meet one or more specifications). In some embodiments, such characterization may involve assessment of one or more of metal-hydroxide retention, degree of phosphorylation, heterogeneity of phosphorylation, signaling activity, and/or efficacy.

Exemplary Characterization of Phosphate Content

In some embodiments, degree of phosphorylation (e.g., of fusion polypeptides of the present disclosure and/or preparations thereof) is characterized. A variety of methods are available for measurement of degree of phosphorylation (e.g., the average number of phosphate molecules per polypeptide). For example, in some embodiments, degree of phosphorylation can be determined by a colorimetric method. In some embodiments, a colorimetric method is or comprises a malachite green assay. Without wishing to be bound by any one theory, a malachite green assay is based on quantification of a green complex formed between Malachite green, molybdate, and free orthophosphate which can be measured (e.g., using a spectrophotometer or plate reader).

In some embodiments, degree of phosphorylation (e.g., the average number of phosphate molecules per polypeptide) is 0.5-7, 1-7, 2-7, 3-7, 4-7, 5-7, 6-7, 0.5-6, 0.5-5, 0.5-4, 1-6, 2-6, 3-6, 4-6, 5-6, 0.5-10, 0.5-9, 0.5-8, 1-10, 1-9, 1-8, 2-10, 2-9, 2-8, 3-10, 3-9, 3-8, 4-10, 4-9, 4-8, 5-10, 5-9, 5-8, 6-10, 6-9, or 6-8. In some embodiments, degree of phosphorylation (e.g., the average number of phosphate molecules per polypeptide) is 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 7.10, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.

In some embodiments, heterogeneity of phosphorylation of fusion polypeptides of the present disclosure and/or preparations thereof are characterized. In some embodiments, heterogeneity of phosphorylation is a measurement of the degree of phosphorylation within a given preparation of fusion polypeptide. In some embodiments, heterogeneity of phosphorylation is a measurement of the degree of phosphorylation across a plurality of preparations of fusion polypeptide. In some embodiments, heterogeneity of phosphorylation is a measurement of location of particular phosphate groups on a polypeptide within a given preparation of fusion polypeptide. In some embodiments, heterogeneity of phosphorylation is a measurement of location of particular phosphate groups on a polypeptide across a plurality of preparations of fusion polypeptide.

A variety of technologies is available for measurement of heterogeneity of phosphorylation. For example, in some embodiments, degree of phosphorylation can be determined by a chromatography method. In some embodiments, a chromatography method comprises ion-exchange chromatography. In some embodiments, for example, a chromatography method comprises analytical anion-exchange chromatography. Anion-exchange chromatography is a form of ion exchange where a negatively charged biomolecule (e.g., a phosphorylated form of a fusion polypeptide disclosed herein) binds to a positively charged resin. In some embodiments, anion-exchange chromatography can be used to resolve polypeptides with different numbers of phosphorylated amino acid residues (e.g., differentially phosphorylated polypeptides). Without wishing to be bound by any one theory, polypeptide phosphorylation confers variability in a polypeptide's charge, permitting separation of differentially phosphorylated polypeptides using ion-exchange chromatography (e.g., anion-exchange chromatography). Use of a gradient elution buffer (e.g., a buffer with increasing salt concentrations) to elute from the ion exchange (e.g., anion exchange) column permits separation of differentially phosphorylated polypeptides. In some embodiments, a buffer is, for example, a Tris buffer. In some embodiments, a linear gradient of Tris buffer is utilized. In some embodiments, a linear gradient of Tris buffer comprises over a linear gradient from 20 mM Tris, pH 7.1 to 20 mM Tris, 525 mM NaCl, pH 7.1 over a pre-defined period of time. In some embodiments, a linear gradient is conducted over a period of 1 minute, 5 minutes, 10 minutes, 15 minutes, 20 minutes, 22 minutes, 24 minutes, 26 minutes, 28 minutes, 30 minutes, 32 minutes, 34 minutes, 36 minutes, 38 minutes, 40 minutes, or longer.

In some embodiments, differentially phosphorylated polypeptides are dephosphorylated. In some embodiments, dephosphorylation comprises use of a phosphatase (e.g., a lambda phosphatase). In some embodiments, a fusion polypeptide is incubated with a phosphatase for a period of time and at a temperature that permits activity of said phosphatase and dephosphorylation of said fusion polypeptide. In some embodiments, dephosphorylation occurs at an incubation temperature of approximately 25° C., 26° C., 27° C., 28° C., 29° C., 30° C., 31° C., 32° C., 33° C., 34° C., 35° C., or higher. In some embodiments, dephosphorylation occurs for an incubation time of 25 minutes, 30 minutes, 35 minutes, 40 minutes, 45 minutes, 50 minutes, 55 minutes, 60 minutes, 65 minutes, or longer. In some embodiments, dephosphorylation occurs for an incubation time of 25-65 minutes, 30-60 minutes, 35-55 minutes, 40-50 minutes, 30-65 minutes, 35-65 minutes, 40-65 minutes, 45-65 minutes, 50-65 minutes, or 55-65 minutes.

In some embodiments, differentially phosphorylated polypeptides are dephosphorylated prior to separation. In some embodiments, differentially phosphorylated polypeptides of the present disclosure are assessed relative to an appropriate reference standard (e.g., a dephosphorylated and/or non-phosphorylated form of a fusion polypeptide).

In some embodiments, after separation of differentially phosphorylated polypeptides (e.g., by ion-exchange chromatography), the amount of each differentially phosphorylated polypeptide is measured. In some embodiments, the amount of each differentially phosphorylated polypeptide is measured according to a variety of methods available in the art. In some embodiments, for example and without limitation, differentially phosphorylated polypeptides are measured using a malachite green assay, analytical ion exchange, spectrophotometer, colorimetric assays, and/or western blot.

Exemplary Characterization of Metal-Hydroxide Retention

In some embodiments, fusion polypeptides of the present disclosure, when exposed to a metal-hydroxide (e.g., aluminum hydroxide) forms a complex therewith. In some embodiments, retention of a fusion polypeptide of the present disclosure on a metal-hydroxide (e.g., metal-hydroxide retention) is characterized. A variety of methods are available to measure metal-hydroxide retention. In some embodiments, for example and without limitation, metal-hydroxide retention can be measured by ellipsometry, surface plasmon resonance, optical waveguide lightmode spectroscopy, attenuated total internal reflectance-infrared spectroscopy, circular dichroism spectroscopy (CD), total internal reflectance-infrared spectroscopy (TIRF), and other high resolution microscopy techniques.

In some embodiments, metal-hydroxide retention is characterized using an in vitro assay. For example, fusion polypeptides at a known concentration are mixed with an excess of metal-hydroxide. The concentration of free, non-complexed fusion polypeptides is quantified and compared to a standard curve to determine metal-hydroxide retention. The concentration of free, non-complexed fusion polypeptide can be assessed according to a variety of method known to those of skill in the art. For example, and without limitation, in some embodiments, free, non-complexed, fusion polypeptides are quantified by enzyme-linked immunosorbent assay (ELISA), western blot, bicinchoninic acid assay, or Bradford assay.

In some embodiments, at least 10%, 15%, 20%, 25%, 30%, 35%, 40%, 45%, 50%, 55%, 60%, 65%, 70%, 75%, 80%, 85%, 90%, 95%, 99%, or 100% of fusion-polypeptide, when mixed with a metal-hydroxide, forms a complex therewith (e.g., is retained).

Exemplary Characterization of Signaling Activity

In some embodiments, fusion polypeptides (and/or complexes thereof) as described herein are characterized for activity (e.g., signaling activity). In some embodiments, activity is characterized by assessing signaling activity (e.g., signaling competency) compared to an appropriate reference standard. An appropriate reference standard can be, for example, a wild-type polypeptide and/or a fusion polypeptide lacking a metal-hydroxide binding polypeptide.

A variety of methods are available to assess signaling competency. In some embodiments, for example, signaling competency is assessed using an in vitro- or in vivo-based activity assay.

In some embodiments, signaling activity is assessed with an in vitro activity assay. In some embodiments, an in vitro activity assay comprises measuring activation or inhibition of downstream signaling of a fusion polypeptide. In some embodiments, measuring activation or inhibition of downstream activity comprises use of a reporter (e.g., a reporter assay). In some embodiments, a reporter assay measures activity using a detectable molecule (e.g., a reporter) that correlates with fusion polypeptide activity.

In some embodiments, a reporter comprises a fluorescent, bioluminescent, and/or other detectable probe known to those of skill in the art. In some embodiments, a reporter comprises use of a gene reporter. A gene reporter, for example, can be activated upon signaling elicited from a polypeptide. For example, upon activation of gene reporter transcription, a detectable product or enzyme that can be activated upon addition of substrate, generating a detectable product and/or by-product, can be utilized. In some embodiments, an enzyme useful in accordance with a reporter assay is, for example, luciferase or an alkaline phosphatase (e.g., secreted alkaline phosphatase, SEAP). In some such embodiments, a HEK-blue-IL12 reporter assay is utilized.

In some embodiments, signaling activity is assessed with an in vivo activity assay. In some embodiments, a fusion polypeptide is administered to a subject (e.g., a mouse, non-human primate, human, etc.) and activity is assessed. In some embodiments, activity is assessed, for example, by measuring activation or inhibition of downstream signaling of a fusion polypeptide as compared to an appropriate reference standard (e.g., activity of a wild-type polypeptide). A variety of methods are available to measure activation or inhibition of downstream signaling of a fusion polypeptide. For example, and without limitation, differential gene expression, protein expression, and/or alterations in post-translational modifications induced by a fusion polypeptide can be measured.

Exemplary Efficacy Characterization

In some embodiments, efficacy can be characterized according to a variety of methods that are available. In some embodiments, for example, a fusion polypeptide (or complex thereof) as described herein is administered (e.g., by intratumoral or peritumoral injection) to a subject (e.g., mouse, non-human primate, human, etc.) and efficacy is determined in comparison to an appropriate reference standard. An appropriate reference standard can be, for example, a wild-type polypeptide and/or a polypeptide lacking a metal-hydroxide binding polypeptide, or having a metal-hydroxide binding polypeptide in a non-binding (e.g., non-phosphorylated) state.

In some embodiments, efficacy is determined pre-clinically in an animal model (e.g., in mice, rats, non-human primates, etc.). In some embodiments, a fusion polypeptide is administered (e.g., by intratumoral or peritumoral injection) to an animal model. For example, in some embodiments, an animal model is an animal model with a tumor (e.g., an animal model of cancer). In some embodiments, a cancer animal model is generated by inoculating said animal model with tumor cells. In some embodiments, an animal model is inoculated with tumor cells at the flank region. In some embodiments, an animal model is inoculated with tumor cells in a clinically relevant region (e.g., a mammary fat pad).

In some embodiments, an animal model of cancer is administered a fusion polypeptide of the present disclosure. In some embodiments, an animal model of cancer is administered a reference standard (e.g., a wild-type polypeptide and/or a polypeptide lacking a metal-hydroxide binding polypeptide). In some embodiment, a variety of available, pre-determined measurements for efficacy known in the art, such as, for example, tumor volume and/or percent survival are assessed over time relative to an appropriate reference standard (e.g., a wild-type polypeptide and/or a polypeptide lacking a metal-hydroxide binding polypeptide).

In some embodiments, efficacy of a fusion polypeptide is determined clinically. In some embodiments, a fusion polypeptide is administered (e.g., by intratumoral, peritumoral injection, or into a tumor-draining lymph node) to a subject with a tumor. In some embodiments, a variety of available, pre-determined measurements for efficacy known in the art, such as, for example, tumor volume and/or percent survival are assessed over time relative to a subject with a tumor administered reference standard (e.g., a treatment in the art of known efficacy and/or placebo).

Compositions

Preparations of Fusion Polypeptides

In some embodiments, the present disclosure, among other things, provides fusion polypeptide preparations. Fusion polypeptide preparations are preparations comprising a fusion polypeptide that, in some embodiments, is purified from a cell culture production of said fusion polypeptide described herein. In some embodiments, a fusion polypeptide preparation comprises an unphosphorylated form of a fusion polypeptide. In some embodiments, a fusion polypeptide preparation comprises a phosphorylated form of the fusion polypeptide. In some embodiments, a fusion polypeptide preparation comprises a mixture of both unphosphorylated and phosphorylated forms of a fusion polypeptide.

In some embodiments, a fusion polypeptide preparation is a preparation comprising pharmaceutical-grade fusion polypeptide. In some embodiments, a fusion polypeptide preparation is a preparation comprising fusion polypeptide which its one or more characterization attributes are assessed and determined to meet a release and/or acceptance criteria (e.g., as described herein). Examples of such product quality attributes include, but are not limited to, degree of phosphorylation and/or heterogeneity of phosphorylation.

In some embodiments, a fusion polypeptide preparation comprises a phosphorylated form of a fusion polypeptide and a kinase used to phosphorylate a fusion polypeptide (e.g., as described herein). In some embodiments, a kinase is removed from a fusion polypeptide preparation.

In some embodiments, a phosphorylated fusion polypeptide preparation comprises fusion polypeptides with varying degrees of phosphorylation. In some embodiments, the degree of phosphorylation (e.g., the average number of phosphate molecules per polypeptide) of a preparation of fusion polypeptide is 0.5-7, 1-7, 2-7, 3-7, 4-7, 5-7, 6-7, 0.5-6, 0.5-5, 0.5-4, 1-6, 2-6, 3-6, 4-6, 5-6, 0.5-10, 0.5-9, 0.5-8, 1-10, 1-9, 1-8, 2-10, 2-9, 2-8, 3-10, 3-9, 3-8, 4-10, 4-9, 4-8, 5-10, 5-9, 5-8, 6-10, 6-9, or 6-8. In some embodiments, the degree of phosphorylation (e.g., the average number of phosphate molecules per polypeptide) of a preparation of fusion polypeptide is 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 7.10, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.

In some embodiments, the present disclosure, among other things, provides a fusion polypeptide preparation comprising a fusion polypeptide-metal hydroxide complex. In some embodiments, a preparation comprising a fusion polypeptide-metal hydroxide complex comprises any of a variety of suitable metal-hydroxide known in the art. For example, and without limitation, a metal-hydroxide may be an aluminum hydroxide or an iron hydroxide. In some embodiments, a fusion polypeptide-metal hydroxide complex comprises a mass ratio of fusion polypeptide to metal hydroxide (e.g., aluminum hydroxide), for example as defined by metal (e.g., aluminum) mass. In some embodiments, the ratio, is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

In some embodiments, the present disclosure, among other things, provides a pharmaceutical composition comprising a fusion polypeptide disclosed herein. In some embodiments, the pharmaceutical composition is formulated as a fusion polypeptide-metal hydroxide complex. In some embodiments, a pharmaceutical composition comprises a pharmaceutically acceptable diluent, carrier, solubilizer, emulsifier, preservative, and/or adjuvant.

In some embodiments, acceptable pharmaceutical composition formulation materials preferably are nontoxic to recipients at the dosages and concentrations employed. In some embodiments, formulation material(s) are for subcutaneous and/or intravenous administration. In some embodiments, formulation material(s) are for local administration (e.g., intratumoral or peritumoral administration). In some embodiments, a pharmaceutical composition can contain formulation materials for modifying, maintaining or preserving, for example, the pH, osmolality, viscosity, clarity, color, isotonicity, odor, sterility, stability, rate of dissolution or release, adsorption or penetration of fusion polypeptides. In some embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, a pharmaceutical composition comprises PBS; 20 mM NaOAC, pH 5.2, 50 mM NaCl; and/or 10 mM NAOAC, pH 5.2, 9% Sucrose. In some embodiments, an optimal pharmaceutical composition will be determined by one skilled in the art depending upon, for example, the intended route of administration, delivery format and desired dosage. See, for example, Remington's Pharmaceutical Sciences, supra. In some embodiments, such compositions may influence the physical state, stability, rate of in vivo release and rate of in vivo clearance of a fusion polypeptide-metal hydroxide complex.

In some embodiments, a primary vehicle or carrier in a pharmaceutical composition can be either aqueous or non-aqueous in nature. For example, in some embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In some embodiments, neutral buffered saline or saline mixed with serum albumin are further exemplary vehicles. In some embodiments, pharmaceutical compositions comprise Tris buffer of about pH 7.0-8.5, or acetate buffer of about pH 4.0-5.5, which can further include sorbitol or a suitable substitute therefore. In some embodiments, a composition comprising a fusion polypeptide metal hydroxide complex or a fusion polypeptide is prepared for storage by mixing the selected composition having the desired degree of purity with optional formulation agents (Remington's Pharmaceutical Sciences, supra) in the form of a lyophilized cake or an aqueous solution. Further, in some embodiments, a composition comprising a fusion polypeptide-metal hydroxide complex or a fusion polypeptide is formulated as a lyophilizate using appropriate excipients such as sucrose.

Use

Methods of Treatment

In one aspect, the present disclosure relates to methods of treating a subject with a medical condition. In some embodiments, the present disclosure relates to methods of treating a subject with a tumor (e.g., a subject with cancer). In general, methods of treatment are aimed at reducing tumor volume, reducing and/or preventing metastases, prolonging survival, and/or curing the condition. Appropriate subjects or individuals receiving a fusion polypeptide or fusion polypeptide metal hydroxide complex of the present disclosure include, for example, humans or other mammals (e.g., mice, rats, rabbits, dogs, horses, cats, pigs, or non-human primates) that have a tumor (e.g., cancer).

In some embodiments, a method of treating a subject with a tumor comprises a step of: treating a subject with a complex comprising: a fusion polypeptide comprising an immunomodulatory polypeptide that comprises an immune agonist moiety and a metal-hydroxide binding polypeptide and a metal hydroxide. In some embodiments, a method of treating a subject with a tumor comprises administering a fusion polypeptide comprising: an immunomodulatory polypeptide that comprises an immune agonist moiety and a metal-hydroxide binding polypeptide, wherein a fusion polypeptide is formulated with a metal hydroxide.

In some embodiments, a complex as described herein is administered as a monotherapy. In some embodiments, a complex as described herein is administered in combination with a second therapeutic. In some embodiments, a complex as described herein is administered to a subject wherein a subject has received or is receiving therapy with at least one additional therapeutic.

Fusion polypeptides and/or preparations and/or complexes thereof of the present disclosure, among other things, are useful for treating a subject with a tumor. Non-limiting examples of diseases associated with a tumor include cancer (e.g., carcinoma, sarcoma, metastatic diseases or hematopoietic neoplastic disorders). A tumor, including a metastatic tumor, can arise from a plurality of primary tumor types. For example, and without limitation, in some embodiments, a tumor or metastatic tumor can arise from a primary tumor of the kidney (e.g., renal cell carcinoma), head and neck (e.g., head and neck squamous cell carcinoma), prostate, breast (e.g., triple-negative), colon, skin (e.g., melanoma, merkel cell carcinoma, cutaneous T-cell lymphoma, cutaneous squamous cell carcinoma, basal cell carcinoma), lung (e.g., non-small cell lung cancer), and pancreas. Accordingly, fusion polypeptides and preparations thereof disclosed herein, including fusion polypeptide metal-hydroxide complexes and preparations thereof, can be administered to subject who has cancer.

It will be appreciated by those skilled in the art that amounts of a fusion polypeptide-metal hydroxide complex, fusion polypeptide or a preparation thereof sufficient to reduce tumor growth and size, or a therapeutically effective amount, will vary not only on the particular compounds or preparations selected, but also with the route of administration, the nature of the condition being treated, and the age and condition of the patient, and will ultimately be at the discretion of the patient's physician or pharmacist and/or based upon clinical guidelines. The length of time during which the compounds used in the instant method will be given varies on an individual basis and/or be based upon clinical guidelines.

In some embodiments, a method of treating a subject with a tumor (e.g., cancer) comprises a step of treating the subject with a complex comprising a fusion polypeptide comprising an immunomodulatory polypeptide that comprises an immune agonist moiety and a metal-hydroxide binding polypeptide and a metal hydroxide. In some embodiments, a fusion polypeptide and a metal-hydroxide are formulated together. Formulated together, for example, comprises a pre-formed complex of fusion polypeptide and metal-hydroxide. In some embodiments, a fusion polypeptide and metal-hydroxide are mixed immediately prior to administration.

In some embodiments, a method of treating a subject with a tumor (e.g., cancer) comprises treating a subject with a complex wherein a complex is administered by intratumoral injection. In some embodiments, a method of treating a subject with a tumor (e.g., cancer) comprises treating a subject with a complex wherein a complex is administered by peritumoral injection. In some embodiments, a method of treating a subject with a tumor (e.g., cancer) comprises treating a subject with a complex wherein a complex is administered to a tumor-draining lymph node or lymph nodes.

Methods of the present invention often involve administration of a therapeutically effective amount of a particular agent. A therapeutically effective amount is an amount sufficient to achieve (in principle, for a subject of comparable characteristics, such as species, body type, size, extent of disease or disorder, degree or type of symptoms, history of responsiveness, and/or overall health) an intended biological or medical response or therapeutic benefit in a tissue, system or subject. For example, a desirable response may include one or more of: delaying or preventing the onset of a medical condition, disease or disorder, slowing down or stopping the progression, aggravation, or deterioration of the symptoms of the condition, bringing about ameliorations of the symptoms of the condition, and curing the condition.

When combinations of therapeutic agents are administered, the amount of any individual agent required in the combination may be different from the amount required of that same agent to achieve its therapeutic effect alone. In some cases, synergies between or among therapeutic agents used in a combination may reduce amounts required; in other cases, inhibitory interactions may increase amounts required. Thus, in general, therapeutically effective amounts of a combination of agents may utilize different absolute amounts of the agents than constitute therapeutically effective amounts of the agents individually.

Combination Therapies

In some embodiments, fusion polypeptide metal-hydroxide complexes or preparations thereof as disclosed herein are administered in combination with a second therapeutic agent. A second therapeutic agent may be selected from a variety of available anti-tumor agents known in the art. In some embodiments, a second therapeutic agent is administered prior to administration of a fusion polypeptide metal-hydroxide complex. In some embodiments, a second therapeutic agent is administered concurrently with a fusion polypeptide metal-hydroxide complex. In some embodiments, a second therapeutic agent is administered after administration with a fusion polypeptide metal-hydroxide complex.

For example, in some embodiments, a second therapeutic is radiation (e.g., ionizing radiation). In some embodiments, an amount of ionizing radiation administered is between about 1 Gy and about 1,000 Gy, about 5 Gy and about 900 Gy, about 10 Gy to about 800 Gy, about 10 Gy to about 700 Gy, about 10 Gy to about 600 Gy, about 10 Gy to about 500 Gy, about 10 Gy to about 400 Gy, about 10 Gy to about 300 Gy, about 10 Gy to about 200 Gy, about 10 Gy to about 100 Gy, about 5 Gy and about 15 Gy, between about 7.5 Gy and about 12 Gy, or between about 10 Gy and about 12 Gy. In some embodiments, an amount of ionizing radiation administered is about 12 Gy. In some embodiments, an amount of ionizing radiation is greater than about 10, 20, 30, 40, 50, 60, 70, 80, 90, 100, 200, 300, 400, 500, or 1,000 Gy. In some embodiments, an amount of ionizing radiation is less than about 1,000, 900, 800, 700, 600, 500, 400, 300, 200, 100, 90, 80, 70, 60, or 50 Gy.

For example, in some embodiments, a second therapeutic agent is a chemotherapeutic agent. In some embodiments, a chemotherapeutic agent may be a targeted therapy (e.g., BRAF inhibitor, MEK inhibitor, etc.). In some embodiments, a chemotherapeutic agent may be any approved chemotherapeutic agent. For example, and without limitation, a chemotherapeutic agent can be one or more of adriamycin, anastrozole, cyclophosphamide, docetaxel, doxifluridine, doxorubicin, erlotinib, fluorouracil, gemcitabine, imatinib, iressa, letrozole, methotrexate, paclitaxel, tarceva, and trastuzumab. A chemotherapeutic agent may be administered according approved and/or known regimen in the art.

For example, in some embodiments, a second therapeutic agent is an anti-tumor antibody. In some embodiments, an anti-tumor antibody is an immune modulator. In some embodiments, an immune modulator is a checkpoint inhibitor. In some embodiments, a checkpoint inhibitor is an antibody or a functional fragment thereof. In some embodiments, an antibody targets one or more of PD-1, PD-L1, CTLA-4, TIM3, TIGIT, and/or LAG3. In some embodiments, an antibody targets PD-1 (e.g., pembrolizumab). An anti-tumor antibody may be administered according to any approved and/or known regimen in the art.

For example, in some embodiments, a second therapeutic agent is a surgical tumor resection. In some embodiments, a fusion polypeptide metal-hydroxide complex is administered prior to surgical tumor resection. In some embodiments, a fusion polypeptide metal-hydroxide complex is administered to tissue after tumor resection, which tissue may include, for example, remaining tumor (e.g., tumor cells). In some embodiments, a fusion polypeptide metal-hydroxide complex is administered to tissue which cannot be removed by surgical tumor resection, or tissue proximal to the resection, during said resection.

For example, in some embodiments, a second therapeutic agent is or comprises cell therapy. In some embodiments, a cell therapy is or comprises natural killer (NK) cells. In some embodiments, a cell therapy is or comprises tumor infiltrating lymphocytes (TILs). In some embodiments, a cell therapy is or comprises macrophages or other myeloid cells. In some embodiments, a cell therapy is or comprises cells that have been expanded ex vivo. In some embodiments, a cell therapy is or comprises Chimeric Antigen Receptor (CAR) effector cell therapy (e.g., CAR T cells). CARs are genetically-engineered, artificial transmembrane receptors, which confer a selected specificity for a ligand of choice onto an immune effector cell (e.g. a T cell, natural killer cell or other immune cell) and which results in activation of the effector cell upon recognition and binding to the ligand. Often, such ligand specificity is achieved by engineering the antigen specificity of a monoclonal antibody into the CAR, thereby targeting the CAR T cell to the antigen recognized by the antibody.

In some embodiments, chimeric antigen receptor-expressing effector cells (e.g., CAR-T cells) are cells that are derived (e.g., isolated) from a patient with a disease or condition and genetically modified in vitro to express at least one CAR with an arbitrary specificity to a ligand. The cells perform at least one effector function (e.g. induction of cytokines) that is stimulated or induced by the specific binding of the ligand to the CAR and that is useful for treatment of the same patient's disease or condition. The effector cells may be T cells (e.g. cytotoxic T cells or helper T cells). One skilled in the art, reading the present disclosure, will appreciate that, in some embodiments, cells other than T cells (e.g., natural killer cells, stem cells, etc) may be engineered to express CARs, so that a chimeric antigen receptor effector cell may comprise an effector cell other than a T cell. In some embodiments, a CAR effector cell is a T cell (e.g. a cytotoxic T cell); in some embodiments, such CAR-T cell exerts its effector function (e.g. a cytotoxic T cell response) on a target cell when brought in contact or in proximity to the target or target cell (e.g. a cancer cell) (see e.g., Chang and Chen (2017) Trends Mol Med 23(5):430-450). In some embodiments, a cell therapy (e.g., a CAR effector cell therapy) utilizes of Tumor Infiltrating Lymphocytes (TILs). TILs target cancer cells. In some embodiments, TILs are isolated from a subject with cancer and expanded ex vivo. In some such embodiments, TILs are isolated and expanded ex vivo after surgical resection of the tumor. In some embodiments, before administration of TILs, a subject is treated with a lymphodepleting conditioning regimen (Rohaan, Maartje W et al. "Adoptive cellular therapies: the current landscape." *Virchows Archiv: an international journal of pathology* vol. 474,4 (2019): 449-461).

In some embodiments, a cell therapy (e.g., a CAR effector cell therapy) utilizes Natural Killer (NK) cells. Natural killer (NK) cells are an essential part of tumor immunosurveillance, evidenced by higher cancer susceptibility and metastasis in association with diminished NK activity in mouse models and clinical studies. In some embodiments, for example, using an array of germline-encoded surface receptors, NK cells are able to recognize and rapidly act against malignant cells without prior sensitization (iu, S., Galat, V., Galat4, Y. et al. NK cell-based cancer immunotherapy: from basic biology to clinical development. *J Hematol Oncol* 14, 7 (2021)).

In some embodiments, fusion polypeptide metal-hydroxide complexes or preparations thereof as disclosed herein are administered to a subject who has received or is receiving a therapy with at least one additional therapeutic. An additional therapeutic agent may be selected from a variety of anti-tumor agents known in the art. In some embodiments, an additional therapeutic agent is administered prior to administration of a fusion polypeptide metal-hydroxide complex. In some embodiments, an additional therapeutic agent is administered concurrently with a fusion polypeptide metal-hydroxide complex. In some embodiments, an additional therapeutic agent is administered after administration with a fusion polypeptide metal-hydroxide complex.

For example, in some embodiments, an additional therapeutic is radiation (e.g., ionizing radiation). In some embodiments, an amount of ionizing radiation administered is between about 1 Gy and about 1,000 Gy, about 5 Gy and about 900 Gy, about 10 Gy to about 800 Gy, about 10 Gy to about 700 Gy, about 10 Gy to about 600 Gy, about 10 Gy to about 500 Gy, about 10 Gy to about 400 Gy, about 10 Gy to about 300 Gy, about 10 Gy to about 200 Gy, about 10 Gy to about 100 Gy, about 5 Gy and about 15 Gy, between about 7.5 Gy and about 12 Gy, or between about 10 Gy and about 12 Gy. In some embodiments, an amount of ionizing radiation administered is about 12 Gy. In some embodiments, an amount of ionizing radiation is greater than about 10, 20, 30, 40, 50, 60, 70, 80, 90, 100, 200, 300, 400, 500, or 1,000 Gy. In some embodiments, an amount of ionizing radiation is less than about 1,000, 900, 800, 700, 600, 500, 400, 300, 200, 100, 90, 80, 70, 60, or 50 Gy.

For example, in some embodiments, an additional therapeutic agent is a chemotherapeutic agent. In some embodiments, an additional therapeutic agent is or comprises a targeted therapy (e.g., BRAF inhibitor, MEK inhibitor, etc.). In some embodiments, a chemotherapeutic agent may be any approved chemotherapeutic agent. For example, and without limitation, a chemotherapeutic agent can be one or more of adriamycin, anastrozole, cyclophosphamide, docetaxel, doxifluridine, doxorubicin, erlotinib, fluorouracil, gemcitabine, imatinib, iressa, letrozole, methotrexate, paclitaxel, tarceva, and trastuzumab. A chemotherapeutic agent may be administered according to any approved and/or known regimen in the art. In some embodiments, an additional therapeutic agent is an anti-tumor antibody. In some embodiments, an anti-tumor antibody is an immune modulator. In some embodiments, an immune modulator is a checkpoint inhibitor. In some embodiments, a checkpoint inhibitor is an antibody or a functional fragment thereof. In some embodiments, an antibody targets one or more of PD-1, PD-L1, CTLA-4, TIM3, TIGIT, and/or LAG3. In some embodiments, an antibody targets PD-1 (e.g., pembrolizumab). An anti-tumor antibody may be administered according to any approved and/or known regimen in the art. For example, in some embodiments an additional therapeutic agent is or comprises cell therapy. In some embodiments, a cell therapy is or comprises Chimeric Antigen Receptor (CAR) effector cell therapy (e.g., CAR T cells). CARs are genetically-engineered, artificial transmembrane receptors, which confer a selected specificity for a ligand of choice onto an immune effector cell (e.g. a T cell, natural killer cell or other immune cell) and which results in activation of the effector cell upon recognition and binding to the ligand. Often, such ligand specificity is achieved by engineering the antigen specificity of a monoclonal antibody into the CAR, thereby targeting the CAR T cell to the antigen recognized by the antibody.

In some embodiments, chimeric antigen receptor-expressing effector cells (e.g., CAR-T cells) are cells that are derived (e.g., isolated) from a patient with a disease or condition and genetically modified in vitro to express at least one CAR with an arbitrary specificity to a ligand. The cells perform at least one effector function (e.g. induction of cytokines) that is stimulated or induced by the specific binding of the ligand to the CAR and that is useful for treatment of the same patient's disease or condition. The effector cells may be T cells (e.g. cytotoxic T cells or helper T cells). One skilled in the art, reading the present disclosure, will appreciate that, in some embodiments, cells other than T cells ((e.g., natural killer cells, stem cells, etc) may be engineered to express CARs, so that a chimeric antigen receptor effector cell may comprise an effector cell other than a T cell. In some embodiments, a CAR effector cell is a T cell (e.g. a cytotoxic T cell); in some embodiments, such CAR-T cell exerts its effector function (e.g. a cytotoxic T cell response) on a target cell when brought in contact or in proximity to the target or target cell (e.g. a cancer cell) (see e.g., Chang and Chen (2017) Trends Mol Med 23(5):430-450). In some embodiments, a cell therapy (e.g., a CAR effector cell therapy) utilizes of Tumor Infiltrating Lymphocytes (TILs). TILs target cancer cells. In some embodiments, TILs are isolated from a subject with cancer and expanded ex vivo. In some such embodiments, TILs are isolated and expanded ex vivo after surgical resection of the tumor. In some embodiments, before administration of TILs, a subject is treated with a lymphodepleting conditioning regimen (Rohaan, Maartje W et al "Adoptive cellular therapies: the current landscape." *Virchow's Archiv: an international journal of pathology* vol. 474,4 (2019): 449-461).

In some embodiments, a cell therapy (e.g., a CAR effector cell therapy) utilizes Natural Killer (NK) cells. Natural killer (NK) cells are an essential part of tumor immunosurveillance, evidenced by higher cancer susceptibility and metastasis in association with diminished NK activity in mouse models and clinical studies. In some embodiments, for example, using an array of germline-encoded surface receptors, NK cells are able to recognize and rapidly act against malignant cells without prior sensitization (iu, S., Galat, V., Galat4, Y. et al. NK cell-based cancer immunotherapy: from basic biology to clinical development. *J Hematol Oncol* 14, 7 (2021)).

In some embodiments, a cell therapy (e.g., a CAR effector cell therapy) comprises myeloid cells. In some embodiments, myeloid cells are or comprise macrophages. Macrophages have been shown to take up alum.

EXEMPLIFICATION

Example 1: Optimization of Exemplary Metal-Hydroxide Binding Polypeptides (e.g., Alum Binding Polypeptide (ABP)) Sequence for Increased Phosphorylation and Aluminum Hydroxide Binding Methods Gene synthesis—Genes were synthesized at ATUM Bio (Newark, CA) and cloned into the pD2610-v10 vector. Human Fam20C (Uniprot Q8IXL6) was cloned with its native signal peptide and a linker-KDEL sequence (GGGSKDEL) for intracellular retention fused at the c-terminus. Single-chain human IL12 constructs were cloned with a human IL2 signal peptide and mature human IL12B/p40 (Uniprot P29460) fused to mature human IL12A/p35 (Uniprot P29459) through a $(G_4S)_3$ linker. Single-chain mouse IL12 constructs were cloned with a human IL2 signal peptide and mature mouse IL12B/p40 (Uniprot P43432) fused to mouse IL12A/p35 (Uniprot P43431) through a $(G_4S)_3$ linker. Various alum binding polypeptide (ABP) sequences were genetically fused to the c-terminus of mouse and human IL12 followed by a $His_6$ tag for affinity purification.

Polypeptide expression and purification—Plasmids encoding human or mouse IL12 constructs were transiently transfected in suspension HEK-293 cells either with or without co-transfection with the human Fam20C-KDEL plasmid. In most co-transfections, a 4:1 mass ratio of IL12 plasmid to Fam20C-KDEL plasmid was used. Supernatants were harvested and IL12 fusion polypeptides purified by affinity chromatography on NiSepharose Excel (Cytiva 17-3712-02). Eluted fusion polypeptides were formulated in Tris-buffered saline (TBS), pH 7.4 and purity determined on a Perkin Elmer GXII capillary electrophoresis system. Polypeptide aggregation was assessed by HPLC-SEC with a 300 Å pore size. Where needed, proteins were further purified by FPLC-SEC on a HiLoad 16/600 or 26/600 Superdex 200 pg column (Cytiva 28-9893-36) and monomeric peak fractions were pooled.

In some cases, fusion polypeptides were further polished by anion exchange chromatography to enrich for highly phosphorylated species. Fusion polypeptides in TBS were diluted 3-fold in WFI and loaded on a HiTrap Q Sepharose column. Samples were washed with 1% Tx-13 in 0.33×TBS followed by 15 column volumes of 20 mM Tris, pH 8.1. Samples were eluted with a linear gradient from 20 mM Tris, pH 8.1 to 20 mM Tris, pH 8.1, 600 mM NaCl over 20 column volumes. Selected fractions were pooled and buffer exchanged into TBS.

Malachite green assay—The average number of phosphate molecules per polypeptide was determined using the Pierce Phosphoprotein Estimation Assay Kit (23270) according to manufacturer's instructions. The phosphorylated protein standard Phosvitin was resuspended in TBS and diluted from 100 to 2.5 μg/mL to generate a standard curve. Each test polypeptide was diluted in TBS to 300 μg/mL and 100 μg/mL. 50 μL of each standard or test agent was mixed with 50 μL of 2.0N NaoH in a flat bottom, 96 well plate (Griener 655101) for alkaline hydrolysis of phosphate from seryl and threonyl residues. Samples were incubated at either 65° C. for 30 minutes or 37° C. for 1 hour, then neutralized by adding 50 μL of 4.7N HCL to each well and mixing for 30 seconds on a shaker. 50 μL of phosphate reagent comprised of one volume ammonium molybdate solution and 3 volumes of malachite green solution was then added to each well and mixed for 30 seconds. Samples were incubated at room temperature for 30 minutes, then absorbance measured at 650 nm. The number of phosphate molecules per test agent was derived based on the known phosphate content in the Phosvitin standard curve.

Aluminum hydroxide (alum) retention assay—Binding and retention of fusion polypeptides to aluminum hydroxide was tested in vitro. Test polypeptides at a final concentration of 100-250 μg/mL in TBS were mixed with a 10-fold mass excess of aluminum hydroxide as defined by metal mass (Invivogen Cat # alu-vac-250) or TBS only as a control to a final volume of 50 μL. Fusion polypeptide/alum mixtures were resuspended thoroughly by pipetting and incubated at room temperature for 30 minutes. Halfway through the incubation, the mixtures were resuspended again by pipetting. The fusion polypeptide/alum mixtures or polypeptide only controls were then diluted 20× in elution buffer containing a final concentration of 1 mM phosphate, 20% mouse serum to a final volume of 1 mL. Diluted samples were incubated at 37° C. with gentle rotating for 24-48 hours. At each timepoint, 50 μL of sample was removed and centrifuged at 18,000×g for 10 minutes to pellet the aluminum hydroxide. Cleared supernatant was transferred to a new tube and stored at 4° C. until ready for analysis. The concentration of free polypeptide in each supernatant sample was quantified using a mouse IL12p70 ELISA kit (R&D Systems m1270). All dilutions were made in TBS+1% BSA+0.1% Tween-20. Test agents were used for standard curves with a top concentration of 1 ng/mL and 2× dilutions and supernatant samples were diluted to a theoretical concentration of 1 ng/mL and 0.5 ng/mL if all polypeptide was released.

SAX-10 HPLC assay—Fusion polypeptide phosphorylation was also assessed by analytical anion-exchange chromatography on a Thermo ProPac SAX-10 column (4×250 mM, 10 μm). Samples were diluted 4-fold in 20 mM Tris, pH 7.1 and loaded on the column at a 1.0 mL/min flow rate. Samples were eluted over a linear gradient from 20 mM Tris, pH 7.1 to 20 mM Tris, 525 mM NaCl, pH 7.1 over 28 minutes. In some cases, fusion polypeptides were dephosphorylated with lambda protein phosphatase (New England Biolabs, P0753L) prior to running on the column. 50 μg of fusion polypeptide was incubated with 10×PMP buffer, 10 mM $MnCL_2$, and 2-4 μL phosphatase at 30° C. for 30-60 minutes.

Syngeneic tumor models—B16F10 cells were grown in DMEM+10% FBS at 37° C., 5% $CO_2$. C57BL/6 mice aged 7-9 weeks were inoculated with $1\times10^6$ B16F10 cells in 0.1 mL of PBS solution at the right flank region. When tumors reached ~75 $mm^3$, mice were randomized and injected intratumorally with 20 μL vehicle or 5-7.7 μg mIL12-ABP that had been mixed and pre-incubated with 25-50 μg aluminum hydroxide as defined by metal mass for 30 minutes at room temperature. In some groups, 200 μg anti-PD1 (Bioxcell BP0273) in a 50 μL volume was injected intraperitoneally on days 0, 3, 6, and 9. Tumor volume and body weight were measured 3× weekly for the duration of the study and mice were euthanized when their tumor volume reach 2000 $mm^3$. In some studies, two tumors were inoculated in each animal with $1\times10^6$ B16F10 cells injected in the right flank and $1\times10^5$ cells injected in the left flank. In these dual flank studies, the mIL12-ABP/alum complex or controls were injected in the larger right flank tumor only.

Results

Figure 3A:
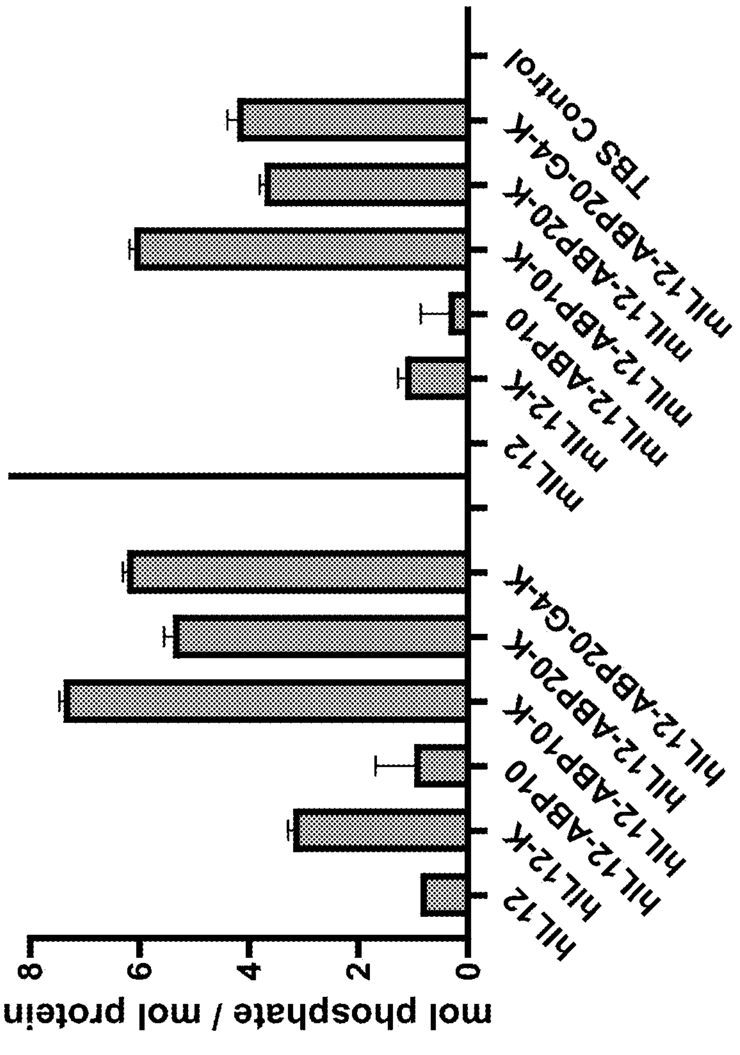

Single-chain human and mouse IL12 constructs were generated containing the mature IL12B and IL12A sequences linked by a $(G_4S)_3$ linker with a c-terminal $His_6$ tag for affinity purification. Alum binding polypeptide containing variants (IL12-ABP) were cloned by inserting nucleotide sequences encoding various ABP sequences c-terminal to IL12 and before the His tag. A first set of human and mouse IL12-ABP fusion polypeptides were transiently expressed in 100 mL HEK cultures either with or without co-transfection with a plasmid encoding human Fam20C kinase with a c-terminal KDEL sequence for intracellular retention. Fusion polypeptides were purified by Ni-NTA chromatography and average phosphorylation levels per fusion polypeptide assessed by malachite green assay (FIG. 3A). hIL12-ABP and mIL12-ABP fusion polypeptides co-expressed with Fam20C (denoted as "-K") had significantly higher phosphate levels compared to fusion polypeptides without Fam20C co-expression or wild-type hIL12 or mIL12 lacking the ABP co-expressed with Fam20C. While all ABP sequences were phosphorylated, fusion polypeptides with the ABP10 sequence had reproducibly higher phosphorylation levels than the other ABP variants tested.

Figure 3B:
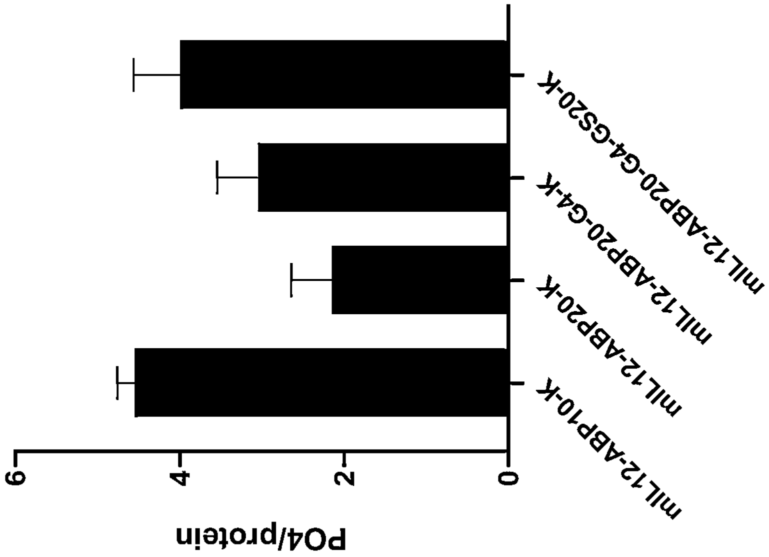
Figure 4A:
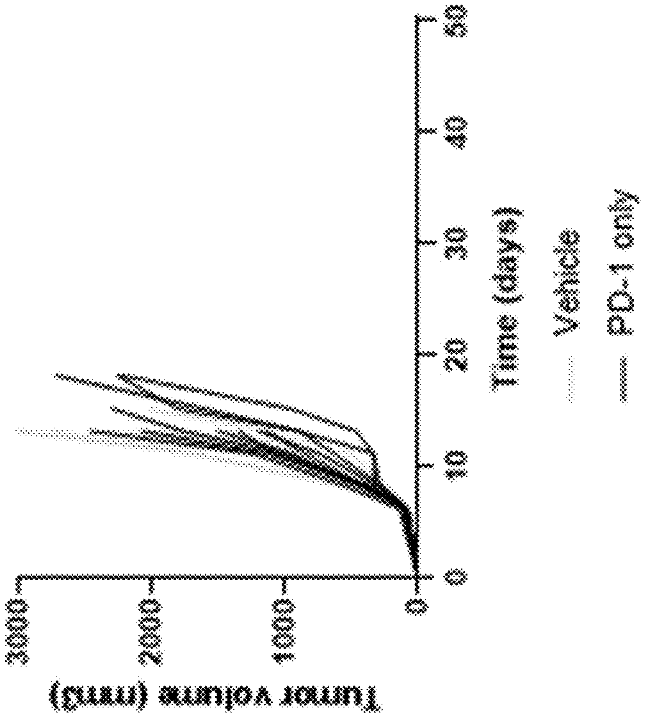
FIGS. 4A-4G demonstrate an exemplary in vivo study of ABP10 verse exemplary metal-hydroxide binding polypeptides of the present disclosure. Mouse IL12-ABP polypeptides were tested in a dual flank B16F10 syngeneic tumor model in combination with systemic PD-1 blockade. Vehicle treatment was utilized as a control.
Figure 4B:
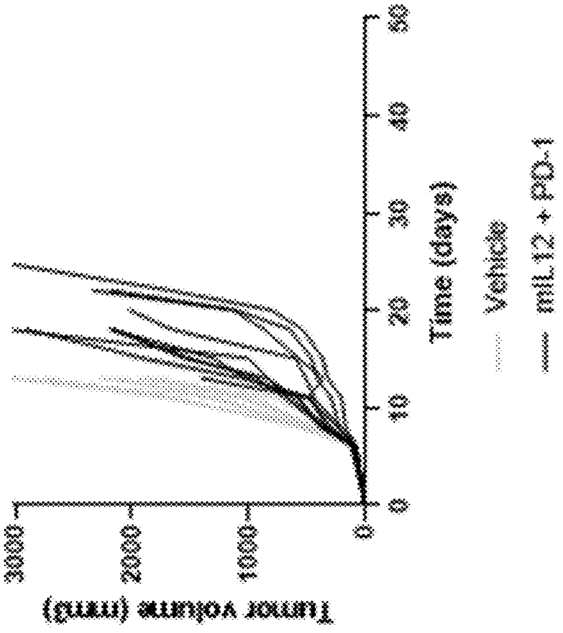
Figure 4C:
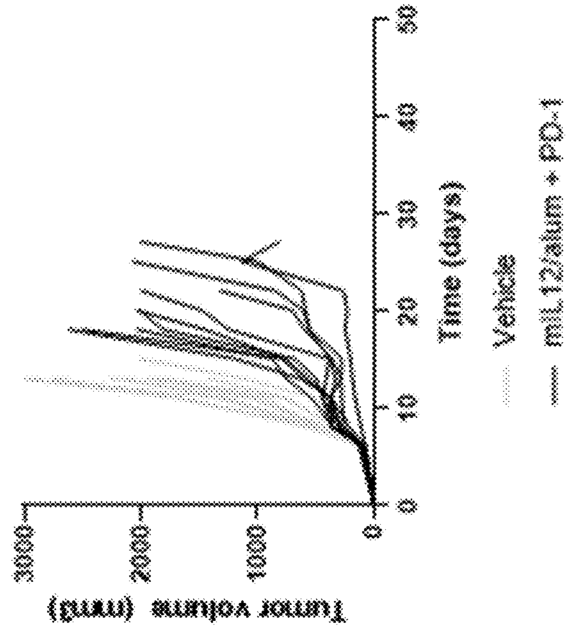
Figure 4D:
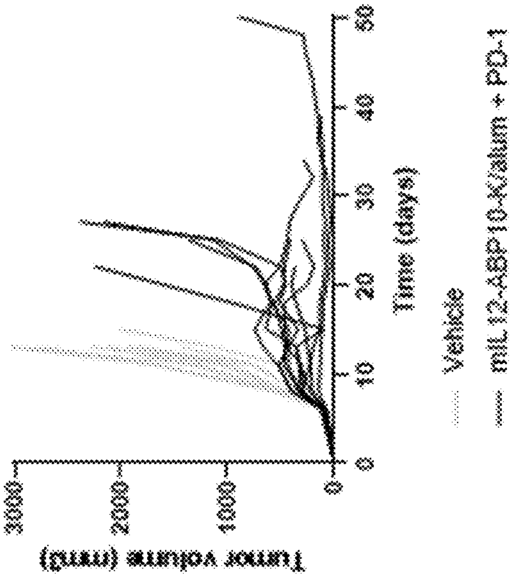
Figure 4E:
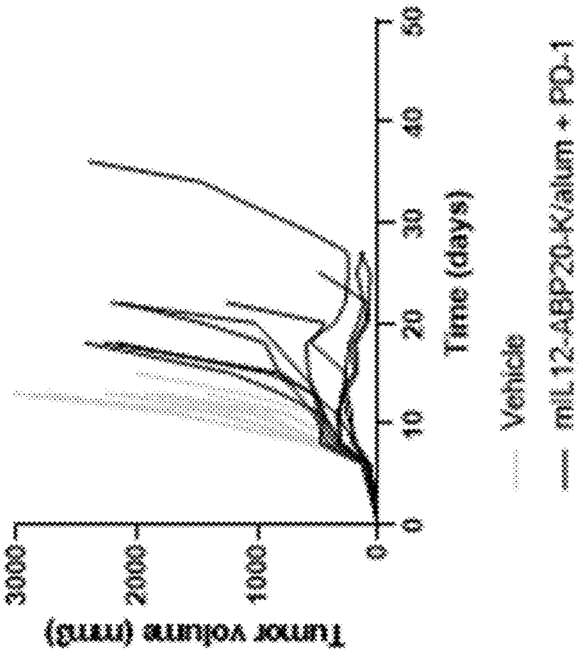
Figure 4F:
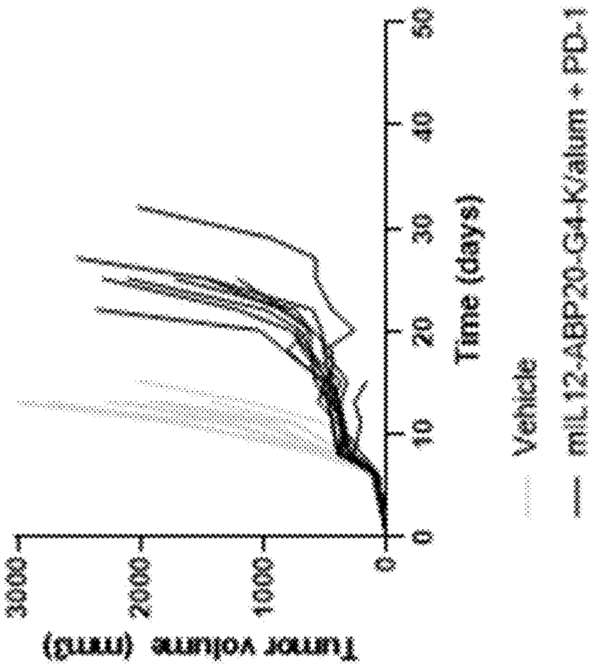
Figure 4G:
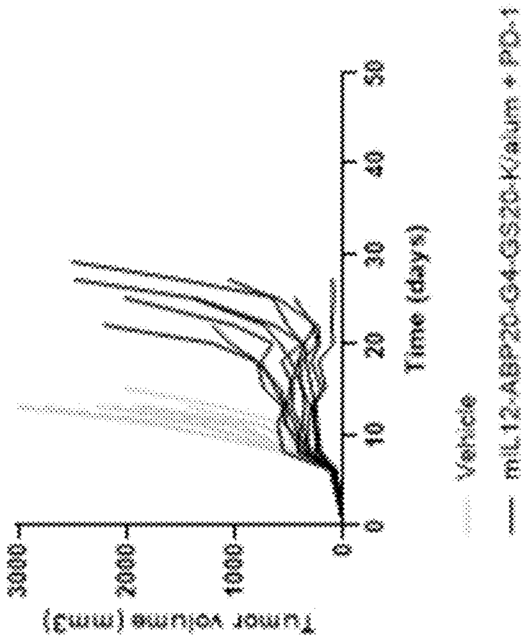

Mouse IL12-ABP variants were expressed at 1 L scale in transient HEK with Fam20C co-expression and purified by sequential Ni-NTA and SEC chromatography. In the malachite green assay, mIL12-ABP10 again had the highest phosphorylation followed in order by ABP20-G4-G520, ABP20-G4, and ABP20 (FIG. 3B). Mouse IL12-ABP fusion polypeptides were then tested in a dual flank B16F10 syngeneic tumor model in combination with systemic PD-1 blockade. 5 μg mIL12 or mIL12-ABP was mixed with 25 μg aluminum hydroxide as defined by metal mass and incubated for 30 minutes prior to injection into the right flank tumor on Day 6 post tumor implantation. All mIL12-ABP/alum complexes delayed tumor growth compared to PD-1 alone or mIL12+PD-1, but the greatest delays were observed with mIL12-ABP10 suggesting that increased phosphorylation can improve in vivo efficacy after a single injection when complexed with alum (FIGS. 4A-4G).

Figure 6A:
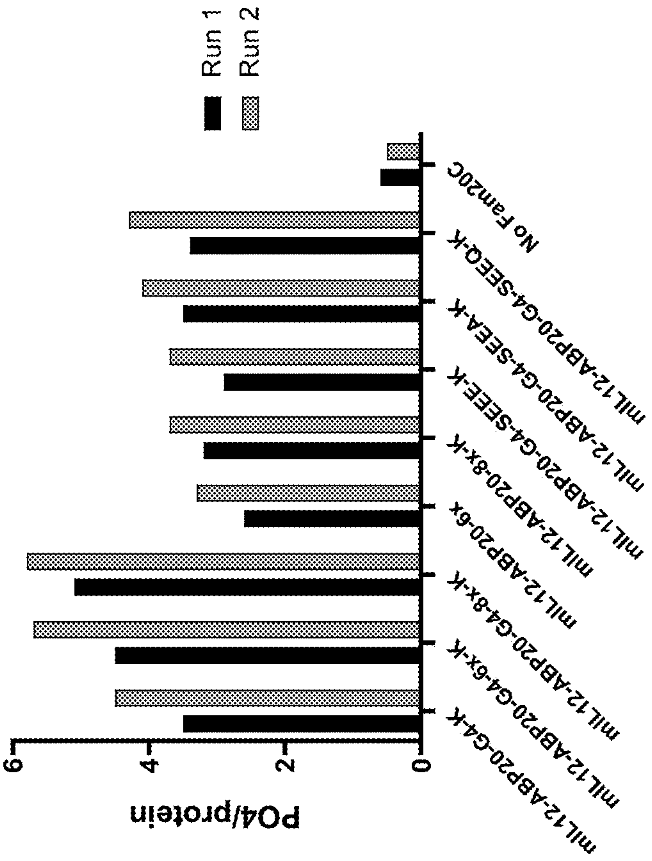
FIG. 6A and FIG. 6B demonstrate analysis of phosphorylation levels using a malachite green assay of exemplary, purified fusion polypeptides. All ABPs demonstrated significantly higher phosphorylation compared to negative controls (no Fam20C or TBS). Runs 1 and 2 of FIG. 6A are technical replicates of the same experiment.
Figure 6B:
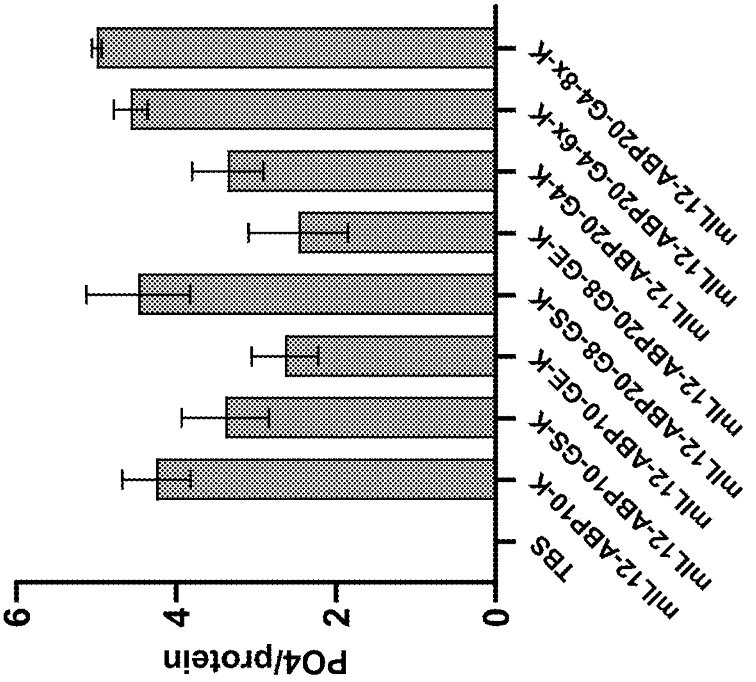

To further enhance ABP phosphorylation, alum retention, and in vivo efficacy, a larger panel of mIL12-ABP constructs was generated with ABP sequences listed in FIG. 5 differing in number of SXE sites, spacing of SXE sites, flanking residues, and linker sequences. Polypeptides were co-transfected with Fam20C in HEK cells and purified by Ni-NTA chromatography. Phosphorylation levels of the purified polypeptides were characterized in the malachite green assay (FIG. 6A and FIG. 6B). While all ABP's had significantly higher phosphorylation compared to negative controls, the highest phosphorylation levels were detected in mIL12 fusion polypeptides comprising ABP10, ABP20-G8-GS, ABP20-G4-6x, and ABP20-G4-8x.

Figure 7A:
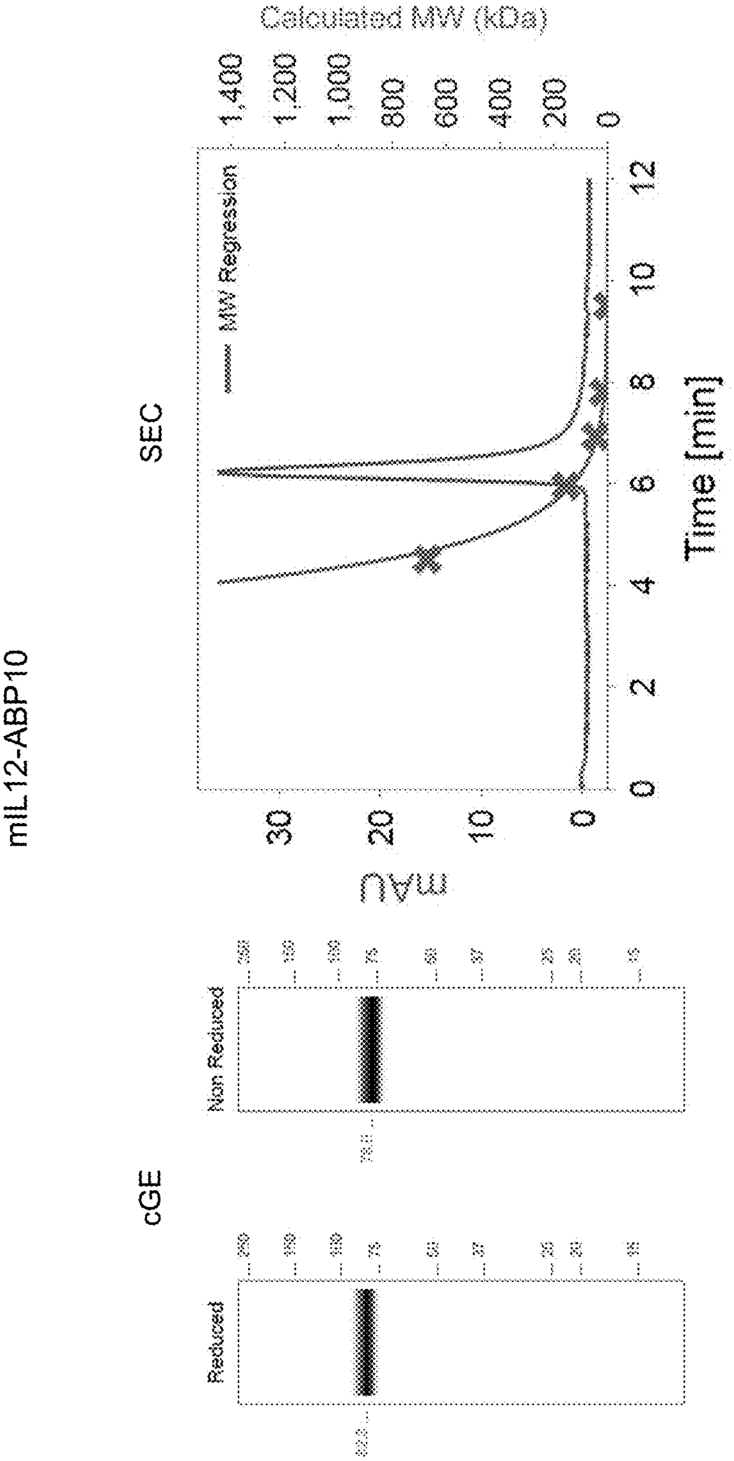
FIGS. 7A-7C show purification of exemplary fusion polypeptides using sequential Ni-NTA affinity and size exclusion chromatography. All polypeptides ran as a single peak on SDS-PAGE and SEC, demonstrating there was no significant degradation or aggregation.
Figure 7B:
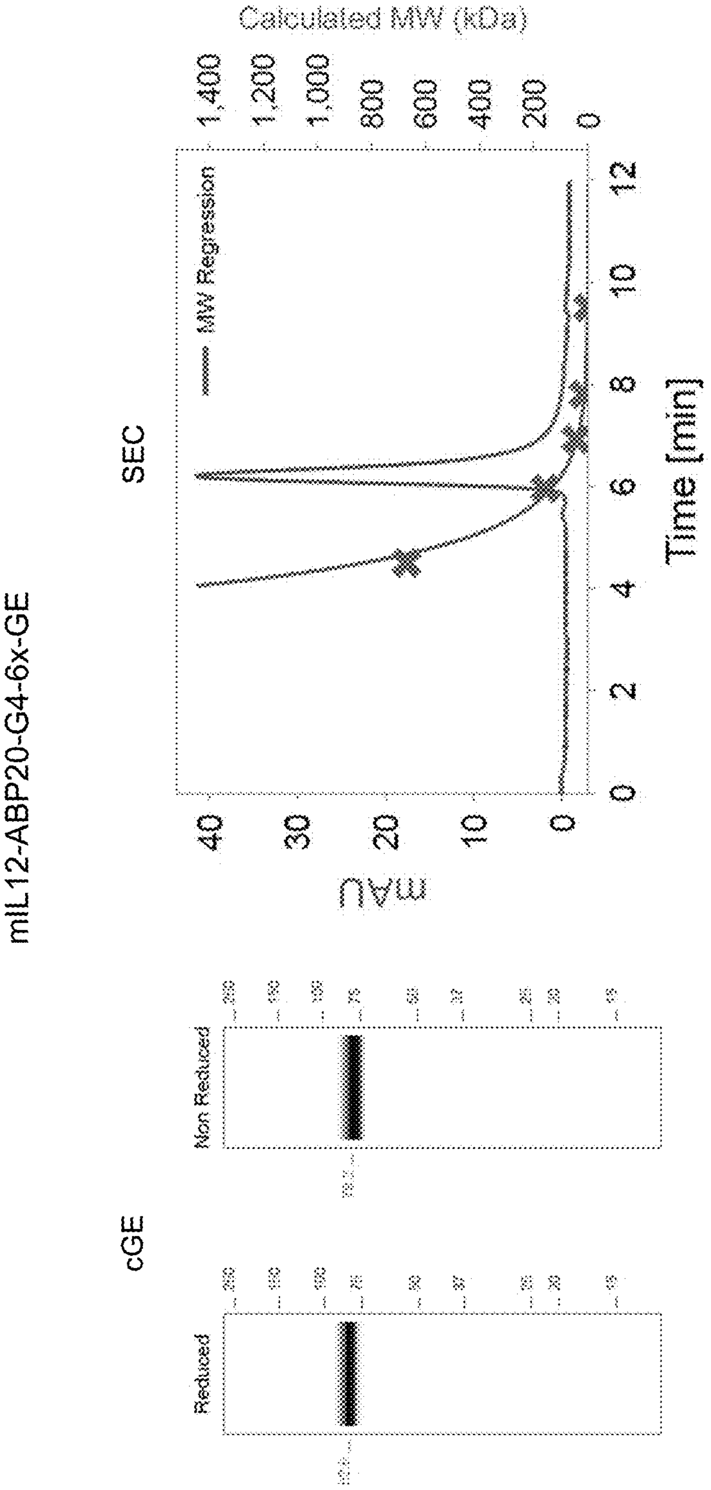
Figure 7C:
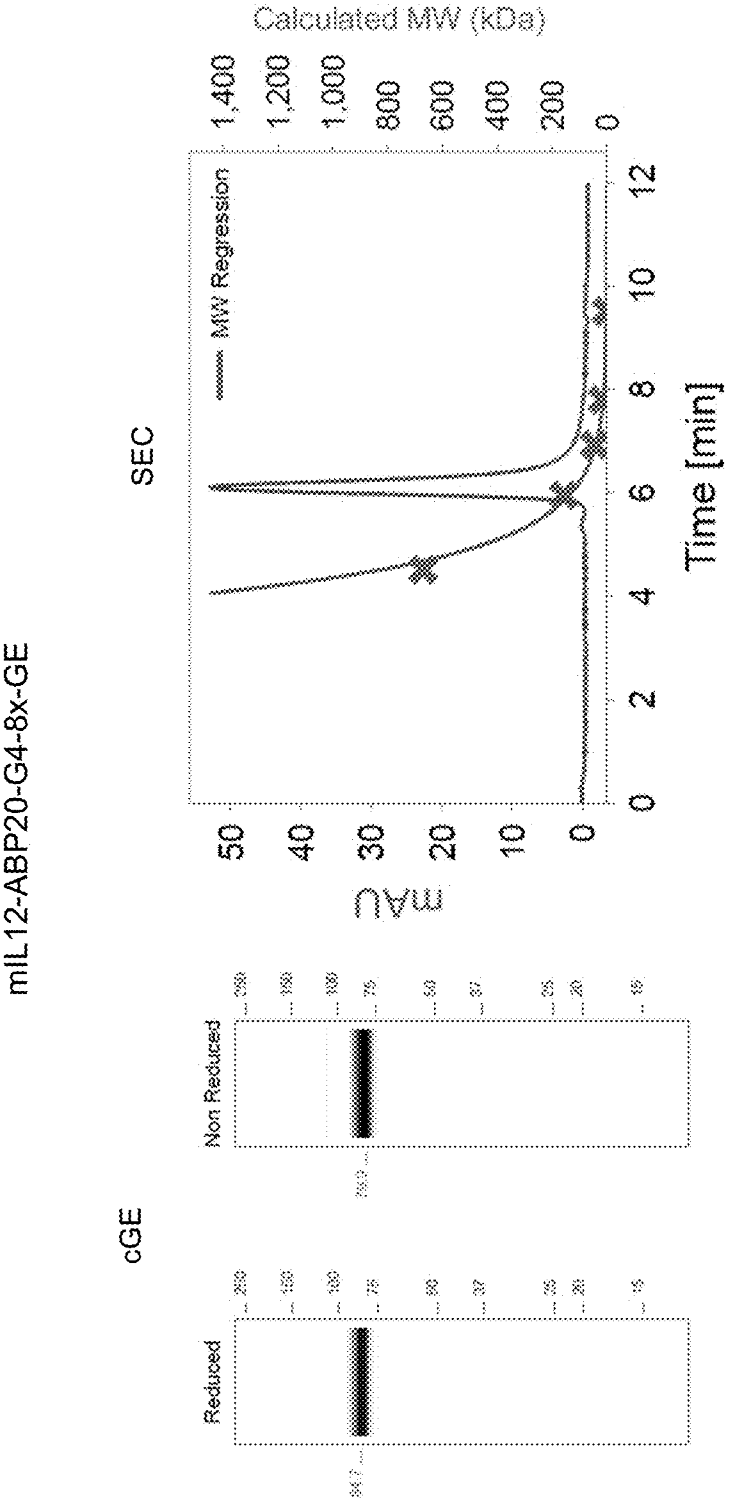
Figure 8:
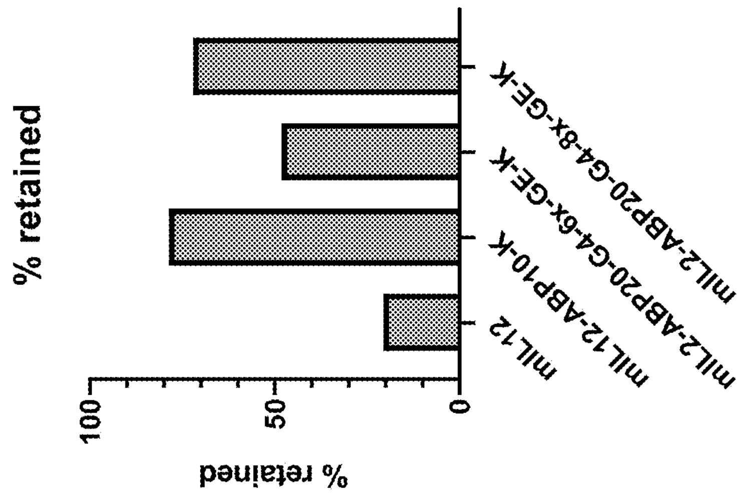
FIG. 8 provides assessment of alum retention for exemplary fusion polypeptides, mIL12-ABP10-K, mIL12-ABP20-G4-6x-GE-K, and mIL-ABP20-G4-8x-GE-K, relative to control, mIL12. All three fusion polypeptides showed greater retention on alum compared to unmodified IL12, mIL12-ABP20-G4-6x-GE was eluted more quickly than both mIL12-ABP10 and mIL12-ABP20-G4-8x-GE.

To reduce the chance of off-target phosphorylation of additional serines in the ABP sequence, the linkers for ABP20-G4-6x and ABP20-G4-8x were changed from GGGGSGGGG to GGGGEGGGG and the serine immediately upstream of the His-tag was removed. These new sequences were referred to as ABP20-G4-6x-GE and ABP20-G4-8x-GE (FIG. 5). mIL12 fused to ABP10, ABP20-G4-6x-GE, or ABP20-G4-8x-GE was co-expressed with Fam20C at 1 L scale in transient HEK. Fusion polypeptides were purified by sequential Ni-NTA affinity and size exclusion chromatography. All fusion polypeptides ran as a single peak on SDS-PAGE and SEC demonstrating that there was no significant degradation or aggregation (FIGS. 7A-7C). The three exemplary fusion polypeptides were tested in an alum retention assay in which fusion polypeptides were incubated with a 10-fold mass excess of aluminum hydroxide as defined by metal mass for 30 minutes in TBS then diluted in elution buffer containing 5 mM phosphate and 20% mouse serum for 24 hours. While all 3 fusion polypeptides had significantly greater retention on alum compared to unmodified IL12, mIL12-ABP20-G4-6x-GE was eluted more quickly than both mIL12-ABP10 and mIL12-ABP20-G4-8x-GE (FIG. 8).

Figure 9A:
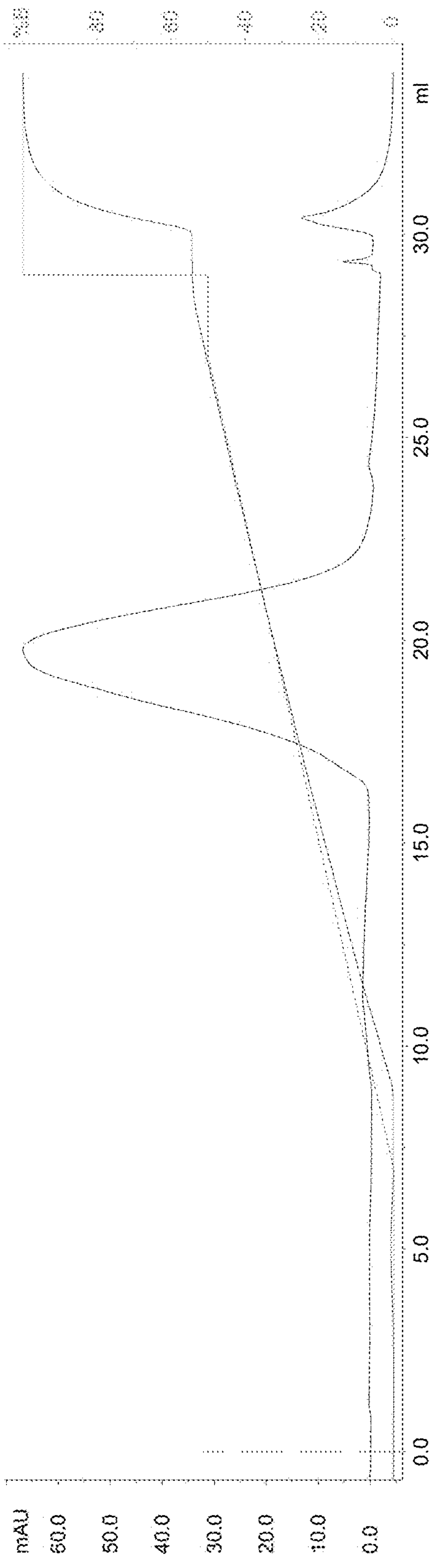
FIG. 9A and FIG. 9B demonstrate exemplary purification of fusion polypeptides. To generate more homogeneously phosphorylated material, mIL12-ABP10-K (FIG. 9A) and mIL12-ABP20-G4-8x-GE-K (FIG. 9B) were further purified by anion exchange chromatography. Samples were eluted with a linear salt gradient and the second half of each elution peak was collected and pooled to eliminate early eluting fractions containing lower levels of phosphorylation.
Figure 9B:
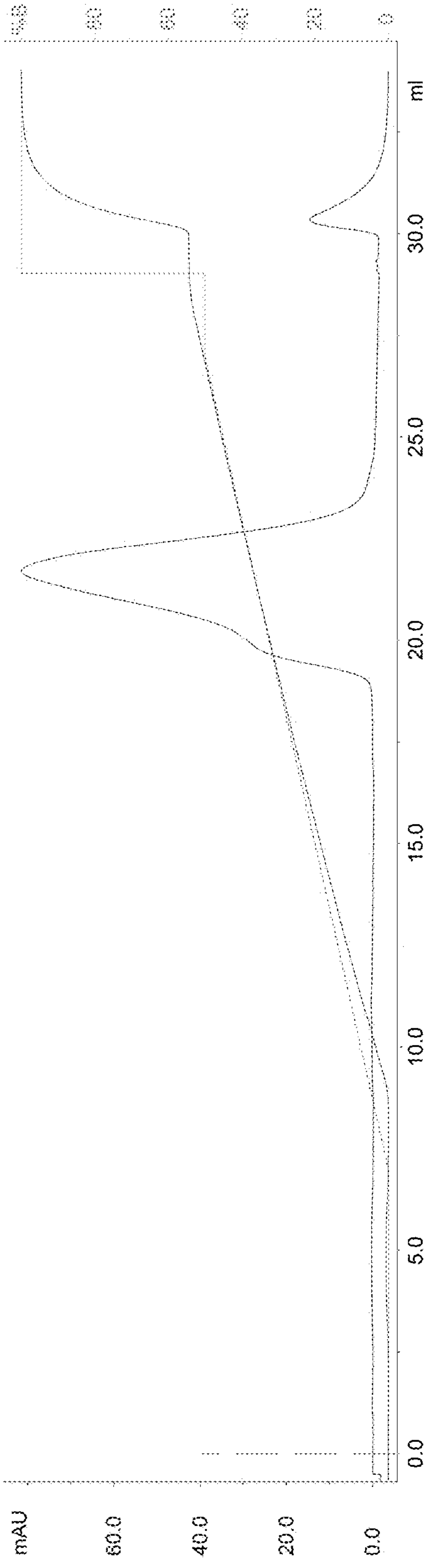
Figure 10A:
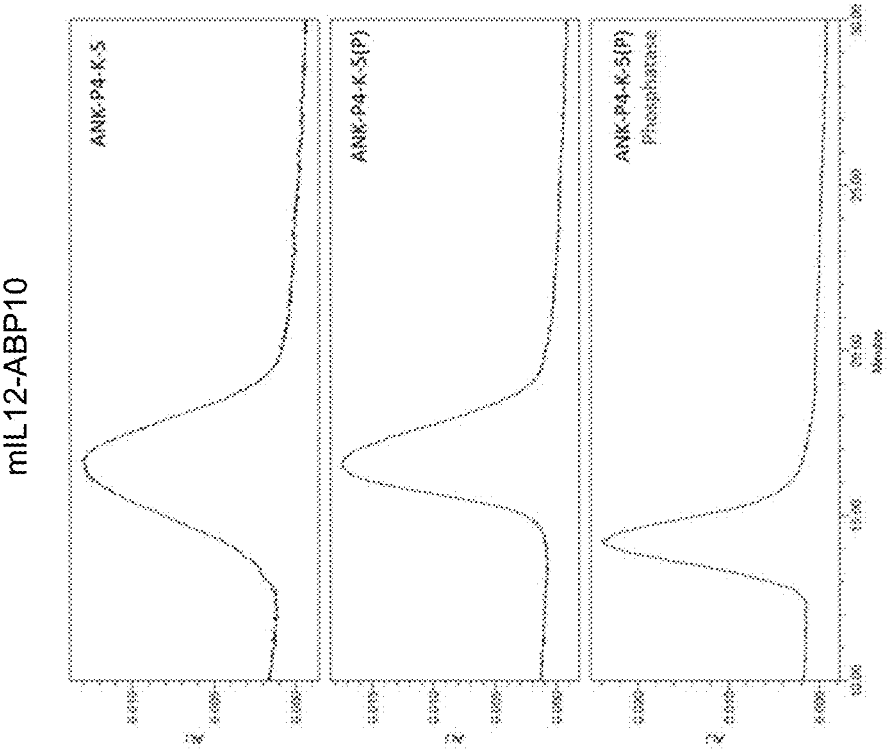
Figure 10B:
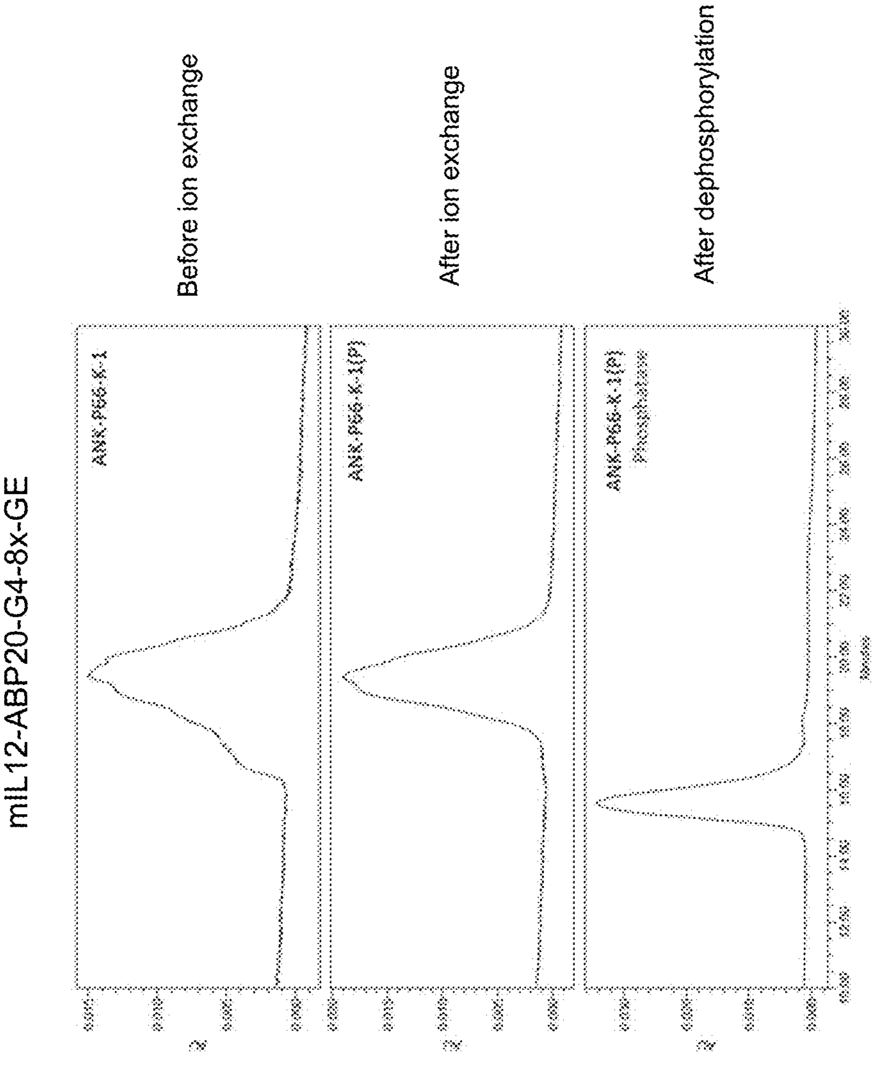

Following transient co-transfection with Fam20C in HEK cells, there is potential for heterogeneity in phosphate levels between IL12-ABP molecules within a given fusion polypeptide sample. In order to generate more homogeneously phosphorylated material, mIL12-ABP10 and mIL12-ABP20-G4-8x-GE were further purified by anion exchange chromatography which is able to separate different phospho-species on the basis of the added negative charge with more heavily phosphorylated fusion polypeptides binding tighter to the column and eluting later. Samples were eluted with a linear salt gradient and the second half of each elution peak was collected and pooled to eliminate early eluting fractions containing lower levels of phosphorylation (FIGS. 9A-9B). The enriched pools of mIL12-ABP10 and mIL12-ABP20-G4-8x-GE after preparative anion exchange chromatography were compared to the original material by analytical ion exchange chromatography (FIGS. 10A-10C). An additional sample of each fusion polypeptide was enzymatically dephosphorylated with phosphatase and run as a control. Prior to anion exchange polishing, both samples have an early eluting fraction that partially overlaps with the dephosphorylated trace. However, after ion exchange polishing, the samples have a more homogeneous profile that elutes later than the dephosphorylated fusion polypeptide suggesting enrichment for fusion polypeptides with higher phosphorylation.

Figure 11A:
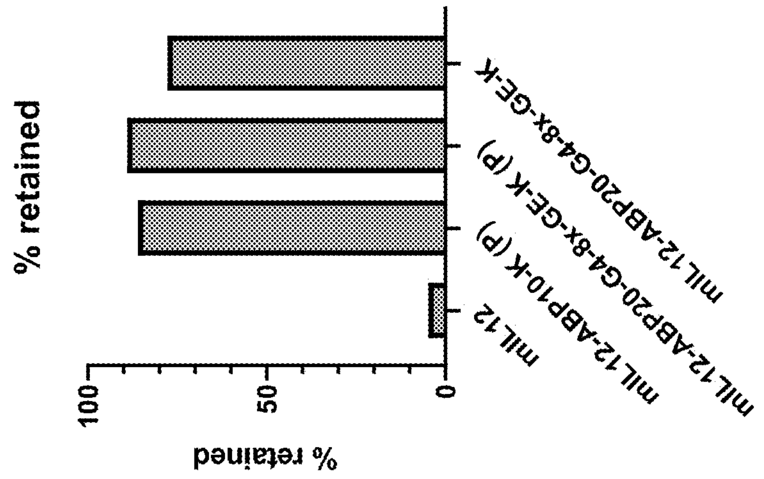
FIG. 11A and FIG. 11B demonstrate exemplary assessment of ion-exchange enriched fusion polypeptides.
Figure 11B:
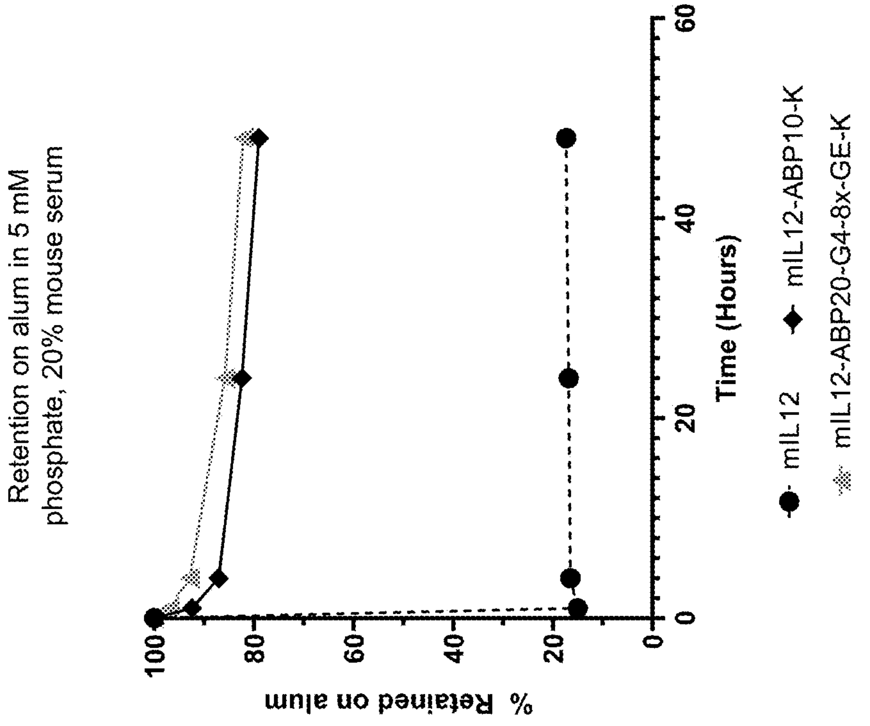

Ion-exchange enriched mIL12-ABP10 and mIL12-ABP20-G4-8x-GE were tested in the alum retention assay along with a sample of mIL12-ABP20-G4-8x-GE prior to ion-exchange polishing (FIG. 11A). Polypeptides were complexed with a 10-fold mass excess of aluminum hydroxide as defined by metal mass then diluted in elution buffer containing 5 mM phosphate and 20% mouse serum for 24 hours before quantifying free polypeptide in the supernatant. The ion exchange purified mIL12-ABP20-G4-8x-GE had the highest retention with 89% bound to alum at 24 hours compared to 86% for mIL12-ABP10 and 78% for the non-ion exchanged material demonstrating that the low phosphate fractions elute off the alum faster. In a second alum retention assay, samples were bound to a 10-fold mass excess of aluminum hydroxide as defined by metal mass then eluted with 5 mM phosphate and 20% mouse serum for up to 48 hours (FIG. 11B). The ion exchange purified mIL12-ABP20-G4-8x-GE again had the highest retention with 82% bound to alum at 48 hours compared to 78% for mIL12-ABP10 and 17% for unmodified mIL12.

Example 2: Cellular Activity of Exemplary Fusion-Polypeptide-Metal Hydroxide Complex Methods HEK-Blue-IL12 potency assay—In vitro IL12 signaling activity was assessed using the HEK-Blue-IL12 reporter assay (Invivogen hkb-il12) according to manufacturer's instructions. This cell line is derived from HEK293 cells stably transfected with human IL12Rβ1 and hIL12Rβ2 and a secreted alkaline phosphatase (SEAP) reporter under the control of a STAT4 inducible promoter. Since mouse IL12 cross-reacts with the human IL12 receptors, this cell line can be used to assess potency of both human and mouse IL12 derived constructs. HEK-Blue-IL12 cells were cultured in DMEM+4.5 g/l glucose, 2 mM L-glutamine, 10% heat inactivated FBS, Pen-Strep (100 U/mL) and 100 ug/mL Normocin and passaged at 70-80% confluency. For potency testing, the same media was used without Normocin.

Test agents or IL12 controls were diluted in assay media to generate a titration series with a top concentration of 10 μg/mL and 3× dilutions. For samples mixed with alum, fusion polypeptides at a final concentration of 50 μg/mL were mixed with a 10× mass excess of aluminum hydroxide as defined by metal mass in TBS and incubated at room temperature for 30 minutes with shaking before diluting in assay media as above. 20 μL of each sample in the titration series was transferred to a 96 well plate and mixed with 180 μL of HEK-Blue-IL12 cell suspension (280,000 cells/mL) for a final top fusion polypeptide concentration of 1 μg/mL and 50,000 cells/well. Plates were then incubated overnight at 37° C. in 5% $CO_2$. The next day, 20 μL of supernatant from each well was transferred to a new plate and mixed with 180 μL of QUANTI-Blue solution (Invivogen rep-qbs), a colorimetric reagent than turns blue in the presence of secreted alkaline phosphatase. Plates were incubated for at 37° C. for 3 hours, then absorbance measured at 620-655 nm.

In some experiments, test agents in TBS were mixed with aluminum hydroxide to a final concentration of 200 μg/mL fusion polypeptide and 2 mg/mL aluminum hydroxide as defined by metal mass, then incubated at RT for 30 minutes. Mixtures were then diluted 5× in elution buffer to a final concentration of 40 μg/mL fusion polypeptide with 1 mM phosphate and 20% mouse serum and incubated at 37° C. with rotating for 24 hours. Samples were centrifuged at 18,000×g at 4° C. for 10 minutes to pellet alum and the supernatant carefully removed and saved. Pellets were resuspended in an equal volume of elution buffer. Supernatant and resuspended alum pellets were then diluted in assay media and tested for activity in the HEK-Blue-IL12 assay as described above.

Figure 12A:
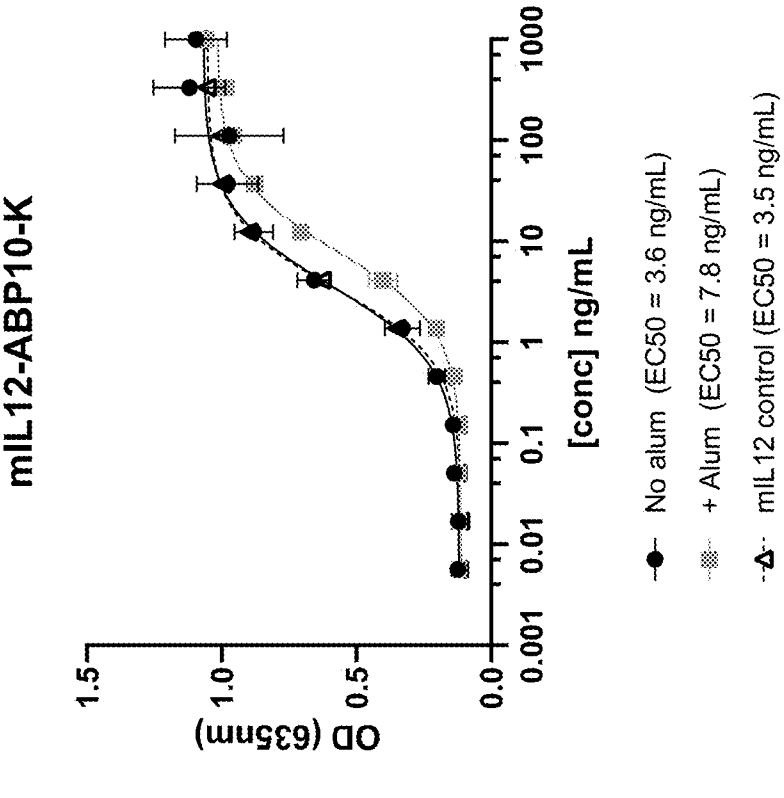
FIG. 12A and FIG. 12B demonstrate assessment of mIL12-ABP10 and mIL12-ABP20-G4-8x-GE in a HEK-Blue-IL12 reporter assay wherein SEAP is expressed in response to IL12 induced signaling.
Figure 12B:
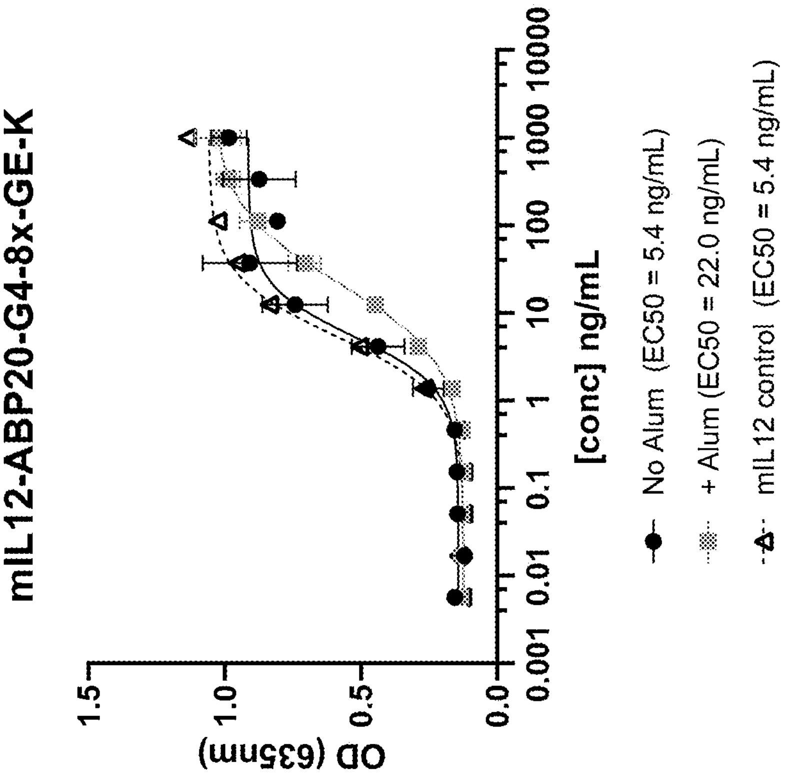

Results mIL12-ABP10 and mIL12-ABP20-G4-8x-GE were tested in a HEK-Blue-IL12 reporter assay that expresses SEAP in response to IL12 induced signaling. The IL12-ABP fusion polypeptides were titrated either alone or after mixing with a 10-fold mass excess of aluminum hydroxide as defined by metal mass in TBS and incubating for 30 minutes. Both fusion polypeptides were active in the assay with EC50 values of 3.6 and 5.4 ng/mL for mIL12-ABP10 and mIL12-ABP20-G4-8x-GE, respectively, compared to 3.5-5.4 ng/mL for unmodified mIL12 (FIGS. 12A-12B). When bound to alum the EC50 values shifted ~2-4 fold with EC50 values of 8 ng/mL for mIL12-ABP10 and 22 ng/mL for mIL12-ABP20-G4-8x. The potency shift is likely a product of steric hindrance in the way the IL12 is presented while complexed with aluminum hydroxide.

Figure 13:
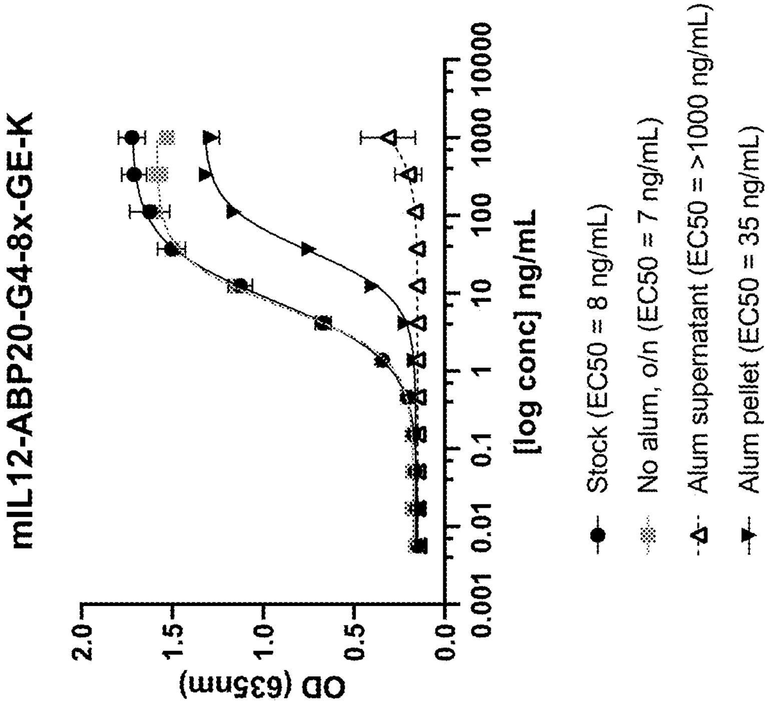
FIG. 13 shows exemplary assessment for the activity of alum bound and eluted fractions of mIL12-ABP20-G4-8x-GE. A supernatant fraction, resuspended alum pellet, and a control sample of mIL12-ABP20-G4-8x-GE incubated overnight in elution buffer without alum were tested in the HEK-Blue-IL12 assay. A control sample without alum had a similar EC50 to previous measurements at 7 ng/mL, a supernatant fraction had an EC50>1000 ng/mL, and an alum pellet was active in the assay with a potency shift of ~5× demonstrating that IL12 remains active while retained on alum for extended time.

To assess activity of the alum bound and eluted fractions, mIL12-ABP20-G4-8x-GE was complexed with a 10-fold mass excess of aluminum hydroxide as defined by metal mass then incubated in elution buffer containing 1 mM phosphate and 20% mouse serum for 24 hours. The alum was then pelleted by centrifugation, supernatant removed, and the pellet resuspended in an equal volume of elution buffer. The supernatant fraction, resuspended alum pellet, and a control sample of mIL12-ABP20-G4-8x-GE incubated overnight in elution buffer without alum were tested in the HEK-Blue-IL12 assay. While the control sample without alum had a similar EC50 to previous measurements at 7 ng/mL, the supernatant fraction had an EC50>1000 ng/mL demonstrating that minimal IL12 eluted off the alum during the extended incubation. In contrast, the alum pellet was active in the assay with a potency shift of ~5× demonstrating that IL12 remains active while retained on alum for extended time (FIG. 13).

Example 3: Use of Fusion-Polypeptide-Metal Hydroxide Complex as Monotherapy and in Combination Therapy Methods Syngeneic tumor models—CT26 cells were cultured in RPMI1640+10% FBS. BALB/c mice aged 7-9 weeks were inoculated subcutaneously with $5\times10^5$ CT26 cells in 0.1 mL PBS at the right flank region. When tumors reached ~75 $mm^3$, mice were randomized and injected intratumorally with 20 μL vehicle or 5 μg mIL12-ABP that had been mixed and pre-incubated with 50 μg aluminum hydroxide as defined by metal mass for 30 minutes at room temperature. Tumor volume and body weight were measured 3× weekly for the duration of the study and mice were euthanized when their tumor volume reach 2000 $mm^3$. Tumor volumes were measured in two dimensions using a caliper, and the volume was calculated using the formula: $V=(L\times W\times W)/2$, where V is tumor volume, L is tumor length (the longest tumor dimension) and W is tumor width (the longest tumor dimension perpendicular to L).

B16F10 cells were grown in DMEM+10% FBS at 37° C., 5% $CO_2$. C57BL/6 mice aged 7-9 weeks were inoculated with $1\times10^6$ B16F10 cells in 0.1 mL of PBS solution at the right flank region. When tumors reached ~75 $mm^3$, mice were randomized and injected intratumorally with 20 μL vehicle or 7.7 μg mIL12-ABP that had been mixed and pre-incubated with 50 μg aluminum hydroxide as defined by metal mass for 30 minutes at room temperature. In some groups, 200 μg anti-PD1 (Bioxcell BP0273) in a 50 μL volume was injected intraperitoneally on days 0, 3, 6, and 9. Tumor volume and body weight were measured 3× weekly for the duration of the study and mice were euthanized when their tumor volume reach 2000 $mm^3$.

4T1 cells were grown in RPMI1640+10% FBS at 37° C., 5% $CO_2$. BALB/c mice aged 7-9 weeks were inoculated in the right mammary fat pad with $3\times10^5$ 4 T1 cells in 0.1 mL PBS. When tumors reached ~75 $mm^3$, mice were randomized and injected intratumorally with 20 μL vehicle or 5 μg mIL12-ABP that had been mixed and pre-incubated with 50 μg aluminum hydroxide as defined by metal mass for 30 minutes at room temperature. Tumor volume and body weight were measured 3× weekly. On day 28 post-tumor inoculation, mice were euthanized and metastases counted in the lung.

Figure 14A:
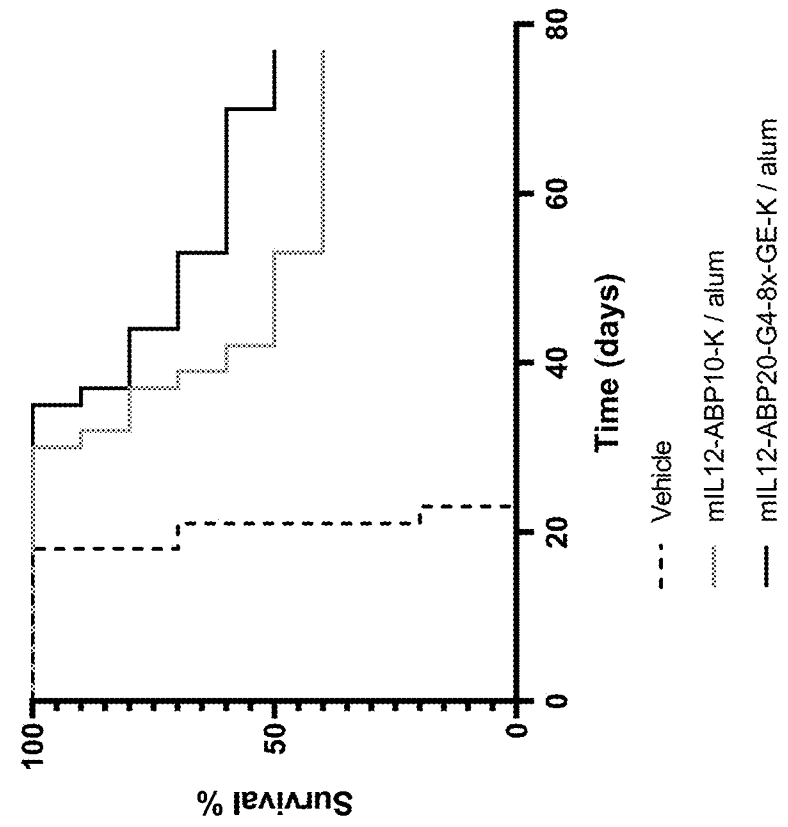
FIGS. 14A-14C demonstrate efficacy of mIL12-ABP10-K/alum and mIL12-ABP20-G4-8x-GE-K/alum as a single shot monotherapy in a CT26 colorectal cancer model.
Figure 14B:
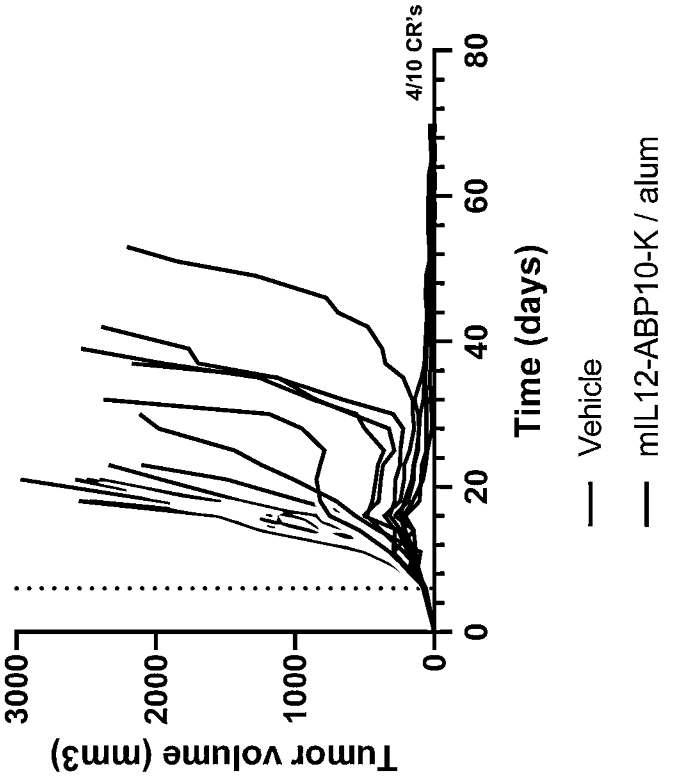
Figure 14C:
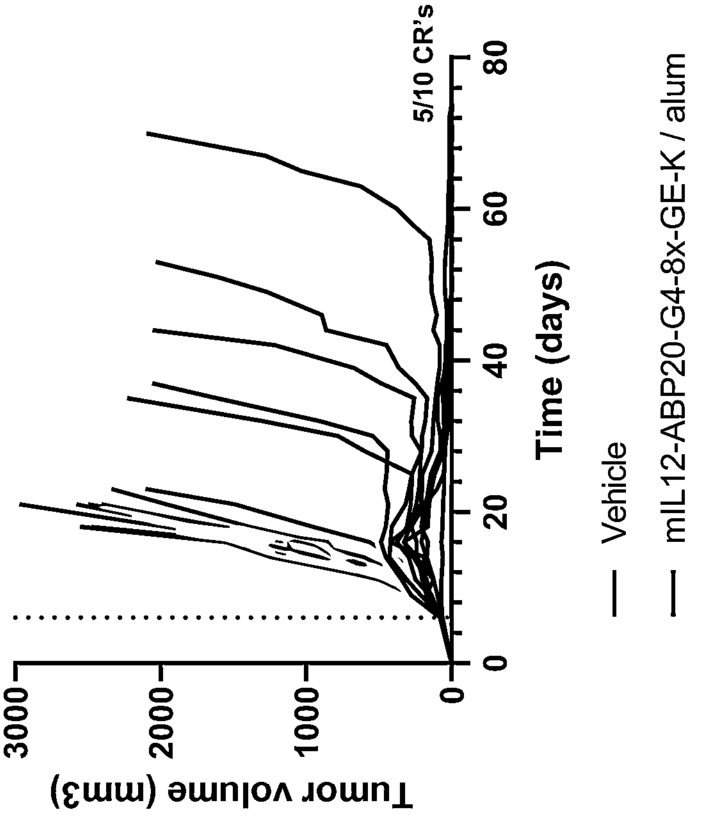
Figure 15A:
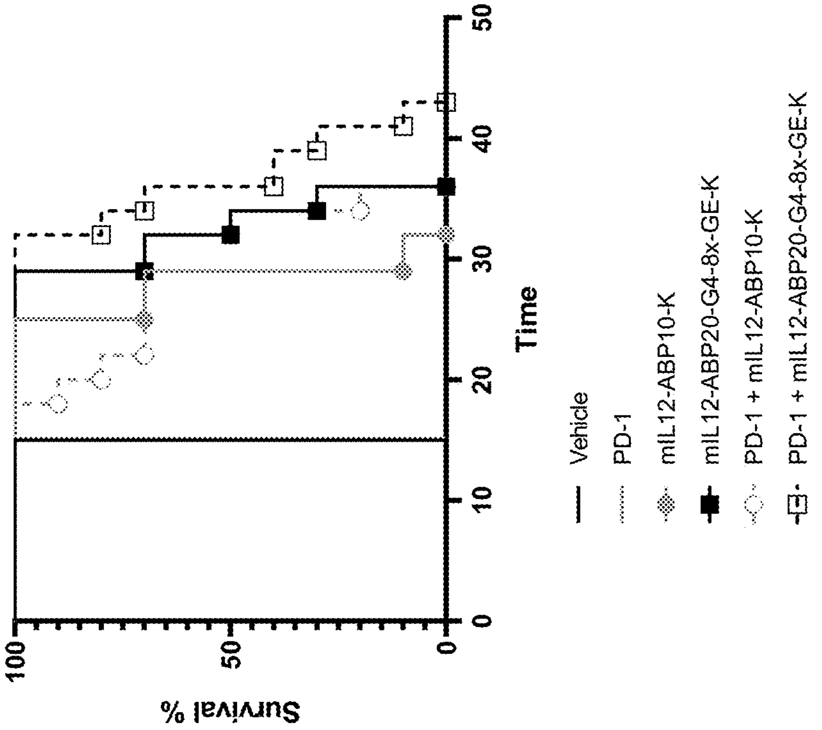
FIGS. 15A-15E demonstrate exemplary fusion polypeptides, as a monotherapy and in combination with an anti-PD-1 antibody, delays refractory B16F10 tumors. 7.7 μg of either mIL12-ABP10 or mIL12-ABP20-G4-8x-GE complexed with 50 μg alum was injected intratumorally on Day 6 and 13 following tumor inoculation. In some animals, anti-PD1 antibody was administered intraperitoneally on Day 0, 3, 6, & 9 in combination with either mIL12-ABP10 or mIL12-ABP20-G4-8x-GE. Vehicle treatment or anti-PD-1 antibody as a monotherapy were used as controls. Tumor delay was further extended in groups receiving the combination treatment with systemic PD-1 blockade. In both the monotherapy and PD-1 combination groups, the median survival was longer in mice treated with mIL12-ABP20-G4-8x-GE compared to mIL12-ABP10.
Figure 15B:
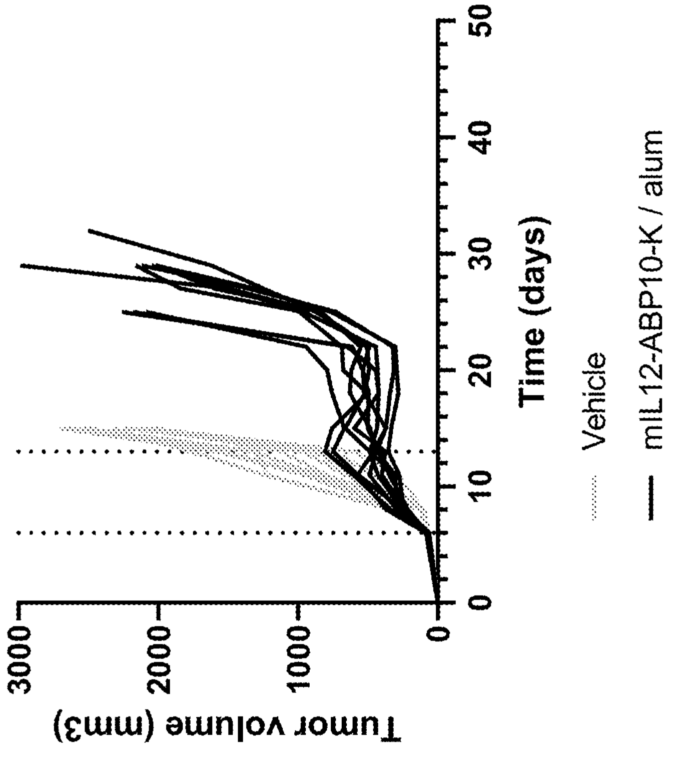
Figure 15C:
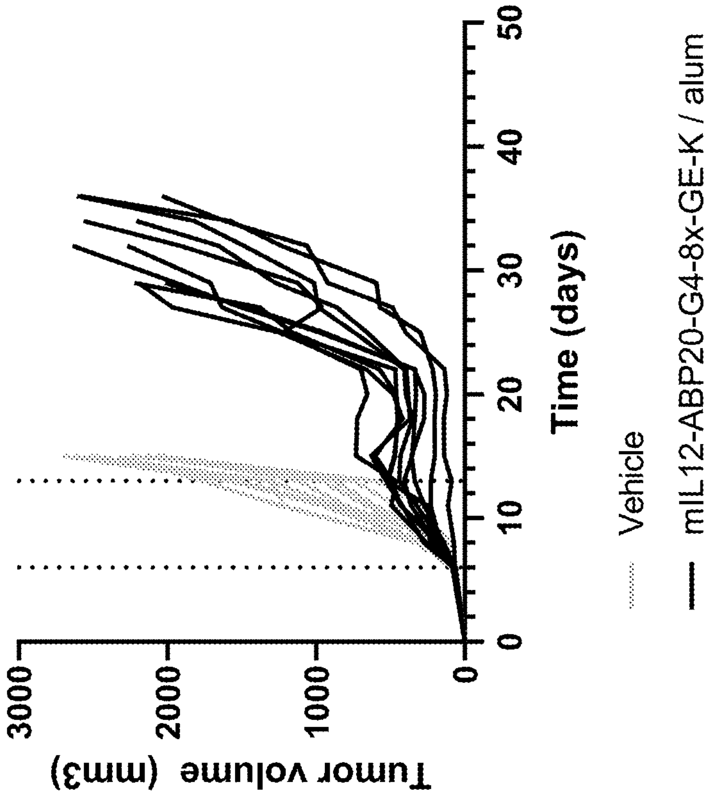
Figure 15D:
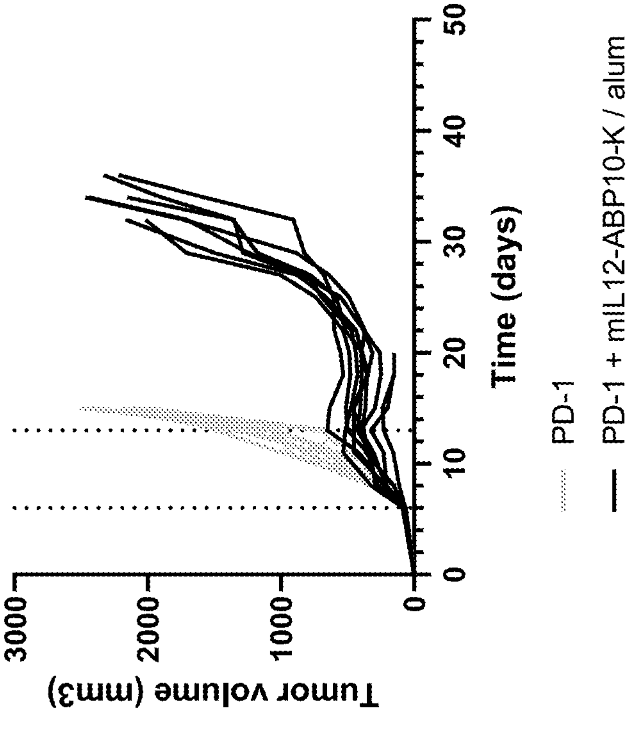
Figure 15E:
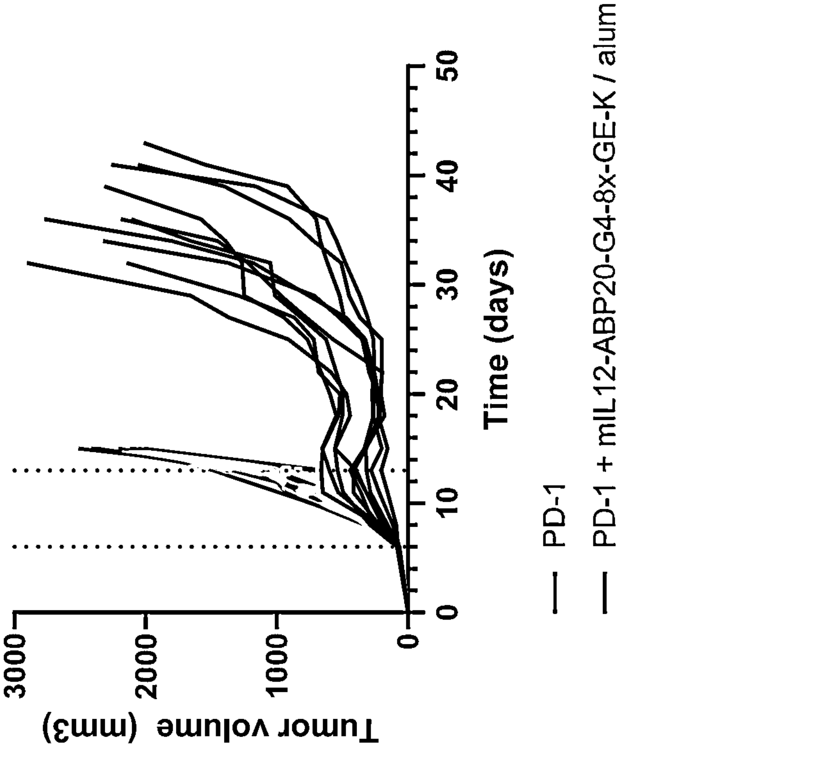

Results mIL12-ABP10 and mIL12-ABP20-G4-8x-GE were compared in multiple syngeneic tumor models. Fusion polypeptides were mixed with a 10-fold mass excess of aluminum hydroxide as defined by metal mass in TBS and incubated at RT for 30 minutes to form a fusion polypeptide-aluminum hydroxide complex prior to injecting in the animals. In the CT26 colorectal cancer model, a single intratumoral injection of 5 μg of either mIL12-ABP or mIL12-ABP20-G4-8x-GE fusion polypeptides complexed with 50 μg alum as defined by metal mass on Day 6 post tumor inoculation led to significant tumor delays and regressions compared to vehicle treated mice. Complete responses with no measurable tumor were observed in 4/10 mice treated with mIL12-ABP10+alum and 5/10 mice treated with mIL12-ABP20-G4-8x-GE+alum (FIGS. 14A-14C).

Figure 16A:
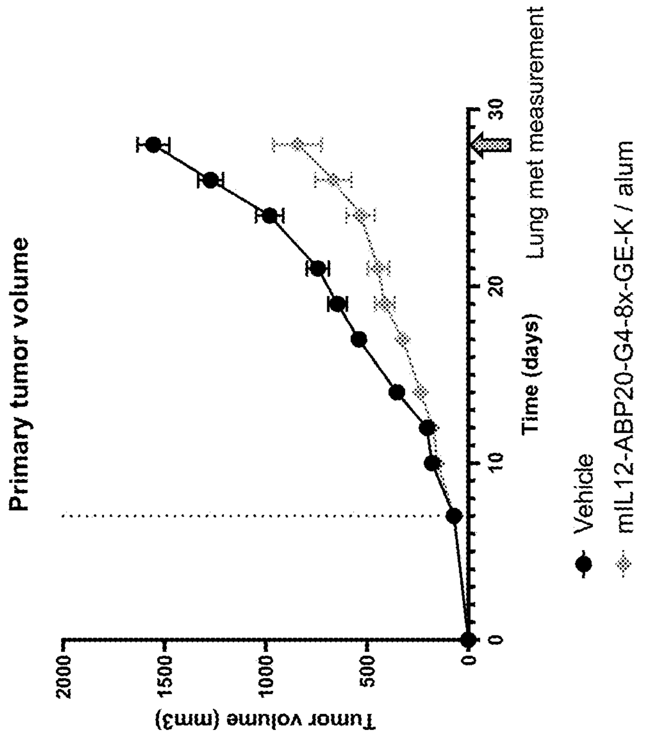
FIG. 16A and FIG. 16B demonstrate exemplary fusion polypeptide metal-hydroxide complex, mIL12-ABP20-G4-8x-GE-K/alum, reduces spontaneous metastases formation in an orthotopic 4T1 breast cancer model. Tumor-bearing mice were treated with a single intratumoral injection of 5 μg of mIL12-ABP polypeptides complexed with 50 μg alum on Day 7 post tumor inoculation.
Figure 16B:
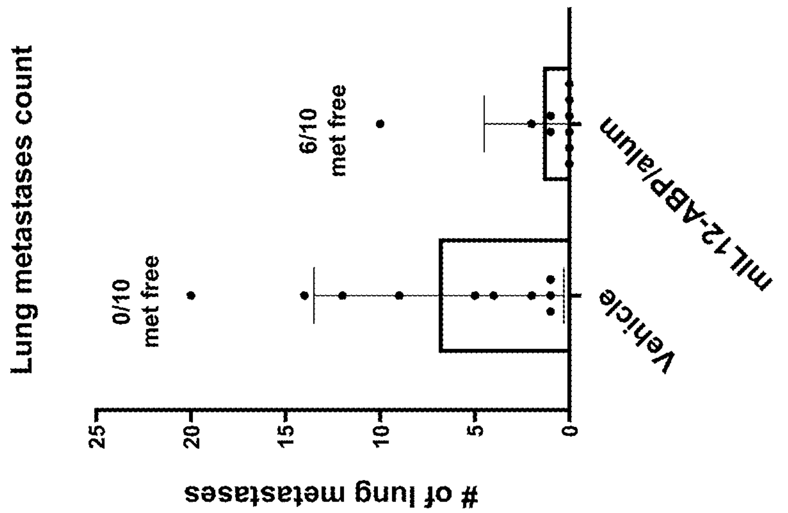

In a second study in the refractory B16F10 tumor model, 7.7 μg of either mIL12-ABP10 or mIL12-ABP20-G4-8x-GE complexed with 50 μg alum as defined by metal mass was injected intratumorally on Day 6 and 13 following tumor inoculation. In some animals, anti-PD1 antibody was also administered intraperitoneally on Day 0, 3, 6, & 9. Both mIL12-ABP agents complexed with alum significantly delayed tumor growth compared to vehicle. The tumor delay was further extended in groups receiving the combination treatment with systemic PD-1 blockade. In both the monotherapy and PD-1 combination groups, the median survival was longer in mice treated with mIL12-ABP20-$G_4$-8x-GE compared to mIL12-ABP10 (FIGS. 15A-15E).

mIL12-ABP20-G4-8x-GE was also tested in an orthortopic 4T1 model that forms spontaneous lung metastases (FIGS. 16A-16B). Tumor-bearing mice were treated with a single intratumoral injection of 5 μg of mIL12-ABP fusion polypeptide complexed with 50 μg alum as defined by metal mass on Day 7 post tumor inoculation. mIL12-ABP20-G4-8x-GE/alum treatment led to growth delay of the primary tumor compared to IT injection of vehicle (FIG. 16A). On Day 28, animals were sacrificed and metastases counted in the lung. While 10/10 vehicle treated mice had at least one lung metastasis, 6/10 of the mice in the mIL12-ABP20-G4-8x-GE/alum treated mice were metastases-free demonstrating that local injection of the mIL12-ABP/alum complex had also induced anti-tumor effects against distal, non-injected lesions (FIG. 16B).

Figure 17A:
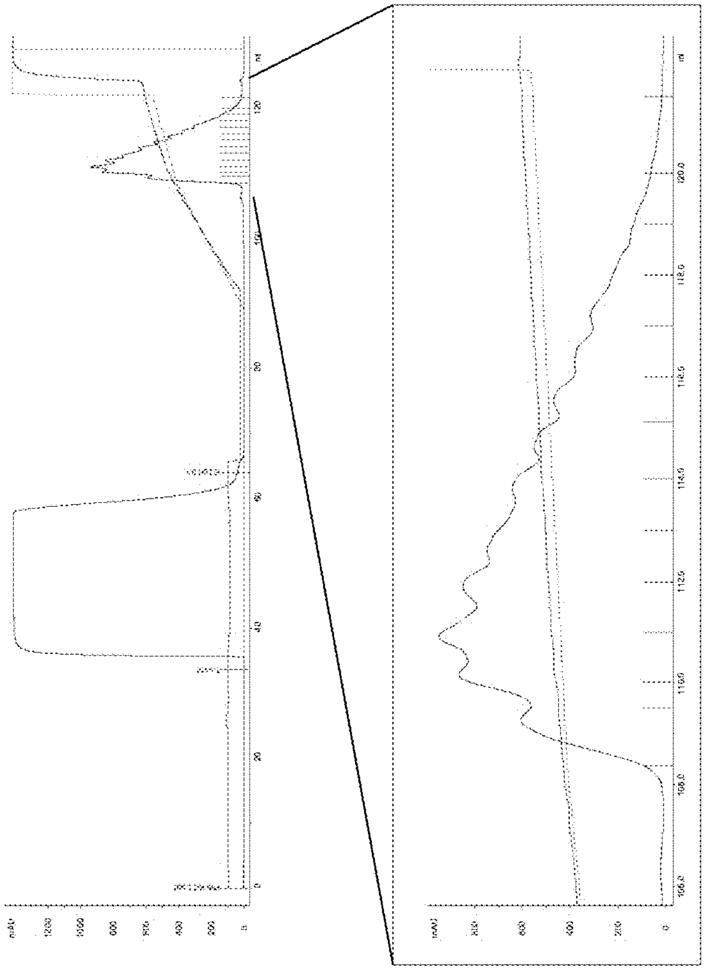
Figure 18A:
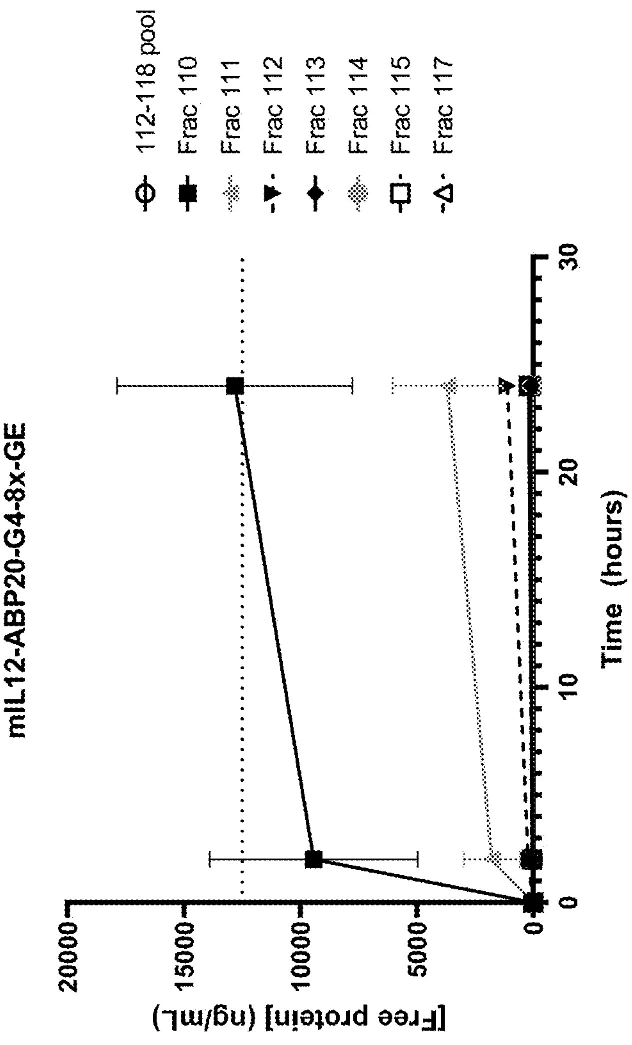
FIG. 18A and FIG. 18B provide exemplary assessment of alum retention on individual fractions of exemplary fusion polypeptide, mIL12-ABP20-G4-8x-GE. Fractions eluted earlier off the anion exchange resin and containing lower phosphorylation levels had lower retention on alum compared to later eluting fractions with higher phosphorylation levels.
Figure 18B:
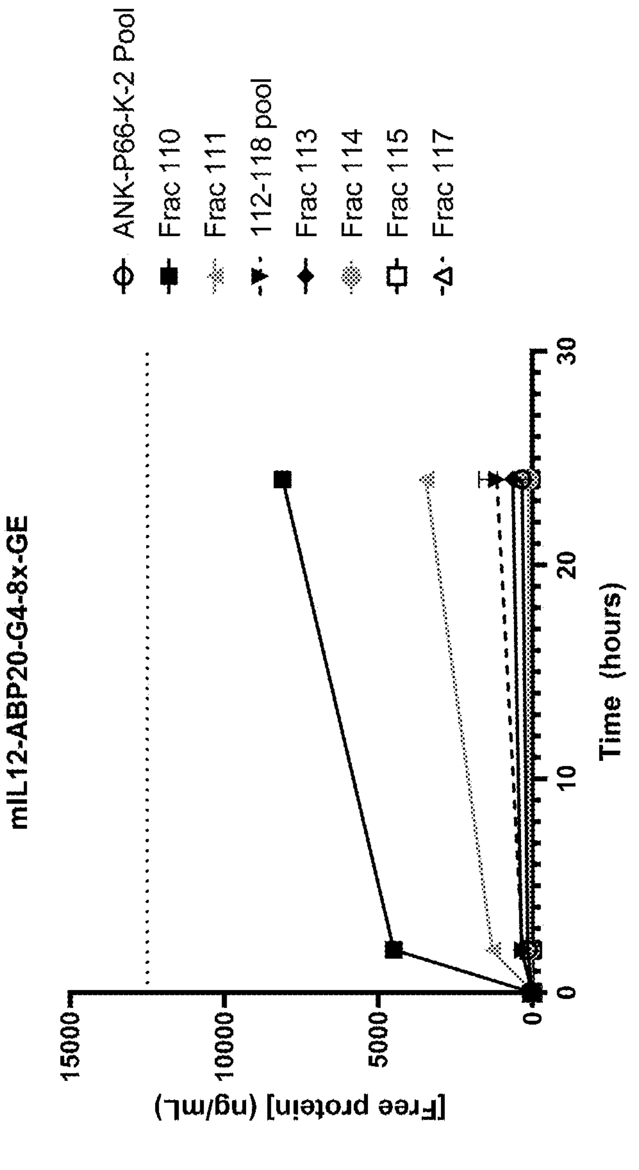
Figure 19A:
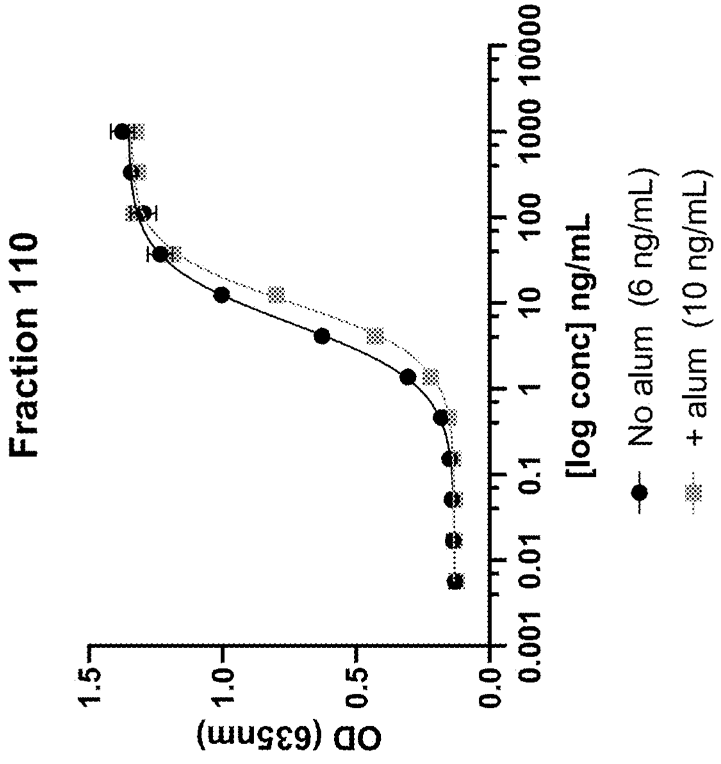
FIGS. 19A-19D provide exemplary assessment of signaling competency on individual fractions of exemplary fusion polypeptide, mIL12-ABP20-G4-8x-GE. Individual fractions were tested in the HEK-Blue-IL12 reporter assay either alone or complexed with a 10-fold mass excess of aluminum hydroxide as defined by metal mass.
Figure 19B:
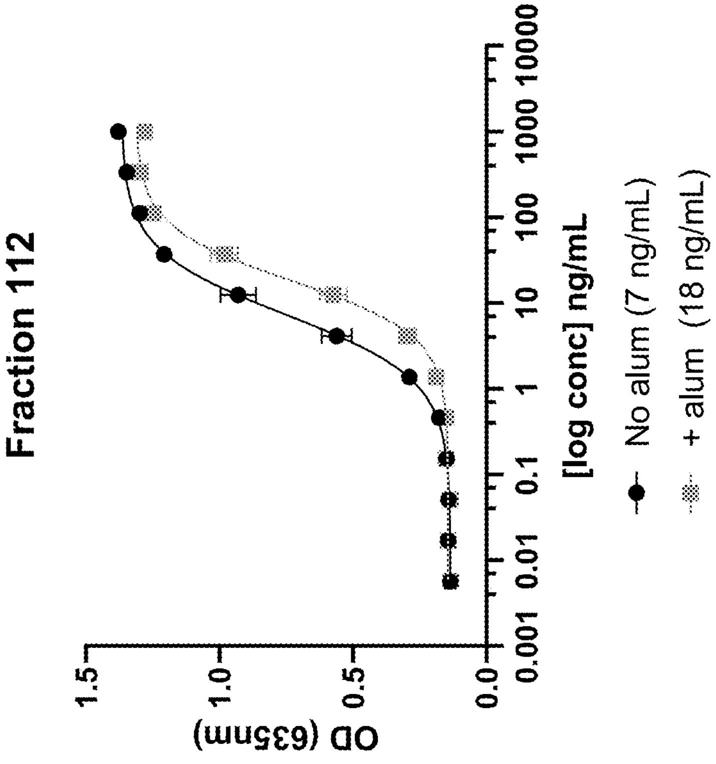
Figure 19C:
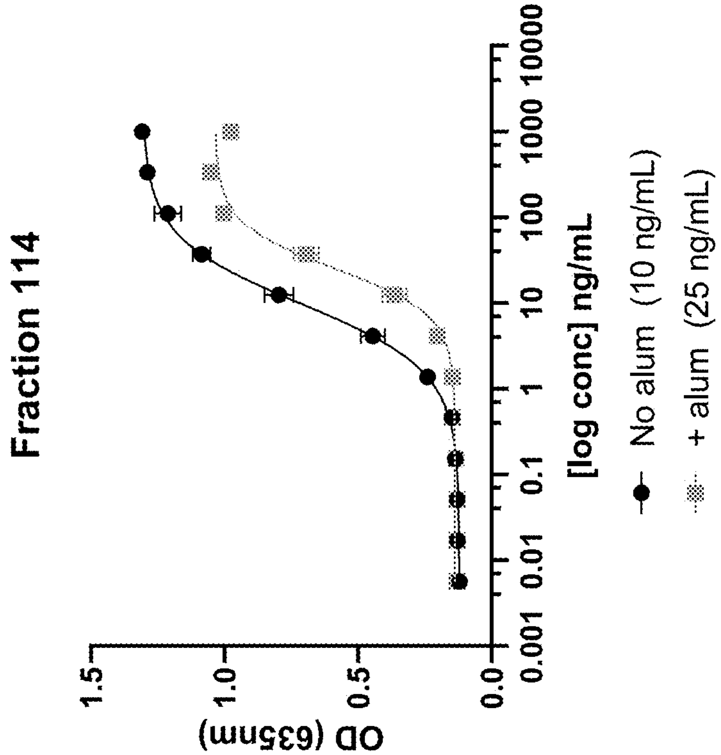
Figure 19D:
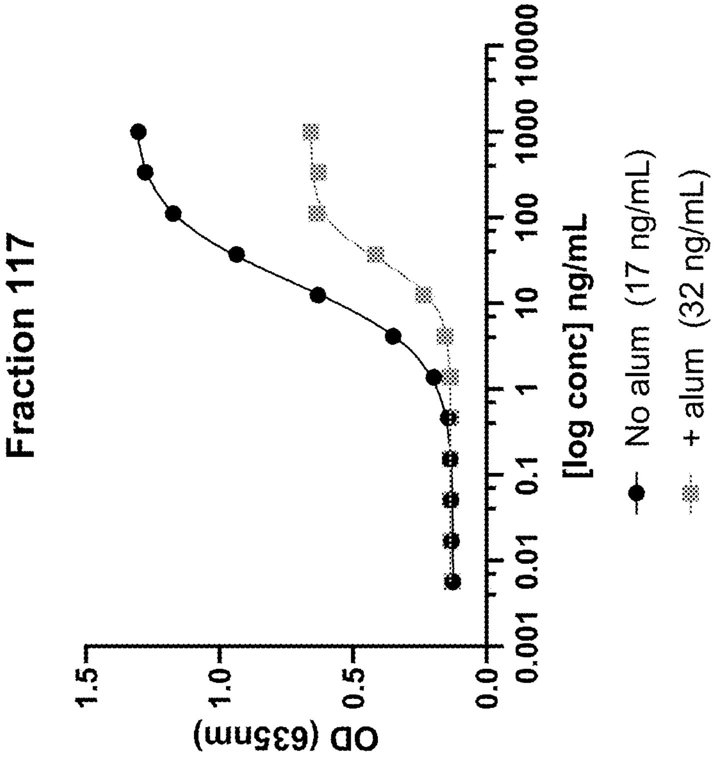

Example 4: Identification of an Optimal Level of Phosphorylation on mIL12-ABP mIL12-ABP20-G4-8x-GE was co-expressed with Fam20C-KDEL transiently in HEK as described above. Fusion polypeptide was purified by Ni-NTA chromatography and size exclusion chromatography, then run on a HiTrap Q Sepharose anion exchange column with a linear salt elution gradient. Individual elution fractions were collected and phosphate levels measured by malachite green assay. Average phosphate levels per fraction ranged from 2 to 7 with lower phosphorylated fusion polypeptide eluting earlier and highly phosphorylated fractions retained longer on the column (FIGS. 17A-17B). Individual fractions were then assessed in the alum retention assay. Fusion polypeptides were bound to a 10-fold mass excess of aluminum hydroxide as defined by metal mass then eluted in solution containing 1 mM phosphate and 50% mouse serum. There was a clear trend where fractions eluting earlier off the anion exchange resin and containing lower phosphorylation levels had lower retention on alum compared to later eluting fractions with higher phosphorylation levels. Fraction 110 with 2.4 phosphates per fusion polypeptide had <50% fusion polypeptide retained on alum at 24 hours and fraction 111 with 3.7 phosphates per fusion polypeptide had ~80% fusion polypeptide retained on alum. Fractions 112 and 113 with 4.6 and 5.8 phosphates per fusion polypeptide respectively were highly retained with >95% bound to alum at 24 hours. Fractions 114-117 with >6 phosphates per fusion polypeptide had no measurable free fusion polypeptide eluting off alum in the assay (FIGS. 18A-18B).

Individual fractions were also tested in the HEK-Blue-IL12 reporter assay either alone or complexed with a 10-fold mass excess of aluminum hydroxide as defined by metal mass (FIGS. 19A-19D). Fractions 110 and 112 had similar peak activity levels with or without alum and 2-3 fold shifts in EC50 when bound to alum. In contrast, fraction 114 and 117 had reduced peak activity when complexed with alum. This suggests that beyond a certain point, excess phosphorylation on the fusion polypeptide can decrease functional activity in the presence of alum Together, these data, summarized in FIG. 20, suggest that there may be an optimal levels of phosphorylation per murine fusion polypeptide at ~4-6 with less than that having insufficient alum retention and >6 losing activity in functional assays.

Example 5: Production and Characterization of Tagless Human IL12-ABP20-G4-8x-GE Genes were synthesized encoding single-chain human IL12-ABP20-G4-8x-GE comprising mature human IL12B/p40 (Uniprot P29460) fused to mature human IL12A/p35 (Uniprot P29459) through a $(G_4S)_3$ linker with the ABP20-G4-8x-GE peptide at the c-terminus. Unlike the mouse constructs, the fusion polypeptides were cloned without the c-terminal His tag, instead ending in a single serine residue. Human IL12-ABP20-G4-8x-GE constructs and Fam20C-KDEL genes were cloned into a single vector with two expression cassettes with different promoters selected to express the hIL12-ABP20-G4-8x-GE fusion polypeptide at an 8-fold higher level than Fam20C-KDEL. Fusion polypeptides were stably transfected in CHO cells using the ATUM Leap-In-Transposase system and stable pools selected. After 14 day expression in a fed-batch culture, supernatants were harvested and purified by multiple chromatography steps including anion exchange chromatography capture and size exclusion chromatography polishing. After purification, the untagged hIL12-ABP20-G4-8x-GE was >97% pure as measured by SDS-PAGE and SEC.

Figure 21A:
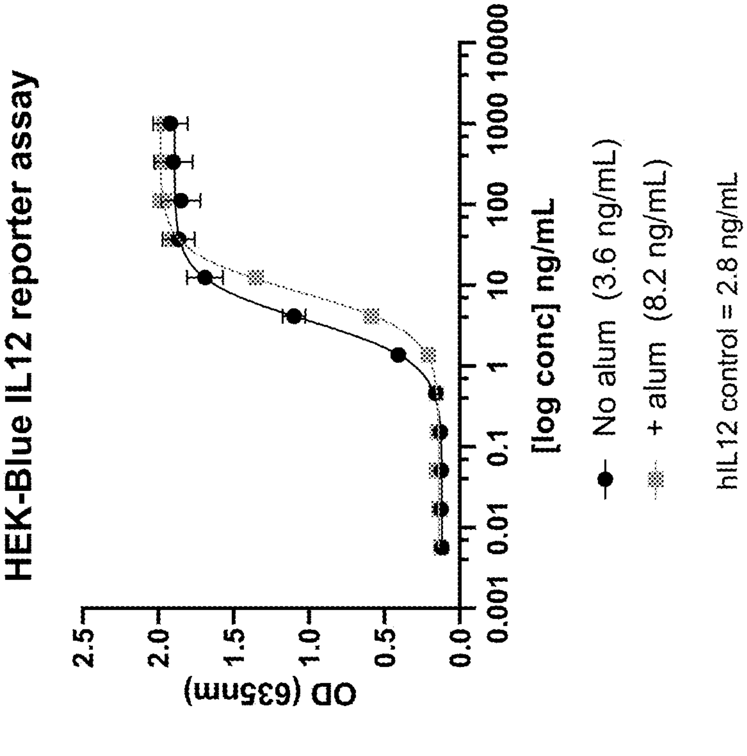
FIGS. 21A-21C demonstrate that human IL12-ABP material is active and retained on alum.
Figure 21B:
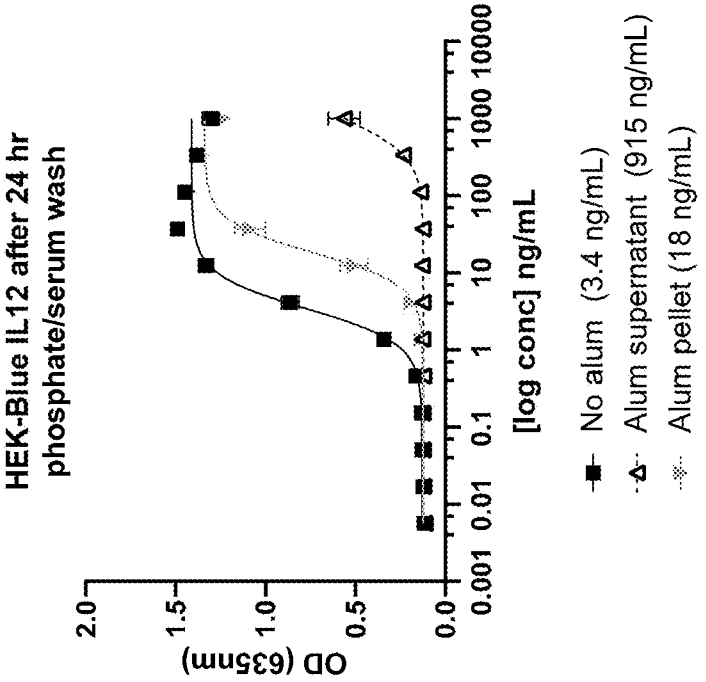
Figure 21C:
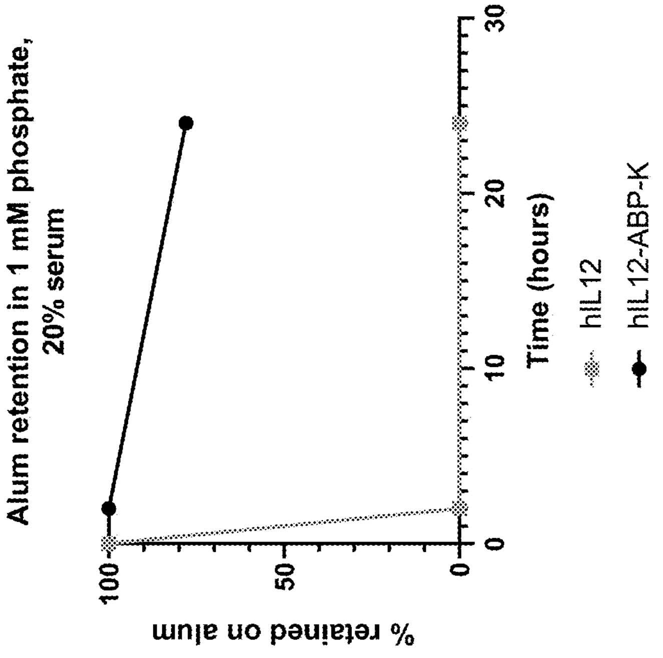

Human IL12-ABP20-G4-8x-GE is active in the HEK-Blue-IL12 assay with an EC50 of 3.6 ng/mL alone or 8.2 ng/mL when complexed with aluminum hydroxide (FIG. 21A). Following incubation of the fusion polypeptide/alum complex in elution buffer containing 1 mM phosphate and 20% mouse serum, the supernatant EC50 shifts>300-fold suggesting minimal fusion polypeptide elution after 24 hours, while the pellet maintained activity with a 5×EC50 shift (FIG. 21B). In a separate alum retention assay, hIL12 or hIL12-ABP was bound to a 10-fold mass excess of aluminum hydroxide as defined by metal mass then diluted in elution buffer containing 1 mM phosphate and 20% mouse serum with free fusion polypeptide detected by ELISA (FIG. 21C). —80% of the hIL12-ABP20-G4-8x-GE is retained on the alum at 24 hours compared to 0% for unmodified IL12.

A second lot of human IL12-ABP20-G4-8x-GE was prepared as described above and further purified by anion exchange chromatography and eluted with a linear salt gradient. Individual elution fractions were collected and phosphate levels were measured by malachite green assay. Average phosphate levels per fraction ranged from 5.8 to 8.8 with lower phosphorylated fusion polypeptide eluting earlier and highly phosphorylated fractions retained longer on the column (FIG. 22).

Figure 23:
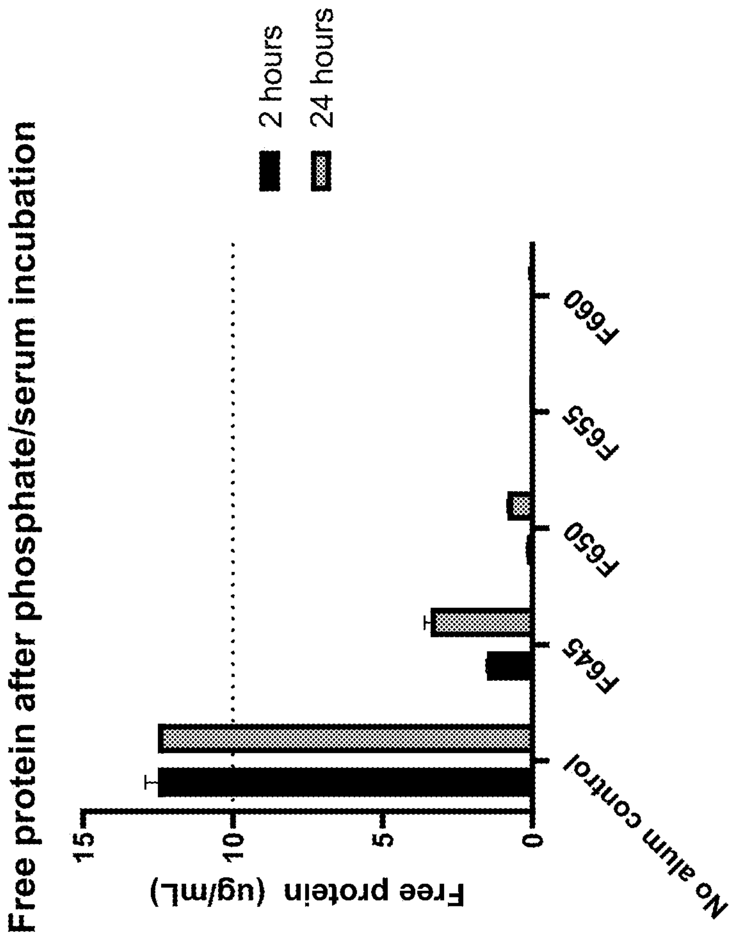
FIG. 23 presents exemplary results of an assessment of binding and retention of purified fractions of an exemplary human IL12-ABP20-G4-8x-GE on aluminum hydroxide. Human IL12-ABP20-G4-8x-GE purification fractions that eluted earlier off the anion exchange resin and containing lower phosphorylation levels had lower retention on aluminum hydroxide compared to later eluting fractions with higher phosphorylation levels.

Individual fractions were assessed in an alum retention assay in which fusion polypeptides were bound to a 10-fold mass excess of aluminum hydroxide as defined by metal mass then eluted in solution containing 1 mM phosphate and 40% serum (FIG. 23). Similar to the murine IL12-ABP20-G4-8x-GE protein, fractions of human IL12-ABP20-G4-8x-GE eluting earlier off the anion exchange resin and containing lower phosphorylation levels had lower retention on alum compared to later eluting fractions with higher phosphorylation levels.

Figure 24:
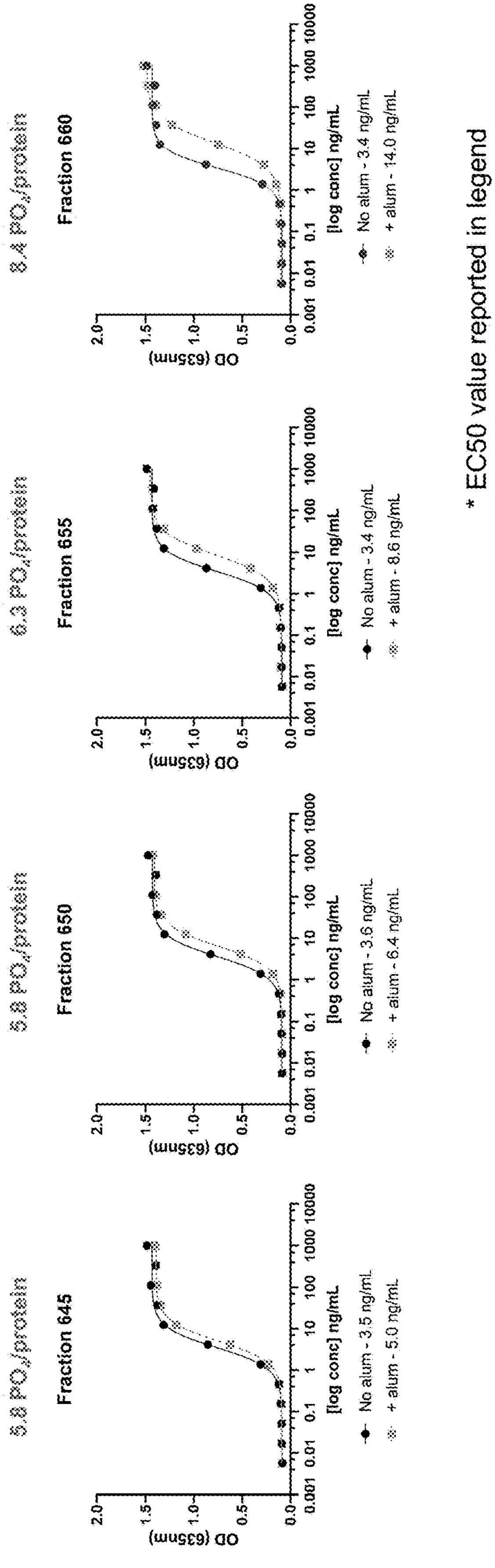
FIG. 24 presents exemplary results of an assessment of the ability of purified fractions of an exemplary human IL12-ABP20-G4-8x-GE to induce IL12-based signaling using a HEK-Blue-IL12 reporter assay either alone or complexed with a 10-fold mass excess of aluminum hydroxide as defined by metal mass.

Individual fractions were also tested in the HEK-Blue-IL12 reporter assay either alone or complexed with a 10-fold mass excess of aluminum hydroxide as defined by metal mass (FIG. 24). In the absence of aluminum hydroxide complexation, all tested fractions had similar potency in the assay with EC50 values between 3.4-3.6 ng/mL. Following aluminum hydroxide complexation, earlier eluting fractions with lower phosphorylation had lower EC50 values (5 and 6.4 ng/mL for fraction 645 and 650, respectively), while later eluting fractions with higher phosphorylation levels had more significant shifts in the EC50 (8.6 and 14 ng/mL for fractions 655 and 660, respectively). All tested fractions had similar maximal activity in the assay either with or without aluminum hydroxide complexation.

Together, fractions 650-660 were identified as having a particularly beneficial balance of alum retention and IL12 signaling activity. Thus, preparations characterized by about 5.8 phosphates or more (e.g., about 5.8 to more than about 8.4) per fusion polypeptide showed particularly desirable properties. Additional assessments may be performed to confirm such properties, including, for example, further in vitro and/or in vivo assessments. In some such studies, fractions 650-660 (or other reasonably comparable preparations—e.g., from another batch, or produced via a different process but achieving comparable phosphorylation characteristics, etc.) may be pooled or otherwise combined for assessment; alternatively or additionally, these fractions (or other reasonably corresponding preparations) may be separately assessed.

Example 6: Production and Characterization of Canine IL12-ABP20-G4-8x-GE-his The present Example documents production and activity of a beneficially phosphorylated preparation of an IL-12 fusion polypeptide as described herein, and of metal hydroxide complexes thereof. Among other things, the present Example documents that preparations of this fusion polypeptide which are characterized by about 5.5 phosphates or more (e.g., about 5.5 to more than about 8.3) per fusion polypeptide showed a particularly desirable balance of alum-binding and IL-12 signaling activities.

An exemplary gene cassette encoding for single-chain canine-IL12-ABP20-G4-8x-GE was synthesized at ATUM Bio and cloned into the pD2610-v5 expression vector. The exemplary canine IL12-ABP20-G4-8x-GE sequence comprises mature canine IL12B/p40 (Uniprot Q28268) fused to mature canine IL12A/p35 (Uniprot F1PPC0) through a $(G_4S)_3$ linker with the ABP20-G4-8x-GE peptide and His tag at the C-terminus. The exemplary construct was transiently co-transfected in suspension HEK-293 cells with a human Fam20C-KDEL plasmid at a 4:1 mass ratio. Supernatants were harvested and IL12 fusion polypeptides purified by affinity chromatography on NiSepharose Excel resin (Cytiva 17-3712-02) followed by FPLC-SEC on a HiLoad 16/600 Superdex 200 pg column (Cytiva 28-9893-36) to remove aggregates. The exemplary canine IL12-ABP20-G4-8x-GE protein was further polished by anion exchange chromatography on a HiTrap Q Sepaharose column to enrich for differentially phosphorylated species and eluted with a linear salt gradient. Selected fractions were assessed for numbers of phosphate per protein using a malachite green assay, IL12 signaling potency using a HEK-Blue-IL12 assay, and aluminum hydroxide binding using an alum retention assay with protocols described above (FIG. 25).

Figure 26:
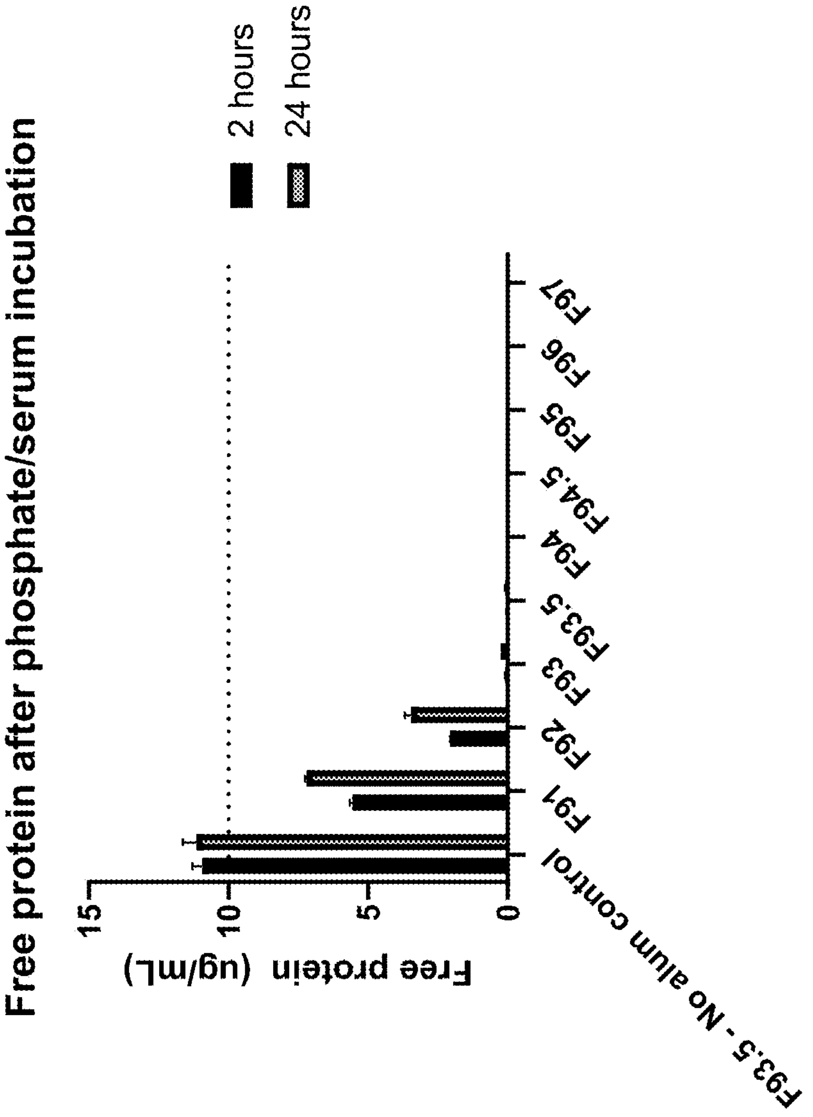
FIG. 26 presents results of an assessment of binding and retention of purified fractions of an exemplary canine-IL12-ABP20-G4-8x-GE on aluminum hydroxide. Canine-IL12-ABP20-G4-8x-GE purification fractions that eluted earlier off the anion exchange resin and containing lower phosphorylation levels had lower retention on aluminum hydroxide compared to later eluting fractions with higher phosphorylation levels.

Average phosphate levels in each fraction ranged from 0.4 to 11.3 $PO_4$/protein with lower phosphorylated proteins eluting earlier and highly phosphorylated proteins retained longer on the column. Individual fractions were then assessed in an alum retention assay in which polypeptides were bound to a 10-fold mass excess of aluminum hydroxide as defined by metal mass then eluted in solution containing 1 mM phosphate and 40% serum with free protein quantified over time using a canine IL12p40 ELISA kit (R&D Systems). A trend was observed where fractions eluting earlier off the anion exchange resin and containing lower phosphorylation levels had lower retention on alum compared to later eluting fractions with higher phosphorylation levels (FIG. 26). Fractions 91 & 92 with 2.0 and 4.5 $PO_4$/protein respectively had the lowest retention with 28% of the IL12 polypeptide in fraction 91 and 65% in fraction 92 retained on the alum at 24 hours. Fractions 93 and 93.5 with 5.5 and 6.5 phosphates per fusion polypeptide respectively were highly retained with >95% bound to alum at 24 hours. Fractions 94-98 with >6.5 phosphates per fusion polypeptide had no measurable free fusion polypeptide eluting off alum in the assay.

Figure 27:
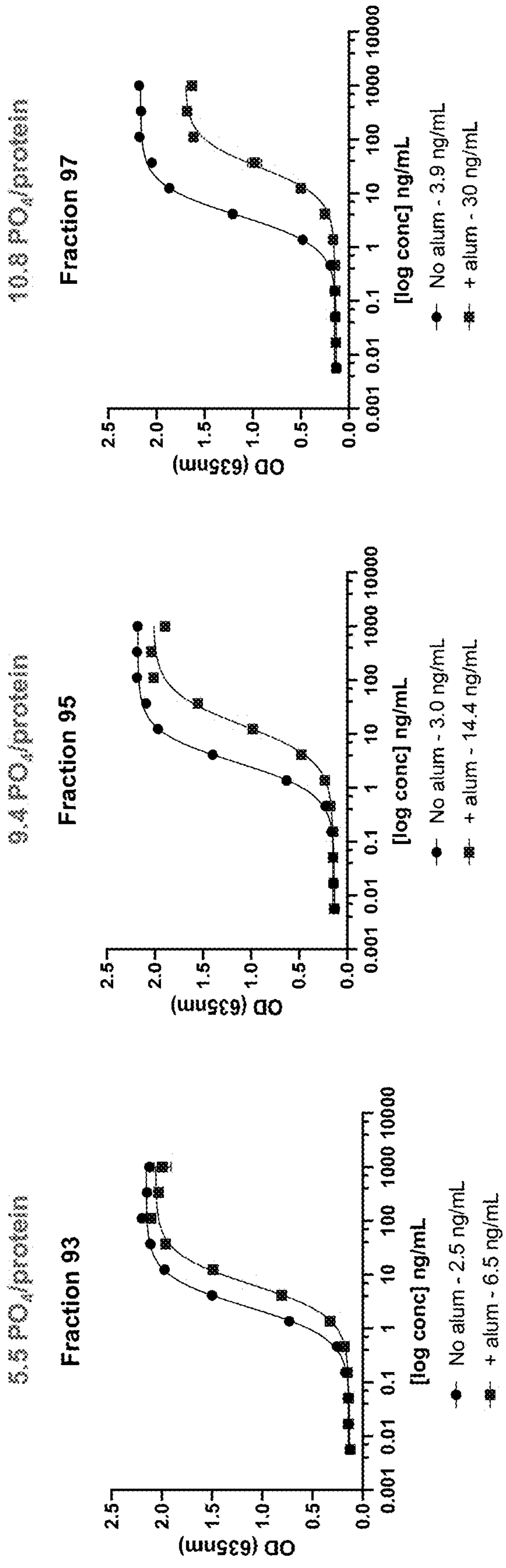
FIG. 27 presents results of an assessment of the ability of purified fractions of an exemplary canine-IL12-ABP20-G4-8x-GE to induce IL12-based signaling using a HEK-Blue-IL12 reporter assay either alone or complexed with a 10-fold mass excess of aluminum hydroxide as defined by metal mass.

Individual fractions were also tested in a HEK-Blue-IL12 reporter assay either alone or complexed with a 10-fold mass excess of aluminum hydroxide as defined by metal mass (FIG. 27). Fractions had similar EC50 values when tested as free protein but different potency when complexed on alum with fractions containing high levels of $PO_4$ having larger increases in EC50 after alum complexation. Fractions 93-94.5 were identified as having a particularly beneficial balance of alum retention and IL12 signaling activity. Thus, preparations characterized by about 5.5 phosphates or more (e.g., about 5.5 to more than about 8.3) per fusion polypeptide showed particularly desirable properties. Additional assessments may be performed to confirm such properties, including, for example, further in vitro and/or in vivo assessments (e.g., in an appropriate animal system—e.g., in this case, in dogs). In some such studies, fractions 93-94.5 (or other reasonably comparable preparations—e.g., from another batch, or produced via a different process but achieving comparable phosphorylation characteristics, etc.) may be pooled or otherwise combined for assessment; alternatively or additionally, these fractions (or other reasonably corresponding preparations) may be separately assessed.

Example 7: Exemplary Canine Studies

The present Example documents further assessment of technologies of the present disclosure (e.g., IL-12 fusion polypeptides, fusion polypeptide preparations). For example, the present Example provides further confirmation and/or assessment of phosphate content, metal-hydroxide retention, signaling activity, efficacy, and/or potency, etc. Among other things, the present Example documents assessment and/or further confirmation of use of IL-12 fusion polypeptides and fusion polypeptide preparations of the present disclosure in a subject, including in a non-human subject, including, for example, a rodent, a mouse, a rat, a rabbit, a monkey, a dog, a cat, a horse, a sheep, cattle, a primate, and/or a pig. Technologies of the present disclosure (e.g., IL-12 fusion polypeptides, fusion polypeptide preparations) are assessed using any suitable animal model known in the art (see, e.g., Paoloni M et al. Defining the Pharmacodynamic Profile and Therapeutic Index of NHS-IL12 Immunocytokine in Dogs with Malignant Melanoma. PLoS One. 2015; 10 (6):e0129954; Cutrera J et al. Safe and effective treatment of spontaneous neoplasms with interleukin 12 electro-chemo-gene therapy. J Cell Mol Med. 2015; 19(3):664-675; Cutrera J et al. Safety and efficacy of tumor-targeted interleukin 12 gene therapy in treated and non-treated, metastatic lesions. Curr Gene Ther. 2015; 15(1):44-54; Von Rueden S K et al. Cancer-Immunity Cycle and Therapeutic Interventions-Opportunities for Including Pet Dogs With Cancer. Front Oncol. 2021; 11:773420. Published 2021 Nov. 19).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A fusion polypeptide comprising:
   (a) an immunomodulatory polypeptide that comprises a functional IL-12 moiety, wherein the IL-12 comprises:
      (i) an IL-12B moiety having an amino acid sequence of at least 95% sequence identity to the amino acid sequence of SEQ ID NO: 23, and
      (ii) an IL-12A moiety having an amino acid sequence of at least 95% sequence identity to the amino acid sequence of SEQ ID NO: 24; and
   (b) a metal-hydroxide binding polypeptide comprising:
      an amino acid sequence having at least 95% sequence identity to the amino acid sequence of SEQ ID NO: 84, and
      having 8 serine-glutamic acid-glutamic acid phosphorylation site motifs.

2. The fusion polypeptide of claim 1, wherein the IL-12B moiety comprises an amino acid sequence having at least 98% sequence identity to the amino acid sequence of SEQ ID NO: 23.

3. The fusion polypeptide of claim 1, wherein the IL-12A moiety comprises an amino acid sequence having at least 98% sequence identity to the amino acid sequence of SEQ ID NO: 24.

4. The fusion polypeptide of claim 1, wherein the IL-12B moiety comprises an amino acid sequence having at least 99% sequence identity to the amino acid sequence of SEQ ID NO: 23.

5. The fusion polypeptide of claim 1, wherein the IL-12A moiety comprises an amino acid sequence having at least 99% sequence identity to the amino acid sequence of SEQ ID NO: 24.

6. The fusion polypeptide of claim 1, wherein the IL-12B moiety comprises the amino acid sequence of SEQ ID NO: 23.

7. The fusion polypeptide of claim 1, wherein the IL-12A moiety comprises the amino acid sequence of SEQ ID NO: 24.

8. The fusion polypeptide of claim 1, wherein the IL-12B is located N-terminal to the IL-12A.

9. The fusion polypeptide of claim 1, wherein the IL-12A is located N-terminal to the IL-12B.

10. The fusion polypeptide of claim 1, wherein the IL-12B and IL-12A portions are linked via a linker.

11. The fusion polypeptide of claim 10, wherein the linker is an amino acid linker consisting of glycine and serine residues.

12. The fusion polypeptide of claim 10, wherein the linker comprises a sequence selected from GS, SEG, GGS, GGGGS (SEQ ID NO: 131), GGGGSGGGG (SEQ ID NO: 135), and GGGGEGGGG (SEQ ID NO: 122).

13. The fusion polypeptide of claim 12, wherein the linker comprises a (G4S) 3 (SEQ ID NO: 3) sequence.

14. The fusion polypeptide of claim 13, wherein the IL-12 comprises a single chain IL-12B linked N-terminal to IL-12A via a linker comprising a (G4S) 3 (SEQ ID NO: 3) sequence.

15. The fusion polypeptide of claim 1, wherein the metal-hydroxide binding polypeptide is phosphorylated, or is suitable to be phosphorylated by a kinase.

16. The fusion polypeptide of claim 15, wherein the kinase is a Fam20C kinase.

17. The fusion polypeptide of claim 1, wherein the fusion polypeptide forms a complex when exposed to a metal-hydroxide.

18. The complex of claim 17, wherein the metal hydroxide is aluminum hydroxide.

19. A fusion polypeptide comprising:

(a) an immunomodulatory polypeptide that comprises an IL-12 moiety, wherein the IL-12 comprises:

(i) an IL-12B moiety having the amino acid sequence of SEQ ID NO: 23, and (ii) an IL-12A moiety having the amino acid sequence of SEQ ID NO: 24; and (b) a metal-hydroxide binding polypeptide comprising the amino acid sequence of SEQ ID NO: 84.

20. A fusion polypeptide comprising the amino acid sequence of SEQ ID NO: 39.

* * * * *